(12) United States Patent
Murdin et al.

(10) Patent No.: US 7,553,493 B2
(45) Date of Patent: Jun. 30, 2009

(54) CHLAMYDIA FLAGELLAR PROTEIN ANTIGEN

(75) Inventors: Andrew D. Murdin, Richmond Hill (CA); Raymond P. Oomen, Aurora (CA); Joe Wang, North York (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 11/905,430

(22) Filed: Oct. 1, 2007

(65) Prior Publication Data

US 2008/0095793 A1   Apr. 24, 2008

Related U.S. Application Data

(62) Division of application No. 09/868,987, filed on Oct. 1, 2001, now Pat. No. 7,297,341.

(51) Int. Cl.
   A61K 39/118   (2006.01)
   A61K 39/02    (2006.01)
   C12P 21/04    (2006.01)
   C12P 21/06    (2006.01)
   C07H 21/04    (2006.01)

(52) U.S. Cl. ............ 424/263.1; 424/184.1; 424/190.1; 424/192.1; 435/69.1; 435/69.7; 536/23.7

(58) Field of Classification Search .......... None
See application file for complete search history.

(56) References Cited

U.S. PATENT DOCUMENTS

| | | | |
|---|---|---|---|
| 6,521,745 B1 * | 2/2003 | Murdin et al. | 536/23.1 |
| 6,559,294 B1 | 5/2003 | Griffais et al. | |
| 6,693,087 B1 | 2/2004 | Murdin et al. | |
| 6,808,713 B1 | 10/2004 | Murdin et al. | |
| 6,822,071 B1 | 11/2004 | Stephens et al. | |
| 7,019,125 B2 | 3/2006 | Murdin et al. | |
| 7,070,792 B2 | 7/2006 | Murdin et al. | |
| 7,081,245 B2 | 7/2006 | Murdin et al. | |
| 2002/0082402 A1 | 6/2002 | Murdin et al. | |
| 2002/0094340 A1 | 7/2002 | Murdin et al. | |
| 2002/0094965 A1 | 7/2002 | Murdin et al. | |
| 2002/0099188 A1 | 7/2002 | Murdin et al. | |
| 2002/0132994 A1 | 9/2002 | Murdin et al. | |
| 2003/0100706 A1 | 5/2003 | Murdin et al. | |
| 2004/0254130 A1 | 12/2004 | Murdin et al. | |

FOREIGN PATENT DOCUMENTS

| EP | 0784059 A | 7/1997 |
|---|---|---|
| WO | WO 99/27105 A | 6/1999 |
| WO | WO 00/27994 | 5/2000 |

OTHER PUBLICATIONS

Accession No. B72030, Apr. 23, 1999.*
U.S. Appl. No. 09/857,128, filed Sep. 20, 2001, Murdin et al.
U.S. Appl. No. 09/471,194, filed Dec. 23, 1999, Murdin et al.
U.S. Appl. No. 09/523,647, filed Mar. 10, 2000, Murdin et al.
U.S. Appl. No. 09/522,606, filed Mar. 10, 2000, Murdin et al.
U.S. Appl. No. 09/609,243, filed Jun. 30, 2000, Murdin et al.
U.S. Appl. No. 09/662,813, filed Sep. 15, 2000, Murdin et al.
U.S. Appl. No. 09/663,362, filed Sep. 15, 2000, Murdin et al.
U.S. Appl. No. 09/663,360, filed Sep. 15, 2000, Murdin et al.
U.S. Appl. No. 09/663,361, filed Sep. 15, 2000, Murdin et al.
U.S. Appl. No. 09/662,814, filed Sep. 15, 2000, Murdin et al.
U.S. Appl. No. 09/662,812, filed Sep. 15, 2000, Murdin et al.
U.S. Appl. No. 09/709,473, filed Nov. 13, 2000, Murdin et al.
U.S. Appl. No. 09/709,474, filed Nov. 13, 2000, Murdin et al.
U.S. Appl. No. 09/709,384, filed Nov. 13, 2000, Murdin et al.
U.S. Appl. No. 09/747,349, filed Dec. 22, 2000, Murdin et al.
Niman et al., PNAS USA, 1983, vol. 80: 4949-4953.
Current Protocols in Immunology, 1997, unit 9.7.1, 9.7.5, 9.7.16, 9.7.19.
Reece et al., 1994 J. Immunol., vol. 172, 241-254.
Hillier et al., Genome Research, vol. 6, No. 9, pp. 807-828, 1996.
Allen et al., Journal of Immunology, 1991, 147, 674-679.
Batteiger et al., 1996, Infection and Immunity, 64, 2839-2841.
Murdin et al., J. Infectious Diseases, 2000, 181, Suppl. 3: S552-S557.
Verma et al., 1997, Nature, vol. 389, p. 239.
Miller et al., The FASB Journal, 1995, 9: 190-199.
Rudinger et al., in "Peptide Hormones", edited by Parsons, J.A., University Park Press, Jun. 1976, p. 6.
Burgess et al., The Journal of Cell Biology, 111: 2129-2138, 1990.
Lazar et al., Molecular and Cellular Biology, 8(3), 1247-1252, 1988.
Jobling et al., Mol. Microbiol., 1991, 5(7): 1755-1767.
Howard R.F., Jacobson K.C., Rickel E., Thurman, Analysis of inhibitory epitopes in the Plasmodium falciparum rhoptry protein RAP-1 including identification of a second inhibitory epitope, J. Infect. Immun., Jan. 1998, 66(1): 380-6 (abstract).
AbD Serotec Excerpt from technical brochure from www.ab-direct.com.
Ayyildiz, Technical Approach to Generate Polyclonal Antibodies against Bacterially expressed GST-PYK-C, Tr. J. Medical Sciences, 29 (1999), 355-360 (abstract).
Cassill J.A., Whitney M., Jaozeiro C.A., Becker A., Zuker C.S., Isolation of Drosophila genes encoding G protein-coupled receptor kinases, Proc. Nat. Acad. Sci. USA, Dec. 15, 1991, 88(24): 11067-70 (pp. 11067 and 11068).

(Continued)

Primary Examiner—Robert B Mondesi
Assistant Examiner—Padma V Baskar

(57) ABSTRACT

The present invention provides purified and isolated polynucleotide molecules that encode *Chlamydia* polypeptides which can be used in methods to prevent, treat, and diagnose *Chlamydia* infection. In one form of the invention, the polynucleotide molecules encode polypeptides CPN100988 RY-68 (SEQ ID Nos:13 and 26).

24 Claims, 96 Drawing Sheets

OTHER PUBLICATIONS

Lutzelschwab R., Klambt C., Rossa R., Schmidt O., A Protein Product of the Drasophila recessive tumor gene, 1(2) giant gl, potentially has cell adhesion properties, EMBO J., Jun. 1987, 6(6): 1791-1797 (pp. 1791 and 1792).

Schoneck R, Plumas-Marty B, Taibi A, Billaut-Mulot O, Loyens M, Gras-Masse H, Capron A, Ouassi A, Trypanosoma cruzi cDNA encodes a tandemly repeated domain structure characteristic of small stress proteins an glutathione S-transferases, Biol Cell., 1994, 80(1): 1-10, (pp. 1 and 2).

Philippe B, Brion JP, Coppens E, Octave JN, Generation of a monoclonal antibody to the carboxy-terminal domain of tau by immunization with the amino-terminal domain of the amyloid precursor protein, J. Neurosci. Res., Dec. 15, 1996, 46(6): 709-19 (abstract).

Yu H, Nakano Y, Yamashita Y, Oho T and Koga T, Effects of antibodies against cell surface protein antigen PA-c-glucosyltransferase fusion proteins on glucan synthesis and cell adhesion of Streptococcus mutans, Infect. Immunol., Jun. 1997, 2292-2298, vol. 65, No. 6 (Abstract).

Zhou FC, Xu Y, Bledsoe S, Lin R, Kelley MR, Serotonin transporter antibodies: production, characteristic, and localization in the brain, Brain Res. Mol. Brain Res., Dec. 31, 1996, 43(1-2): 267-78, (Abstract).

Boehringer Mannheim Biochemicals (1991 Catalog p. 557).
Stratagene (1991 Product Catalog, p. 66).
Promega (1993/1994 catalog, pp. 90-91), or New England Biolabs (catalog 1986/1987, pp. 60-62).
Gibco BRL (Catalogue & Reference Guide 1992, p. 292).
Grayston et al. (1995) Journal of Infectious Diseases 168:1231.
Campos et al. (1995) Investigation of Ophthalmology and Visual Science 36:1477.
Grayston et al. (1990) Journal of Infectious Diseases 161: 618.
Marrie (1993) Clinical Infectious Diseases. 18:501.
Wang et al. (1986) Chamydial Infections. Cambridge University Press, Cambridge. p. 329.
Saikku et al. (1988) Lancet; ii:983.
Thom et al. (1992) JAMA 268:68.
Linnanmaki et al. (1993) Circulation 87: 1130.
Saikku et al. (1992) Annals Internal Medicine 116:499.
Melnick et al. (1993) American Journal of Medicine 95: 499.
Shor et al. (1992) South African Medical Journal 82: 158.
Kuo et al. (1993) Journal of Infectious Diseases 167:841.
Kuo et al. (1993) Arteriosclerosis and Thrombosis 13: 1501.
Campbell et al. (1995) Journal of Infectious Diseases 172:585.
Chiu et al (1997) Circulation. 96(7) :2144-2148.
Ramirez et a). (1996) Annals of Internal Medicine 125:979.
Jackson et al. Abst. K121, p272, 36th ICAAC, Sep. 15-18, 1996, New Orleans.
Fong et al. (1997) Journal of Clinical Microbiolology 35:48.
Hahn DL, et al. Evidence for *Chlamydia pneumoniae* infection in steriod-dependent asthma. Ann Allergy Asthma Immunol. Jan. 1998; 80(1): 45-49.
Hahn DL, et al. "Association of *Chlamydia pneumoniae* IgA antibodies with recently symptomatic asthma". Epidemiol Infect. Dec. 1996; 117(3): 513-517.
Bjornsson E, at el. Serology of chlamydia in relation to asthma and bronchial hyperresponsiveness Scand .7 Infect Dis. 1956; 28(1): 63-69.
Hahn DL. "Treatment of *Chlamydia pneumoniae* infection in adult asthma: a before-after trial" J Fam Pract. Oct. 1995; 41(4):345-351.
Allegra L. et al., "Acute exacerbations of asthma in adults: Role of *Chlamydia pneumoniae* infection", Eur Respir J Dec. 1994, 7(12) 2165-2168.
Hahn DL, et al. Association of *Chlamydia pneumoniae* (strain TWAR) infection with wheezing, asthmatic bronchitis, and adult-onset asthma JAMA. Jul. 10, 1991; 266(2): 225-230.
Pal et al. (1996) Infection and Immunity.64:5341.
Jones et al. (1995) Vaccine 13:715.

Igietseme et al (1993) Regional Immunology 5:317.
Magee et al (1993) Regional Immnology 5: 305.
Landers et al (1991) Infection & Immunity 59:3774.
Magee et al (1995) Infection & Immunity 63:516.
Cotter et al. (1995) Infection and Immunity 63:4704.
Campbell et al. (1990) Infection and Immunity 58:93.
McCafferty et al (1995) Infection and Immunity 63:2387-9.
Gaydos et al. Similarity of *Chlamydia pneumonlae* strains in the Variable Domain IV Region of the Major Outer Membrane Protein Gene; Infection and Immunity; 60(12) :5319-5323.
Wiedmann-Al-Ahmad M, et al. "Reactions of polyclonal and neutralizing anti-p54 monoclonal antibodies with an isolated, species-specific 54-kilodalton protein of *Chlamydia pneumoniae*" Clin Diagn lab Immunol. Nov. 1997; 4(6:700-704).
Hughes et al., 1992. Infect. Immun. 60(9) :3497.
Dion et al., 1990. Virology 179:474-477.
Snijders et al., 1991. J. Gen. Virol. 72:557-565.
Langeveld et al., Vaccine 12(15) :1473-1480, 1994.
Kunkel et al. Proc. Natl. Acad. Sci. USA (1985) 82:488.
Casey & Davidson, Nucl. Acid Res.. (1977) 4:1539.
Cagnon et al, Protein Engineering (1991) 4(7) :843.
Takase et al. J. Bact. (1987) 169:5692.
Perez Melgosa et al, Infect Immun. (1994) 62:880.
Watson et al., Nucleic Acids Res (1990) 18:5299.
Watson et al. Microbiology (1995) 141:2489.
Melgosa at al., "Outer membrane complex proteins of *Chlamydia pneumoniae*" FEMS Microbiol Lett., NL, Amsterdam, Sep. 1993; 112 (2:199-204).
Campbell et al., .J. Clin. Microbiol. (1990) 28 :1261.
Iijima et al., Characterization if *Chlamydai pneumoniae* species-specific proteins immunodominant in humans. J. Clin. Microbiol., Mar. 1994, 32(3:583-588.
Http://chlamydia-www.berkley.edu:4231/.
Bachmaier et al., Science (1999) 283:1335.
Ausubel et al. "Current Protocols in Molecular Biology", John Wiley & Sons Inc., vol. 1, 1993, 15 sheets.
Silhavy et al., "Experiments with gene fusions", Cold Spring Harbor Laboratory Press, 1984, pp. 191-195.
Davis et al., "A Manual for Genetic Engineering: Advanced Bacterial Genetics" Cold Spring Harbor Laboratory Press, 1980, pp. 174-176.
Database Genembl (online) Jul. 22, 1998, Stephens et al., "*Chlamydia trachomatis* section 45 of 87 of the complete genome", XP002133142, Accession No. AE001318.
Stephens et al. "Genome Sequence of an Obligate Intracellular Pathogen of Humans:*Chlamydia trachomatis*", Science, vol. 282, Oct. 23, 1998, pp. 754-579, XP002104802.
Database Genembl (online), Mar. 15, 1999, Kalman et al., "*Chlamydia pneumoniae* section 57 of 103 of the complete genome", XP002133143, Accession No. AE001641.
Kalman et al., "Comparative Genomes of *Chlamydia pneumoniae* and *C. trachomatis*", Nature Genetics, vol. 21, Apr. 1999, pp. 385-389, Accession No. XP00853883.
Gu L. et al. "Cloning and characterization of a secY homolog from *Chlamydia trachomatis*", Molecular and General Genetics, vol. 243, No. 4, May 25, 1994, pp. 482-487, Accession XP000864462.
Melgosa MP et al., "Isolation and characterization of a gene encoding a *Chlamydia pneumoniae* 76-kilodalton protein containing a species-specific epitope", Infection and Immunity US, American Society for Microbiology, Washington vol. 62, No. 3, Mar. 1, 1994, pp. 880-886, XP002059939.
Watson MW et al., The nucleotide sequence of the 60kDa cysteine rich outer membrane protein of *Chlamydia pneumoniae* strain IOL-207, Nucleic Acids Research (1990), vol. 18, No. 17, p. 5299, XP00891318.
Melgosa MP et al., "Sequence analysis of the major outer membrane protein gene of *Chlamydia pneumoniae*", Infection and Immunity (1991), vol. 59, No. 6, pp. 2195-2199, XP000891319.

\* cited by examiner

Restriction enzyme analysis of CPN100686 (RY 54 - SEQ ID NO. 1)

Figure 1C (Continued)

```
                         Hpy188IX
                           MnlI    |
   CviRI          NspV  HinfI|     |   ApoI
   FokI|          TaqI  TfiI|  |Tsp509I            BsmAI   MseI
   ||             |     |||     |                  |       |
       GCAAATGTTCTTGTATTCGAAAGAATCCGAGAGGAATTTTTATTGTCTCAAAGTCTTAA
   481 ---------+---------+---------+---------+---------+---------+ 540
       ACGTTTACAAGAACATAAGCTTTCTTAGGCTCTCCTTAAAAATAACAGAGTTTCAGAATT CviJI   CviJI
                           BsaJI     |    NlaIV|    HinfI
              SfcI         StyI      |    MwoI ||   TfiI           SfcI
              |            |         |    |    ||   |              |
       AAAATCTGTAGAAAAAGGATATACCAAGGCTTTTGGAGCCATTTTTGATTCTAACTTGAC
   541 ---------+---------+---------+---------+---------+---------+ 600
       TTTTAGACATCTTTTTCCTATATGGTTCCGAAAACCTCGGTAAAAACTAAGATTGAACTG BbvCI
              Bpu10I
              DdeI                         CviJI
       CviJI   |        BseMII             HaeIII    BslI
       HaeI    |        MnlI       |       EcoO109I |EcoNI|
       TaaI HaeIII | MboII    |    | BfaI  Sau96I   | MseI |
       |    |    |    |       |    |    |    |     | |    |
       TACAGTATTGGCCTCAGCACTTCTTTTCTTCCTAGATACAGGGCCTATTAAAGGGTTTGC
   601 ---------+---------+---------+---------+---------+---------+ 660
       ATGTCATAACCGGAGTCGTGAAGAAAAGAAGGATCTATGTCCCGGATAATTTCCCAAACG ApoI
                                                          Tsp509I
                                                          MboII|
                                                          BcefI||
                 ApoI                                     NlaIII|||
                 MboII                                    Hpy178III |||
                 Tsp509I      EarI    CviJI    RcaI       |    |    |||
                 |            |       |        |          |    |    |||
       TTTGACATTGATTTTAGGAATTTTCTCTTCAATGTTTACGGCTCTTTTCATGACTAAATT
   661 ---------+---------+---------+---------+---------+---------+ 720
       AAACTGTAACTAAAATCCTTAAAAGAGAAGTTACAAATGCCGAGAAAAGTACTGATTTAA NdeI
                           FokI       CviRI    |
            NlaIII         SimI   |   TaaI     ||       XmnI
            |              |      |   |        ||       |
       TTTCTTCATGCTGTGGATGAATAAGACCCAACATACACAGTTGCATATGATGAATAAGTT
   721 ---------+---------+---------+---------+---------+---------+ 780
       AAAGAAGTACGACACCTACTTATTCTGGGTTGTATGTGTCAACGTATACTACTTATTCAA
```

Figure 1D (Continued)

```
                    Hpy178III
                       SmlI|                              Hpy178III
                       MnlI||                    CviJI        |
                       SfaNI||                   Bce83I       |
              NlaIII   | ||       CviRI    FokI|     |        |
                 |     | ||        |         |  ||   |        |
        CGTGGGGATAAAGCATGATTTCTTGAGAGGATGCAAAAAACTTTGGGCTGTTTCTGGAAG
    781 ---------+---------+---------+---------+---------+---------+ 840
        GCACCCCTATTTCGTACTAAAGAACTCTCCTACGTTTTTTGAAACCCGACAAAGACCTTC

ApoI
                                                    EcoRI
                                                    Tsp509I
                                                    ScrFI  |
                                                    CviJI  |
                                                    EcoRII |
                             Sth132I    AvaI    NlaIV|    |
                                |        |        || |    |
        TGTTTTTCTTTTAGGTTGCGTTGCTCTCGGGTTTGGAGCCTGGAATTCCGTTTTGGGAAT
    841 ---------+---------+---------+---------+---------+---------+ 900
        ACAAAAAGAAAATCCAACGCAACGAGAGCCCAAACCTCGGACCTTAAGGCAAAACCCTTA

DraI
           MseI|
           MnlI||               MseI             NlaIII       SfaNI
            |||                  |                 |            |
        GGATTTTAAAGGAGGGTATGCCTTTACCTTTAATCCAAAAGAGCATGGCATCAGCGATGT
    901 ---------+---------+---------+---------+---------+---------+ 960
        CCTAAAATTTCCTCCCATACGGAAATGGAAATTAGGTTTTCTCGTACCGTAGTCGCTACA

Hpy178III
                                            MboII      BfaI|
                                            AluI|      XbaI||
                          CviRI    SfcI     CviJI|     BsmAI|||
                           |        |         ||         | |||
        TGCTCAAATGCGTGGCAAAGTTGTGCATAAACTACAGGAAGCTGGTCTTTCTTCTAGAGA
    961 ---------+---------+---------+---------+---------+---------+ 1020
        ACGAGTTTACGCACCGTTTCAACACGTATTTGATGTCCTTCGACCAGAAAGAAGATCTCT

BsaBI
                            DpnI  |
                         Sau3AI   |
                      AlwI        |
                   Hpy188IX|      |
                   Tth111II|      |
                      DpnI  ||     |
                    BstYI  |||     |                      AluI
                    Sau3AI |||     |                      CviJI
         Eco57I MboII      |||     |                    HindIII  |
            |     |   |    |||     |                         |   ||
        CTTCCGTATTCAAACATTTGGATCTTCAGAAAAGATCAAAATCTATTTTAGTGATAAAGC
    1021 ---------+---------+---------+----------+---------+---------+ 1080
        GAAGGCATAAGTTTGTAAACCTAGAAGTCTTTTCTAGTTTTAGATAAAATCACTATTTCG
```

Figure 1F (Continued)

```
                                       NlaIII
                                     Hpy178III |
                                  Tsp509I  |   |
                                    MseI|  |   |
              TspRI    HhaI        |  | |  |             CviRI
   BcefI      MwoI    |MwoI  |  |RcaI |  |       CviJI  MwoI   |
       |         |    ||  |  ||    |  |  |         |      |    |
       GCAATATGCTTTCAGTGCCGTATGCGCTTTAATTCATGACCTTTTGGCTACCTGTGCAGT
 1321  ---------+---------+---------+---------+---------+---------+ 1380
       CGTTATACGAAAGTCACGGCATACGCGAAATTAAGTACTGGAAAACCGATGGACACGTCA
CviJI
                            ApoI                Cac8I   |
               BsgI       Tsp509I  MboII        CviRI   |      MwoI
                  |           |      |             | |  |         |
       CTTGTTTATAGCACATTTCTTTTTGAAGAAAATTCAAATAGATTTGCAAGCCATTGGTGC
 1381  ---------+---------+---------+---------+---------+---------+ 1440
       GAACAAATATCGTGTAAAGAAAAACTTCTTTTAAGTTTATCTAAACGTTCGGTAACCACG DpnI
                                       BclI  |      DpnI
    MseI       TaaI          MseI      Sau3AI|   Sau3AI |Hpy178III
       |          |             |          | |       | ||        |
       TTTAATGACTGTATTGGGGTATTCATTAAACAATACTTTGATCATTTTGATCGTATTCG
 1441  ---------+---------+---------+---------+---------+---------+ 1500
       AAATTACTGACATAACCCCATAAGTAATTTGTTATGAAACTAGTAAAAACTAGCATAAGC SfaNI
                                          NlaIII |
                                            NspI |
          DpnI                              NsiI ||
       Sau3AI |     MboII                  CviRI |||     MseI
           | |         |                       | |||        |
       TGAAGATCGCCAAGCGAACCTGTTTACCCCTATGCATGTTTTAGTTAATGATGCCCTTCA
 1501  ---------+---------+---------+---------+---------+---------+ 1560
       ACTTCTAGCGGTTCGCTTGGACAAATGGGGATACGTACAAAATCAATTACTACGGGAAGT AciI
              Fnu4HI
                TauI    MslI         AluI
       MaeII  CviJI|    TaaI|        CviJI                  MseI
           |     ||       ||             |                     |
       AAAGACGTTCAGCCGCACGGTAATGACAACAGCTACAACTCTATCAGTTTTGTTAATGCT
 1561  ---------+---------+---------+---------+---------+---------+ 1620
       TTTCTGCAAGTCGGCGTGCCATTACTGTTGTCGATGTTGAGATAGTCAAAACAATTACGA NlaIV
               CviJI|
             Fnu4HI ||        MnlI
               TauI ||      Tsp509I      CjePI            HinfI
       BseRI AciI|  ||        MseI|      CviRI     |   MboII  TfiI
           |    ||  ||           ||          |     |       |     |
       TTTGTTTATAGGCGGCTCCTCTGTCTTTAATTTTGCATTTATTATGACCATAGGGATTCT
 1621  ---------+---------+---------+---------+---------+---------+ 1680
       AAACAAATATCCGCCGAGGAGACAGAAATTAAAACGTAAATAATACTGGTATCCCTAAGA
```

Figure 1G (Continued)

```
                  BsmAI                          AvaII
     BfaI  CjePI  BsmBI   CviRI          MnlI Sau96I
       |     |     |        |              |    |
       TCTAGGAACTTTATCGTCTCTTTATATTGCACCACCTCTGTTGTTGTTTATGGTCCGTAA
1681   ---------+---------+---------+---------+---------+---------+ 1740
       AGATCCTTGAAATAGCAGAGAAATATAACGTGGTGGAGACAACAACAAATACCAGGCATT
                       MseI
                  TaaI  |           AflIII

RsaI  |  |   MseI   MaeII
                |   |  |    |       |
       AGAAAATCGCTCAAAATAAGTACCGTTAAACTTAATCTAACGTGTAGCAATATAAAAATC
1741   ---------+---------+---------+---------+---------+---------+ 1800
       TCTTTTAGCGAGTTTTATTCATGGCAATTTGAATTAGATTGCACATCGTTATATTTTTAG

NlaIV
                         CviJI|
                         HaeIII|
                         EcoO109I||        ApoI        Hpy188IX
                         Sau96I||       Tsp509I   ApoI    |
     BsmFI    PshAI      BsmFI |||       MseI  |  Tsp509I |
       |        |          |   |||        |    |    |     |
       TCCTTTGGGACTTTAGTCCCAAAGGCCCCTGTGGTATTAAATTTATGACAAATTCAGATA
1801   ---------+---------+---------+---------+---------+---------+ 1860
       AGGAAACCCTGAAATCAGGGTTTCCGGGGACACCATAATTTAAATACTGTTTAAGTCTAT

ATGC
1861   ---- 1864
       TACG
```

Restriction enzyme analysis of CPN100696 (RY 55 - SEQ ID NO. 2)

Figure 2B (Continued)

```
                                              HinfI
                            ApoI              TfiI
   HinfI        BccI        Tsp509I           BsaAI  |
   TfiI    HphI CjeI  |     FokI   |          MaeII| |
    |       |   | |   |      |     |           ||  |
    GGTGAATCTACTCATAGGATGGGCAAAGACAAAATTTATTCAACCTATACGTGAATCAAA
241 ---------+---------+---------+---------+---------+---------+ 300
    CCACTTAGATGAGTATCCTACCCGTTTCTGTTTTAAATAAGTTGGATATGCACTTAGTTT Tsp509I
              Cac8I    |
              AluI     |            ApoI
   AluI       CviJI    |            EcoRI
   CviJI Hpy178III |   |     CjePI  Tsp509I
    |     |       ||   |      |      |
    GCTCTTTCAATCCAGAGCTTGCCAAATTACCCTGCTCGTTTTAGGAATTCTTTTGGTTGT
301 ---------+---------+---------+---------+---------+---------+ 360
    CGAGAAAGTTAGGTCTCGAACGGTTTAATGGGACGAGCAAAATCCTTAAGAAAACCAACA CjeI
         MboII   |
         NlaIII| |                                  CjeI
   CjePI     || |           BsrI              NsiI|
   MwoI| NspI| |            CviJI| BslI       CviRI ||   BbvI
    ||   ||  |               ||  |             | ||   |
    TGCTGGATTAGCATGTATGTTTATCTTCCATAGCCAGTTAGGGGCAAATGCATTTTGGTT
361 ---------+---------+---------+---------+---------+---------+ 420
    ACGACCTAATCGTACATACAAATAGAAGGTATCGGTCAATCCCCGTTTACGTAAAACCAA MaeIII
       Fnu4HI         MaeIII BfaI |
       TseI|          MseI  |SpeI| |    MslI         HindIII
        ||              |    ||  | |     |            |
    GATTATTCCTGCTGCCATAGGATTGATTAAGTTACTAGTTACATCATTATGTTTTGATGA
421 ---------+---------+---------+---------+---------+---------+ 480
    CTAATAAGGACGACGGTATCCTAACTAATTCAATGATCAATGTAGTAATACAAAACTACT Hpy188IX
   RsaI      |
   BsrGI |   |
   TatI  |   |
   AluI  |   |                                      DpnI
   CviJI |   |     NlaIII BspMI BslI    AarI        Sau3AI |
    |    |   |       |     |    |        |          |    ||
    AGCTTGTACATCTGAAAAACTCATGGTTTTCCAAAAATGGGCAGGTGTTTTAGAAGATCA
481 ---------+---------+---------+---------+---------+---------+ 540
    TCGAACATGTAGACTTTTTGAGTACCAAAAGGTTTTTACCCGTCCACAAAATCTTCTAGT
```

Figure 2D (Continued)

```
                        Hpy188IX
                          DpnI  |
                     Sau3AI |   |
                  RsaI    | |   |
              BsaAI  |    | |   |
               SunI  |    | |   |
             MaeII|  |    | |   |              Tsp509I
             FokI||  |    | |   |               TaaI  |

||| |    | | |                    | |
    GGGATGCTACTTTCCACGTACGAGATCAGATGTAAAGAGCAACAGTAATTATTTTCTACA
721 ---------+---------+---------+---------+---------+---------+ 780
    CCCTACGATGAAAGGTGCATGCTCTAGTCTACATTTCTCGTTGTCATTAATAAAAGATGT

TspRI
   TaaI  |        NlaIII
    |  |           |
    CTGTTGTAATAAAATCATGT
781 ---------+---------+ 800
    GACAACATTATTTTAGTACA
```

Restriction enzyme analysis of CPN100709 (RY 57 - SEQ ID NO. 3)

Figure 3C (Continued)

```
                                                   Hpy178III
                                              DdeI    |
                                  TspRI    MnlI  |    |     BseMII
        AlwI Hpy188IX              BtsI   | BccI |  | | Hin4I  |
         |    |                     |     |  |   |  | |  |     |
             TCTTGTTGGACTTTCTGACACCACCACCACTGCTTTCGCCCATCTCTCAGGAGGACAAAT
   481   ---------+---------+---------+---------+---------+---------+ 540
             AGAACAACCTGAAAGACTGTGGTGGTGGTGACGAAAGCGGGTAGAGAGTCCTCCTGTTTA

Hpy178III
                                    CviJI             Tsp509I  |
                            Bpu10I    |           ApoI    |    |
                RsaI         DdeI     |        Tsp509I    |    |
           TatI  |           CviJI    |          MnlI  MseI|   |
            | |              | |      |           |    |  ||   |
             CCAGCGTGTACTTCTGGCAAGAGCCTTAGCCTCCTACCCTGAAATTTTAATTCTTGATGA
   541   ---------+---------+---------+---------+---------+---------+ 600
             GGTCGCACATGAAGACCGTTCTCGGAATCGGAGGATGGGACTTTAAAATTAAGAACTACT

Tth111II
                 Hpy178III   |
                   DpnI |    |                                  AluI
                 Sau3AI |    |         ApoI                     CviJI
        CviJI      AlwI |    |      Tsp509I MseI               BciVI  |
          |         |   |    |          |    |                  |  | |
             GCCGACGACAAACATTGATCCTGACAATCAACAAAGAATTTTAAGTATCCTAAAAAAGCT
   601   ---------+---------+---------+---------+---------+---------+ 660
             CGGCTGCTGTTTGTAACTAGGACTGTTAGTTGTTTCTTAAAATTCATAGGATTTTTTCGA

BsiHKAI
              Bsp1286I
               BseSI  |
               CviRI  |                DpnI
              ApaLI   |              Sau3AI |
              BsaAI|  |           Hpy178III| |
             MaeII||  |               HphI|| |
              RsaI||| |              MboII ||| |
             SunI |||| |             MaeIII    |    |||    |
             TaaI |||| |              BstXI    |    |||    |        Tsp509I      MseI
               | |||| |                MslI    |    |||    |           |          |
             CAACCGTACGTGCACCATTCTTATGGTAACTCACGATCTTCACCATACGACGAATTACTT
   661   ---------+---------+---------+---------+---------+---------+ 720
             GTTGGCATGCACGTGGTAAGAATACCATTGAGTGCTAGAAGTGGTATGCTGCTTAATGAA

BcgI
                               CviRI                       TaqI   MseI
                                 |                          |      |
             TAATAAAGTTTTTTATATGAACAAAACTTTGCACTTCATTGGCAGACACTTCGACCTTAA
   721   ---------+---------+---------+---------+---------+---------+ 780
             ATTATTTCAAAAAATATACTTGTTTTGAAACGTGAAGTAACCGTCTGTGAAGCTGGAATT
```

Restriction enzyme analysis of CPN100710 (RY 58 - SEQ ID NO. 4)

Figure 4B (Continued)

```
                              DpnI
              CviRI         CjePI|                  HinfI
              NlaIII        Sau3AI||                TfiI
              NspI          TaqI|||       BsmAI
               |             ||||          |         | |
       AAACTTGTTAGAGAAACCTTACATGCAACAAGTCGATCTTTCCCAAAATGTCTCGCTGAT
361    ---------+---------+---------+---------+---------+---------+ 420
       TTTGAACAATCTCTTTGGAATGTACGTTGTTCAGCTAGAAAGGGTTTTACAGAGCGACTA CviJI
           CviJI                       Pfl1108I            TaqII|
           CjePI |                     CjeI |      BslI MseI  ||
             | |                        | |        |     |   ||
       TCAAGGAAAGCCTTGCTGTAATCAACATACCACGAACTACGACACCCACACTTGGTTAAG
421    ---------+---------+---------+---------+---------+---------+ 480
       AGTTCCTTTCGGAACGACATTAGTTGTATGGTGCTTGATGCTGTGGGTGTGAACCAATTC MseI                 MaeIII
       RleAI  CjeI|   BsmAI        CjeI  |          MseI
        |      ||     |              |   |           |
       CCCTAAAAACCTTAAAGTCCAAGTGGAGACTATCGTTACCACTTTAAGTAAAAAATATCC
481    ---------+---------+---------+---------+---------+---------+ 540
       GGGATTTTTGGAATTTCAGGTTCACCTCTGATAGCAATGGTGAAATTCATTTTTTATAGG HaeIV
               Hin4I
         HinfI   |
         MnlI|   |
         ThaI||  |
       BsbI ||| |                                 AvaII
       CjeI ||| |                                 Sau96I
       PleI ||| |                          AluI    |
        |   ||| |         BsrDI            CviJI   |   MnlI
        |   ||| |           |                |     |    |
       TCAACACGCGACTCTATATCAAAGCAATGGAGAGAAACTTCTGTTAGCTTTGGACCAACT
541    ---------+---------+---------+---------+---------+---------+ 600
       AGTTGTGCGCTGAGATATAGTTTCGTTACCTCTCTTTGAAGACAATCGAAACCTGGTTGA BsaJI
                                                          BstDSI
            ApoI                                          NcoI
            Tsp509I                     MnlI              StyI
              |                          |                 |
       CAATGAGGAAATTCTTACGATTACCTCCAAAGCGAAACAACGCCATATTTTAGTTTCCCA
601    ---------+---------+---------+---------+---------+---------+ 660
       GTTACTCCTTTAAGAATGCTAATGGAGGTTTCGCTTTGTTGCGGTATAAAATCAAAGGGT
```

Figure 4D (Continued)

```
                               HaeIV           NlaIII
                               Hin4I           TaqII|
      AluI                     NlaIV       |   Hpy178III||
      CviJI     Eco57I         AvaII|      |   RcaI    |||
    BfaI  |MaeIII    |         Sau96I|     |   BsmFI|  |||
      |    |    |    |            ||       |      || |||
         CTAGCTTTCCGTTACGGAAGCAAGGGACCGAATATCATTCATGATGTTTCTTTCTCTGTC
    961  ---------+---------+---------+---------+---------+---------+ 1020
         GATCGAAAGGCAATGCCTTCGTTCCCTGGCTTATAGTAAGTACTACAAAGAAAGAGACAG

MnlI
                     HinfI  AvaII  |
         BccI        TfiI   Sau96I |   BslI              MseI
          |           |       |    |    |                 |
         TATGATGGCGACTTTATAGGAATCATAGGACCAAACGGAGGGGGGAAAAGCACCTTAACG
    1021 ---------+---------+---------+---------+---------+---------+ 1080
         ATACTACCGCTGAAATATCCTTAGTATCCTGGTTTGCCTCCCCCCTTTTCGTGGAATTGC DpnI
                                         NlaIV
                                    BamHI |
                                    BstYI |
                                    Sau3AI|                     BsmI
                                    Hpy188IX|         BbsI      FauI
         Tsp509I        Cac8I       BslI ||     XmnI  |Sth132I|
         MseI|          CviJI  |    AlwI ||| |  AlwI  |    |MboII ||
           ||             |    |       |  |||  |    |   |    |   |  ||
         ATGTTAATTTTGGGCTTGCTTACTCCTACATTCGGATCCTTGAAGACTTTCCCTTCGCAT
    1081 ---------+---------+---------+---------+---------+---------+ 1140
         TACAATTAAAACCCGAACGAATGAGGATGTAAGCCTAGGAACTTCTGAAAGGGAAGCGTA SacII
         AciI|
       MspA1I|
         ThaI|
         AciI ||
        BsaJI ||
        BstDSI||
           | ||
         TCCGCGGGGAAACAAACCCATT
    1141 ---------+---------+-- 1162
         AGGCGCCCCTTTGTTTGGGTAA
```

Restriction enzyme analysis of CPN100711 (RY 59 - SEQ ID NO. 5)

Figure 5B (Continued)

```
                                    DpnI
                              BstYI  |
                              Sau3AI |
                              EarI|  |
                           Hpy178III| |
                HinfI              || |
                PpiI  |            || |
               MaeIII|  |          || |
                TaaI|  |           || |
              Tsp45I|  |           || |
               AlwNI||  |   BfaI|| |
               MboII||  |   XbaI||||          ApoI
                PleI|  |  |AlwI ||||        Tsp509I
                   ||  || |   ||||            |
         GATATTACAGGAACTGTGACTCTTCTAGATCCTAATGGCAACTTATATCAAAATTCTTAT
     181 ---------+---------+---------+---------+---------+---------+ 240
         CTATAATGTCCTTGACACTGAGAAGATCTAGGATTACCGTTGAATATAGTTTTAAGAATA MboII
                   EcoRV|
                   HphI ||
                BbsI    ||
                ThaI    ||                                      MaeIII
                AciI    ||      Tsp509I  CviRI    MwoI            |
                   || |||        |        |        |             |
         CTTGGTGAAGACCGCGATATCACTCTTTTCAATATAGACAATTCTGCAAGTGGGGCAGTT
     241 ---------+---------+---------+---------+---------+---------+ 300
         GAACCACTTCTGGCGCTATAGTGAGAAAAGTTATATCTGTTAAGACGTTCACCCCGTCAA HphI          ApoI                         ScrFI
         CviJI |MaeIII      Tsp509I    AluI            EcoRII |
         MwoI  |  |Tsp45I   BslI  |    CviJI           NlaIV| |
           || |  |  |         |    |                     |  |||
         ACAGCCACGAATGTCACCCTTCAAGGGAATTTAGGAGCTAAAAAAGGATATTTAGGAACC
     301 ---------+---------+---------+---------+---------+---------+ 360
         TGTCGGTGCTTACAGTGGGAAGTTCCCTTAAATCCTCGATTTTTTCCTATAAATCCTTGG
```

Figure 5D (Continued)

```
                                HinfI
                                CjeI|
                                HphI|
                        Hpy188IX||                                       Fnu4HI
                           PleI ||                                         CjeI|
                           ApoI|  |||                                    MspAlI|
                        Tsp509I|  |||                    BbvI              TseI|
                       Hpy178III||  |||              NlaIII  |            SfaNI||
                           TaqI  ||  |||                MnlI  |   |CviJI   AciI|||
                              |  ||  |||                  |   |   |          ||||
                     AAAGAAGTATCTCGAAATTCTGACTCATTCACCTATCATGGCAGAGGCTATACCGCTGCT
              601    ---------+---------+---------+---------+---------+---------+ 660
                     TTTCTTCATAGAGCTTTAAGACTGAGTAAGTGGATAGTACCGTCTCCGATATGGCGACGA Eco57I
                               BbvI    |
                              AceIII|  |
                                MnlI|  |         Fnu4HI
                                ApoI|| |          AluI|
                              Tsp509I|| |          CviJI|                  MaeIII
                   MwoI    FokI   ||| |            TseI|                   Tsp45I
                      |       |   ||| |             ||                         |
                     GTGGATGCCAAACCTCGCCAAGAATTTATTTTAGGAGCTGCCTTCAGTCAGGTTTTTGGT
              661    ---------+---------+---------+---------+---------+---------+ 720
                     CACCTACGGTTTGGAGCGGTTCTTAAATAAAATCCTCGACGGAAGTCAGTCCAAAAACCA MaeIII
                                                                Tsp45I
                        Hpy188IX                         Bpu10I     |
                           HphI|                           DdeI     |
                          HinfI ||PleI                     CviJI|   |         BseMII
                              | || |                           ||   |              |
                     CACGCCGAGTCTGAATATCACCTTGACAACTATAAGCATAAAGGCTCAGGTCACTCTACA
              721    ---------+---------+---------+---------+---------+---------+ 780
                     GTGCGGCTCAGACTTATAGTGGAACTGTTGATATTCGTATTTCCGAGTCCAGTGAGATGT Cac8I                                       CviJI
                               MboII                                       HaeIII
                             Tth111II|                        TaaI          BsaI|
                              SfaNI  ||                       Hin4I|       BsmAI|
                                  |  ||                          ||           ||
                     CAAGCATCTCTTTATGCTGGCAATATCTTCTATTTTCCTGCGATACGGTCTCGGCCTATT
              781    ---------+---------+---------+---------+---------+---------+ 840
                     GTTCGTAGAGAAATACGACCGTTATAGAAGATAAAAGGACGCTATGCCAGAGCCGGATAA BsaJI BslI
                       StyI PflMI                  CviRI NlaIII
                          |    |                       |    |
                     CTATTCCAAGGTGTGGCGACCTATGGTTATATGCAACATGACACCACAACCTACTATCCT
              841    ---------+---------+---------+---------+---------+---------+ 900
                     GATAAGGTTCCACACCGCTGGATACCAATATACGTTGTACTGTGGTGTTGGATGATAGGA
```

Figure 5F (Continued)

```
                                          Fnu4HI
                                          AluI|
                                          CviJI|
                                          MspA1I|
            AluI                          PvuII|        HinfI
            CviJI           BbvI          TseI| RsaI    TfiI
              |              |             ||    |       |
         GCATTAGCTTGGCGTGAGATTATTCTATATAATAAAGTATCAGCTGCGTACCTCCCTGTG
    1141 ---------+---------+---------+---------+---------+---------+ 1200
         CGTAATCGAACCGCACTCTAATAAGATATATTATTTCATAGTCGACGCATGGAGGGACAC Hpy178III
             DdeI   |
       MnlI  |      |       BseMII                            MaeII
        |    |      |          |                                |
         ATTCTCAGGAATAATCCAAAAGCGACCTATGAAGTTCTCTCTACAAAAGAAAAGGGCAAC
    1201 ---------+---------+---------+---------+---------+---------+ 1260
         TAAGAGTCCTTATTAGGTTTTCGCTGGATACTTCAAGAGAGATGTTTTCTTTTCCCGTTG BsgI
                                                           HphI |
                                                           ApoI|  |
                                                           Tsp509I| |
                                                      BanII   || |
                                                      BsiHKAI || |
                                                      Bsp1286I|| |
                                                      SacI   || |
                                                      AluI | || |
                                                      CviJI | || |
                                                    Hin4I | | || |
                                                  AceIII | | | || |
                                                  BbvI|  | | | || |
                                                CviRI || | | | || |
                                           BstAPI  |   || | | | || |
                                            MwoI   |   || | | | || |
                                            MnlI|  |   || | | | || |
                                           BssSI|| |   || | | | || |
                                            AluI||| |   || | | | || |
            AclI                           CviJI||| |   || | | | || |
            MaeII                          Fnu4HI||| |   || | | | || |
            HincII  |                      TseI|  ||| |   || | | | || |
              ||                                ||||||    || | | | || |
         GTAGTCAACGTTCTCCCTACAAGAAACGCAGCTCGTGCAGAGGTGAGCTCTCAAATTTAT
    1261 ---------+---------+---------+---------+---------+---------+ 1320
         CATCAGTTGCAAGAGGGATGTTCTTTGCGTCGAGCACGTCTCCACTCGAGAGTTTAAATA
```

Restriction enzyme analysis of CPN100877 (RY 61 - SEQ ID NO. 6)

Figure 6B (Continued)

```
                                                      BseMII
                                        Hpy178III    MaeII|
                          Cac8I         Bsu36I  |MaeIII  ||
             MseI         BcgI|   MaeIII    |   | MnlI   ||
        CviRI |           CviJI|| Tsp45I DdeI   |  |Tsp45I||
            | |             |||    |      |    |  |     ||
        CGATAACTCTGCATTAAATAAAGCCTGCTTCAATGTGACCTCAGGAAGTGTGACGTTCGC
301     ---------+---------+---------+---------+---------+---------+ 360
        GCTATTGAGACGTAATTTATTTCGGACGAAGTTACACTGGAGTCCTTCACACTGCAAGCG

Hpy178III
                                       Bsu36I   |    BseMII
                NlaIII    MseI   SspI  DdeI  |  MnlI  |   CviJI
                   |       |      |     |    |   |    |    |
        AGGAAATCATCATGGGTTATATTTTAATAATATTTCCTCAGGAACTACAAAGGAAGGGGC
361     ---------+---------+---------+---------+---------+---------+ 420
        TCCTTTAGTAGTACCCAATATAAAATTATTATAAAGGAGTCCTTGATGTTTCCTTCCCCG

SmlI
                   DpnI |
          Bce83I   BstYI|       Tth111II
          RsaI  |  Sau3AI|       MaeII  |
        TatI |  |  AlwI | |     MnlI |  |   BcefI
           | |  |    |  | |       |  |  |     |
        TGTACTTTGTTGCCAAGATCCTCAAGCAACGGCACGTTTTTCTGGGTTCTCCACGCTCTC
421     ---------+---------+---------+---------+---------+---------+ 480
        ACATGAAACAACGGTTCTAGGAGTTCGTTGCCGTGCAAAAAGACCCAAGAGGTGCGAGAG MseI
                   Sth132I  |
                   MspI     |
                   NciI     |
                   ScrFI    |
                   BanII|   |
                  Bsp1286I| |
                   BsaJI || |
                   CviJI||| |          FokI
        Hpy188IX     ||||  |     BsmAI  |   CviRI
              |      ||||  |         |  |    |
        TTTTATTCAGAGCCCCGGAGATATTAAAGAACAGGGATGTCTCTATTCAAAAAATGCACT
481     ---------+---------+---------+---------+---------+---------+ 540
        AAAATAAGTCTCGGGGCCTCTATAATTTCTTGTCCCTACAGAGATAAGTTTTTTACGTGA Tsp509I                                       EciI
          MseI   |                                          AciI|
            |    |                                             ||
        TATGCTCTTAAACAATTATGTAGTGCGTTTTGAACAAAACCAAAGTAAGACTAAAGGCGG
541     ---------+---------+---------+---------+---------+---------+ 600
        ATACGAGAATTTGTTAATACATCACGCAAAACTTGTTTTGGTTTCATTCTGATTTCCGCC
```

Figure 6C (Continued)

```
                                                Hin4I
                                        HinfI           Hpy188IX
        AluI                            TfiI    BsmAI
        CviJI        MaeIII  SfcI       Pfl1108I|       BsmBI
          |            |       |          |     ||      |      |
            AGCTATTAGTGGGGCGAATGTTACTATAGTAGGCAACTACGATTCCGTCTCTTTCTATCA
    601     ---------+---------+---------+---------+---------+---------+  660
            TCGATAATCACCCCGCTTACAATGATATCATCCGTTGATGCTAAGGCAGAGAAAGATAGT MnlI
             CviJI   |           BsmFI           NlaIV
             BsmI|   |           MboII           AvaII  |
             Fnu4HI||            Hin4I  |        EcoO109I|
             CviRI|||    Eco57I  |      |        Psp5II  |
             TseI||||    BbvI|   |      |        Sau96I |SfcI    CviRI
              ||||         ||    |      |          |     |         |
            GAATGCAGCCACTTTTGGAGGTGCTATCCATTCTTCAGGTCCCCTACAGATTGCAGTAAA
    661     ---------+---------+---------+---------+---------+---------+  720
            CTTACGTCGGTGAAAACCTCCACGATAGGTAAGAAGTCCAGGGGATGTCTAACGTCATTT RsaI
                             CjePI          Hpy178III           CjeI|
                             CjeI    |         DrdII            TatI||
                   CviRI     |       |         MnlI     |  CviJI    |||
                     |       |       |         ||       |    |      |||
            TCAGGCAGAGATAAGATTTGCACAAAATACTGCCAAGAATGGTTCTGGAGGGGCTTTGTA
    721     ---------+---------+---------+---------+---------+---------+  780
            AGTCCGTCTCTATTCTAAACGTGTTTTATGACGGTTCTTACCAAGACCTCCCCGAAACAT Hpy188IX
                             DpnI  |
               BccI          BclI  |  |
               BpmI|         Sau3AI|  |                    MnlI
      Hpy188IX    ||         BsaBI |  |                 Hpy178III|
      CjePI  |    ||         HphI| |  |        BsmI       TaqI   ||
         |   |    ||            ||| | |          |          |    |||
            CTCCGATGGTGATATTGATATTGATCAGAATGCTTATGTTCTATTTCGAGAAAATGAGGC
    781     ---------+---------+---------+---------+---------+---------+  840
            GAGGCTACCACTATAACTATAACTAGTCTTACGAATACAAGATAAAGCTCTTTTACTCCG Eco57I
                               BbsI|
                               MboII|
                         CviJI  ||           Hpy178III
                         BsaXI| ||             BslI
             SfcI  MnlI  Hin4I| ||           BpmI  |     TatI
               |     |     || ||               ||     |
            ATTGACTACTGCTATAGGTAAGGGAGGGGCTGTCTGTTGTCTTCCCACTTCAGGAAGTAG
    841     ---------+---------+---------+---------+---------+---------+  900
            TAACTGATGACGATATCCATTCCCTCCCCGACAGACAACAGAAGGGTGAAGTCCTTCATC
```

Figure 6D (Continued)

```
                BsrI                                                    TaqII
     RsaI        |      MaeIII                                  XmnI|
     ScaI |      |      Tsp45I     Hpy188IX         TaaI        CjeI    ||
       | |       |        |          |               |           |      ||
         TACTCCAGTTCCTATTGTGACTTTCTCTGACAATAAACAGTTAGTCTTTGAAAGAAACCA
 901     ---------+---------+---------+---------+---------+---------+   960
         ATGAGGTCAAGGATAACACTGAAAGAGACTGTTATTTGTCAATCAGAAACTTTCTTTGGT

AvaII
                                                              EcoO109I
                                                              Psp5II
                                                              Sau96I
                                                              Sse8647I
                       CviJI          Eco57I                   EarI    |
                       NlaIV|          BfaI  |               Hpy178III |
                       EciI ||         CjeI  |    MboII       SfaNI|   |
                       AciI|  ||       MwoI  |    DdeI|       MnlI ||  |
                         || ||          ||   |     ||          |   ||  |
         TTCCATAATGGGTGGCGGAGCCATTTATGCTAGGAAACTTAGCATCTCTTCAGGAGGTCC
 961     ---------+---------+---------+---------+---------+---------+  1020
         AAGGTATTACCCACCGCCTCGGTAAATACGATCCTTTGAATCGTAGAGAAGTCCTCCAGG

ApoI
                           Tsp509I
                           CviRI   |        ApoI              AluI
                            NdeI   |       Tsp509I            CviJI
                              |    | |        |                |
         TACTCTATTTATCAATAATATATCATATGCAAATTCGCAAAATTTAGGTGGAGCTATTGC
1021     ---------+---------+---------+---------+---------+---------+  1080
         ATGAGATAAATAGTTATTATATAGTATACGTTTAAGCGTTTTAAATCCACCTCGATAACG

DpnI
                          Sau3AI  |
                          Hin4I   |  |                             BsaJI
          MnlI    BsrI    |   |   |     BpmI       Tsp509I          StyI
           |       |      |||         |              |               |
         CATTGATACTGGAGGGGAGATCAGTTTATCAGCAGAGAAAGGAACAATTACATTCCAAGG
1081     ---------+---------+---------+---------+---------+---------+  1140
         GTAACTATGACCTCCCCTCTAGTCAAATAGTCGTCTCTTTCCTTGTTAATGTAAGGTTCC

Hpy178III
           MspI   AluI  TaaI            SfaNI         ApoI        |
          BsaWI|  CviJI FokI|           BccI         Tsp509I      |
           ||    |      ||              |   |          |          |
         AAACCGGACGAGCTTACCGTTTTTGAATGGCATCCATCTTTTACAAAATGCTAAATTCCT
1141     ---------+---------+---------+---------+---------+---------+  1200
         TTTGGCCTGCTCGAATGGCAAAAACTTACCGTAGGTAGAAAATGTTTTACGATTTAAGGA
```

Figure 6H (Continued)

```
                                           SfaNI
                              SimI         AluI  |
       BspMI         Hpy178III |           CviJI |
       DpnI          BsaI   |  |     TaqI  |  |        TaqI
       BstYI |       BsmAI  |  |     NsiI| |  |        DpnI|
       Sau3AI |   CviRI  |  |  |     CviRI||  |        Sau3AI ||
       Hpy188IX| |MseI   |  |  |     NlaIII|  |        MnlI  | || CviJI
       | ||  | |  |      |  |  |     | ||   |  |        |  | ||   |
       CAGATCCTTAATGCAGGTTCAAGAGACCCATGCATCGAGCTTACAGACAGATCGAGGGCT
1921   ---------+---------+---------+---------+---------+---------+ 1980
       GTCTAGGAATTACGTCCAAGTTCTCTGGGTACGTAGCTCGAATGTCTGTCTAGCTCCCGA

ApoI
                        Tsp509I
                        MboII  |
               Tsp509I   |     |
       ClaI     |        |     |                                NlaIV
       TaqI     |        |     |                                RsaI
       DpnI|   AlwI|     |     |                     BbsI  BanI |
       Sau3AI ||BccI||   |     | XmnI  NlaIII  Hpy188IX  MnlI |MboII| |
       | ||   |||   ||   |     |      |       |          |  | ||   ||
       GTGGATCGATGGAATTGGGAATTTCTTCCATGTATCTGCCTCCGAAGACAATATAAGGTA
1981   ---------+---------+---------+---------+---------+---------+ 2040
       CACCTAGCTACCTTAACCCTTAAAGAAGGTACATAGACGGAGGCTTCTGTTATATTCCAT

TaaI       AciI                          DpnI  Bpu10I
       KpnI|      MspA1I                        Sau3AI |  DdeI
       | |        |                             | |    |
       CCGTCATAACAGCGGTGGATATGTTCTATCTGTAAATAATGAGATCACACCTAAGCACTA
2041   ---------+---------+---------+---------+---------+---------+ 2100
       GGCAGTATTGTCGCCACCTATACAAGATAGACATTTATTACTCTAGTGTGGATTCGTGAT

BccI
       TaqI  |              BsmAI                AciI
       |     |              |                    |
       TACTTCGATGGCATTTTCCCAACTCTTTAGTAGAGACAAGGACTATGCGGTTTCCAACAA
2101   ---------+---------+---------+---------+---------+---------+ 2160
       ATGAAGCTACCGTAAAAGGGTTGAGAAATCATCTCTGTTCCTGATACGCCAAAGGTTGTT

AlwI              BslI
                       Hin4I  |                BfaI|
                       DpnI   |                AvrII|  XmnI
                       Sau3AI |                BsaJI|  SspI|
                       MmeI | |                StyI| |MnlI ||
                       | | | |                  ||| |  |  ||
       CGAATACAGAATGTATTTAGGATCGTATCTCTATCAATATACAACCTCCCTAGGGAATAT
2161   ---------+---------+---------+---------+---------+---------+ 2220
       GCTTATGTCTTACATAAATCCTAGCATAGAGATAGTTATATGTTGGAGGGATCCCTTATA
```

Figure 6I (Continued)

```
                                        HinfI
                                        TfiI
                            Hpy178III    |
                            MaeII   |    |   MboII
               MaeIII       Bce83I  |    |   |Hpy178III|
               ThaI|  Sth132I  |    |    |   |  SmlI   |  |
                 ||      |  |  |    |    |   |    |    |  ||
            TTTCCGTTATGCTTCGCGTAACCCTAATGTAAACGTCGGGATTCTCTCAAGAAGGTTTCT
     2221   ---------+---------+---------+---------+---------+---------+ 2280
            AAAGGCAATACGAAGCGCATTGGGATTACATTTGCAGCCCTAAGAGAGTTCTTCCAAAGA MnlI                        NlaIII
                         |                            |
            TCAAAATCCTCTTATGATTTTTCATTTTTTGTGTGCTTATGGTCATGCCACCAATGATAT
     2281   ---------+---------+---------+---------+---------+---------+ 2340
            AGTTTTAGGAGAATACTAAAAAGTAAAAAACACACGAATACCAGTACGGTGGTTACTATA HphI
                                           AluI|
                                           CviJI|
                                           MspA1I|
               ApoI                        PvuII|       MunI         SfcI
               Tsp509I                     CjeI||       Tsp509I      CviJI|
                  |                          |||          |            ||
            GAAAACAGACTACGCAAATTTCCCTATGGTGAAAAACAGCTGGAGAAACAATTGTTGGGC
     2341   ---------+---------+---------+---------+---------+---------+ 2400
            CTTTTGTCTGATGCGTTTAAAGGGATACCACTTTTTGTCGACCTCTTTGTTAACAACCCG BanI
                        NlaIII                        MboII    |
                        NspI                          BsaJI    | |
                  MwoI  SphI                          StyI     | |
            MnlI  CjeI  |Cac8I |                      Bbs I    | |
            BpmI |AciI  | |Hin4I |      MnlI  BplI    FokI     | |
             |    ||    | | ||   |       |     |       |       | | |
            TATAGAGTGCGGAGGGAGCATGCCTCTATTGGTATTTGAGAACGGAAGACTTTTCCAAGG
     2401   ---------+---------+---------+---------+---------+---------+ 2460
            ATATCTCACGCCTCCCTCGTACGGAGATAACCATAAACTCTTGCCTTCTGAAAAGGTTCC Bsp24I
                                                    CjeI
                                                    CjePI
            BccI                                    BsmAI |
            NlaIV |             Tsp509I   NlaIII BsmBI | BcefI
              |   |                |        |       | | |    |
            TGCCATCCCATTTATGAAACTACAATTAGTTTATGCTTATCATGGAGATTTCAAAGAGAC
     2461   ---------+---------+---------+---------+---------+---------+ 2520
            ACGGTAGGGTAAATACTTTGATGTTAATCAAATACGAATAGTACCTCTAAAGTTTCTCTG
```

Figure 6J (Continued)

```
                    CviJI
                   HaeIII
                    BccI  |
                    EaeI  |
                   GdiII  |
             PstI   |  |          CjeI
           CviRI |  |  |         CjePI|              ClaI
         SfcI |  |  |  |       Bsp24I||     MseI     TaqI         RsaI  BfaI
           | |  |  |  |          |||       |        |             |     |
           GACTGCAGATGGCCGTAGATTTAGTAATGGGAGTTTAACATCGATTTCTGTACCTCTAGG
     2521 ---------+---------+---------+---------+---------+---------+ 2580
           CTGACGTCTACCGGCATCTAAATCATTACCCTCAAATTGTAGCTAAAGACATGGAGATCC

FokI
                         Cac8I                     BseMII    |
                          AluI |    Hpy178III  RsaI    |    |
            MnlI          CviJI |    DdeI   |TatI      |    |
              |             | |      |  |    |  |      |    |
           CATACGCTTTGAGAAGCTGGCACTTTCTCAGGATGTACTCTATGACTTTAGTTTCTCCTA
     2581 ---------+---------+---------+---------+---------+---------+ 2640
           GTATGCGAAACTCTTCGACCGTGAAAGAGTCCTACATGAGATACTGAAATCAAAGAGGAT

BbvI
                              DpnI|
                              NlaIV|         Fnu4HI
                              BamHI ||         AluI|
                              BstYI ||         CviJI|            AciI
                              Sau3AI||   NlaIII TseI|          PleI|HinfI
          Hpy178III     AlwI   | ||   AlwI |MnlI||            BsmAI ||HphI|
              |          |    | ||    |   | ||  |||             |   ||   ||
           TATTCCTGATATTTTCCGTAAGGATCCCTCATGTGAAGCTGCTCTGGTGATTAGCGGAGA
     2641 ---------+---------+---------+---------+---------+---------+ 2700
           ATAAGGACTATAAAAGGCATTCCTAGGGAGTACACTTCGACGAGACCACTAATCGCCTCT Hpy178III
                                  BsaAI      |
                                 MaeII|      |
                                  AflIII ||   |
                    CviJI      Fnu4HI  |  ||   |
              ScrFI   |          TseI|  |  ||   |  NlaIII            SimI
            EcoRII |  |          MspI ||  | ||BbvI | NspI  Sth132I   BscGI|
              |  |  |             |   ||  |  ||  |   |      |           ||
           CTCCTGGCTTGTTCCGGCAGCACACGTATCAAGACATGCTTTTGTAGGGAGTGGAACGGG
     2701 ---------+---------+---------+---------+---------+---------+ 2760
           GAGGACCGAACAAGGCCGTCGTGTGCATAGTTCTGTACGAAAACATCCCTCACCTTGCCC
```

Figure 6K (Continued)

```
                                              MnlI
                                       BanII  |
                                     BsiHKAI  |
                                    Bsp1286I  |
                                        SacI  |                     BsmI
                                        AluI  |  |                  AciI|
                    BseMII              CviJI |  |                  Fnu4HI|
                      MseI   |            DdeI|  |  |   TaqI        TauI|
                        |    |              |  |  |  |    |            ||
              TCGGTATCACTTTAACGACTATACTGAGCTCTTATGTCGAGGAAGTATAGAATGCCGCCC
         2761 ---------+---------+---------+---------+---------+---------+ 2820
              AGCCATAGTGAAATTGCTGATATGACTCGAGAATACAGCTCCTTCATATCTTACGGCGGG

Tsp509I
               BfaI   |
                BslI  |                  ApoI
              NlaIII| |            TaaI Tsp509I          CjeI        BsrDI
                  ||| |              |    |                |            |
              CCATGCTAGGAATTATAATATAAACTGTGGAAGCAAATTTCGTTTTTAGAAGGTTTCCAT
         2821 ---------+---------+---------+---------+---------+---------+ 2880
              GGTACGATCCTTAATATTATATTTGACACCTTCGTTTAAAGCAAAAATCTTCCAAAGGTA

AlwI
                                  CjeI |
                                  MseI | |
                             DpnI    | | |
                           BstYI  |  | | |
                          Sau3AI  |  | | |
                       Hpy178III| |  | | |
                           MspI|| |  | | |
                          BsaWI||| |  | | |                 DpnI
                          BspEI||| |  | | |      BspGI Sau3AI |
                          NlaIV||||  | | |      ScrFI |HaeIV  | |
                  XcmI    DrdII||||| | | |      EcoRII |  |Hin4I |  | AlwI
                    |       ||||||   | | |          |  |    |    |  |   |
              TGCCTGTGTGGTTCCGGATCTTAACTATAAATCCTGGACTATGGATCATAGGCATTGGGT
         2881 ---------+---------+---------+---------+---------+---------+ 2940
              ACGGACACACCAAGGCCTAGAATTGATATTTAGGACCTGATACCTAGTATCCGTAACCCA

Hpy178III
            TaqI
              |
              TTCTCGAACT
         2941 ---------+ 2950
              AAGAGCTTGA
```

Restriction enzyme analysis of CPN100325 (RY 62 - SEQ ID NO. 7)

Figure 7B (Continued)

```
                                                             MaeIII
                                                             Tsp45I
                                                             AluI  |
      BfaI             Tsp509I                      BsrI     CviJI |
    SpeI|              BfaI    |             AceIII SfaNI    TspRI||
     | |                |      |                |     |      |  |||
     AACTAGTCTTACTACTAGCACTAATTTATATGGTGGGGGCATCTATTCCAGTGGAGCTGT
241  ---------+---------+---------+---------+---------+---------+ 300
     TTGATCAGAATGATGATCGTGATTAAATATACCACCCCCGTAGATAAGGTCACCTCGACA

NgoGV
                  NlaIV
           Hpy178III  |                            FokI
              |       ||                            |
     CACGCTAACCAATATATCTGGAACCTTTGGCATTACAGGAAACTCTGTTATCAATACAGC
301  ---------+---------+---------+---------+---------+---------+ 360
     GTGCGATTGGTTATATAGACCTTGGAAACCGTAATGTCCTTTGAGACAATAGTTATGTCG

ScrFI
       BsaJI |
       EcoRII|                                 BtrI BsmAI
    SfaNI | |  | CviRI    FokI          CviRI MaeII| BsmBI
     |    | |  |  |         |             |    | ||  |
     GACATCCCAGGATGCAGATATACAAGGTGGGGGCATTTATGCAACCACGTCTCTCTCAAT
361  ---------+---------+---------+---------+---------+---------+ 420
     CTGTAGGGTCCTACGTCTATATGTTCCACCCCCGTAAATACGTTGGTGCAGAGAGAGTTA

TaqII       Fnu4HI
                              BbvI |          TseI|
                               |  |             ||
     AAATCAATGTAATACACCCATTCTATTTAGCAACAACTCTGCTGCCACTAAAAAAACATC
421  ---------+---------+---------+---------+---------+---------+ 480
     TTTAGTTACATTATGTGGGTAAGATAAATCGTTGTTGAGACGACGGTGATTTTTTTGTAG

MaeIII
                                          PstI
                                      CviRI |
                                      Fnu4HI| |
                          CviJI       SfcI  | |
                          BbvI|       MspA1I| |        Hin4I
                          MwoI||      TseI  | | Hpy178III    |
         Tsp509I    MboII|    ||      AciI  | ||  TaqI   |   |
            |         |  ||   ||       |    |||    | |   |   |
     AACAACAAAGCAAATTGCTGGTGGGGCTATCTTCTCCGCTGCAGTAACTATCGAGAATAA
481  ---------+---------+---------+---------+---------+---------+ 540
     TTGTTGTTTCGTTTAACGACCACCCCGATAGAAGAGGCGACGTCATTGATAGCTCTTATT
```

Figure 7C (Continued)

```
                                                                      SfcI
                                                                      AlwNI|
                              Tsp509I                                 BstAPI|
                              MseI   |                      Fnu4HI    ||
                              MmeI   |                      TseI|     ||
              CviJI   BseMII  ||     |                      MwoI||    ||
        DdeI  |       BpII|| |       |   AciI Hpy188IX      SfcI |    ||  MwoI|
        |     |       ||| |          |   |    |             |  | |    ||  ||
        CTCTCAGCCCATTATTTTCTTAAATAATTCCGCAAAGTCGGAAGCAACTACAGCAGCAAC
541     ---------+---------+---------+---------+---------+---------+ 600
        GAGAGTCGGGTAATAAAAGAATTTATTAAGGCGTTTCAGCCTTCGTTGATGTCGTCGTTG

BseRI
                                         AluI|
                                         CviJI|
                                         Fnu4HI||
                                   BsrDI    |||
        BbvI           AluI        CviJI|CviRI||
        PstI|          CviJI       NgoGV| MwoI||      BbvI
        CviRI ||       MnlI|       NlaIV| TseI||      MaeIII|  MseI
        |   ||         ||          ||| | ||| ||       ||       |
        TGCAGGAAATAAAGATAGCTGTGGAGGAGCCATTGCAGCTAACTCTGTTACTTTAACAAA
601     ---------+---------+---------+---------+---------+---------+ 660
        ACGTCCTTTATTTCTATCGACACCTCCTCGGTAACGTCGATTGAGACAATGAAATTGTTT

Tsp509I        AlwNI                         BpmI
           DraI     |               MnlI  |                BseRI  |
           MseI|    |               CviRI |      BsrI      CviJI  |  |
           ||       |               |     |      |         |      |  |
        TAACCCTGAAATAACCTTTAAAGGAAATTATGCAGAAACTGGAGGAGCGATTGGCTGTAT
661     ---------+---------+---------+---------+---------+---------+ 720
        ATTGGGACTTTATTGGAAATTTCCTTTAATACGTCTTTGACCTCCTCGCTAACCGACATA

DpnI                Sth132I       CviRI
        Sau3AI |   HphI CviJI   BscGI MnlI|  BsmAI          TaaI
        |    |     |    |       |     |  ||  |              |
        TGATCTTACTAATGGCTCACCTCCCCGTAAAGTCTCTATTGCAGACAACGGTTCTGTCCT
721     ---------+---------+---------+---------+---------+---------+ 780
        ACTAGAATGATTACCGAGTGGAGGGGCATTTCAGAGATAACGTCTGTTGCCAAGACAGGA

EcoRV
                           AciI    HaeII          CjeI             |
                       MnlI |      HhaI|          Hin4I ClaI       |
        Hpy178III      MseI |ThaI  Hin4I||BsmAI BpmI    | TaqI     |
        |               |   |      |  |||    |  |       |  |      |
        TTTTCAAGACAACTCTGCGTTAAATCGCGGAGGCGCTATCTATGGAGAGACTATCGATAT
781     ---------+---------+---------+---------+---------+---------+ 840
        AAAAGTTCTGTTGAGACGCAATTTAGCGCCTCCGCGATAGATACCTCTCTGATAGCTATA
```

Figure 7D (Continued)

```
                          CjeI
       ScrFI              MaeIII |                   BccI Tsp509I
      EcoRII |            MboII | |       EarI NlaIII |  CviRI|
         | |                ||| |            |    | |   |    ||
          CTCCAGGACAGGTGCGACTTTCATCGGTAACTCTTCAAAACATGATGGAAGTGCAATTTG
    841   ---------+---------+---------+---------+---------+---------+ 900
          GAGGTCCTGTCCACGCTGAAAGTAGCCATTGAGAAGTTTTGTACTACCTTCACGTTAAAC

CviJI           HhaI                              MaeIII
             |              |                                  |
          CTGTTCAACAGCCCTAACTCTTGCGCCAAACTCCCAACTTATCTTTGAAAACAATAAGGT
    901   ---------+---------+---------+---------+---------+---------+ 960
          GACAAGTTGTCGGGATTGAGAACGCGGTTTGAGGGTTGAATAGAAACTTTTGTTATTCCA

Tsp509I
                                                         CviRI|
                                                   Fnu4HI ||
                          AluI       Tsp509I        AluI| ||
                          CviJI       BbvI  |       CviJI| ||
           CviJI   HindIII |  AceIII|  |        TseI | ||| ||
             |       |     |    ||    |              |    |||  ||
          TACGGAAACCACAGCCACTACAAAAGCTTCCATAAATAATTTAGGAGCTGCAATTTATGG
    961   ---------+---------+---------+---------+---------+---------+ 1020
          ATGCCTTTGGTGTCGGTGATGTTTTCGAAGGTATTTATTAAATCCTCGACGTTAAATACC AatII
                        MaeIII |
                        Tsp45I |
                        BsaHI| |
                        MaeII| |
             MaeIII        || |                   DdeI
              Tsp45I       || |                   AluI|
               BfaI |      || |                   CviJI|
                    |      || |           BseMII  MspA1I|
           BsmAI    SpeI|  || |             |   PvuII|              MseI
             |       ||| ||| |             |    ||                |
          AAATAATGAGACTAGTGACGTCACTATCTCTTTATCAGCTGAGAATGGAAGTATTTTCTT
    1021  ---------+---------+---------+---------+---------+---------+ 1080
          TTTATTACTCTGATCACTGCAGTGATAGAGAAATAGTCGACTCTTACCTTCATAAAAGAA Tth111II             Eco57I
                                         PstI |             ApoI    |
                                        CviRI | |         Tsp509I   |
            DraI       CviRI            SfcI | | |         MaeII   | |
              |           |              |  | | |           |      | |
          TAAAAACAATCTATGCACAGCAACAAACAAATACTGCAGTATTGCTGGAAACGTAAAATT
    1081  ---------+---------+---------+---------+---------+---------+ 1140
          ATTTTTGTTAGATACGTGTCGTTGTTTGTTTATGACGTCATAACGACCTTTGCATTTTAA
```

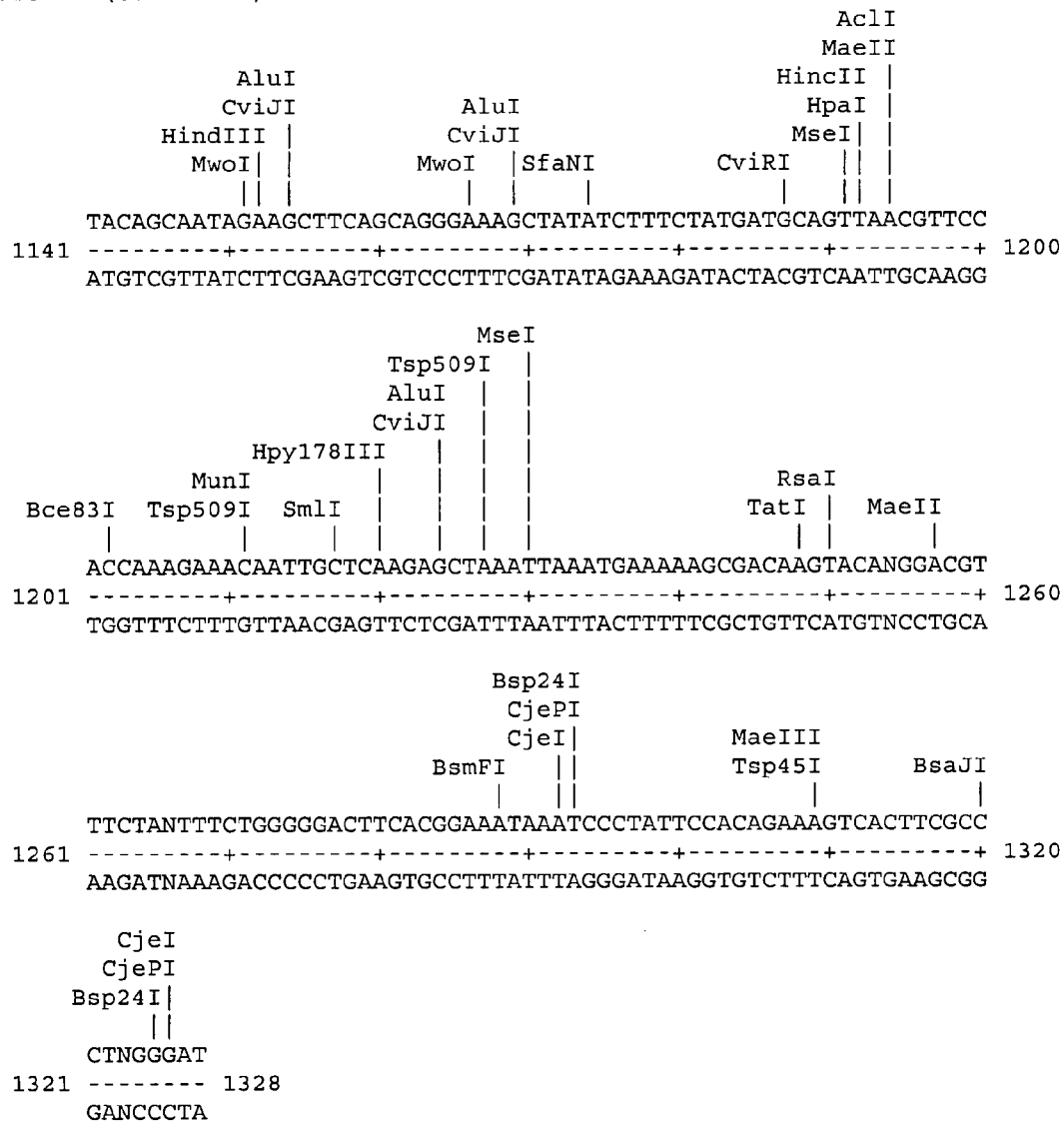

Restriction enzyme analysis of CPN100368 (RY 63 - SEQ ID NO. 8)

```
Figure 8D (Continued)
                                            CjePI
                                   BseMII   |
                                   BseRI  | |
         Tth111II        BstEII    | |
         BsaJI  |        MaeIII    | |
           StyI  |Hpy178III  TaaI  | |              SfcI
         TaaI |  |   DdeI   |Tsp45I| |    HphI     MnlI |
            | |  |     |     |    | |     |         | |
            TACAGTCCAAGGAAACTCAGGAACGGTGACCTTCTCCTCAAATACTGCTACAGATAAAGG
  721       ---------+---------+---------+---------+---------+---------+ 780
            ATGTCAGGTTCCTTTGAGTCCTTGCCACTGGAAGAGGAGTTTATGACGATGTCTATTTCC DpnI                   BfaI
            BstYI |                Cac8I  |                MaeIII
            Sau3AI|  AlwI      SfaNI |    |          HinfI     |PleI
              | | |    |         |   |    |            |       | |
            TGGGGGGATCTACTCAAAAGAAAAGGATAGCACGCTAGATGCCAATACAGGAGTCGTTAC
  781       ---------+---------+---------+---------+---------+---------+ 840
            ACCCCCCTAGATGAGTTTTCTTTTCCTATCGTGCGATCTACGGTTATGTCCTCAGCAATG Hpy188IX
                                              BanII|
                                              BsiHKAI|
                                BscGI        Bsp1286I|
                            Tth111II   |        SacI|
                          CviRI  |     |        AluI||
                     Sth132I|    |     |       CviJI||  BsaBI     Bce83I
                         | ||    |     |           |||    |          |
            CTTCAAATCTAATACTGCAAAGACGGGGGGTGCTTGGAGCTCTGATGACAATCTTGCTCT
  841       ---------+---------+---------+---------+---------+---------+ 900
            GAAGTTTAGATTATGACGTTTCTGCCCCCACGAACCTCGAGACTACTGTTAGAACGAGA Fnu4HI
                                                    Bpu1102I   |
                                                       DdeI    |
                         RsaI                         CviJI|   |
              MspI    SmlI   ScaI                     MspI |   |  BseMII
            BsrFI|   BsbI  |TatI  |Hpy178III         BsrFI| |TseI|MwoI  |
              ||     |      | |      |                ||  ||  || |  |  |
            TACCGGCAACACTCAAGTACTTTTTCAGGAAAATAAAACAACCGGCTCAGCAGCACAGGC
  901       ---------+---------+---------+---------+---------+---------+ 960
            ATGGCCGTTGTGAGTTCATGAAAAAGTCCTTTTATTTTGTTGGCCGAGTCGTCGTGTCCG Sth132I
                 MspI    |
                 NciI    |
            BbvI ScrFI   |                           SfcI
             |    ||     |                            |
            AAATAACCCGGAAGGTTGTGGTGGGGCAATCTGTTGTTATCTTGCTACAGCAACAGACAA
  961       ---------+---------+---------+---------+---------+---------+ 1020
            TTTATTGGGCCTTCCAACACCACCCCGTTAGACAACAATAGAACGATGTCGTTGTCTGTT
```

Figure 8E (Continued)

```
                                              AluI
                                              CviJI
                                      BseMII   |
                             Hpy178III   |     |
                               HinfI     |     |
                               TfiI      |     |
                  CviJI Hpy188IX |        |     |        BfaI
          BsrI     |    DdeI |   |        |     |     SpeI|CjeI
           |       |     |   |   |        |     |       | |   |
          AACTGGATTAGCCATTTCTCAGAATCAAGAAATGAGCTTCACTAGTAATACAACAACTGC
1021   ---------+---------+---------+---------+---------+---------+   1080
          TTGACCTAATCGGTAAAGAGTCTTAGTTCTTTACTCGAAGTGATCATTATGTTGTTGACG CjeI
                                CjeI |
                         MwoI    |   |       Hpy178III
                     DpnI  |     |   |        RsaI                              TaqI
                Sau3AI |   |     |   |     TatI |    |BccI     FokI    CjeI      |
                   | | |   |     |   |      |   |      |        |       |        |
                   GAATGGTGGAGCGATCTACGCTACTAAATGTACTCTGGATGGAAACACAACTCTTACCTT
1081   ---------+---------+---------+---------+---------+---------+   1140
                   CTTACCACCTCGCTAGATGCGATGATTTACATGAGACCTACCTTTGTGTTGAGAATGGAA FokI
                                                   AluI|
        Hpy188IX                                   CviJI|
          DpnI   |                          EciI      ||
        Sau3AI   | |                       AciI|      ||        AlwNI
           | | |                               ||      ||           |
          CGATCAGAATACTGCGACAGCAGGATGTGGCGGAGCTATCTATACAGAAACTGAAGATTT
1141   ---------+---------+---------+---------+---------+---------+   1200
          GCTAGTCTTATGACGCTGTCGTCCTACACCGCCTCGATAGATATGTCTTTGACTTCTAAA MaeIII
                               TaaI
                              Tsp45I
                              NgoGV   |
                              NlaIV   |
                       BscGI    |     |
                     Eco57I |    |     |                                 BsaHI
              Eco57I   |    |    |     |                                  NarI
         Sth132I |     |    |    |     |                                  BanI|
           MseI  |     |    |    |     |                                 Fnu4HI|
          AflII| |     |    |    |     |                                  TauI||
          MboII| |     |    |    |     |                                  AciI|||
           SmlI| |     | RsaI|    |     |                                     ||||
             || |     |  |   |    |     |                                     ||||
          TTCTCTTAAGGGAAGTACGGGAACCGTGACCTTCAGCACAAATACAGCAAAGACAGGCGG
1201   ---------+---------+---------+---------+---------+---------+   1260
          AAGAGAATTCCCTTCATGCCCTTGGCACTGGAAGTCGTGTTTATGTCGTTTCTGTCCGCC
```

Figure 8J (Continued)

```
                              Hpy188IX
                                 AlwNI|
                              BplI    ||
                              HinfI   ||       AluI         MseI
          DpnI         Hpy188IX |     ||      CviJI         AluI  |
          Hin4I|           DdeI |     ||   BseMII           CviJI |
          Sau3AI||         MnlI |     ||   PleI   | HindIII       |
               |||            | |     ||     |    |   |          |
            AGCGATCCTCTGTAATATCTCAGAGTCTGACATAGCTACAAAAAGCTTAACTCTTACTGA
     2161   ---------+---------+---------+---------+---------+---------+ 2220
            TCGCTAGGAGACATTATAGAGTCTCAGACTGTATCGATGTTTTTCGAATTGAGAATGACT MseI        MseI                              BcefI
                   |           |                                  |
            AAATGAGAGTTTAAGTTTCATTAACAATACGGCAAAAAGAAGTGGTGGTGGTATTTATGC
     2221   ---------+---------+---------+---------+---------+---------+ 2280
            TTTACTCTCAAATTCAAAGTAATTGTTATGCCGTTTTTCTTCACCACCACCATAAATACG BseMII
                                TspRI |
                                HinfI ||
                                 TfiI ||
          DdeI         DdeI     BtsI ||              BccI      Sth132I MnlI
           |            |        | |||                |           |     |
            TCCTAAGTGTGTAATCTCAGGCAGTGAATCCATAAACTTTGATGGCAATACTGCTGAAAC
     2281   ---------+---------+---------+---------+---------+---------+ 2340
            AGGATTCACACATTAGAGTCCGTCACTTAGGTATTTGAAACTACCGTTATGACGACTTTG AvaII
                             BseRI                           Sau96I
                              NspV|                 AluI        |
          Hpy178III           TaqI|      TaqI      CviJI   TaaI   BsmAI
             |                 ||         |         |       |      |
            TTCGGGAGGAGCGATTTATTCGAAAAACCTTTCGATTACAGCTAACGGTCCTGTCTCCTT
     2341   ---------+---------+---------+---------+---------+---------+ 2400
            AAGCCCTCCTCGCTAAATAAGCTTTTTGGAAAGCTAATGTCGATTGCCAGGACAGAGGAA BpmI
                                HaeII |
                                HhaI| |
                               NgoGV|| |
                               NlaIV|| |
                               BsaHI||| |
              Hpy178III         NarI||| |
              MnlI              BanI|||| |
             Tsp509I|  |MnlI   MwoI ||||||    CviJI     AciI      MnlI
                  ||   |   |      |||||||       |        |         |
            TACCAATAATTCTGGAGGCAAGGGAGGCGCCATTTATATAGCCGATAGCGGAGAACTTTC
     2401   ---------+---------+---------+---------+---------+---------+ 2460
            ATGGTTATTAAGACCTCCGTTCCCTCCGCGGTAAATATATCGGCTATCGCCTCTTGAAAG
```

Figure 8K (Continued)

```
                                              BseMII      DdeI       BsaXI
                                              NgoGV|BseMII |          AloI|
     DdeI    CviJI     BccI           DdeI    NlaIV|MnlI |  |         PpiI|
      |       |         |              |       ||   ||  | |  |         ||
            CTTAGAGGCTATTGATGGGGATATTACTTTCTCAGGGAACCGAGCGACTGAGGGAACTTC
2461  ---------+---------+---------+---------+---------+---------+  2520
            GAATCTCCGATAACTACCCCTATAATGAAAGAGTCCCTTGGCTCGCTGACTCCCTTGAAG

ScrFI
                                                                AlwNI|
                                                                EcoRII||
                                                                AluI |||
                                                                CviJI|||
                                                               Fnu4HI | |||
                                                                TseI| | |||
                                                               Fnu4HI|| | |||
                                                                CviRI| | |||
                                      ScrFI                      TseI| | | |||
                                      BsaJI|                     Cac8I|| | | |||
                                      EcoRII|                    AluI | | | | |||
                     DpnI             NgoGV||                    CviJI| | | | |||
           Sau3AI     |                NlaIV|||                 HindIII| | | | |||
            TaqI|     |                BanI |||                   DpnI | | | | | |||
     AlwI    |  |     |                MslI | | |||              Sau3AI|DdeI| | | | |||
      |      |  |     |                 |   | | |||               |    | | | | | | |||
            AACTCCCAACTCGATCCATTTAGGTGCCAGGGGCAAGATCACTAAGCTTGCAGCAGCTCC
2521  ---------+---------+---------+---------+---------+---------+  2580
            TTGAGGGTTGAGCTAGGTAAATCCACGGTCCCCGTTCTAGTGATTCGAACGTCGTCGAGG MnlI
                                                                    SfaNI |
                                              AluI    Hpy178III       | |
                        AceIII       DpnI     CviJI     BslI |        | |
                        BbvI|       Sau3AI |  Hin4I |   CviRI|        | |
     BbvI   |   |        AlwI  |     BccI  |   |  MnlI |              | |
      |    ||                  |      |    |   |   |   |              | |
            TGGTCATACGATTTATTTTTATGATCCTATTACGATGGAAGCTCCTGCATCTGGAGGAAC
2581  ---------+---------+---------+---------+---------+---------+  2640
            ACCAGTATGCTAAATAAAAATACTAGGATAATGCTACCTTCGAGGACGTAGACCTCCTTG BseRI                XcmI
                                       AluI|                MnlI |
                 BpmI     BseRI        CviJI|              MnlI  |  |
                  |        |             ||                 |    |  |
            AATAGAGGAGTTAGTCATCAATCCTGTTGTCAAAGCTATTGTTCCTCCTCCCCAACCAAA
2641  ---------+---------+---------+---------+---------+---------+  2700
            TTATCTCCTCAATCAGTAGTTAGGACAACAGTTTCGATAACAAGGAGGAGGGGTTGGTTT
```

Figure 8L (Continued)

```
         AvaII
     Sau96I                          BsmI        Hpy178III
   BsIl     |                     Bce83I   |       SmlI    |     ApoI
  PflMI     |                      MboII   |      CviJI|   |    Tsp509I
     | |    |                         | |        | ||   |     |
     AAATGGTCCTATATAGAAGAAAAACGAATGCTCTTTGTAAGGCTCAAGAGTAAAAAATTC
2701 ---------+---------+---------+---------+---------+---------+ 2760
     TTTACCAGGATATATCTTCTTTTTGCTTACGAGAAACATTCCGAGTTCTCATTTTTTAAG

Eco57I
                 Hpy188IX             ApoI          |
             BcefI    |   Fnu4HI      EcoRI         |
           BbvI  |    |     TseI|    Tsp509I        |
             |   |    |     ||      |           |
     TAAAGGTATTCTCTCAATAGGTTCTGAAGTGCTGCCGTAGAATTCATAAATATCTC
2761 ---------+---------+---------+---------+---------+------ 2816
     ATTTCCATAAGAGAGTTATCCAAGACTTCACGACGGCATCTTAAGTATTTATAGAG
```

Figure 9A
Restriction enzyme analysis of CPN100624 (RY 64 - SEQ ID NO. 9)

```
                                    MseI
                                   NlaIII|
                          AflIII    ||           DraI
                         BspLU11I   ||           SwaI
                           SspI    |NspI|        MseI|
                            |       |  ||         |  ||
        TCAAATATATGAGTTTACTAACTCTGTAATATTCAACATGTTAATAAGCATATTTAAATA
    1   ---------+---------+---------+---------+---------+---------+  60
        AGTTTATATACTCAAATGATTGAGACATTATAAGTTGTACAATTATTCGTATAAATTTAT

Hpy178III
       ApoI       BfaI|
      Tsp509I PsiI XbaI|| Tsp509I
         |     |   |||    |
        TAAATTTATAAACTTCTAGACAACAAATTGATGATTTTTATGACAAACTCTATTTTCAT
   61   ---------+---------+---------+---------+---------+---------+  120
        ATTTAAATATTTGAAGATCTGTTGTTTAACTACTAAAAATACTGTTTGAGATAAAAGTA

HhaI
                                                            TspRI
                           FokI         BsmAI         BtsI   |
                   SimI   | DrdI DdeI    |      BseMII  |    |
                    ||     |    |  |     |        |     |    |
        ATCAAAGTTTGGATGTTTATGCGACCCATTTGTCTCAGCATTTTATCCCACTGCGCTATG
  121   ---------+---------+---------+---------+---------+---------+  180
        TAGTTTCAAACCTACAAATACGCTGGGTAAACAGAGTCGTAAAATAGGGTGACGCGATAC

Hpy178III
                                                      MnlI      |
                  Hpy178III                 Hpy188IX  |  BfaI|
                  BsmFI       |             MnlI   |  |XbaI||
                     |        |               |    |  |  |||
        TTGTTCCTTATCAGGAAATGAAGTCCCTAACCTCGCCTCTTGTCAGATGTCTAGAAAAGA
  181   ---------+---------+---------+---------+---------+---------+  240
        AACAAGGAATAGTCCTTTACTTCAGGGATTGGAGCGGAGAACAGTCTACAGATCTTTTCT
```

Figure 9F (Continued)

```
                    Sth132I              Fnu4HI
              MnlI     |                  TseI|
         MspI   |      |         Sth132I  || NciI
         NciI   |      |         BstAPI|  || ScrFI
         ScrFI  |      |   CviRI     || ||BsaJI|
         BslI|  |  |BbvI    | MwoI   || ||MspI| MseI MseI BfaI
           ||  |   |   |    |  |     || ||  ||  |    |    |
           TCAACCCGGATATAGAAATGCACTCTATGCTGCTCCGGGGATTAACTTAAAACTAGGAGC
    1261 ---------+---------+---------+---------+---------+---------+ 1320
           AGTTGGGCCTATATCTTTACGTGAGATACGACGAGGCCCCTAATTGAATTTTGATCCTCG

Hpy188IX
                                                   DpnI |
                                               Sau3AI | |
                                               BsaBI| | |
                                           Hpy178III| | |
                                                DpnI||| |             DpnI
                                        Sau3AI    | ||| |           BstYI |
                                          SfcI    | ||| |          Sau3AI |
              ApoI               DpnI     |       | ||| |           HaeIV |
              Tsp509I          Sau3AI     |       | ||| |           Hin4I |
              PsiI   |    AlwI   |        |       | ||| |            AlwI |  |
                 |   |      |    |        |       | ||| |               | |  |
           AAGACAGGGTTATAAAATTCTCTTTTATGATCCTATAGATCACGATCAGACGACAACAGA
    1321 ---------+---------+---------+---------+---------+---------+ 1380
           TTCTGTCCCAATATTTTAAGAGAAAATACTAGGATATCTAGTGCTAGTCTGCTGTTGTCT

BsbI
                                         TaaI   |
                                       NgoGV |  |        HinfI
                                       NlaIV |  |         TfiI
                                        BanI |  |   Hpy178III |
                                       BstXI |  |  |   MspI|  |
                           Tsp509I     BsaJI|   |  |   BsaWI|| |
               SfcI    MseI|    HphI BccI StyI| |  |   BspEI|| |
                  |      ||      |    |   ||  | |  |      ||| |
           TCCTATAGTATTTAATTATGAACCCCATCACCTTGGCACCGTGTTGTTTTCCGGAATCAA
    1381 ---------+---------+---------+---------+---------+---------+ 1440
           AGGATATCATAAATTAATACTTGGGGTAGTGGAACCGTGGCACAACAAAAGGCCTTAGTT CjePI
                                                  MboII |
               HinfI                          ApoI  |   |     EarI
                TfiI     CjePI             Tsp509I  |   |  Hpy178III
                 |         |                  |     |   |     |
           TGTAGATTCTAACGCAACAAATCCATTGAACTTCCTATCAAAATTTTCTAACTCTTCACG
    1441 ---------+---------+---------+---------+---------+---------+ 1500
           ACATCTAAGATTGCGTTGTTTAGGTAACTTGAAGGATAGTTTTAAAAGATTGAGAAGTGC
```

Figure 9K (Continued)

```
                            MseI    SimI       CviJI  MseI
                             |       |           |     |
     GCTTTGCCACTATACAGAAATCTTAAAAGGGTCGTCCAAAGCCTTCTTTAATAACCACAC
2461 ---------+---------+---------+---------+---------+---------+ 2520
     CGAAACGGTGATATGTCTTTAGAATTTTCCCAGCAGGTTTCGGAAGAAATTATTGGTGTG

CjePI
                                            Hinfl   Hpy178III  |
                 Hpy178III                  TfiI       TaqI    |
         CviJI      |                BfaI    |        FauI|    |
       BsgI |       |       CjePI    AluI|   |       Sth132I|  |
     BslI   |     BfaI| CviRI  |     CviJI| AciI         |||   |
     PflMI  |     XbaI||MnlI   |      HphI|| BpmI        |||   |
      |  |  |       ||| |      |         ||| |     |     |||   |
     TTTGGTAGCCTCTCTAGACTGCACATTCTTACCAGCTAGAATCACCCGCACTCTCGAACT
2521 ---------+---------+---------+---------+---------+---------+ 2580
     AAACCATCGGAGAGATCTGACGTGTAAGAATGGTCGATCTTAGTGGGCGTGAGAGCTTGA CviJI
                                       HaeI
                                       HaeIII
                                       StuI
                                     ScrFI     |      BstXI
                         TspRI   HhaI BsaJI |  |      BsaI |
             CviJI       BsrDI|  CjeI |EcoRII|  |      BsmAI|
              |            ||    ||   ||  |  |  |      MnlI |  |
              |            ||    ||   ||  |  |  |       |   |  |
     CCAGCCCTTTATCAGTGCCATTGCTCTGCGCTGTTCCCAGGCCTCGTTCCAAGAAACTGG
2581 ---------+---------+---------+---------+---------+---------+ 2640
     GGTCGGGAAATAGTCACGGTAACGAGACGCGACAAGGGTCCGGAGCAAGGTTCTTTGACC BccI                      Hin4I
                   BpmI |                    DpnI  |
             FokI   | |                      BglII |    |
       CjeI   ApoI| | |                      BstYI |    |      CviJI
     BsrI|FokI Tsp509I| |                    Sau3AI|    |      MnlI |
      ||   |    ||  | |                        ||  |    |       |   |
     AGACCATATAAGAAAATTCCATCCAAAACATCCCCTTACAGATCTTTCCTCTCCCATAGG
2641 ---------+---------+---------+---------+---------+---------+ 2700
     TCTGGTATATTCTTTTAAGGTAGGTTTTGTAGGGGAATGTCTAGAAAGGAGAGGGTATCC BslI
                                       PflMI
     Hpy188IX                 NlaIII    |
        |                        |      ||
     CTTCCGTTCTGAATGGAAAACTTCACATCATATCCCCATGCTATGGACTACGGAAATATC
2701 ---------+---------+---------+---------+---------+---------+ 2760
     GAAGGCAAGACTTACCTTTTGAAGTGTAGTATAGGGGTACGATACCTGATGCCTTTATAG
```

Figure 9M (Continued)

```
         Tsp509I
           MseI|
     CviJI   ||
    NgoGV|   ||
    NlaIV|   ||
         ||  ||
        TTGGAGCCTTAATTTTAGGTAAAACTACAATA
3061    ---------+---------+---------+-- 3092
        AACCTCGGAATTAAAATCCATTTTGATGTTAT
```

Restriction enzyme analysis of CPN100633 (RY 65 - SEQ ID NO. 10)

Restriction enzyme analysis of CPN100985 (RY 66 - SEQ ID NO. 11)

Figure 11B (Continued)

```
                            DpnI
                            BclI   |
                            Sau3AI |                   CviJI
                              | |                        |
         TCTCTTTTATGTTTTACTTGTGAAGGAGATGATCATAGGCATTGTGATAGGCTTTGTTTT
    361  ---------+---------+---------+---------+---------+---------+ 420
         AGAGAAAATACAAAATGAACACTTCCTCTACTAGTATCCGTAACACTATCCGAAACAAAA

AlwI
                                              HaeIV |
                                              Hin4I |
                                              DpnI  | |
                         CviRI        BstYI   | | |
          BbvI           Fnu4HI  |    Sau3AI  | | |           HinfI
          BsgI|           TseI|  | MwoI       | | |           TfiI
            ||             |||   |   |         | | |            |
         AGCATTTCCCTTTTATGCTGCACAATCGGCAGGATCTTTCATCACTAACCAACAAGGGAT
    421  ---------+---------+---------+---------+---------+---------+ 480
         TCGTAAAGGGAAAATACGACGTGTTAGCCGTCCTAGAAAGTAGTGATTGGTTGTTCCCTA FokI       HhaI                               NlaIII
          MnlI  |        ThaI             Hin4I         AciI MnlI|
            |  |          |                 |            |   ||
         TCAGGGTTTAGAGGGCGCGACATCCCTGATTTCCATTGAGCAGACCTCTCCGCATGGCAT
    481  ---------+---------+---------+---------+---------+---------+ 540
         AGTCCCAAATCTCCCGCGCTGTAGGGACTAAAGGTAACTCGTCTGGAGAGGCGTACCGTA BstEII
                     Hpy178III                MaeIII
                     MaeIII|                  Tsp45I
          BplI        Tsp45I|    TaqII   HphI   |         TaaI
           |           ||      |       |      |           |
         TTTATACCATTACTTCGTGACTATTATTTTTTGGTTAGTGGGTGGTCACCGTATTGTAAT
    541  ---------+---------+---------+---------+---------+---------+ 600
         AAATATGGTAATGAAGCACTGATAATAAAAAACCAATCACCCACCAGTGGCATAACATTA DpnI
                                    Sau3AI |
                                    Hpy188IX| |
                      Hpy178III     AlwI   | | |
               CviRI          | XmnI|      | | |
                 |            |  ||        | | |
         CTCTTTGTTATTGCAAACTCTTGAAGTCATTCCGATCCATAGTTTCTTTCCTGCCGAGAT
    601  ---------+---------+---------+---------+---------+---------+ 660
         GAGAAACAATAACGTTTGAGAACTTCAGTAAGGCTAGGTATCAAAGAAAGGACGGCTCTA
```

Figure 11D (Continued)

```
                                              BfaI
                                              AvrII|
                                              BsaJI|
                    DrdII                     StyI|
   Tth111II    BsmFI   |                   Bce83I||NlaIV      SmlI
      |          |     |                      |||   |           |
      TTATTTCACTCTTGCTTGGTTCAAAGAAGTCCCCATTATGCTCCTAGGTTCCAACCCTCA
901   ---------+---------+---------+---------+---------+---------+ 960
      AATAAAGTGAGAACGAACCAAGTTTCTTCAGGGGTAATACGAGGATCCAAGGTTGGGAGT

Hpy178III
                  CviJI             SfaNI
                  BfaI  |     HinfI  |
         MnlI     MmeI  |Hpy178III   |
         RsaI  |  AvrII|   MaeIII|   |                    BpmI
         ScaI  |  BsaJI|   Tsp45I|   |       HhaI         HinfI|
      TatI  |  |  StyI |   PleI ||   |   |   Hin4I        TfiI|
         ||  |  |  ||  |    |  ||    |   |    |   |         ||
      AGTACTCTAATCCCCTAGGCTCTTATCGTGACTCTTATCTGGAGATGCGCTCACTTACGA
961   ---------+---------+---------+---------+---------+---------+ 1020
      TCATGAGATTAGGGGATCCGAGAATAGCACTGAGAATAGACCTCTACGCGAGTGAATGCT BplI       TspRI           CjeI
      DdeI  |      TaaI |           HinfI|
      CjeI  |   |HhaI   |      DdeI  TfiI|                      DdeI
         |||  |    |    |        |     ||                        |
      ATCTTAGCGCACTGTTTATGGATTATCTTAGGGAATCTCTCGCATATTCTTTTGTAATCT
1021  ---------+---------+---------+---------+---------+---------+ 1080
      TAGAATCGCGTGACAAATACCTAATAGAATCCCTTAGAGAGCGTATAAGAAAACATTAGA Hpy178III
      HinfI ApoI    |
      TfiI Tsp509I  |
         |   |      |
         AAGAATCTATAAATTCAAGA
1081   ---------+---------+ 1100
         TTCTTAGATATTTAAGTTCT
```

Restriction enzyme analysis of CPN100987 (RY 67 - SEQ ID NO. 12)

Figure 12C (Continued)

```
                  Tsp509I
        SfaNI     CviRI       TaaI
          |        ||          |
      TCTTTCTTCTTGGACTACTGATGCAGAATTACGACAGTTCGTTCATAAGCAAGGGTTAGA
661   ---------+---------+---------+---------+---------+---------+ 720
      AGAAAGAAGAACCTGATGACTACGTCTTAATGCTGTCAAGCAAGTATTCGTTCCCAATCT

TaqII
                                                            BsaAI  |
                                                            SnaBI  |
                  MseI                                      MaeII| |
                    |                                         || |
      GTTTTTAGGTAAAGCATTAACAAAAGAAAACGCTTCTTTTCTATGGTATTTTCTACGTAG
721   ---------+---------+---------+---------+---------+---------+ 780
      CAAAAATCCATTTCGTAATTGTTTTCTTTTGCGAAGAAAAGATACCATAAAAGATGCATC

FokI
          BsiEI                          DraI  |                MslI
          TaqI  Hin4I    TaqI            MseI| |NlaIII   BccI     |
            |    |        |                || |   |        |      |
      GTTAGATGTCGGTCGAGCATATATCGTCGAGCAGACTTTAAAAACATGGTATGACCATCC
781   ---------+---------+---------+---------+---------+---------+ 840
      CAATCTACAGCCAGCTCGTATATAGCAGCTCGTCTGAAATTTTTGTACCATACTGGTAGG

FauI
                    Sth132I|      NlaIII
                    BfaI  ||       NsiI |
      BsmFI   MseI  AciI |  ||    CviRI |  |  DdeI        HindIII
        |      |     |   |  ||      |   |  |   |            |
      CTATGTGGATTATTTTAAGTCCCGCCTAGAACAATGCATGAAAGTCTTAGTGAAATAAAA
841   ---------+---------+---------+---------+---------+---------+ 900
      GATACACCTAATAAAATTCAGGGCGGATCTTGTTACGTACTTTCAGAATCACTTTATTTT AluI            AluI
      CviJI           CviJI
        |               |
      GCTTTATAAGTAAAGATTTAGCTTTATACAAAGTATAGAAAAATAACACG
901   ---------+---------+---------+---------+---------+ 950
      CGAAATATTCATTTCTAAATCGAAATATGTTTCATATCTTTTTATTGTGC
```

Restriction enzyme analysis of CPN100988 (ry68 - SEQ ID NO. 13)

Figure 13B (Continued)

```
              Hpy178III
              DpnI       |
              MnlI       |
         Sau3AI |       | Bpu1102I
        MseI  | |       |   DdeI       BspMI         Hpy188IX
    NlaIV |   | |       |   CviJI|     BpmI  |       CviRI     |
      |   |   | |       |   | |         |    |         |       |
      AACCTTAATGATCTCTGGAGGGTGGCTTAGCAATATGATTTTACGCTTTGCAGGTCAGAT
301   ---------+---------+---------+---------+---------+---------+  360
      TTGGAATTACTAGAGACCTCCCACCGAATCGTTATACTAAAATGCGAAACGTCCAGTCTA

AluI
                                AluI    HinfI               CviJI
                                CviJI   TfiI                CjeI |
                                  |       |                   | ||
      TTTCCAAAACTTCTATAAATGGAAATAAAGAGCTTATGGGAATCTCTCTACCAGAGCTTT
361   ---------+---------+---------+---------+---------+---------+  420
      AAAGGTTTTGAAGATATTTACCTTTATTTCTCGAATACCCTTAGAGAGATGGTCTCGAAA BfaI                                         CviJI
        AvrII|                  CjeI                    HaeIII
        BsaJI|                  FokI |            MspI  |    BslI
         StyI|             DdeI MmeI|         Tth111II  |   |MnlI   |
           ||              |    ||              |       |   |  |    |
      TTTCCAACCTAGGTTCTGCTTACTTAGATTATATCTTTCAACATCCTCCGGCCTATGTTT
421   ---------+---------+---------+---------+---------+---------+  480
      AAAGGTTGGATCCAAGACGAATGAATCTAATATAGAAAGTTGTAGGAGGCCGGATACAAA MboII
         |
      GGTCAGTTTTTCTTCTTTTA
481   ---------+---------+ 500
      CCAGTCAAAAAGAAGAAAAT
```

Figure 14: Identification of T- and B-cell epitopes from the amino acid sequences SEQ ID No. 14; ORF: cpn100686

```
  1 MVSSPILNVP LKNHASVSGK FTHREVSKLA SDLKSGAMSF VPEVLSEETI
 51 SSDLGKKQCT QGIISACCGL AMLIVLMSVY YRFGGVIASG AVLLNLLLIW
101 AALQYLDAPL TLSGLAGIVL AMGMAVDANV LVFERIREEF LLSQSLKKSV
151 EKGYTKAFGA IFDSNLTTVL ASALLFFLDT GPIKGFALTL ILGIFSSMFT
201 ALFMTKFFFM LWMNKTQHTQ LHMMNKFVGI KHDFLRGCKK LWAVSGSVFL
251 LGCVALGFGA WNSVLGMDFK GGYAFTFNPK EHGISDVAQM RGKVVHKLQE
301 AGLSSRDFRI QTFGSSEKIK IYFSDKALSY TKQIRASLLK LTIMSWRYCG
351 IVVRNRPRFL YGNSKRNAKF WSKVSSKLSK KMRYQATIGL LGALAIILLY
401 VSLRFEWQYA FSAVCALIHD LLATCAVLFI AHFFLKKIQI DLQAIGALMT
451 VLGYSLNNTL IIFDRIREDR QANLFTPMHV LVNDALQKTF SRTVMTTATT
501 LSVLLMLLFI GGSSVFNFAF IMTIGILLGT LSSLYIAPPL LLFMVRKENR
551 SK
```

Possible T cell epitope:

427  VLFIAHFFL                (SEQ ID NO: 27)

Possible B cell epitope:

465  RIREDRQAN                (SEQ ID NO: 28)

Figure 15: Identification of T- and B-cell epitopes from the amino acid sequences SEQ ID No. 15; ORF: cpn100696

```
  1 MSSNLHPVGG TGTGAAAPES VLNIVEEIAA SGSVTAGLQA ITSSPGMVNL
 51 LIGWAKTKFI QPIRESKLFQ SRACQITLLV LGILLVVAGL ACMFIFHSQL
101 GANAFWLIIP AAIGLIKLLV TSLCFDEACT SEKLMVFQKW AGVLEDQLDD
151 GILNNSNKIF GHVKTEGNTS RATTPVLNDG RGTPVLSPLV SKIARV
```

Possible T cell epitope:

133   KLMVFQKWA                    (SEQ ID NO: 29)

Possible B cell epitope:

163   VKTEGNTSRAT                  (SEQ ID NO: 30)

Figure 16: Identification of T- and B-cell epitopes from the amino acid sequences SEQ ID No. 16; ORF: cpn100709

```
  1 MTIRILAEGL AFRYGSKGPN IIHDVSFSVY DGDFIGIIGP NGGGKSTLTM
 51 LILGLLTPTF GSLKTFPSHS AGKQTHSMIG WVPQHFSYDP CFPISVKDVV
101 LSGRLSQLSW HGKYKKKDFE AVDHALDLVG LSDTTTTAFA HLSGGQIQRV
151 LLARALASYP EILILDEPTT NIDPDNQQRI LSILKKLNRT CTILMVTHDL
201 HHTTNYFNKV FYMNKTLHFI GRHFDLNRPI LLSSYKNQEF SCSPH
```

Possible T cell epitope:

212   YMNKTLHFI           (SEQ ID NO: 31)

Possible B cell epitopes:

109   SWHGKYKKKDFE        (SEQ ID NO: 32)

166   DEPTTNIDPDNQQR      (SEQ ID NO: 33)

Figure 17: Identification of T- and B-cell epitopes from the amino acid sequences SEQ ID No. 17; ORF: cpn100710

```
  1 MHKVIVFIFL TLYSLKSYGN DVIDKPHVLV SIAPYKFLVE QIAEETCFVY
 51 AIVTNHYDPH TYELPPQQIK ELRQGDLWFR IGEAFGKNLL EKPYMQQVDL
101 SQNVSLIQGK PCCNQHTTNY DTHTWLSPKN LKVQVETIVT TLSKKYPQHA
151 TLYQSNGEKL LLALDQLNEE ILTITSKAKQ RHILVSHGAF GYFCRDYNFS
201 QHTIEKSSHV EPSPKDVARV FRDIEQYKIS SVILLEYSGR RSSAMLADRF
251 HMHTVNLDPY AENVLVNLKT IATTFSSL
```

Possible T cell epitope:

125   WLSPKNLKV                    (SEQ ID NO: 34)

Possible B cell epitope:

55    NHYDPHTYELPPQQIKELRQGD       (SEQ ID NO: 35)

Figure 18: Identification of T- and B-cell epitopes from the amino acid sequences SEQ ID No. 18; ORF: cpn100711

```
  1 MGPGSVLSNH SKEAGGIAIN NVIIDFSEIV PTKDNATVAP PTLKLVSRTN
 51 ADSKDKIDIT GTVTLLDPNG NLYQNSYLGE DRDITLFNID NSASGAVTAT
101 NVTLQGNLGA KKGYLGTWNL DPNSSGSKII LKWTFDKYLR WPYIPRDNHF
151 YINSIWGAQN SLVTVNQGIL GNMLNNARFE DPAFNNFWAS AIGSFLRKEV
201 SRNSDSFTYH GRGYTAAVDA KPRQEFILGA AFSQVFGHAE SEYHLDNYKH
251 KGSGHSTQAS LYAGNIFYFP AIRSRPILFQ GVATYGYMQH DTTTYYPSIE
301 EKNMANWDSI AWLFDLRFSV DLKEPQPHST ARLTFYTEAE YTRIRQEKFT
351 ELDYDPRSFS ACSYGNLAIP TGFSVDGALA WREIILYNKV SAAYLPVILR
401 NNPKATYEVL STKEKGNVVN VLPTRNAARA EVSSQIYLGS YWTLYGTYTI
451 DASMNTLVQM ANGGIRFVF
```

Possible T cell epitope:

312 WLFDLRFSV (SEQ ID NO: 36)

Possible B cell epitope:

240 ESEYHLDNYKHKGSGHST` (SEQ ID NO: 37)

Figure 19: Identification of T- and B-cell epitopes from the amino acid sequences SEQ ID No. 19; ORF: cpn100877

```
  1 MRFSLCGFPL VFSFTLLSVF DTSLSATTIS LTPEDSFHGD SQNAERSYNV
 51 QAGDVYSLTG DVSISNVDNS ALNKACFNVT SGSVTFAGNH HGLYFNNISS
101 GTTKEGAVLC CQDPQATARF SGFSTLSFIQ SPGDIKEQGC LYSKNALMLL
151 NNYVVRFEQN QSKTKGGAIS GANVTIVGNY DSVSFYQNAA TFGGAIHSSG
201 PLQIAVNQAE IRFAQNTAKN GSGGALYSDG DIDIDQNAYV LFRENEALTT
251 AIGKGGAVCC LPTSGSSTPV PIVTFSDNKQ LVFERNHSIM GGGAIYARKL
301 SISSGGPTLF INNISYANSQ NLGGAIAIDT GGEISLSAEK GTITFQGNRT
351 SLPFLNGIHL LQNAKFLKLQ ARNGYSIEFY DPITSEADGS TQLNINGDPK
401 NKEYTGTILF SGEKSLANDP RDFKSTIPQN VNLSAGYLVI KEGAEVTVSK
451 FTQSPGSHLV LDLGTKLIAS KEDIAITGLA IDIDSLSSSS TAAVIKANTA
501 NKQISVTDSI ELISPTGNAY EDLRMRNSQT FPLLSLEPGA GGSVTVTAGD
551 FLPVSPHYGF QGNWKLAWTG TGNKVGEFFW DKINYKPRPE KEGNLVPNIL
601 WGNAVDVRSL MQVQETHASS LQTDRGLWID GIGNFFHVSA SEDNIRYRHN
651 SGGYVLSVNN EITPKHYTSM AFSQLFSRDK DYAVSNNEYR MYLGSYLYQY
701 TTSLGNIFRY ASRNPNVNVG ILSRRFLQNP LMIFHFLCAY GHATNDMKTD
751 YANFPMVKNS WRNNCWAIEC GGSMPLLVFE NGRLFQGAIP FMKLQLVYAY
801 HGDFKETTAD GRRFSNGSLT SISVPLGIRF EKLALSQDVL YDFSFSYIPD
851 IFRKDPSCEA ALVISGDSWL VPAAHVSRHA FVGSGTGRYH FNDYTELLCR
901 GSIECRPHAR NYNINCGSKF RF
```

Possible T cell epitope:

146   ALMLLNNYV                    (SEQ ID NO: 38)

Possible B cell epitope:

581   DKINYKPRPEKEG                (SEQ ID NO: 39)

Figure 20: Identification of T- and B-cell epitopes from the amino acid sequences SEQ ID No. 20; ORF: CPN100325

```
  1 MPSSWKRLLQ VLSHKIAATE SGGGIYAKDI QLQALPGSFT ITDNKVETSL
 51 TTSTNLYGGG IYSSGAVTLT NISGTFGITG NSVINTATSQ DADIQGGGIY
101 ATTSLSINQC NTPILFSNNS AATKKTSTTK QIAGGAIFSA AVTIENNSQP
151 IIFLNNSAKS EATTAATAGN KDSCGGAIAA NSVTLTNNPE ITFKGNYAET
201 GGAIGCIDLT NGSPPRKVSI ADNGSVLFQD NSALNRGGAI YGETIDISRT
251 GATFIGNSSK HDGSAICCST ALTLAPNSQL IFENNKVTET TATTKASINN
301 LGAAIYGNNE TSDVTISLSA ENGSIFFKNN LCTATNKYCS IAGNVKFTAI
351 EASAGKAISF YDAVNVPPKK QLLKS
```

Possible T cell epitope:

226   VLFQDNSAL          (SEQ ID NO: 40)

Possible B cell epitope:

257   NSSKHDG            (SEQ ID NO: 41)

Figure 21: Identification of T- and B-cell epitopes from the amino acid sequences SEQ ID No. 21; ORF: CPN100368

```
  1 MKYSLPWLLT SSALVFSLHP LMAANTDLSS SDNYENGSSG SAAFTAKETS
 51 DASGTTYTLT SDVSITNVSA ITPADKSCFT NTGGALSFVG ADHSLVLQTI
101 ALTHDGAAIN NTNTALSFSG FSSLLIDSAP ATGTSGGKGA ICVTNTEGGT
151 ATFTDNASVT LQKNTSEKDG AAVSAYSIDL AKTTTAALLD QNTSTKNGGA
201 LCSTANTTVQ GNSGTVTFSS NTATDKGGGI YSKEKDSTLD ANTGVVTFKS
251 NTAKTGGAWS SDDNLALTGN TQVLFQENKT TGSAAQANNP EGCGGAICCY
301 LATATDKTGL AISQNQEMSF TSNTTTANGG AIYATKCTLD GNTTLTFDQN
351 TATAGCGGAI YTETEDFSLK GSTGTVTFST NTAKTGGALY SKGNSSLTGN
401 TNLLFSGNKA TGPSNSSANQ EGCGGAILAF IDSGSVSDKT GLSIANNQEV
451 SLTSNAATVS GGAIYATKCT LTGNGSLTFD GNTAGTSGGA IYTETEDFTL
501 TGSTGTVTFS TNTAKTGGAL YSKGNNSLSG NTNLLFSGNK ATGPSNSSAN
551 QEGCGGAILS FLESASVSTK KGLWIEDNEN VSLSGNTATV SGGAIYATKC
601 ALHGNTTLTF DGNTAETAGG AIYTETEDFT LTGSTGTVTF STNTAKTAGA
651 LHTKGNTSFT KNKALVFSGN SATATATTTT DQEGCGGAIL CNISESDIAT
701 KSLTLTENES LSFINNTAKR SGGGIYAPKC VISGSESINF DGNTAETSGG
751 AIYSKNLSIT ANGPVSFTNN SGGKGGAIYI ADSGELSLEA IDGDITFSGN
801 RATEGTSTPN SIHLGARGKI TKLAAAPGHT IYFYDPITME APASGGTIEE
851 LVINPVVKAI VPPPQPKNGP I
```

Possible T cell epitope:

7    WLLTSSALV                    (SEQ ID NO: 42)

Possible B cell epitopes:

162    QKNTSEKDG                  (SEQ ID NO: 43)

538    GNKATGPSNSSANQEG       (SEQ ID NO: 44)

Figure 22: Identification of T- and B-cell epitopes from the amino acid sequences SEQ ID No. 22; ORF: CPN100624

```
  1 MTNSIFISKF GCLCDPFVSA FYPTALCCSL SGNEVPNLAS CQMSRKDISA
 51 FHTSPSFRLN VTPEPLVSSF RPSNLLNGFG HDITQDITIT GNSINSVIDY
101 NYHYEDGGIL ACKNLFISEN KGNLSFERNS SHSSGGALYS VRECWISKNQ
151 NYSFISNAAS LATTTTSGFG GAIHALDSYI TNNLGEGQFL DNVSKNRGGA
201 IYVGVSLSIT DNLGPIVIKK NQTLEDSSFG GGIFCRAVNI ERNYQNIQIN
251 DNASGQGVVY FLPLGVIISS NKEIIEISNH SASSINTASG KLYPGGGGIM
301 CTSLSHENNP KGLIFNNKTA ALSGGVYTRD LSSSKITVRT AFINNSATSG
351 GALINLSGIG STPQNFFLSA DYGDILFNNN TITSSSPQPG YRNALYAAPG
401 INLKLGARQG YKILFYDPID HDQTTTDPIV FNYEPHHLGT VLFSGINVDS
451 NATNPLNFLS KFSNSSRLER GVLAIEDRAA ISCKTLSQTG GILRLGNAAL
501 IRTKGPGSSI NFNAIAINLP SILQSEASAP KFWIYPTLTG STYSEDTSST
551 ITLSGPLTFL NDENENPYDS LDLSEPRKDI PPPLPPRCDC KKIDTSNLIV
601 EAMNLDEHYG YQGIWSPYWM ETTTTTSSTV PEQTNTNHRQ LYVDWTPVGY
651 RPNPERHGEF IANTLWQSAY NALLGIRILP PQNLKEHDLE ASLQGLGLLI
701 NQHNREGRKG FRNHTTGYAA TTSAKTAARH SFSLGFAQMF SKTRERQSPS
751 TTSSHNYFAG LRFDSLLFRD FISTGLSLGY SYGDHHMLCH YTEILKGSSK
801 AFFNNHTLVA SLDCTFPLAR ITRTLELQPF ISAIALRCSQ ASFQETGDHI
851 RKFHPKHPLT DLSSPIGFRS EWKTSHHIPM LWTTEISYVP TLYRKNPEMF
901 TTLLISNGTW TTQATPVSYN SVAAKIKNTS QLFSRVTLSL DYSAQVSSST
951 VGQYLKAESH CTF
```

Possible T cell epitope:

640    QLYVDWTPV          (SEQ ID NO: 45)

Possible B cell epitopes:

701    NQHNREGRKGFRNHTTG    (SEQ ID NO: 46)

741    SKTRERQSPSTTSSHNY    (SEQ ID NO: 47)

Figure 23: Identification of T- and B-cell epitopes from the amino acid sequences SEQ ID No. 23; ORF: CPN100633

```
  1 MTILRNFLTC SALFLALPAA AQVVYLHESD GYNGAINNKS LEPKITCYPE
 51 GTSYIFLDDV RISNVKHDQE DAGVFINRSG NLFFMGNRCN FTFHNLMTEG
101 FGAAISNRVG DTTLTLSNFS YLAFTSAPLL PQGQGAIYSL GSVMIENSEE
151 VTFCGNYSSW SGAAIYTPYL LGSKASRPSV NLSGNRYLVF RDNVSQVYGG
201 AISTHNLTLT TRGPSCFENN HAYHDVNSNG GAIAIAPGGS ISISVKSGDL
251 IFKGNTASQD GNTIHNSIHL QSGAQFKNLR AVSESGVYFY DPISHSESHK
301 ITDLVINAPE GKETYEGTIS FSGLCLDDHE VCAENLTSTI LQDVTLAGGT
351 LSLSDGVTLQ LHSFKQEASS TLTMSPGTTL LCSGDARVQN LHILIEDTDN
401 FVPVRIRAED KDALVSLEKL KVAFEAYWSV YDFPQFKEAF TIPLLELLGP
451 SFDSLLLGET TLERTQVTTE NDAVRGFWSL SWEEYPPSLD KDRRITPTKK
501 TVFLTWNPEI TSTP
```

Possible B cell epitope:

482 WEEYPPSLDKDRRITPTKK          (SEQ ID NO: 48)

Figure 24: Identification of T- and B-cell epitopes from the amino acid sequences SEQ ID No. 24; ORF: cpn100985

```
  1 MGISLPELFS NLGSAYLDYI FQHPPAYVWS VFLLLLARLL PIFAVAPFLG
 51 AKLFPSPIKI GISLSWLAII FPKVLADTQI TNYMDNNLFY VLLVKEMIIG
101 IVIGFVLAFP FYAAQSAGSF ITNQQGIQGL EGATSLISIE QTSPHGILYH
151 YFVTIIFWLV GGHRIVISLL LQTLEVIPIH SFFPAEMMSL SAPIWITMIK
201 MCQLCLVMTI QLSAPAALAM LMSDLFLGII NRMAPQVQVI YLLSALKAFM
251 GLLFLTLAWW FIIKQIDYFT LAWFKEVPIM LLGSNPQVL
```

Possible T cell epitope:

83  YMDNNLFYV                    (SEQ ID NO: 49)

Possible B cell epitope:

78  TQITNYMDNN                   (SEQ ID NO: 50)

Figure 25: Identification of T- and B-cell epitopes from the amino acid sequences SEQ ID No. 25; ORF: cpn100987

```
  1 MKHSKEDDLS RFLPKNLLVE SPHPEEIPLK SLSFTMSWLP TIHPSWITIA
 51 MKEFPPEIQG QLLAWLPEPL VQEILPLLPG ISIAPHRCAP FGAFYLLDML
101 SKKIRPCGIT EEIFLPASSA NAILYYTGPV KIALINCLGL YSIAKELKHI
151 LDKVVIERVK NALSPTEKLF LTYCQSHPMK HLETTNFLSS WTTDAELRQF
201 VHKQGLEFLG KALTKENASF LWYFLRRLDV GRAYIVEQTL KTWYDHPYVD
251 YFKSRLEQCM KVLVK
```

Possible T cell epitope:

220    FLWYFLRRL                            (SEQ ID NO: 51)

Possible B cell epitope:

1      MKHSKEDDLSR                          (SEQ ID NO: 52)

Figure 26: Identification of T- and B-cell epitopes from the amino acid sequences SEQ ID No. 26; ORF: cpn100988

```
  1 MLAFFATSFK SVLFEYSYQS LLLILIVSAP PIILASIVGI MVAIFQAATQ
 51 IQEQTFAFAV KLVVIFGTLM ISGGWLSNMI LRFAGQIFQN FYKWK
```

Possible T cell epitope:

21 LLLILIVSA           (SEQ ID NO: 53)

Possible B cell epitope:

89 QNFYKWK             (SEQ ID NO: 54)

US 7,553,493 B2

*CHLAMYDIA* FLAGELLAR PROTEIN ANTIGEN

REFERENCE TO RELATED APPLICATIONS

This application is a divisional application of U.S. application Ser. No. 09/868,987 filed on Oct. 1, 2001, now U.S. Pat. No. 7,297,341, which claims the benefit of 13 U.S. provisional applications: U.S. Provisional Application Nos. 60/113,280, 60/113,281, 60/113,282, 60/113,283, 60/113, 284, 60/113,285, 60/113,385, all of which were filed Dec. 23, 1998; and U.S. Provisional Application Nos. 60/114,050, 60/114,056, 60/114,057, 60/114,058, 60/114,059, 60/114, 061, all of which were filed Dec. 28, 1998.

FIELD OF INVENTION

The present invention relates to *Chlamydia* antigens and corresponding DNA molecules, which can be used to prevent and treat *Chlamydia* infection in mammals, such as humans.

BACKGROUND OF THE INVENTION

Chlamydiae are prokaryotes. They exhibit morphologic and structural similarities to gram-negative bacteria including a trilaminar outer membrane, which contains lipopolysaccharide and several membrane proteins that are structurally and functionally analogous to proteins found in *E coli*. They are obligate intra-cellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

*C. pneumoniae* is a common human pathogen, originally described as the TWAR strain of *Chlamydia psittaci* but subsequently recognised to be a new species. *C. pneumoniae* is antigenically, genetically and morphologically distinct from other *chlamydia* species (*C. trachomatis*, *C. pecorum* and *C. psittaci*). It shows 10% or less DNA sequence homology with either of *C. trachomatis* or *C. psittaci*.

*C. pneumoniae* is a common cause of community acquired pneumonia, only less frequent than *Streptococcus pneumoniae* and *Mycoplasma pneumoniae* (Grayston et al. (1995) Journal of Infectious Diseases 168:1231; Campos et al. (1995) Investigation of Opthalmology and Visual Science 36:1477). It can also cause upper respiratory tract symptoms and disease, including bronchitis and sinusitis (Grayston et al. (1995) Journal of Infectious Diseases 168:1231; Grayston et al (1990) Journal of Infectious Diseases 161:618; Marrie (1993) Clinical Infectious Diseases. 18:501; Wang et al (1986) Chlamydial infections. Cambridge University Press, Cambridge. p. 329. The great majority of the adult population (over 60%) has antibodies to *C. pneumoniae* (Wang et al (1986) Chlamydial infections. Cambridge University Press, Cambridge. p. 329), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from fomites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against chlamydial infections.

In most instances, *C. pneumoniae* infection is often mild and without complications, and up to 90% of infections are subacute or unrecognized. Among children in industrialized countries, infections have been thought to be rare up to the age of 5 y, although a recent study (E Normann et al, *Chlamydia pneumoniae* in children with acute respiratory tract infections, Acta Paediatrica, 1998, Vol 87, Iss 1, pp 23-27) has reported that many children in this age group show PCR evidence of infection despite being seronegative, and estimates a prevalence of 17-19% in 2-4 y olds. In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 y. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (Saikku et al. (1988) Lancet; ii:983; Thom et al. (1992) JAMA 268:68; Linnanmaki et al. (1993), Circulation 87:1030; Saikku et al. (1992) Annals Internal Medicine 116:273; Melnick et al (1993) American Journal of Medicine 95:499). Moreover, the organisms have been detected in atheromas and fatty streaks of the coronary, carotid, peripheral arteries and aorta (Shor et al. (1992) South African. Medical Journal 82:158; Kuo et al. (1993) Journal of Infectious Diseases 167:841; Kuo et al. (1993) Arteriosclerosis and Thrombosis 13:1500; Campbell et al (1995) Journal of Infectious Diseases 172:585; Chiu et al. Circulation, 1997 (In Press)). Viable *C. pneumoniae* has been recovered from the coronary and carotid artery (Ramirez et al (1996) Annals of Internal Medicine 125:979; Jackson et al. Abst. K121, p 272, $36^{th}$ ICAAC, 15-18 Sep. 1996, New Orleans). Furthermore, it has been shown that *C. pneumoniae* can induce changes of atherosclerosis in a rabbit model (Fong et al (1997) Journal of Clinical Microbiology 35:48). Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbations of asthma in adults, and small-scale studies have shown that prolonged antibiotic treatment was effective at greatly reducing the severity of the disease in some individuals (Hahn D L, et al. Evidence for *Chlamydia pneumoniae* infection in steroid-dependent asthma. Ann Allergy Asthma Immunol. 1998 January; 80(1): 45-49; Hahn D L, et al. Association of *Chlamydia pneumoniae* IgA antibodies with recently symptomatic asthma. Epidemiol Infect. 1996 December; 117(3): 513-517; Bjornsson E, et al. Serology of chlamydia in relation to asthma and bronchial hyperresponsiveness. Scand J Infect Dis. 1996; 28(1): 63-69; Hahn D L. Treatment of *Chlamydia pneumoniae* infection in adult asthma: a before-after trial. J Fam Pract. 1995 October; 41(4): 345-351; Allegra L, et al. Acute exacerbations of asthma in adults: role of *Chlamydia pneumoniae* infection. Eur Respir J. 1994 December; 7(12): 2165-2168; Hahn D L, et al. Association of *Chlamydia pneumoniae* (strain TWAR) infection with wheezing, asthmatic bronchitis, and adult-onset asthma. JAMA. 1991 Jul. 10; 266(2): 225-230).

In light of these results a protective vaccine against *C. pneumoniae* infection would be of considerable importance. There is not yet an effective vaccine for any human chlamydial infection. It is conceivable that an effective vaccine can be developed using physically or chemically inactivated Chlamydiae. However, such a vaccine does not have a high margin of safety. In general, safer vaccines are made by genetically manipulating the organism by attenuation or by recombinant means. Accordingly, a major obstacle in creating an effective and safe vaccine against human chlamydial infection has been the paucity of genetic information regarding *Chlamydia*, specifically *C. pneumoniae.*

Studies with *C. trachomatis* and *C. psittaci* indicate that safe and effective vaccine against *Chlamydia* is an attainable goal. For example, mice which have recovered from a lung infection with *C. trachomatis* are protected from infertility induced by a subsequent vaginal challenge (Pal et al. (1996) Infection and Immunity. 64:5341). Similarly, sheep immunized with inactivated *C. psittaci* were protected from subsequent chlamydial-induced abortions and stillbirths (Jones et al. (1995) Vaccine 13:715). Protection from chlamydial infections has been associated with Th1 immune responses, particularly the induction of INFg—producing CD4+T-cells (Igietsemes et al. (1993) Immunology 5:317). The adoptive transfer of CD4+ cell lines or clones to nude or SCID mice conferred protection from challenge or cleared chronic disease (Igietseme et al (1993) Regional Immunology 5:317; Magee et al (1993) Regional Immunology 5: 305), and in vivo depletion of CD4+T cells exacerbated disease post-challenge (Landers et al (1991) Infection & Immunity 59:3774; Magee et al (1995) Infection & Immunity 63:516). However, the presence of sufficiently high titres of neutralising antibody at mucosal surfaces can also exert a protective effect (Cotter et al. (1995) Infection and Immunity 63:4704).

Antigenic variation within the species *C. pneumoniae* is not well documented due to insufficient genetic information, though variation is expected to exist based on *C. trachomatis*. Serovars of *C. trachomatis* are defined on the basis of antigenic variation in the major outer membrane protein (MOMP), but published *C. pneumoniae* MOMP gene sequences show no variation between several diverse isolates of the organism (Campbell et al (1990) Infection and Immunity 58:93; McCafferty et al (1995) Infection and Immunity 63:2387-9; Gaydos et al (1992) Infection and Immunity 60(12):5319-5323). Regions of the protein known to be conserved in other chlamydial MOMPs are conserved in *C. pneumoniae* (Campbell et al (1990) Infection and Immunity 58:93; McCafferty et al (1995) Infection and Immunity 63:2387-9). One study has described a strain of *C. pneumoniae* with a MOMP of greater that usual molecular weight, but the gene for this has not been sequenced (Grayston et al. (1995) Journal of Infectious Diseases 168:1231). Partial sequences of outer membrane protein 2 from nine diverse isolates were also found to be invariant (Ramirez et al (1996) Annals of Internal Medicine 125:979). The genes for HSP60 and HSP70 show little variation from other chlamydial species, as would be expected. The gene encoding a 76 kDa antigen has been cloned from a single strain of *C. pneumoniae*. It has no significant similarity with other known chlamydial genes (Marrie (1993) Clinical Infectious Diseases. 18:501).

Many antigens recognised by immune sera to *C. pneumoniae* are conserved across all chlamydiae, but 98 kDa, 76 kDa and 54 kDa proteins appear to be *C. pneumoniae*-specific (Campos et al. (1995) Investigation of Opthalmology and Visual Science 36:1477; Marrie (1993) Clinical Infectious Diseases. 18:501; Wiedmann-Al-Ahmad M, et al. Reactions of polyclonal and neutralizing anti-p54 monoclonal antibodies with an isolated, species-specific 54-kilodalton protein of *Chlamydia pneumoniae*. Clin Diagn Lab Immunol. 1997 November; 4(6): 700-704). Immunoblotting of isolates with sera from patients does show variation of blotting patterns between isolates, indicating that serotypes *C. pneumoniae* may exist (Grayston et al. (1995) Journal of Infectious Diseases 168:1231; Ramirez et al (1996) Annals of Internal Medicine 125:979). However, the results are potentially confounded by the infection status of the patients, since immunoblot profiles of a patient's sera change with time post-infection. An assessment of the number and relative frequency of any serotypes, and the defining antigens, is not yet possible.

Accordingly, a need exists for identifying and isolating polynucleotide sequences of *C. pneumoniae* for use in preventing and treating *Chlamydia* infection.

SUMMARY OF THE INVENTION

The present invention provides purified and isolated polynucleotide molecules that encode *Chlamydia* polypeptides which can be used in methods to prevent, treat, and diagnose *Chlamydia* infection. In one form of the invention, the polynucleotide molecules are selected from DNA that encode polypeptides CPN100686 RY 54 (SEQ ID No: 1), CPN100696 RY-55 (SEQ ID No: 2), CPN100709 RY-57 (SEQ ID No: 3), CPN100710 RY-58 (SEQ ID No:4), CPN100711 RY-59 (SEQ ID No: 5), CPN100877 RY-61 (SEQ ID No:6), CPN100325 RY-62 (SEQ ID No:7), CPN100368 RY-63 (SEQ ID No:8), CPN100624 RY-64 (SEQ ID No:9), CPN100633 RY-65 (SEQ ID No:10), CPN100985 RY-66 (SEQ ID No:11), CPN100987 RY-67 (SEQ ID No:12) and CPN100988 RY-68 (SEQ ID No:13). Another form of the invention provides polypeptides corresponding to the isolated DNA molecules. The amino acid sequences of the corresponding encoded polypeptides are shown for CPN100686 RY 54 as SEQ ID No: 14, CPN100696 RY-55 as SEQ ID No: 15, CPN100709 RY-57 as SEQ ID No: 16, CPN100710 RY-58 as SEQ ID No: 17, CPN100711 RY-59 as SEQ ID No: 18, CPN100877 RY-61 as SEQ ID No: 19, CPN100325 RY-62 as SEQ ID No: 20, CPN100368 RY-63 as SEQ ID No: 21, CPN100624 RY-64 as SEQ ID No: 22, CPN100633 RY-65 as SEQ ID No: 23, CPN100985 RY-66 as SEQ ID No: 24, CPN100987 RY-67 as SEQ ID No: 24 and CPN100988 RY-68 as SEQ ID No: 26.

Those skilled in the art will readily understand that the invention, having provided the polynucleotide sequences encoding *Chlamydia* polypeptides, also provides polynucleotides encoding fragments derived from such peptides. Moreover, the invention is understood to provide mutants and derivatives of such polypeptides and fragments derived therefrom, which result from the addition, deletion, or substitution of non-essential amino acids as described herein. Those skilled in the art would also readily understand that the invention, having provided the polynucleotide sequences encoding *Chlamydia* polypeptides, further provides monospecific antibodies that specifically bind to such polypeptides.

The present invention has wide application and includes expression cassettes, vectors, and cells transformed or transfected with the polynucleotides of the invention. Accordingly, the present invention further provides (i) a method for producing a polypeptide of the invention in a recombinant host system and related expression cassettes, vectors, and transformed or transfected cells; (ii) a vaccine, or a live vaccine vector such as a pox virus, *Salmonella typhimurium*, or *Vibrio cholerae* vector, containing a polynucleotide of the invention, such vaccines and vaccine vectors being useful for, e.g., preventing and treating *Chlamydia* infection, in combination with a diluent or carrier, and related pharmaceutical compositions and associated therapeutic and/or prophylactic methods; (iii) a therapeutic and/or prophylactic use of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of *Chlamydia* in a biological sample, which can involve the use of a DNA or RNA molecule, a monospecific antibody, or a polypeptide of the invention; and (v) a method for purifying a polypeptide of the invention by antibody-based affinity chromatography.

BRIEF DESCRIPTION OF THE DRAWINGS

The present invention will be further understood from the following description with reference to the drawings, in which:

FIGS. 14 through 26 show an identification of T and B cell epitopes from the amino acid sequences SEQ ID Nos: 14 to 26.

DETAILED DESCRIPTION OF INVENTION

Figure 1A:
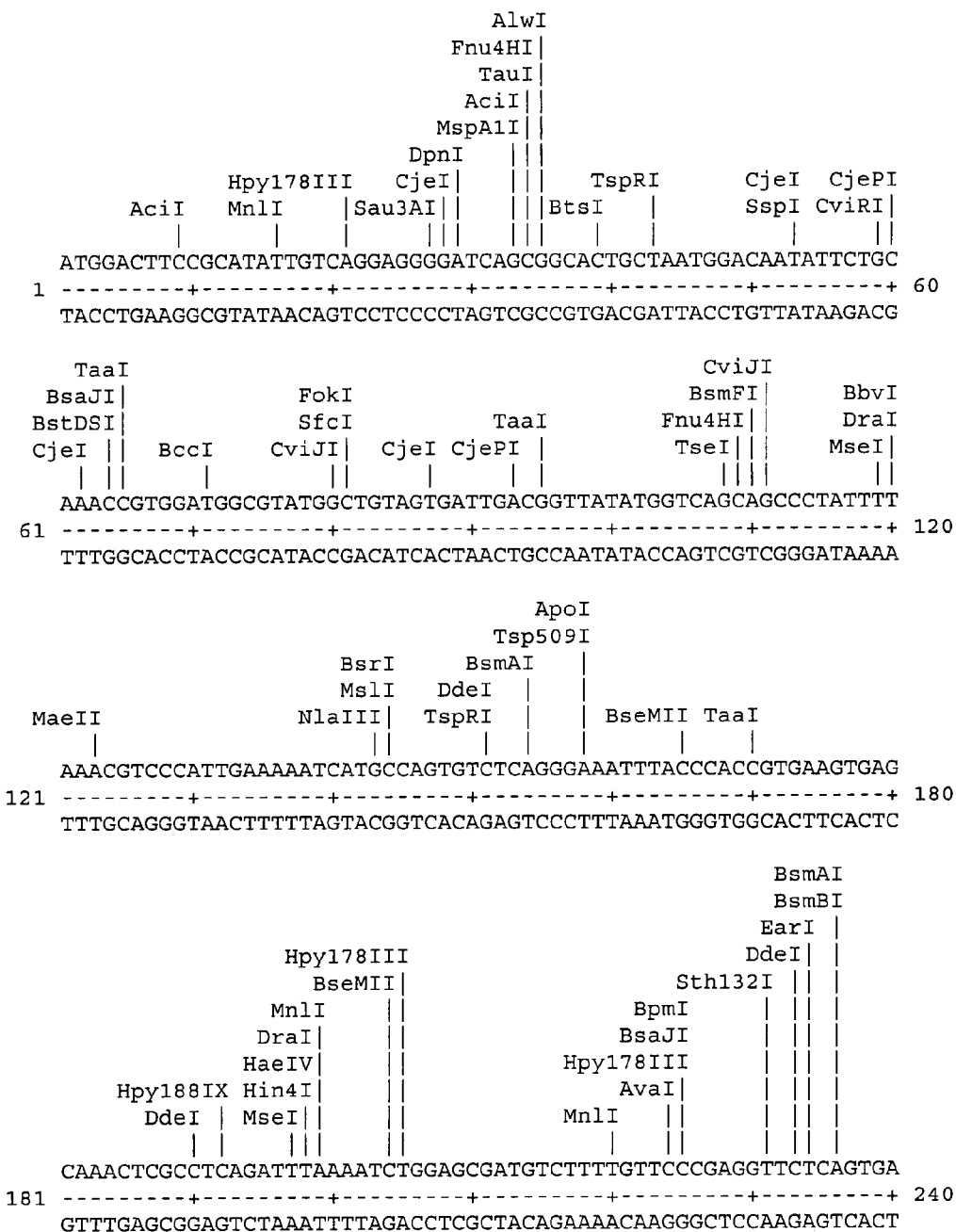
FIG. 1 through 13 show the restriction enzyme analysis of the nucleic acid sequences of the invention.
Figure 1B:
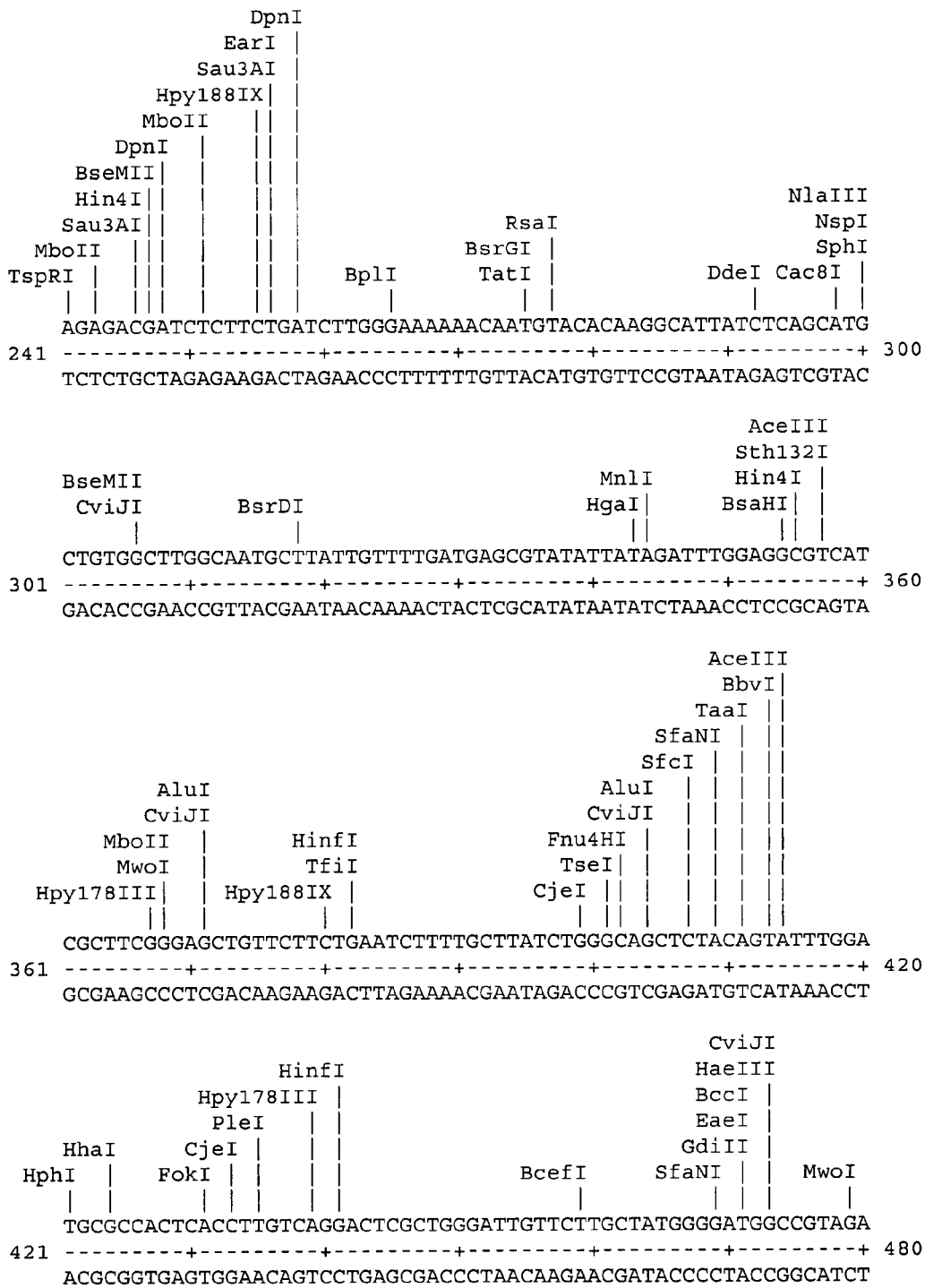
Figure 1E:
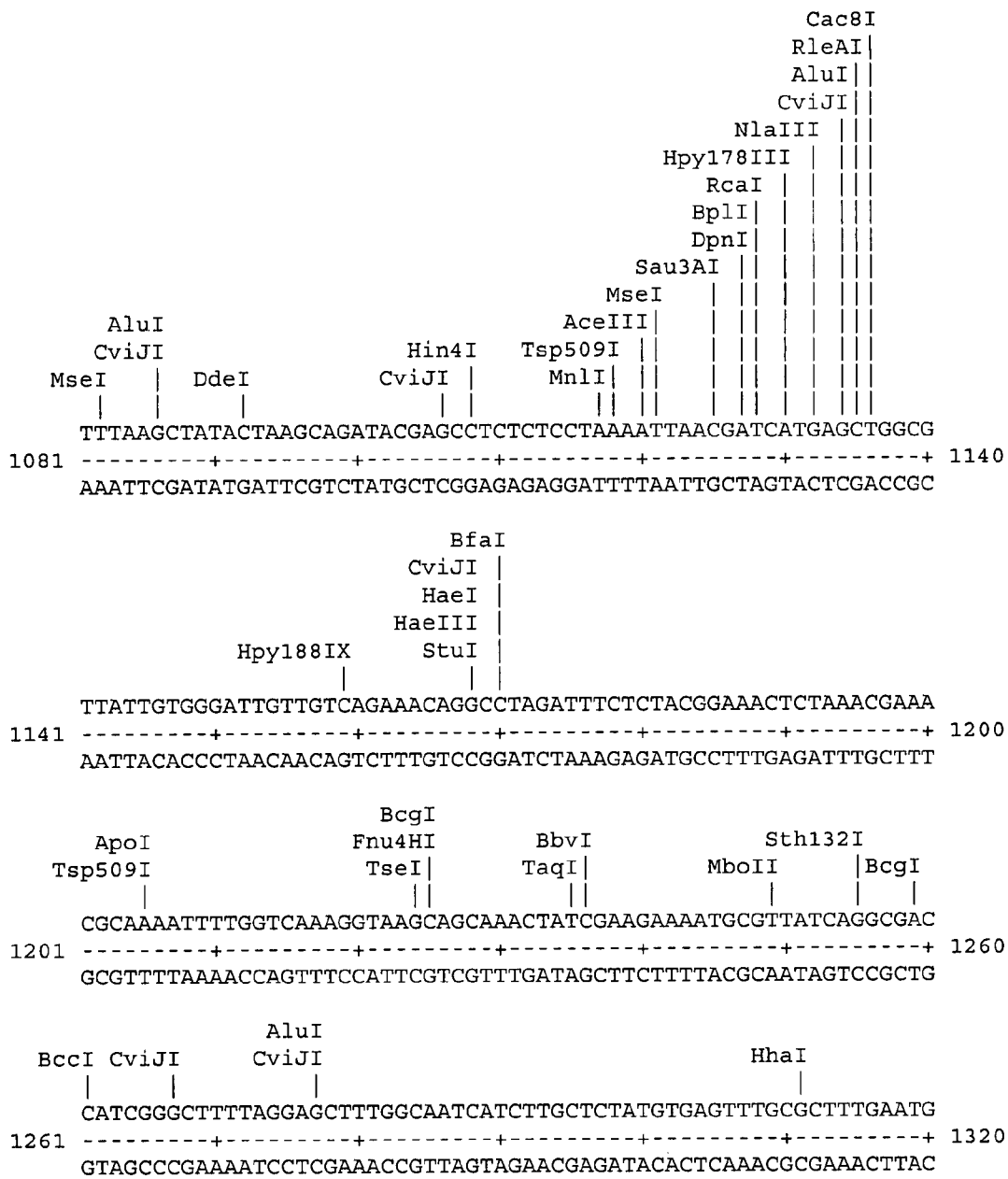
Figure 2A:
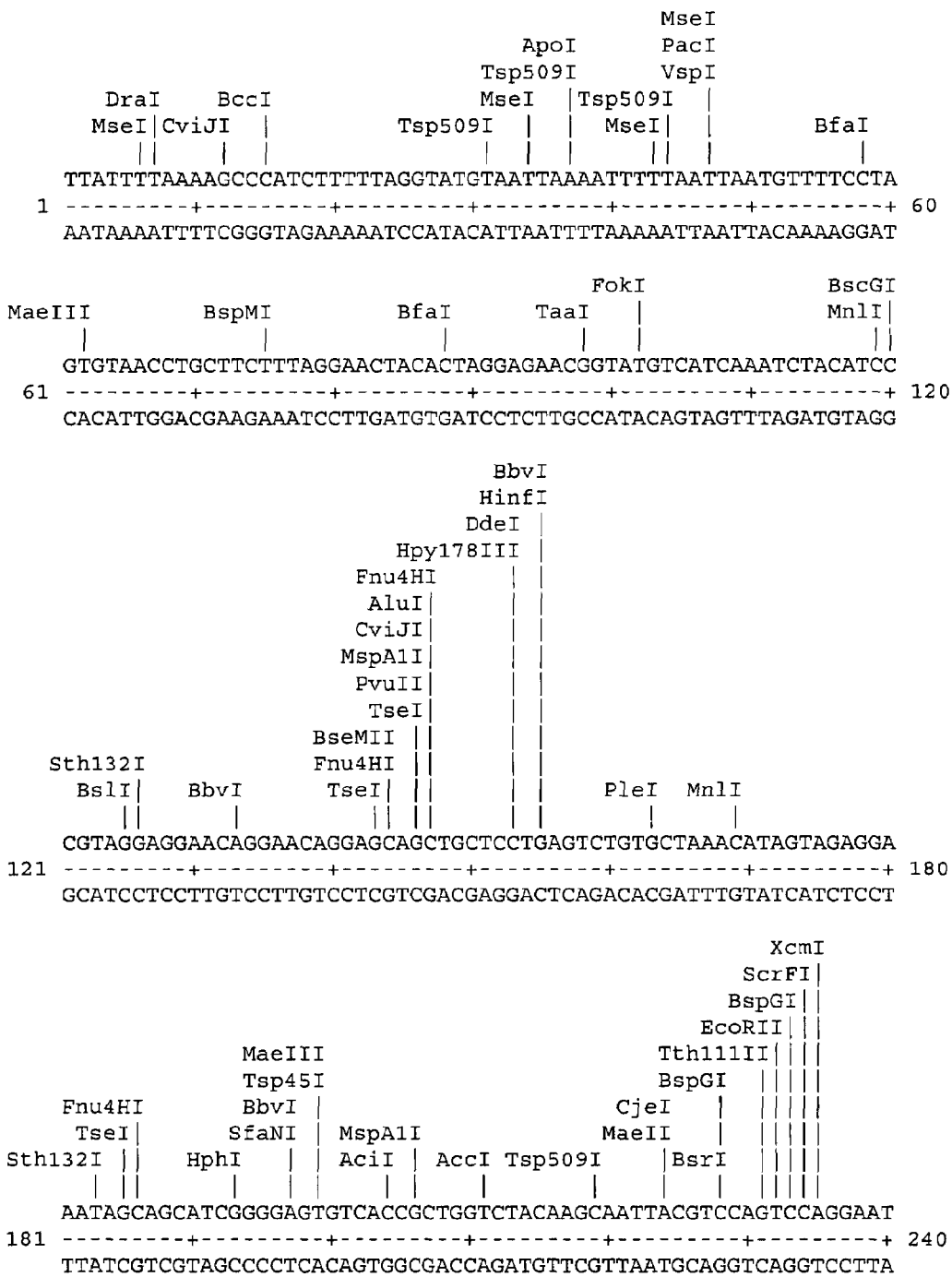
Figure 2C:
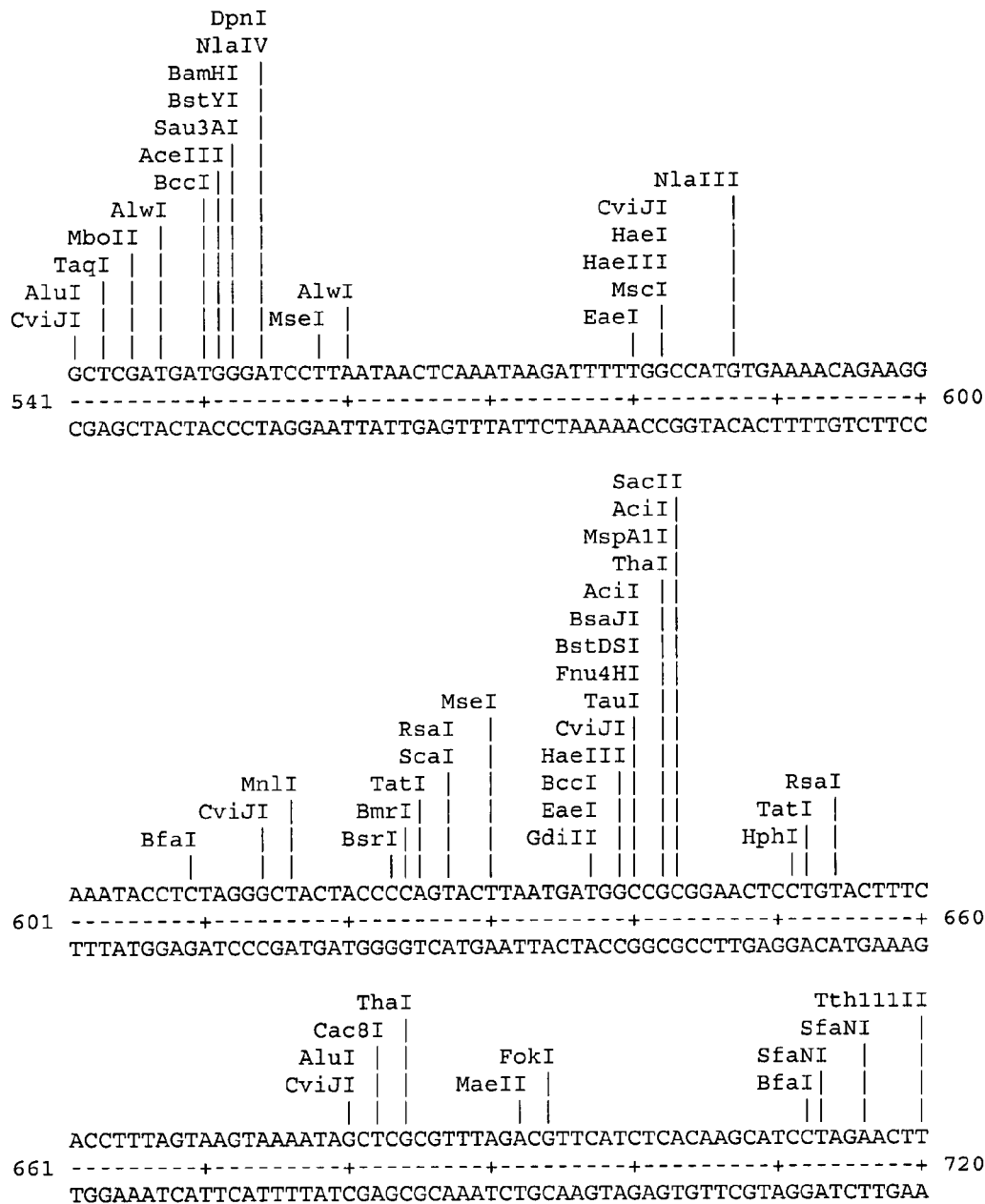
Figure 3A:
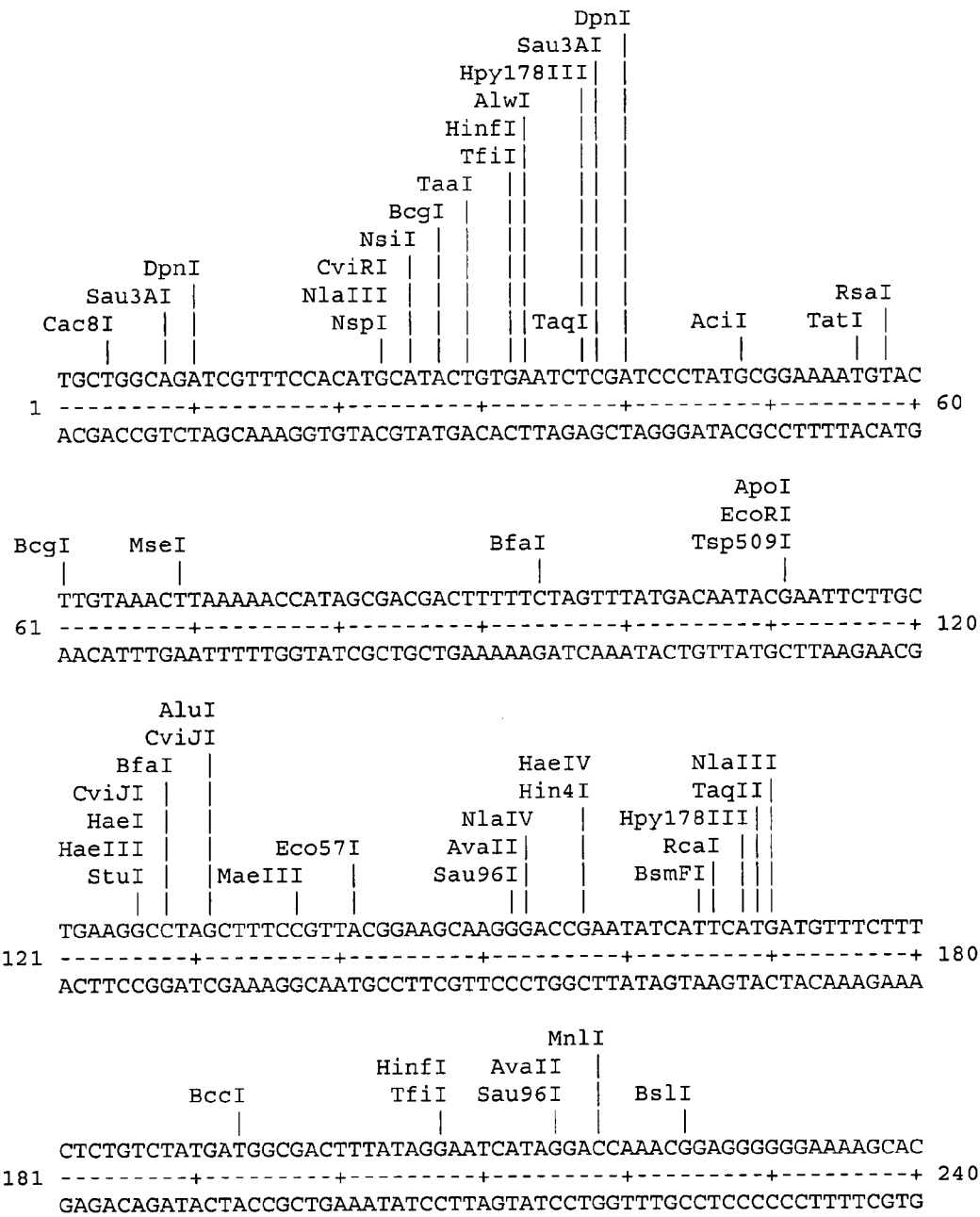
Figure 3B:
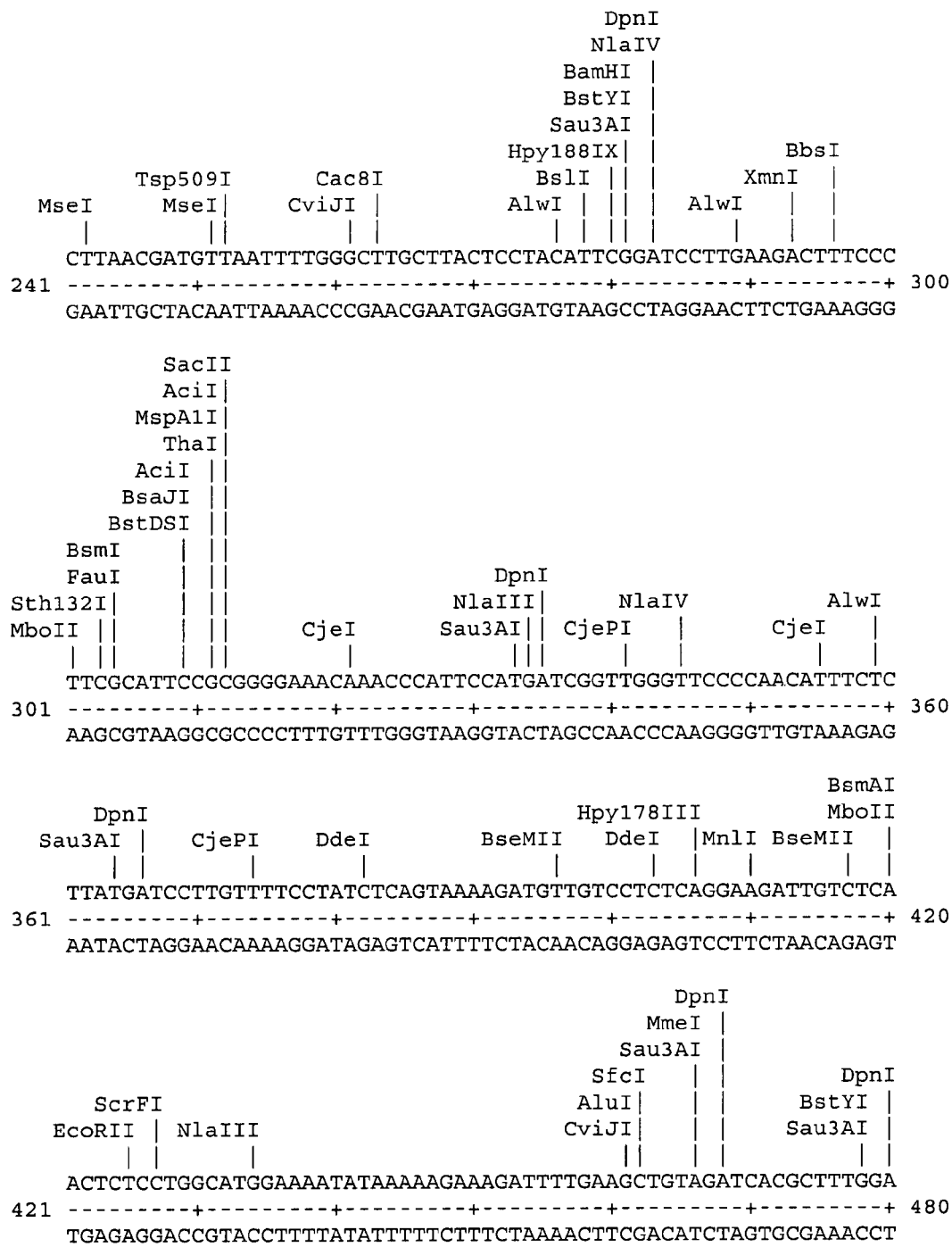
Figure 3D:
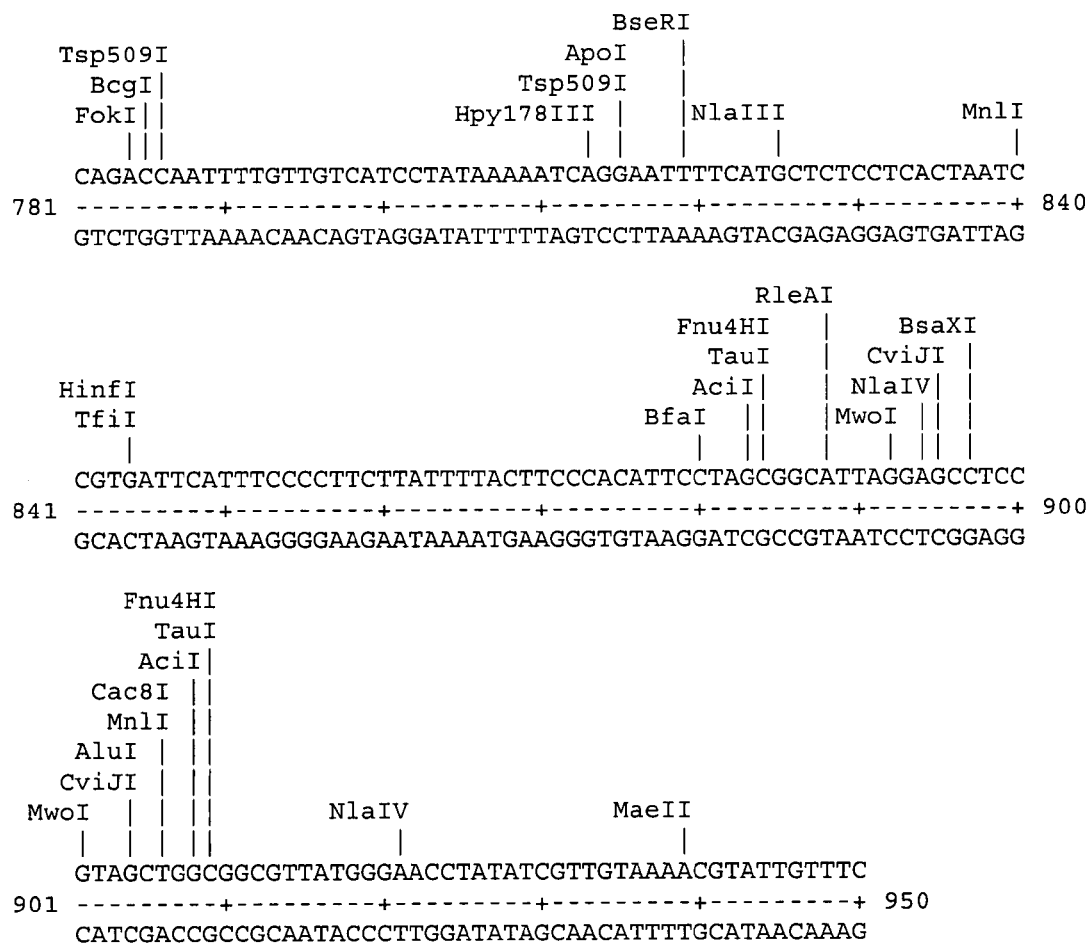
Figure 4A:
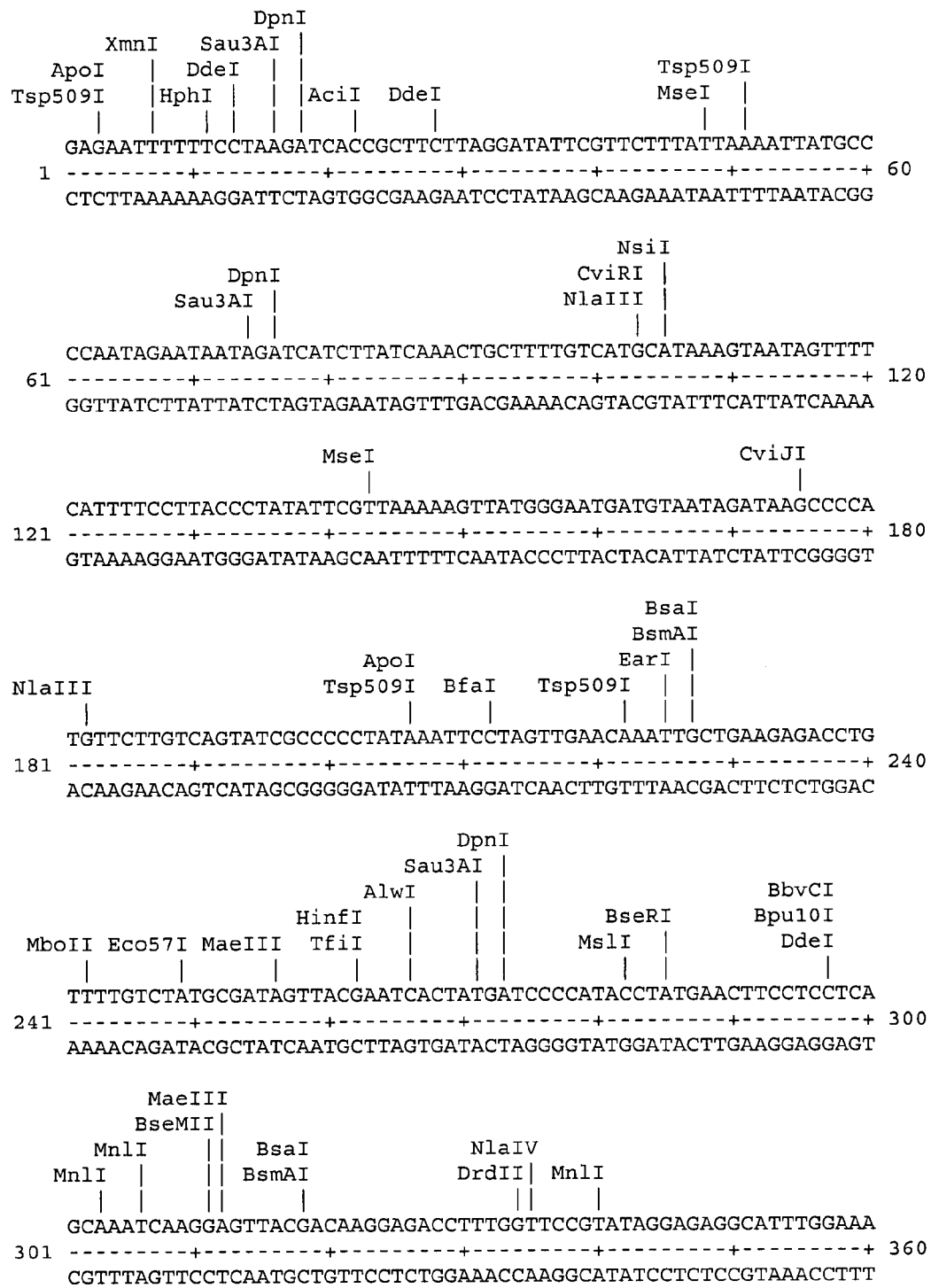
Figure 4C:
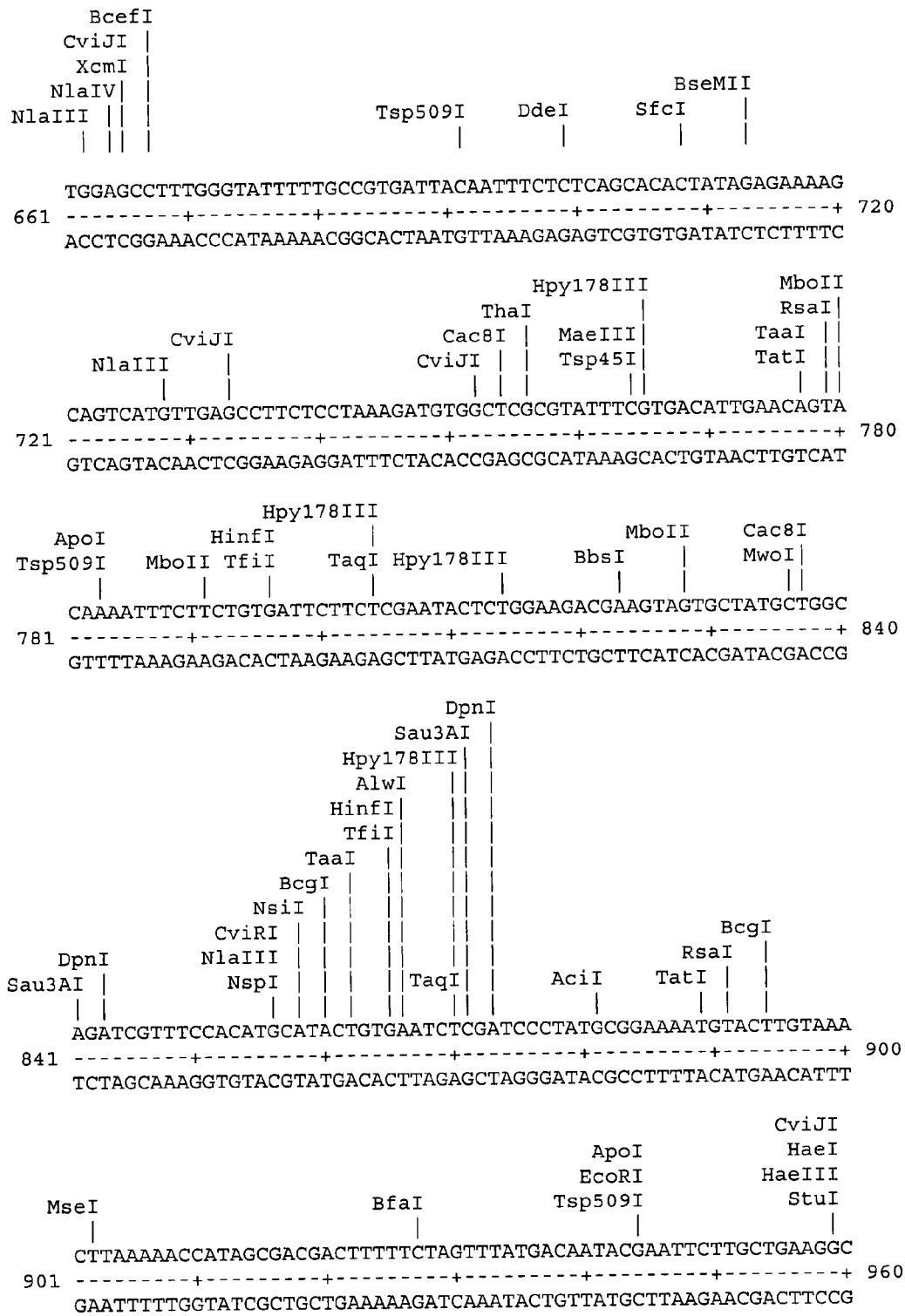
Figure 5A:
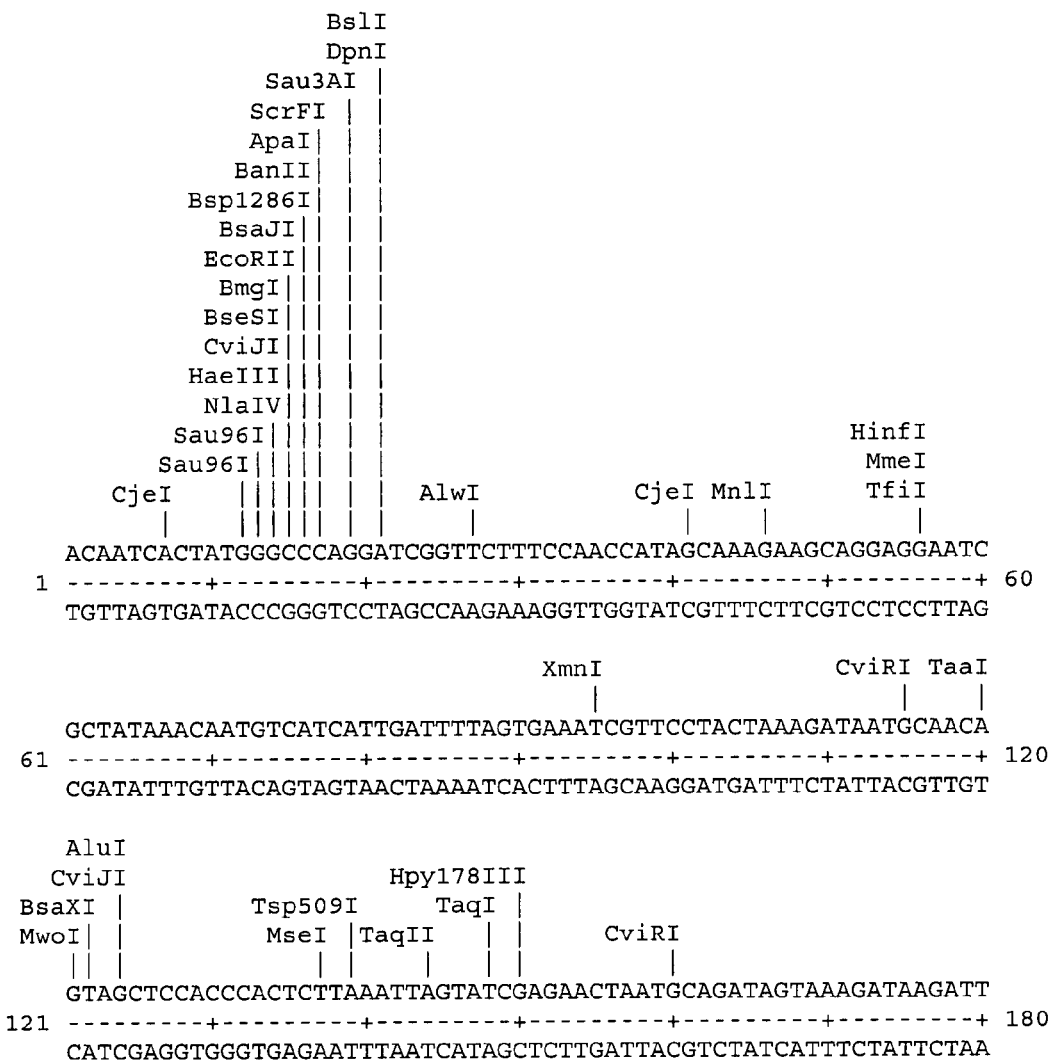
Figure 5C:
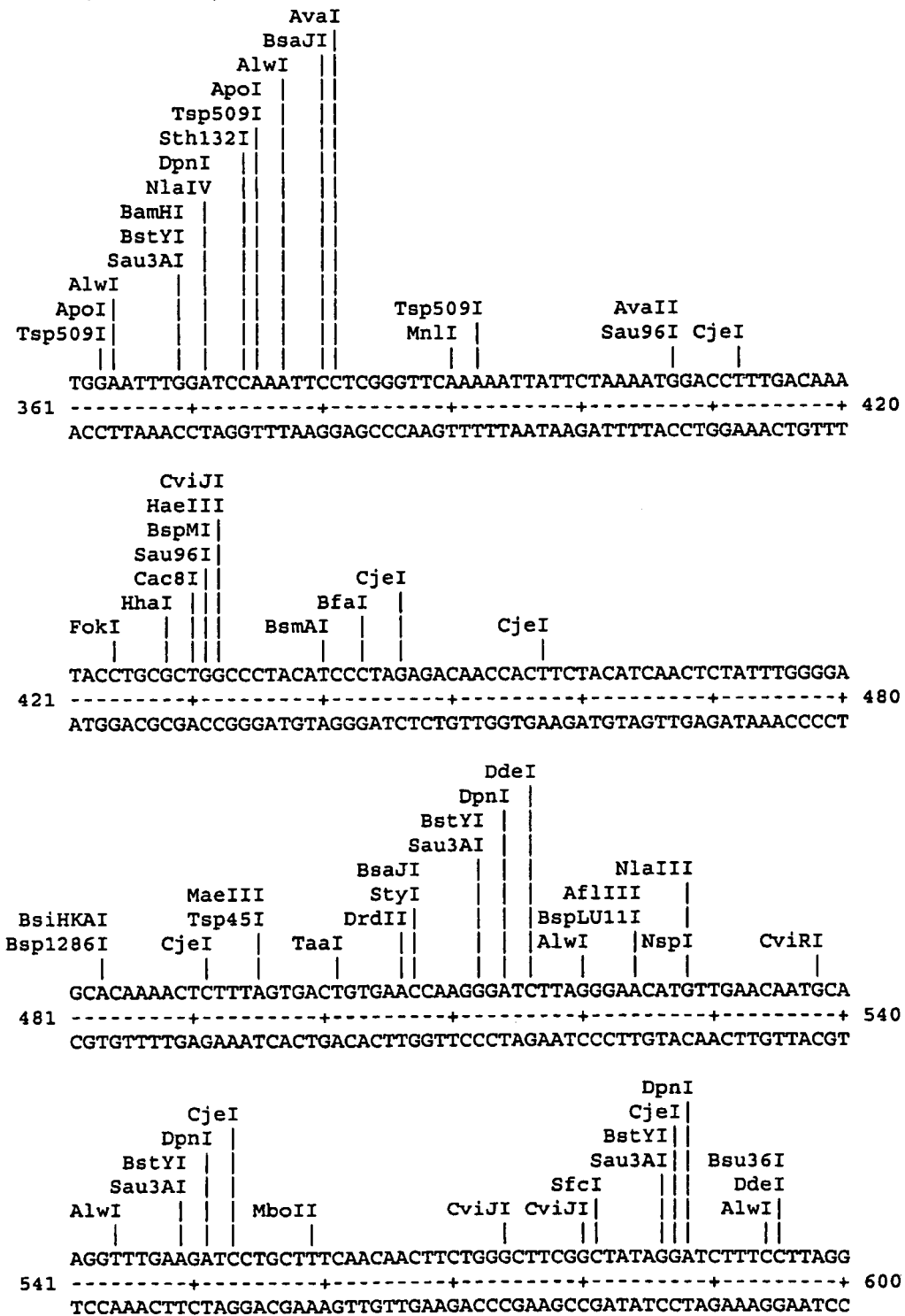
Figure 5E:
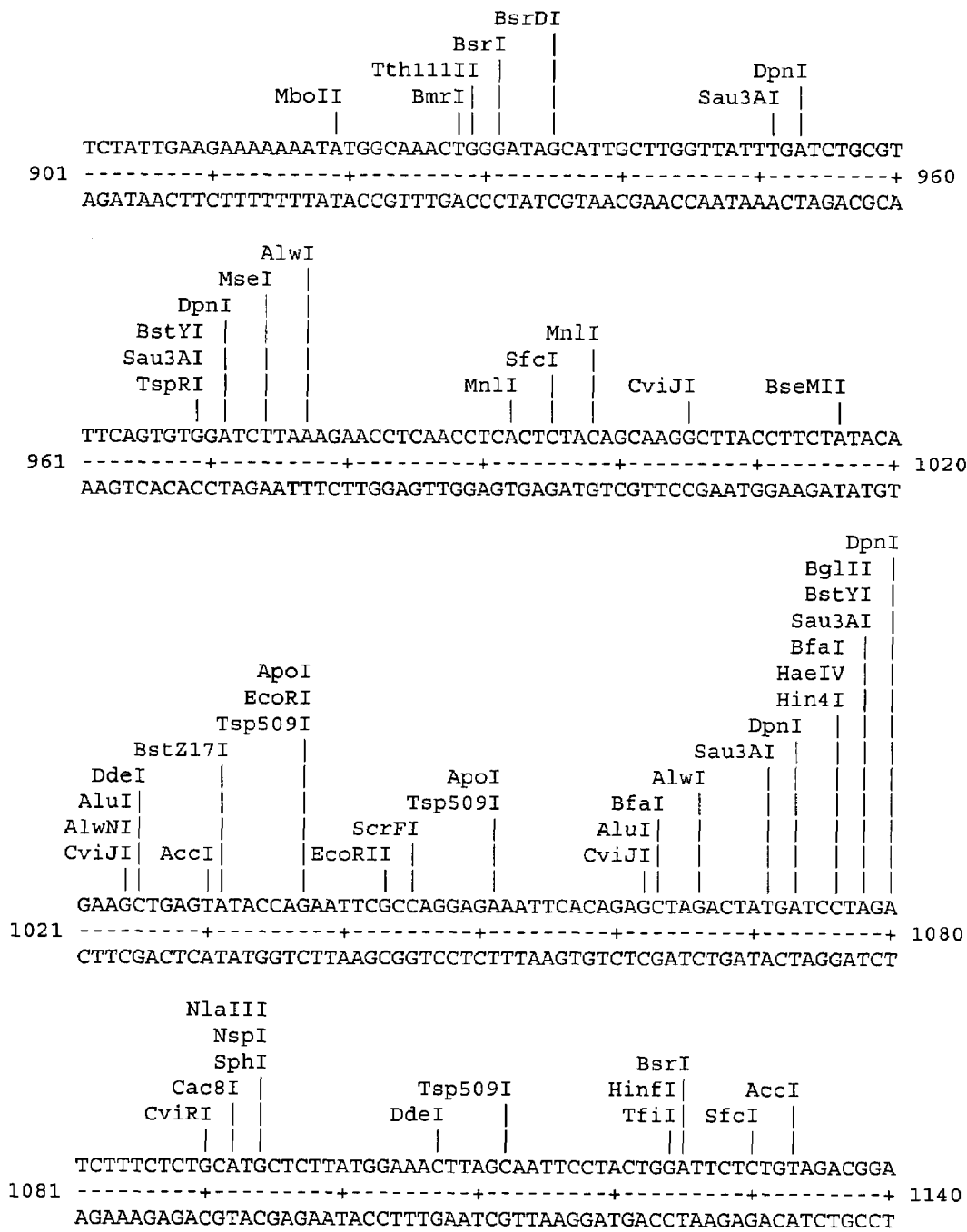
Figure 5G:
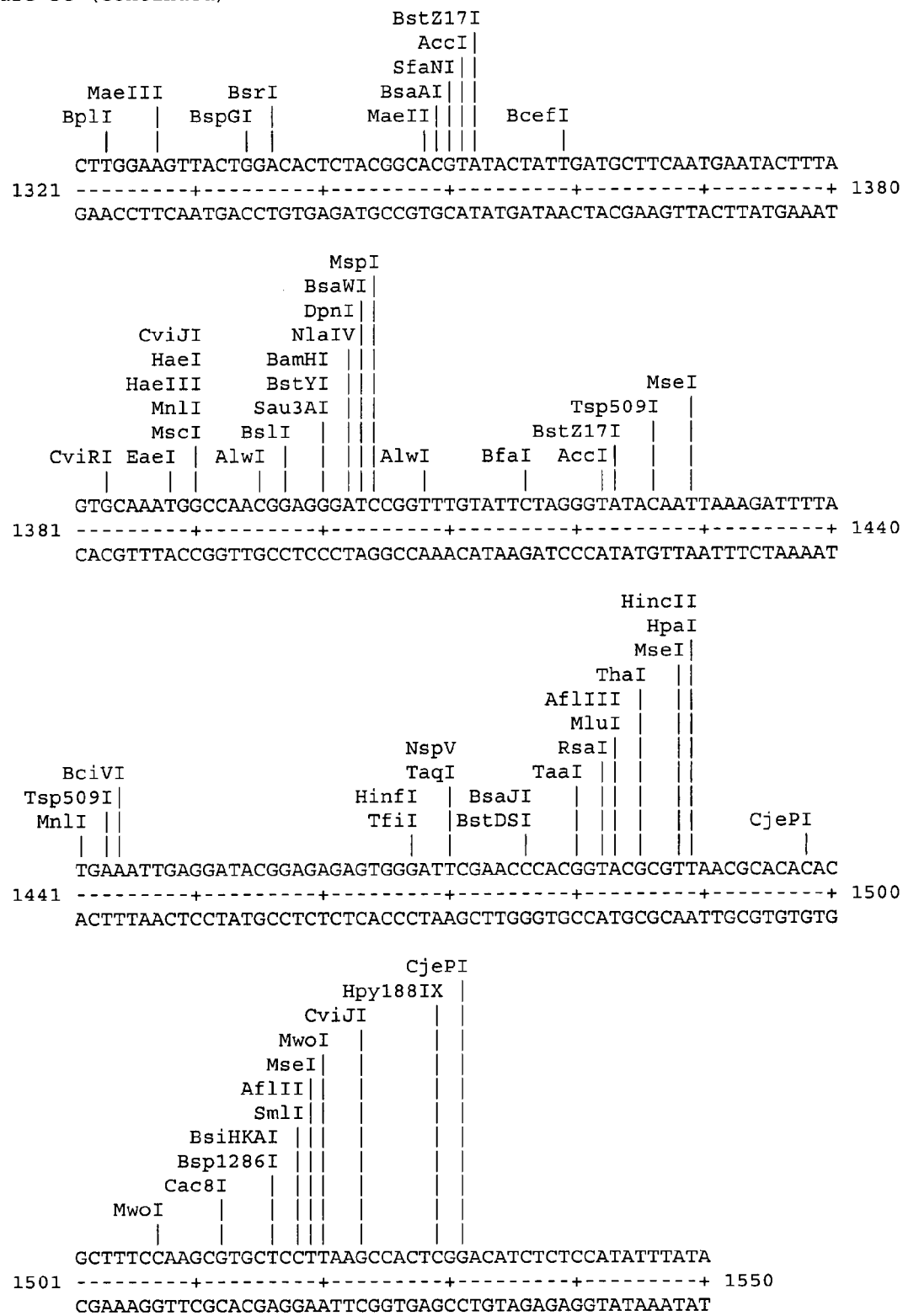
Figure 6A:
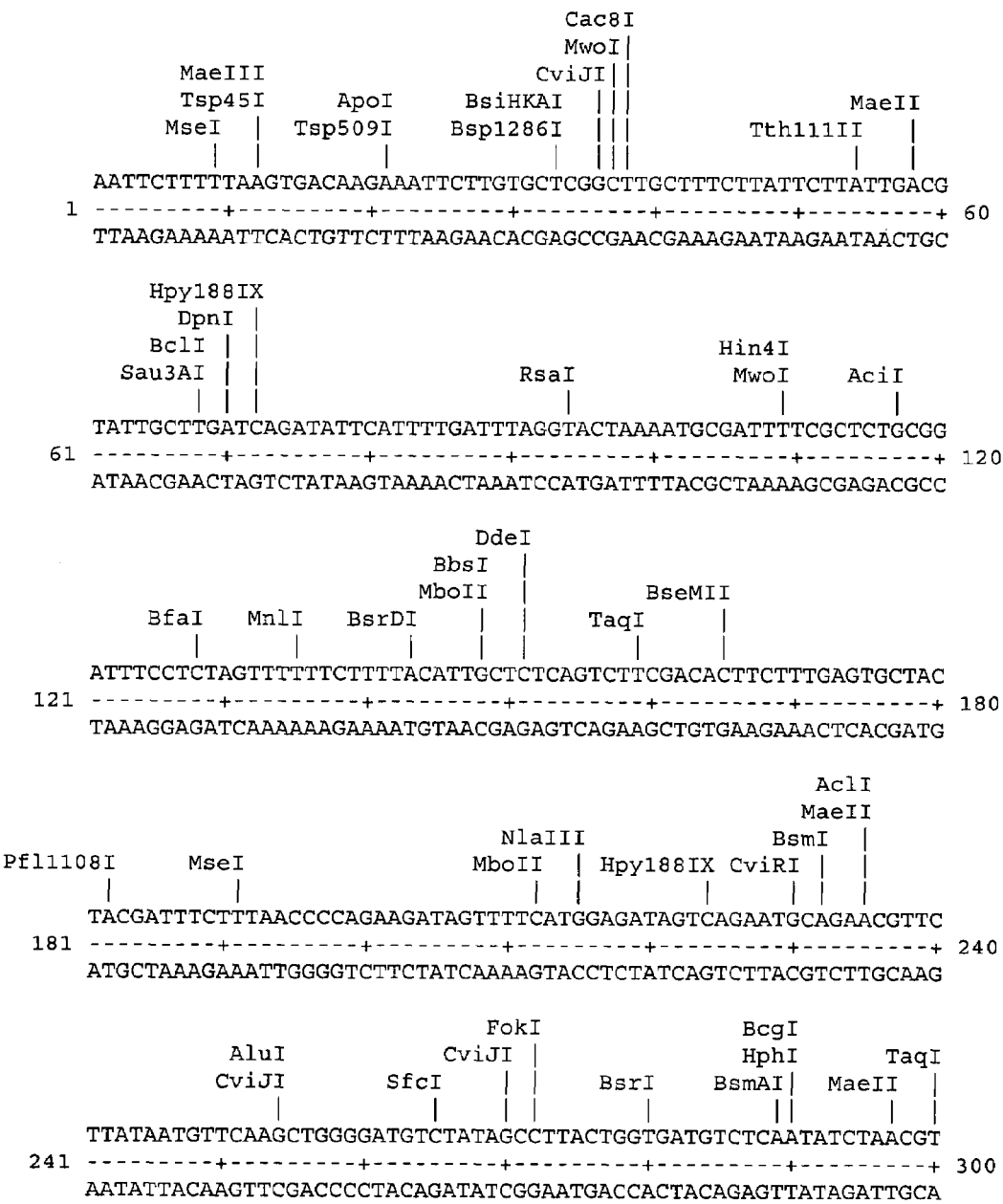
Figure 6E:
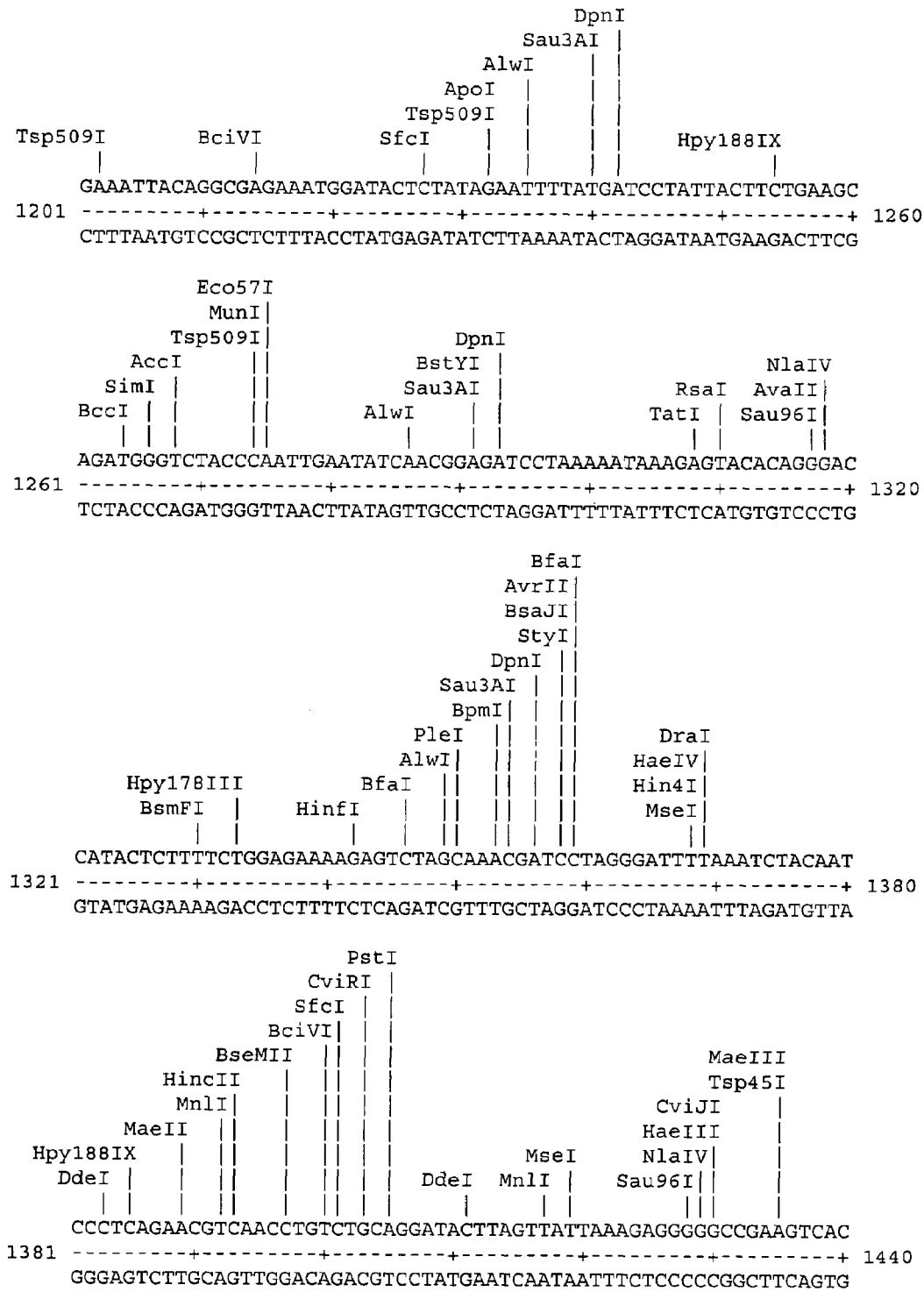
Figure 6F:
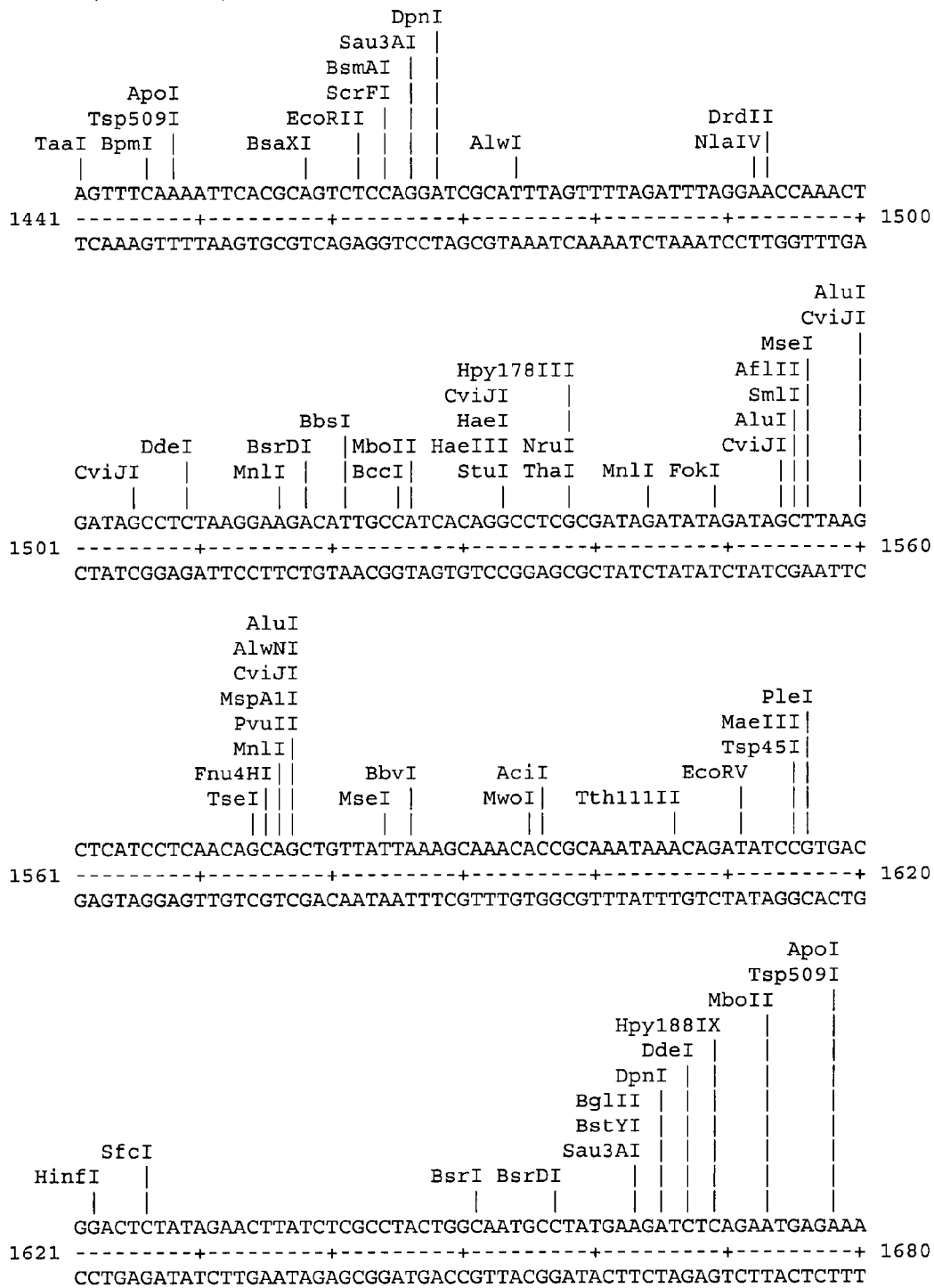
Figure 6G:
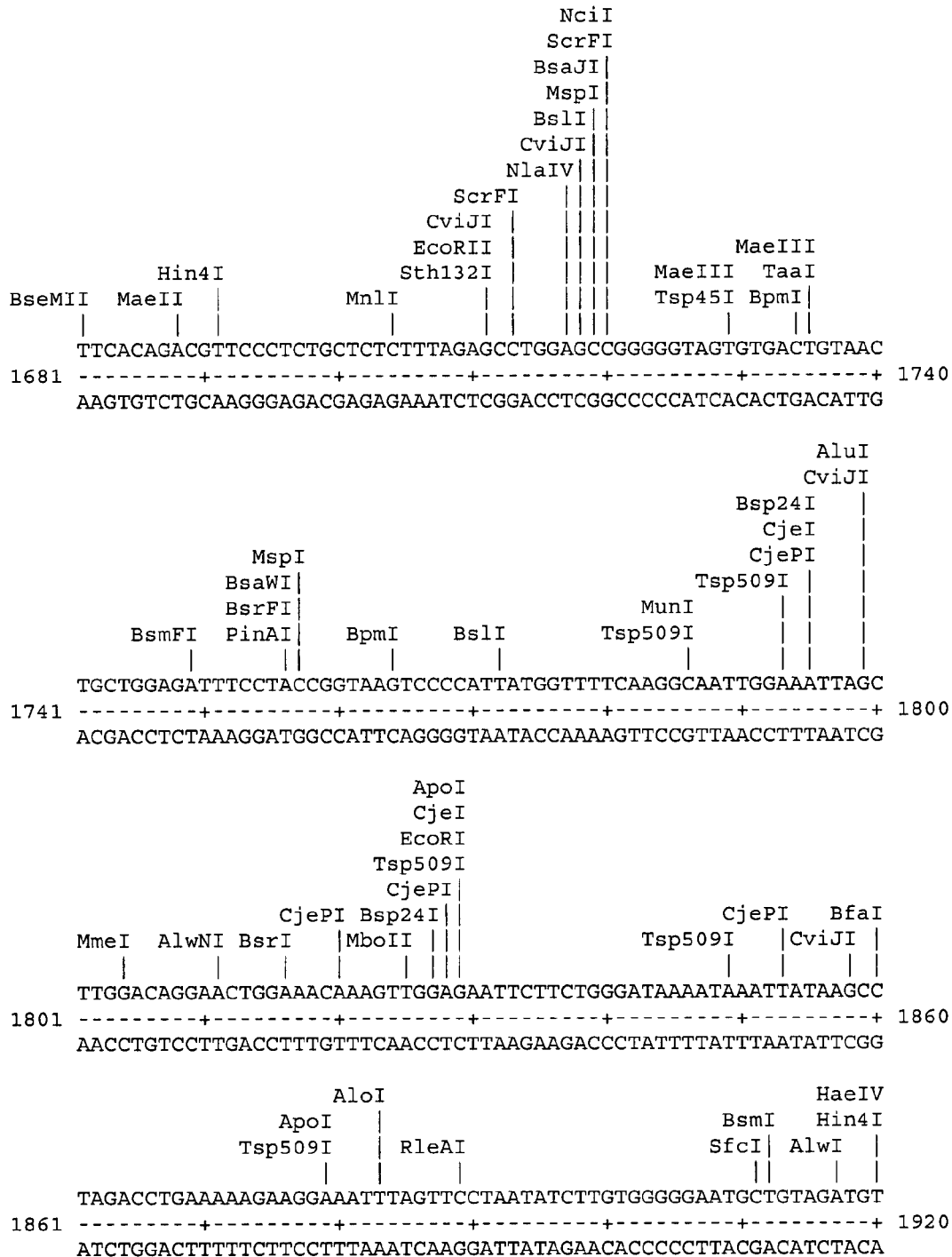
Figure 7A:
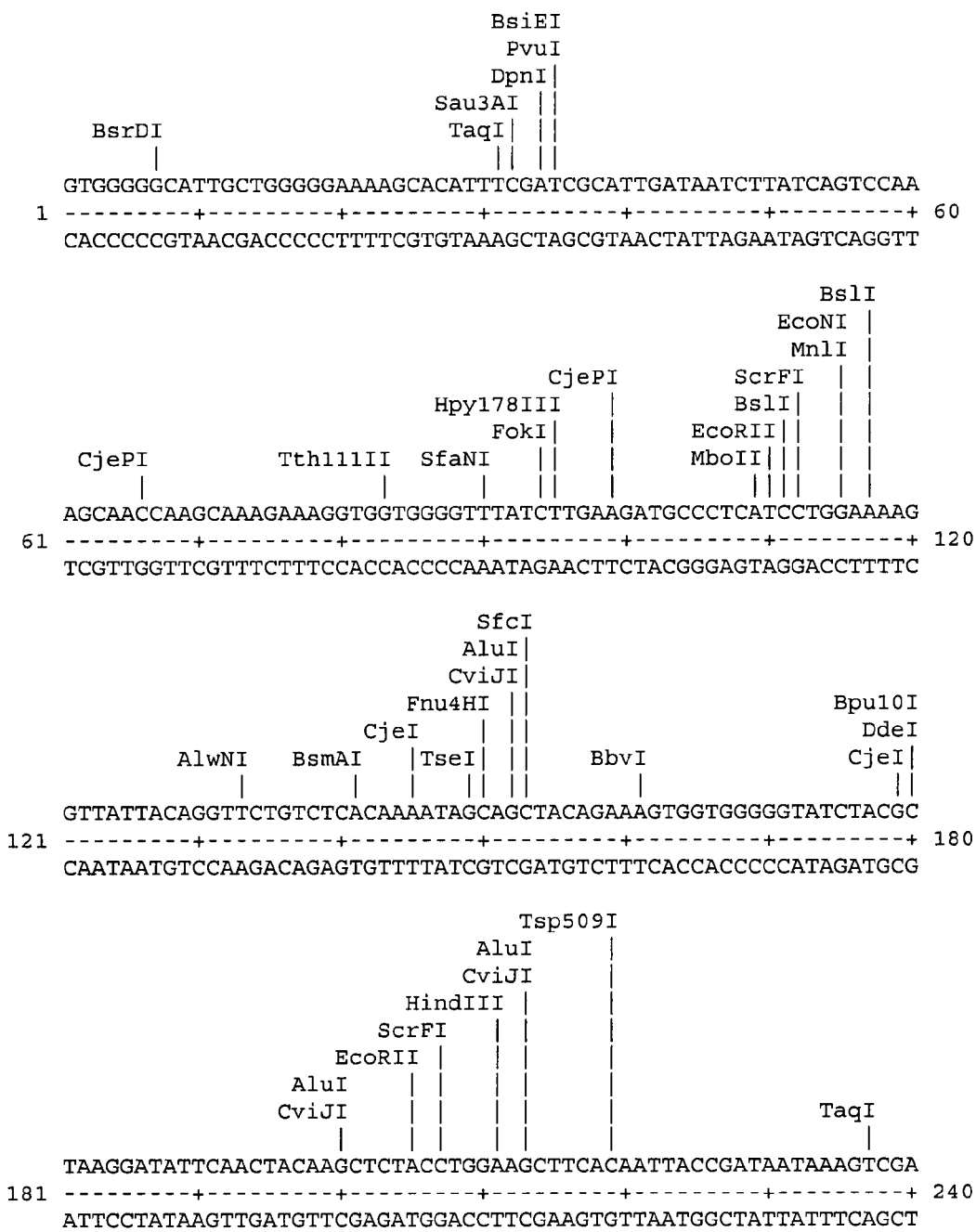
Figure 8A:
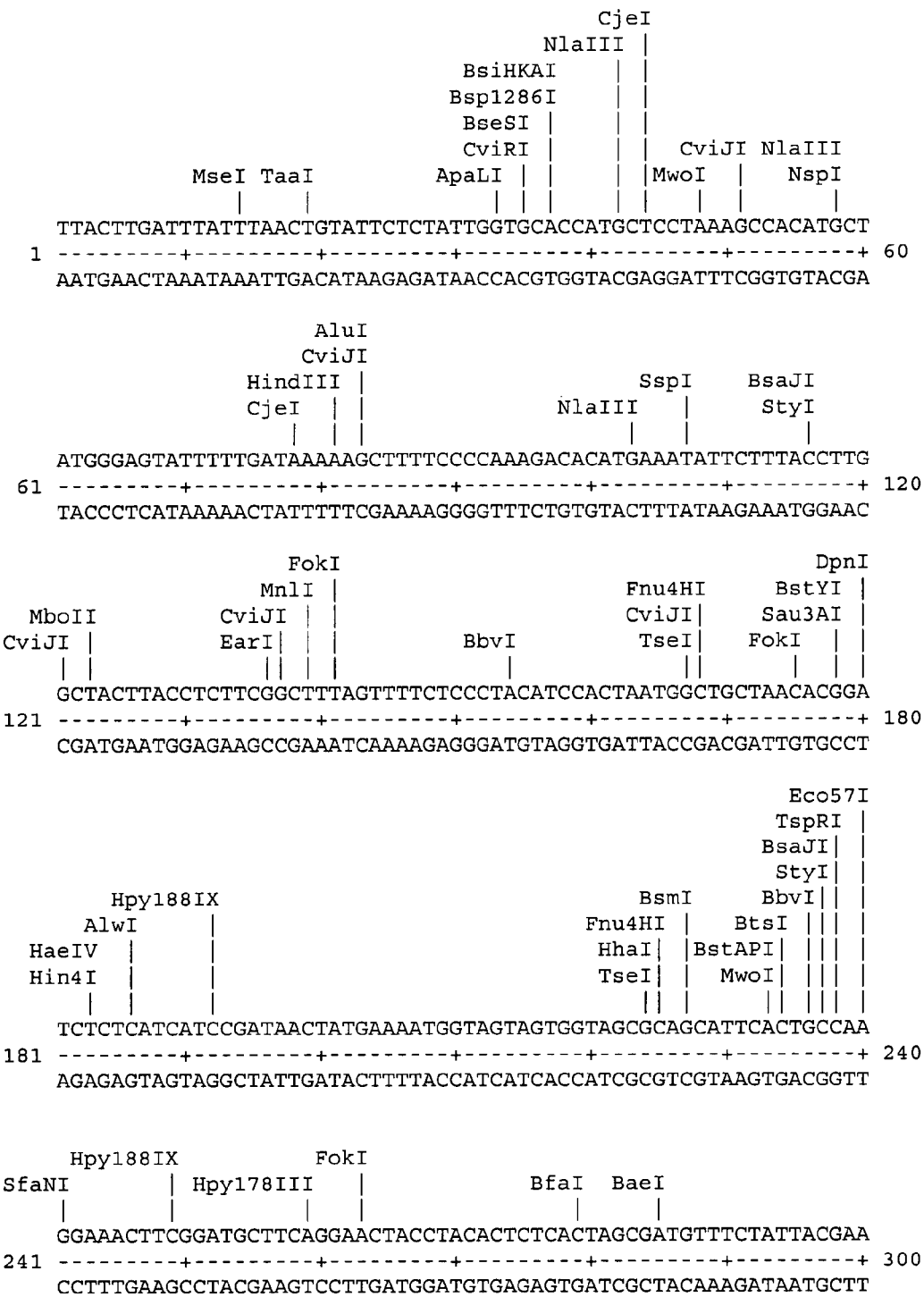
Figure 8B:
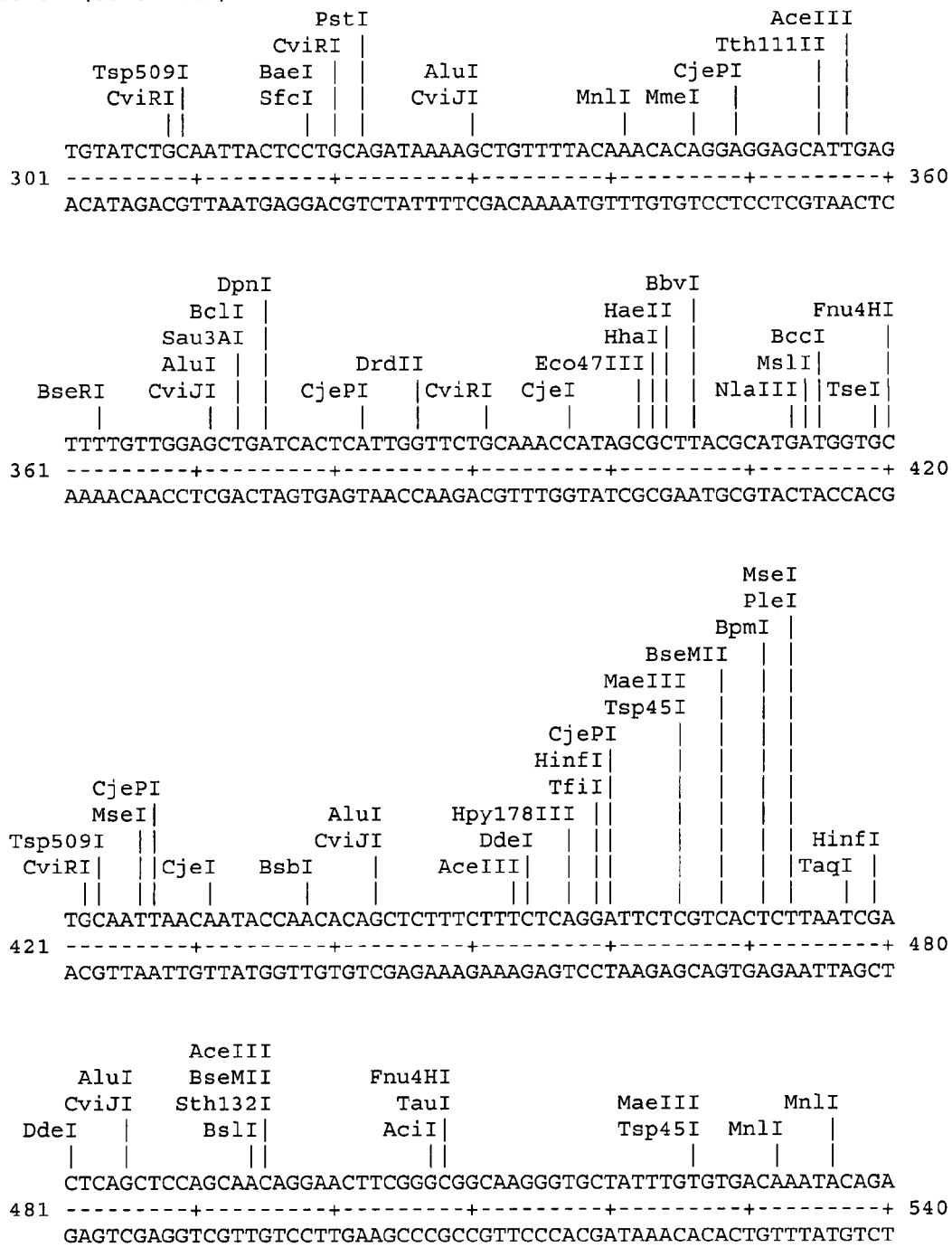
Figure 8C:
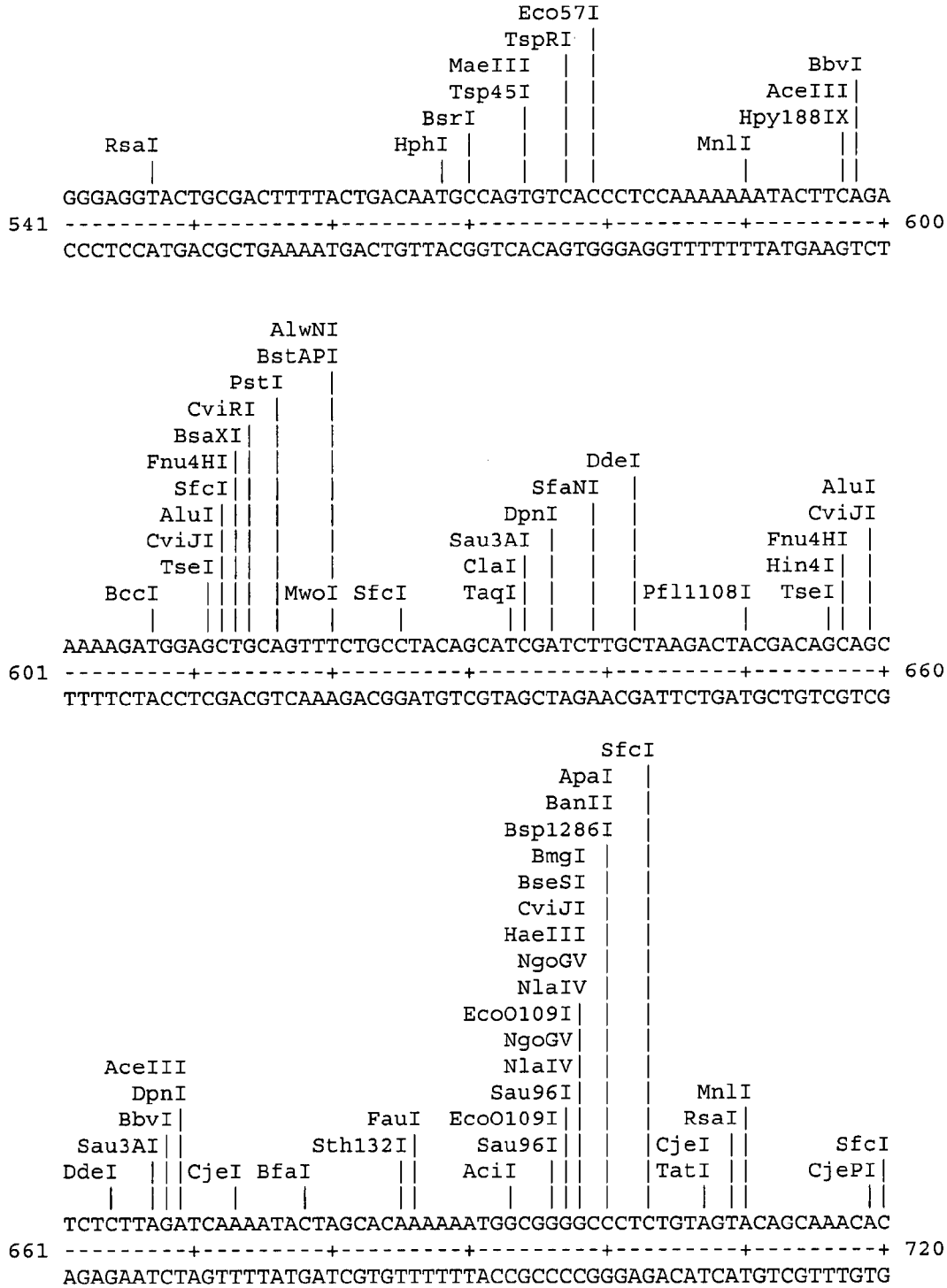
Figure 8F:
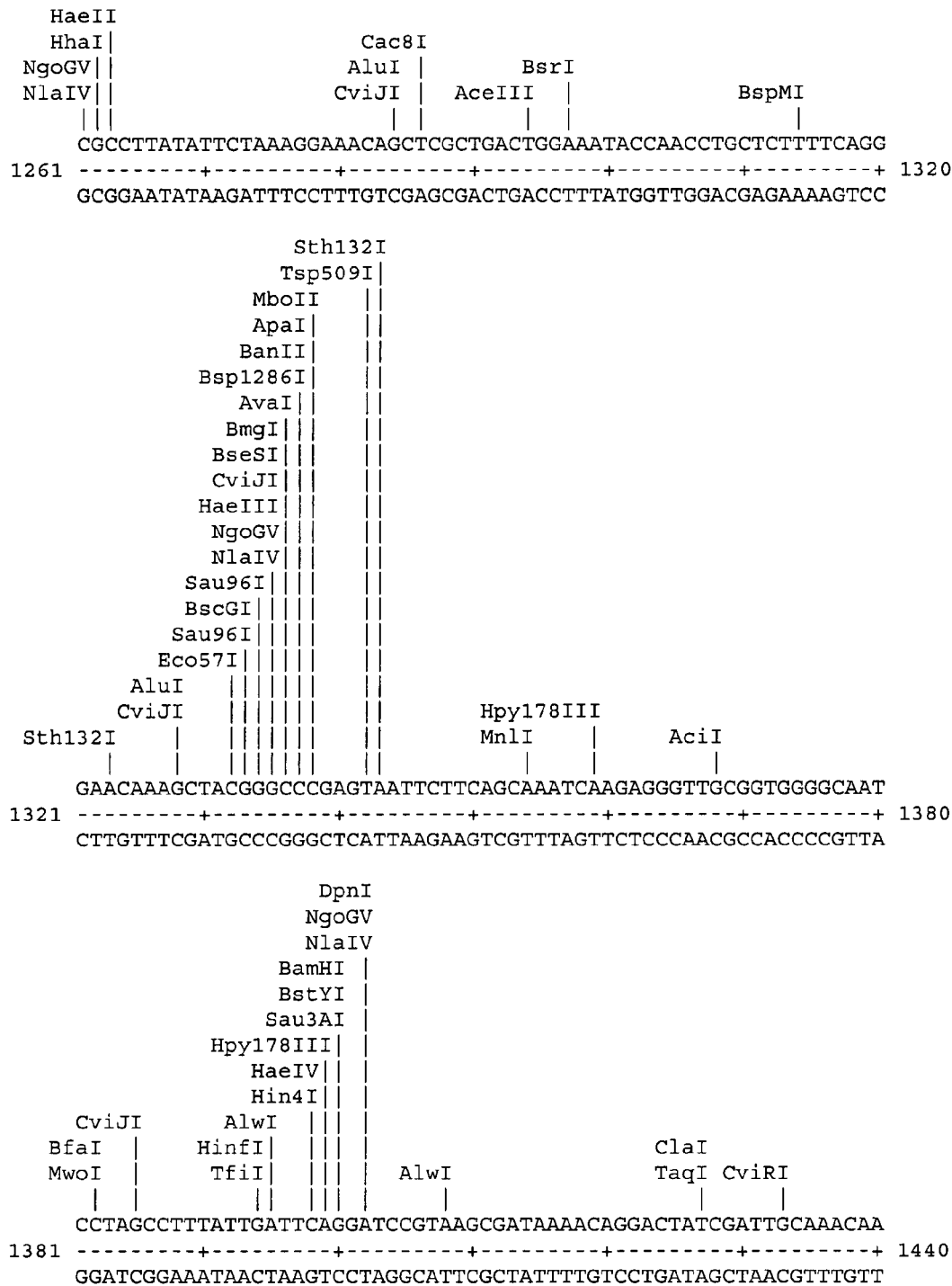
Figure 8G:
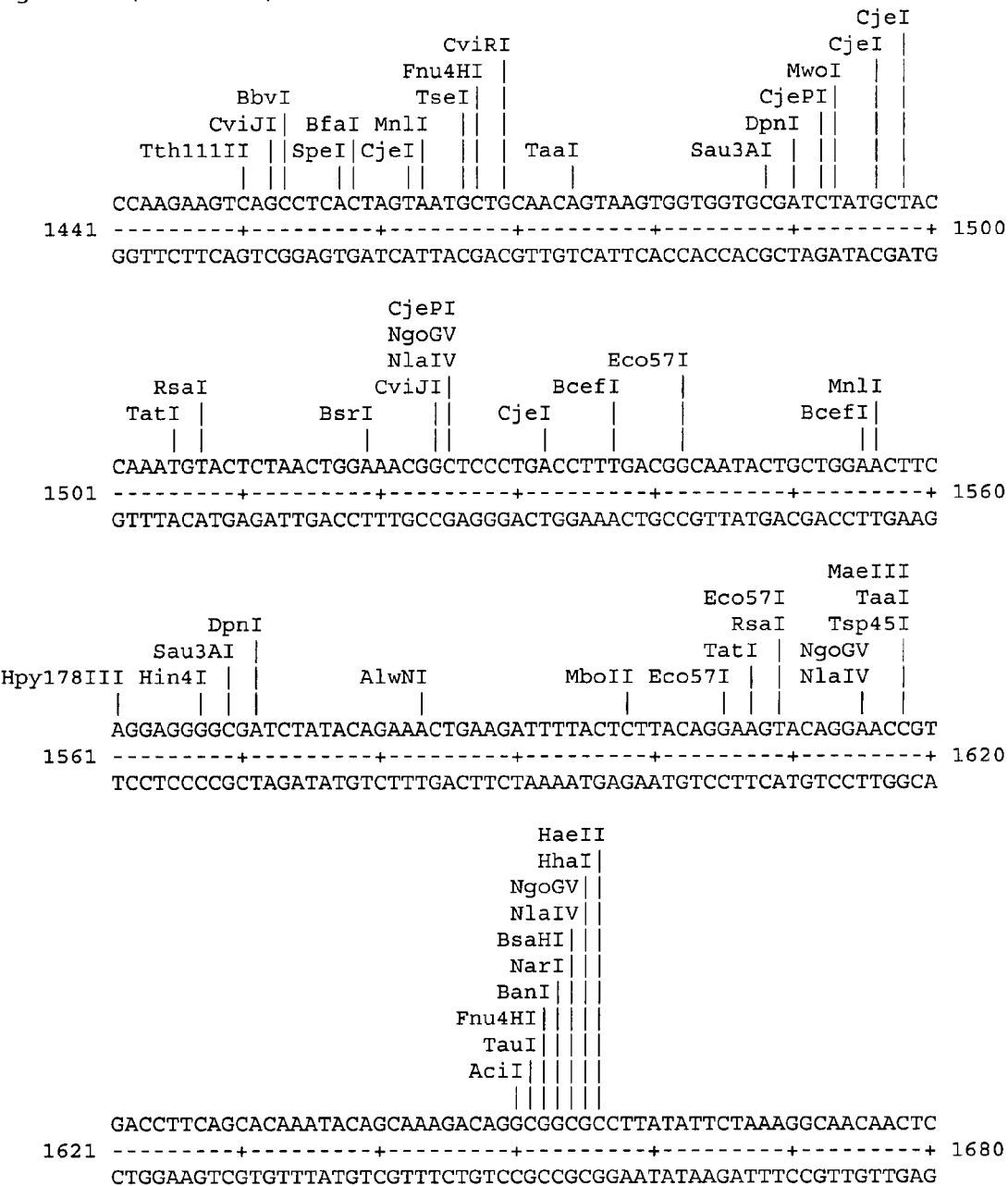
Figure 8H:
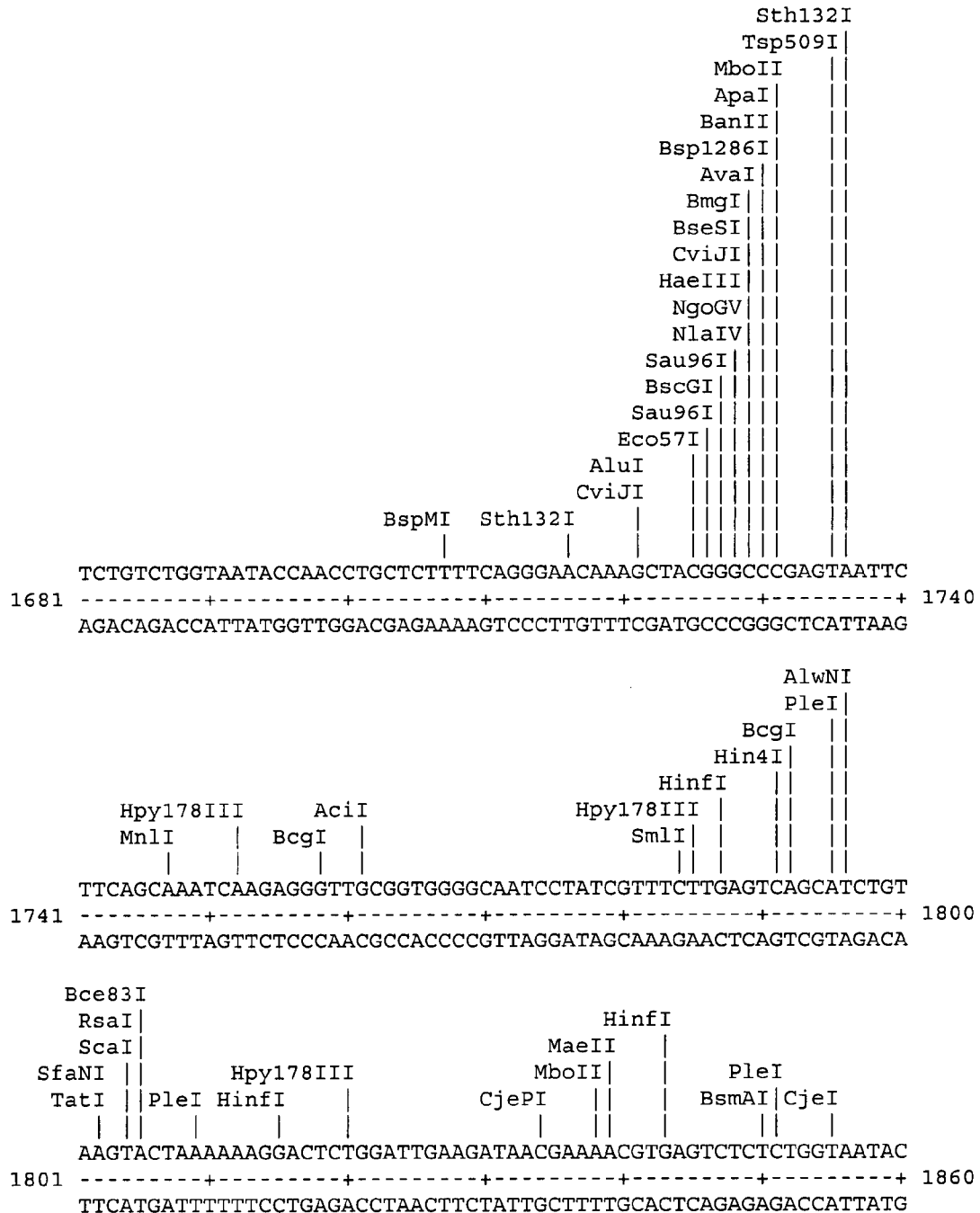
Figure 8I:
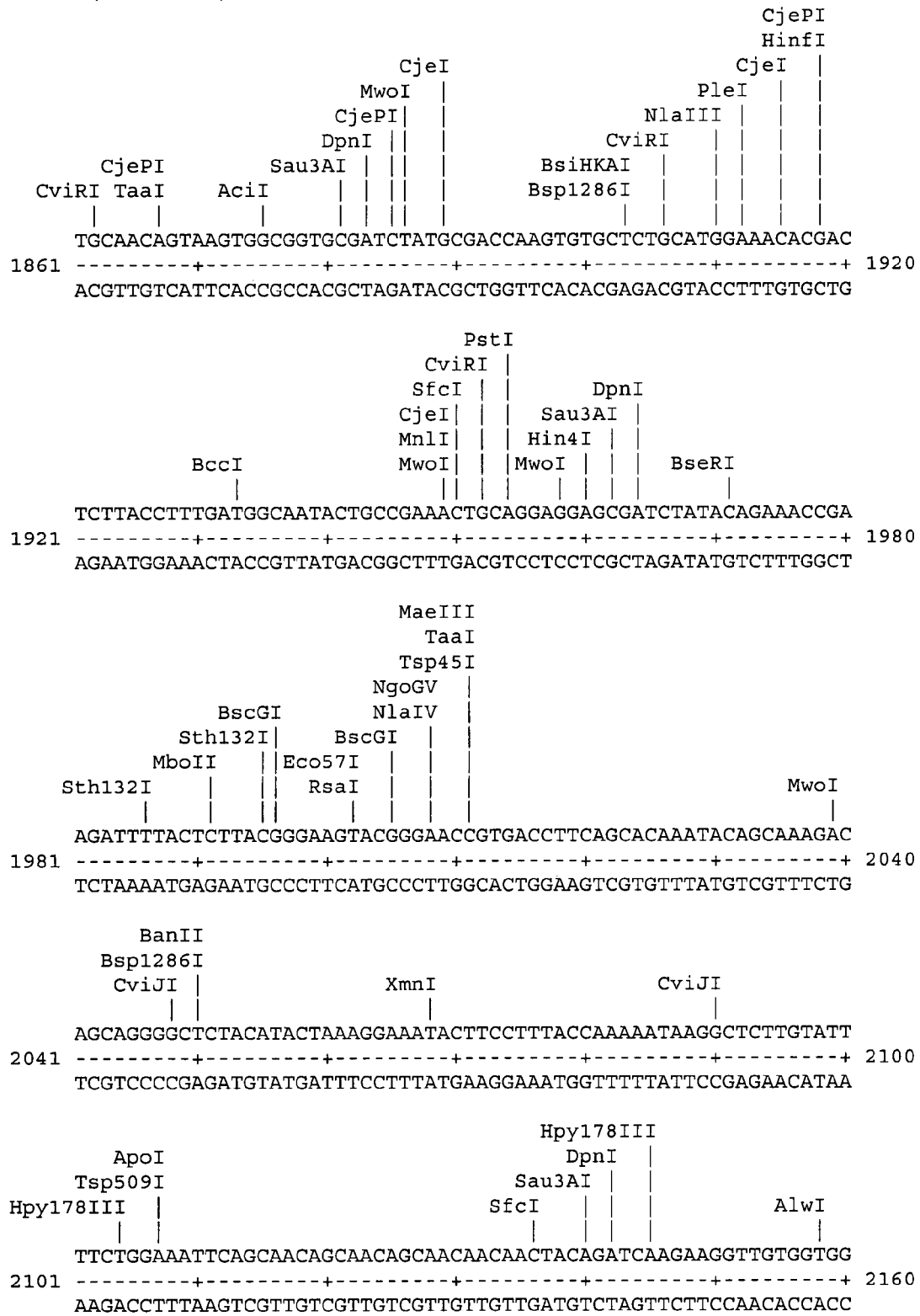
Figure 9B:
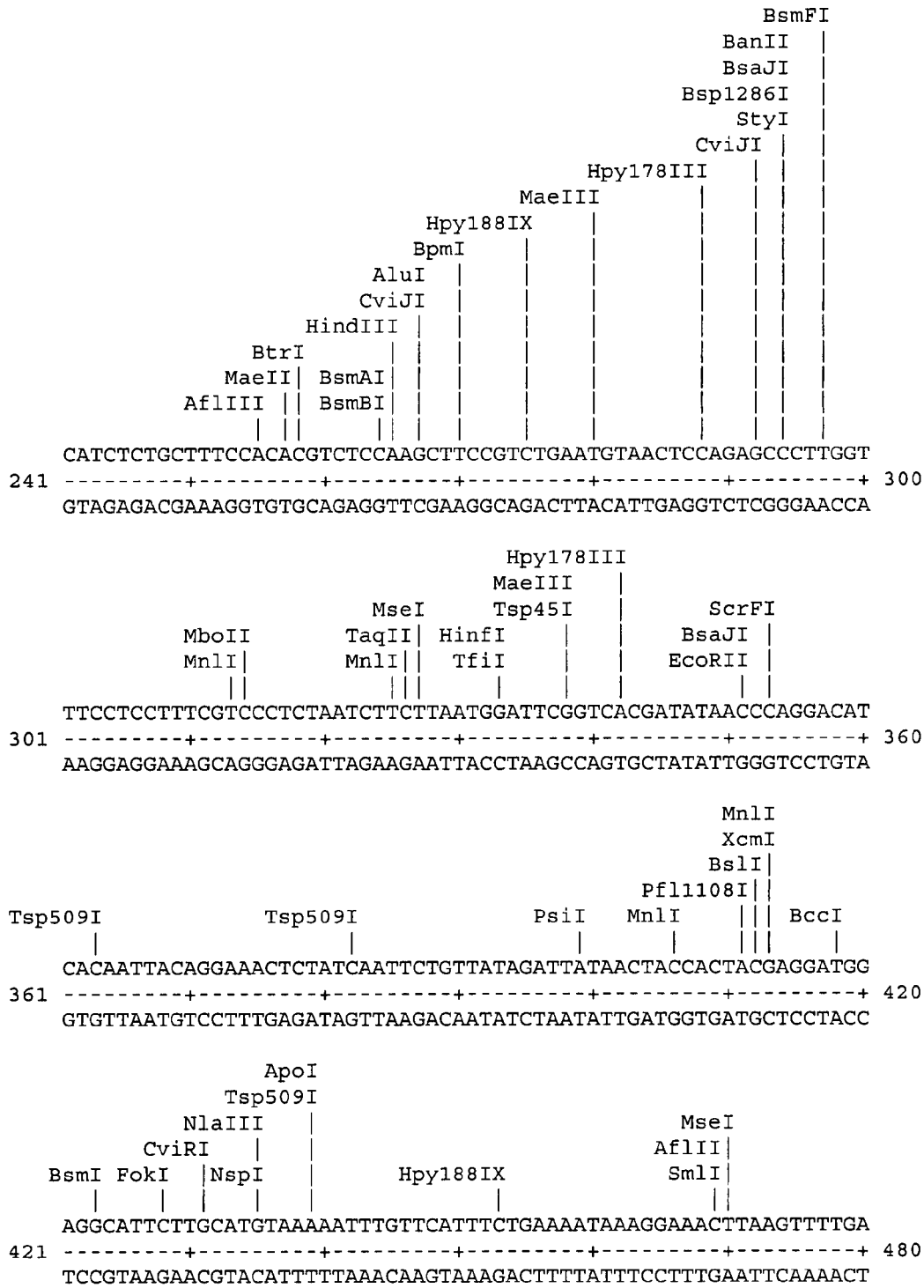
Figure 9C:
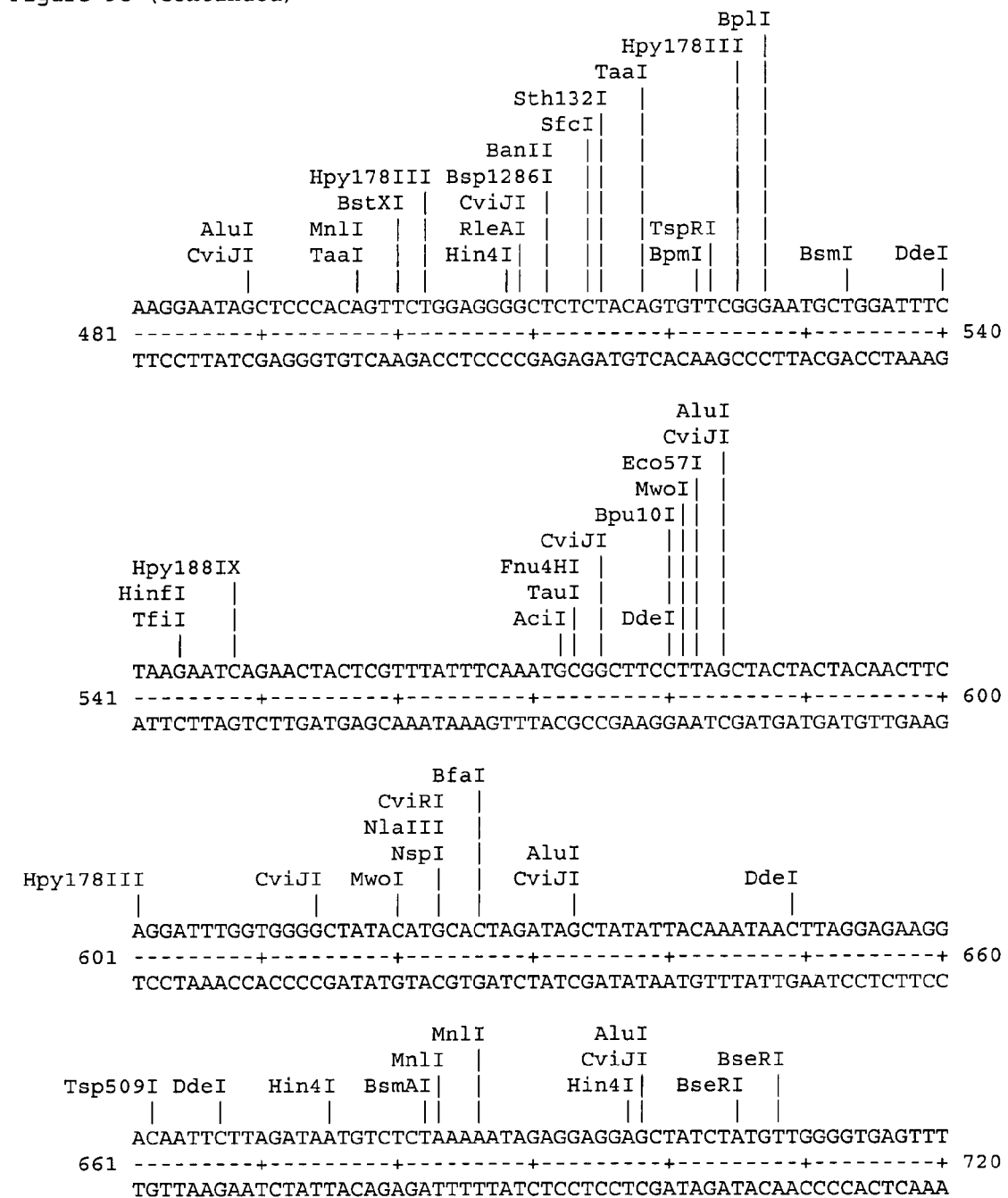
Figure 9D:
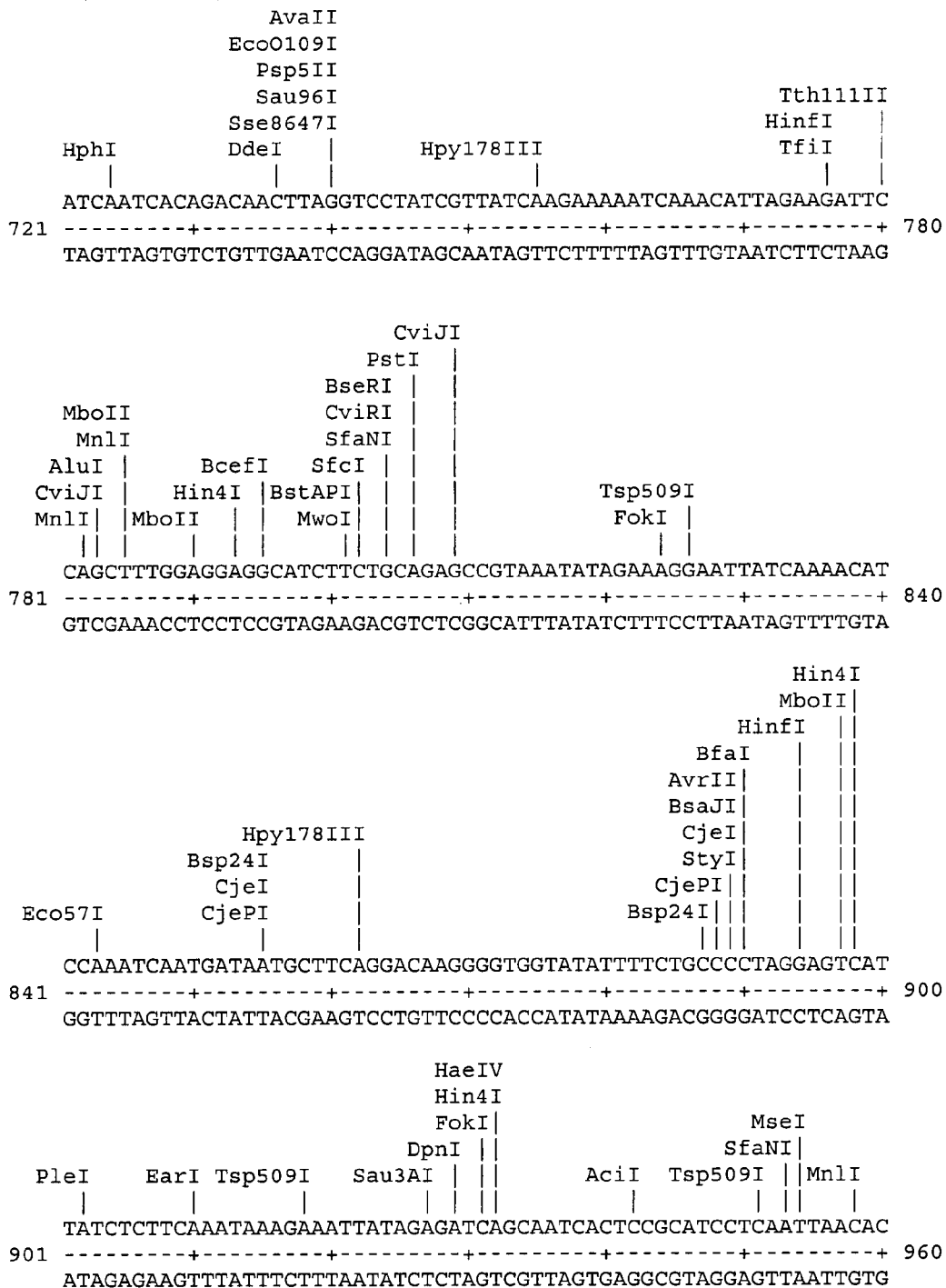
Figure 9E:
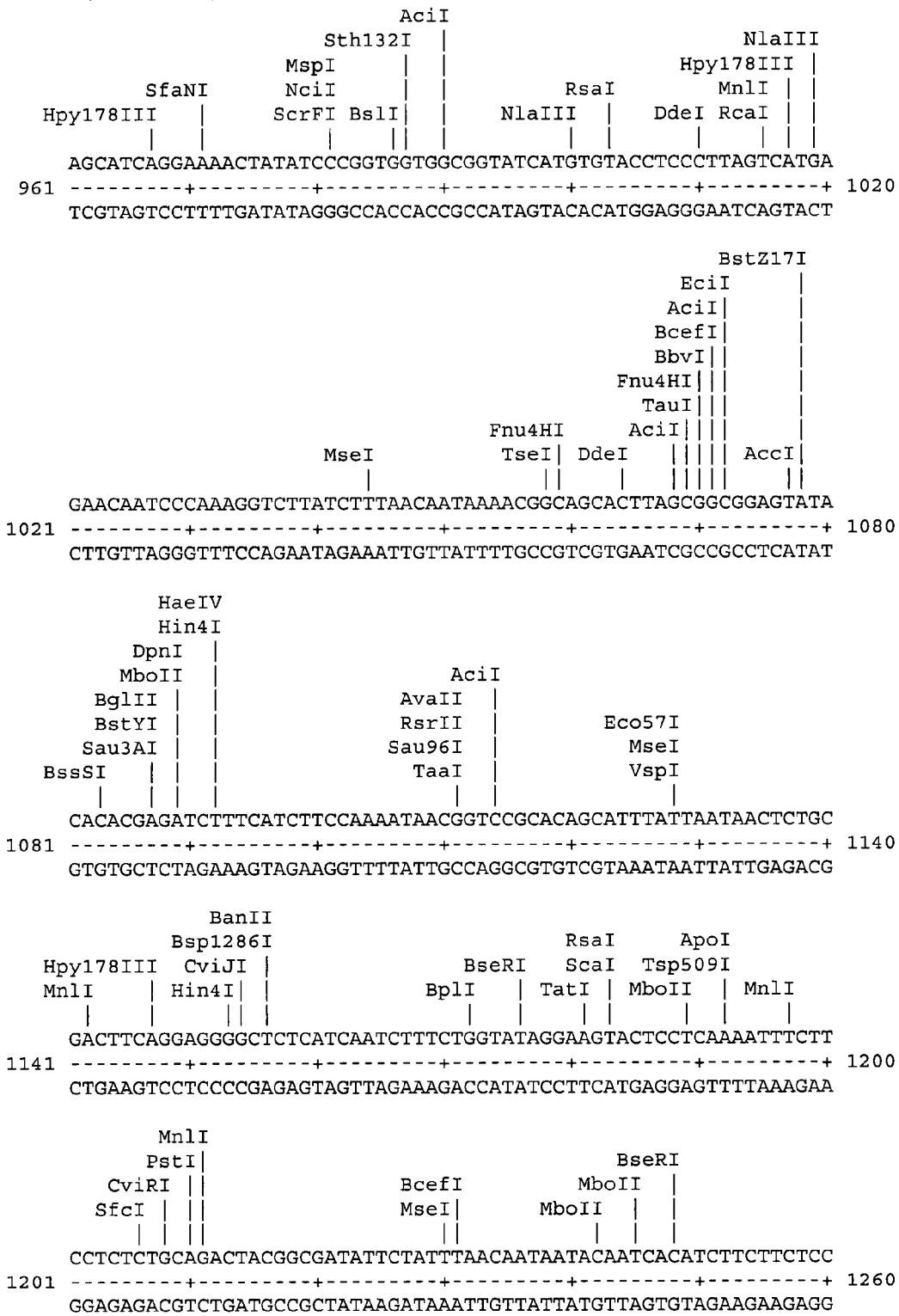
Figure 9G:
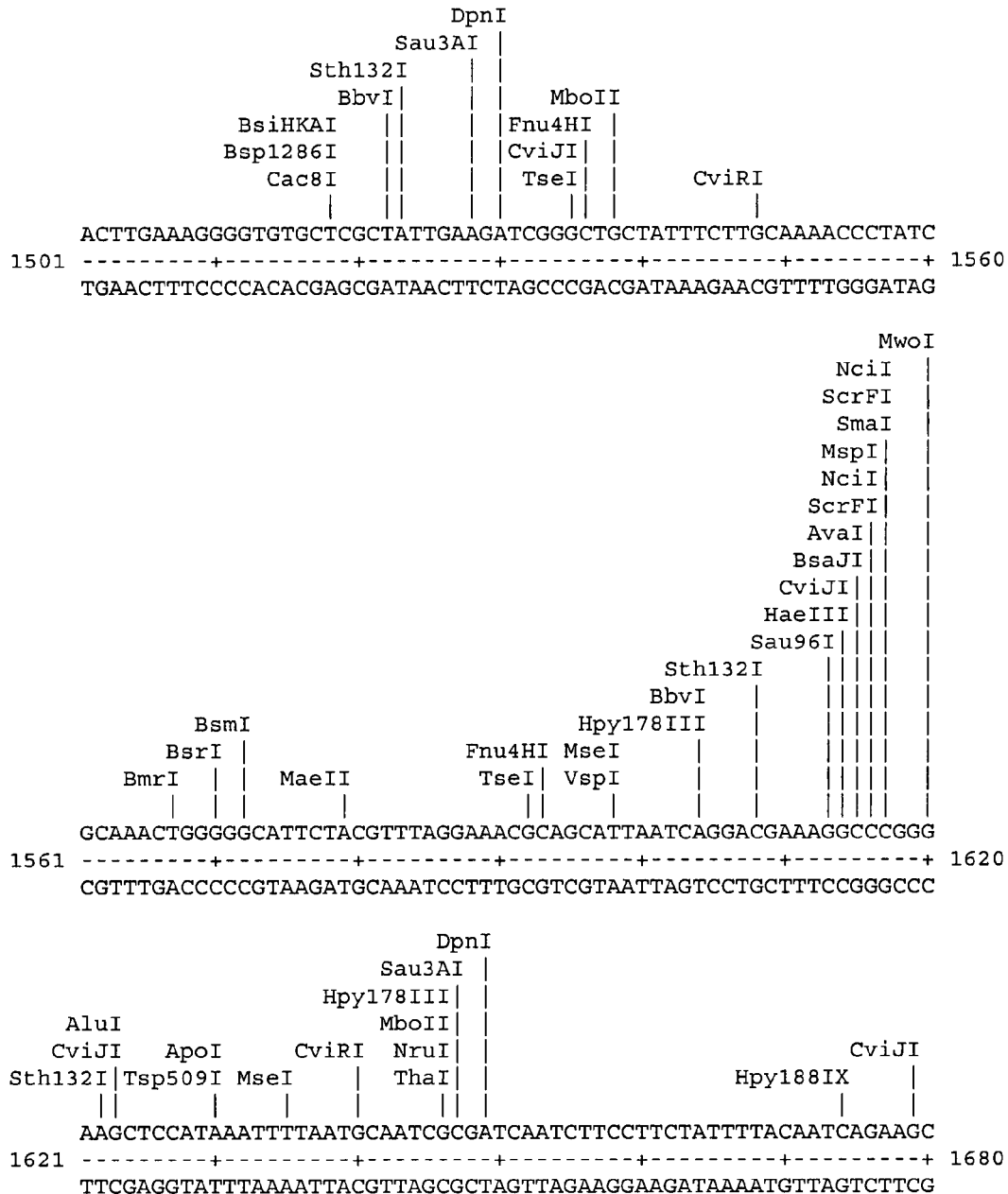
Figure 9H:
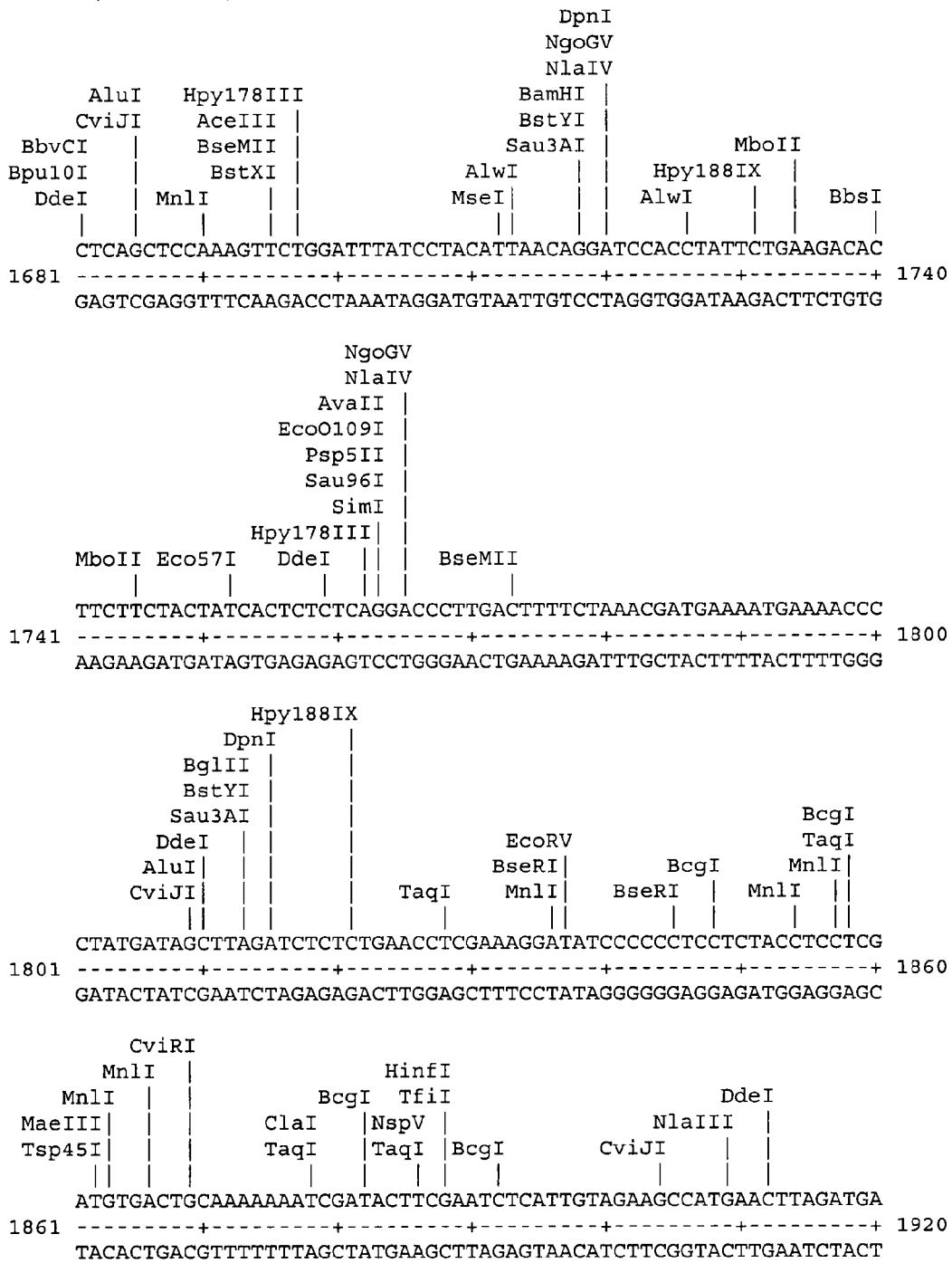
Figure 9I:
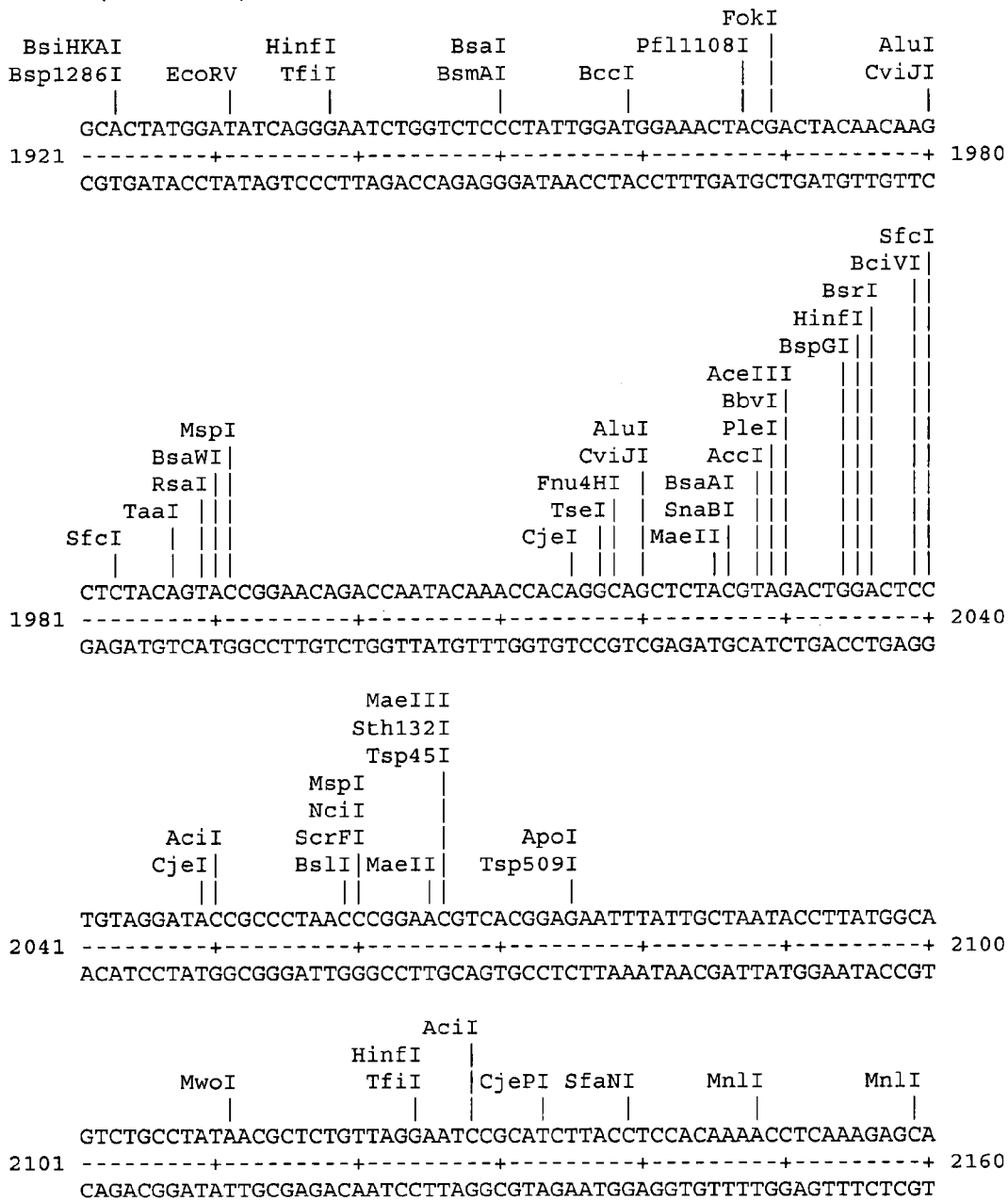
Figure 9J:
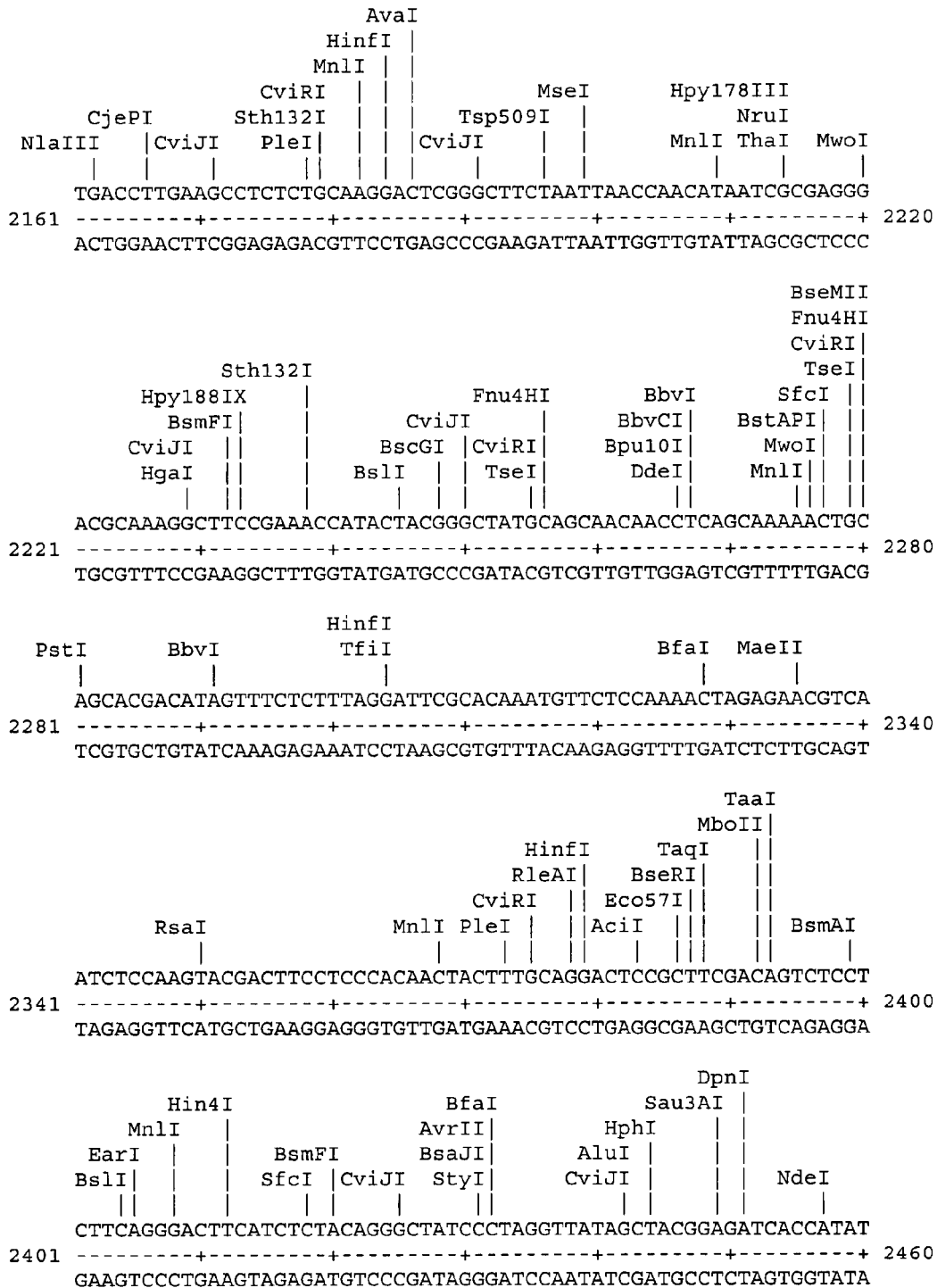
Figure 9L:
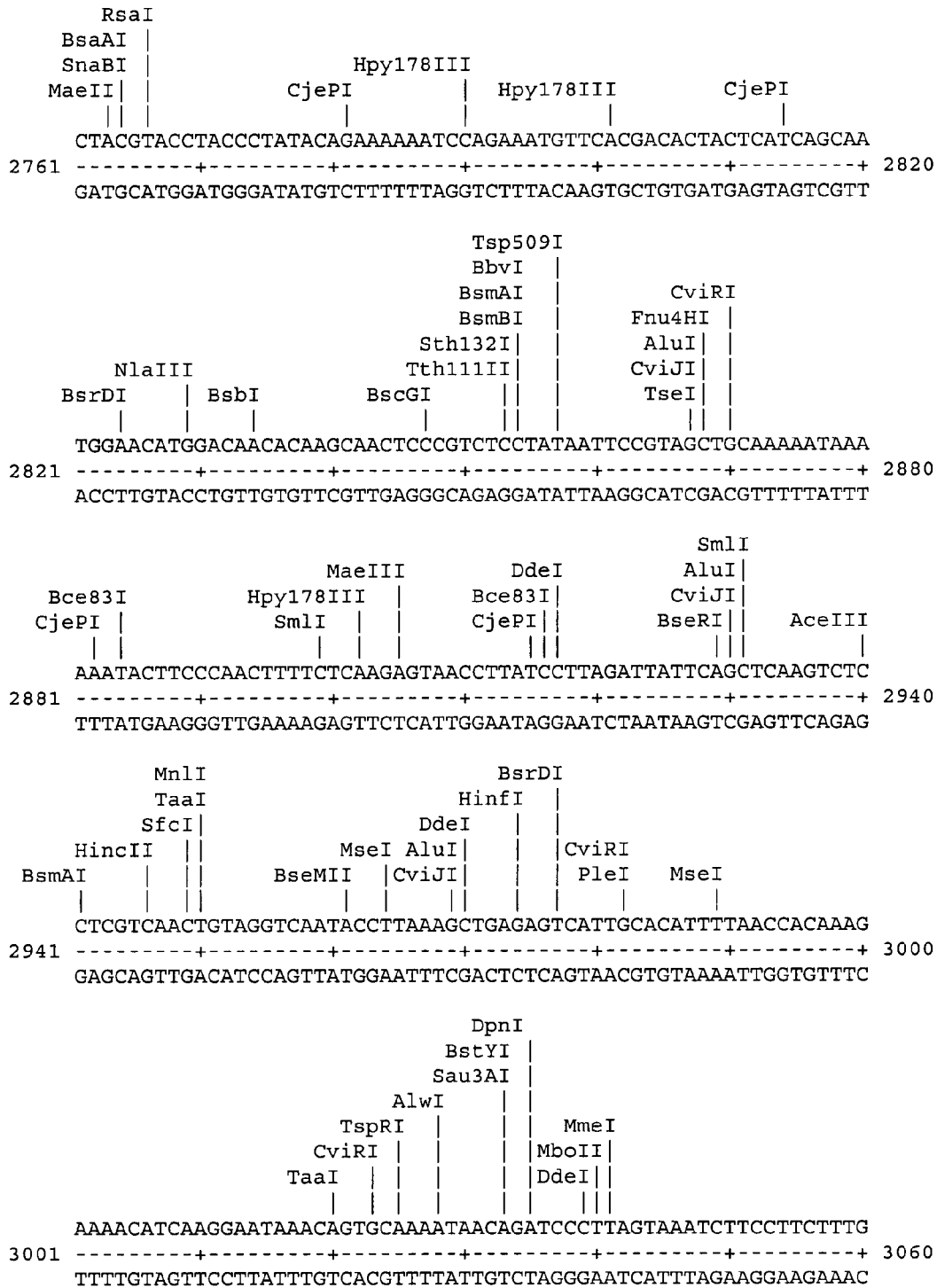
Figure 10A:
Figure 10B:
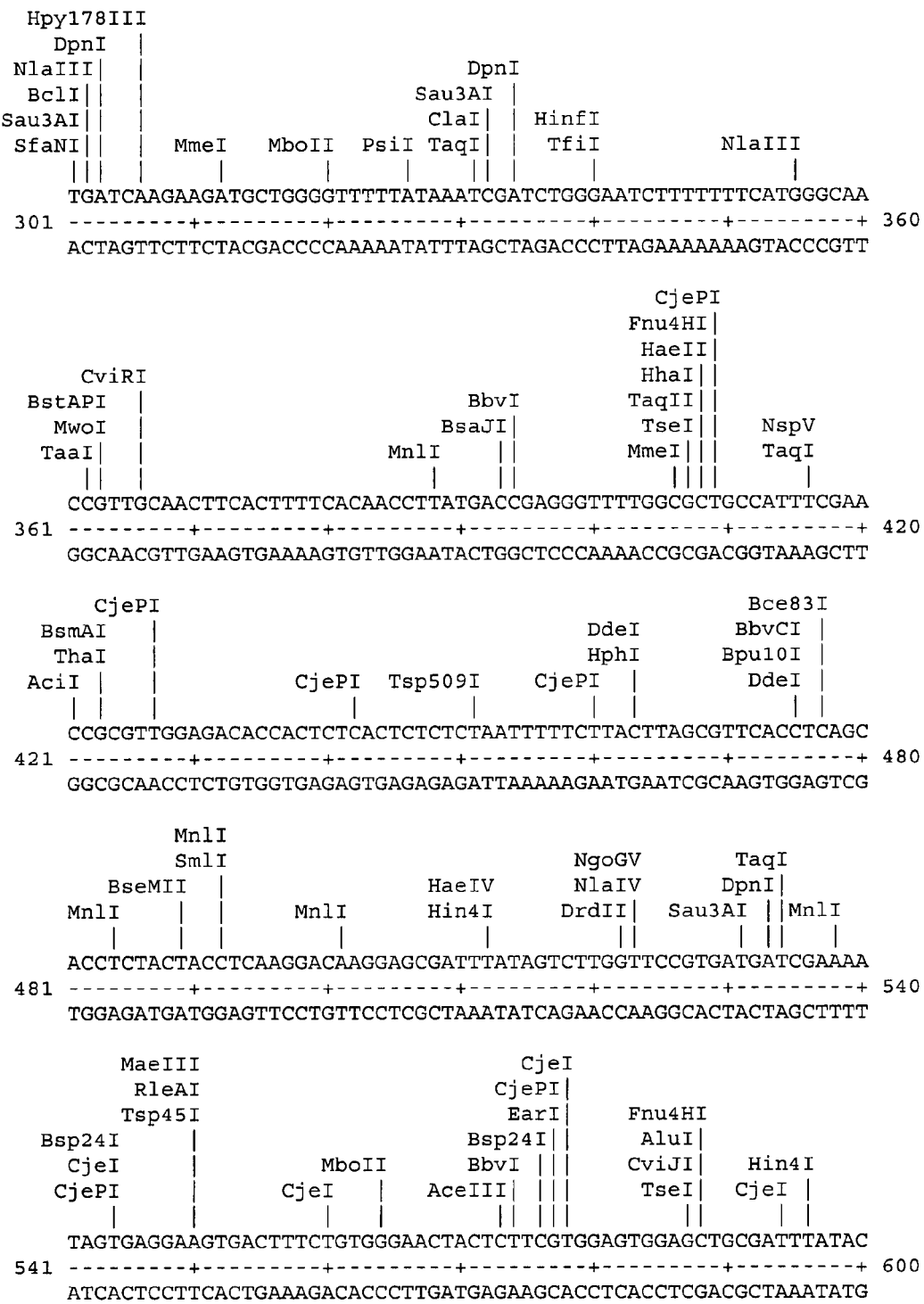
Figure 10C:
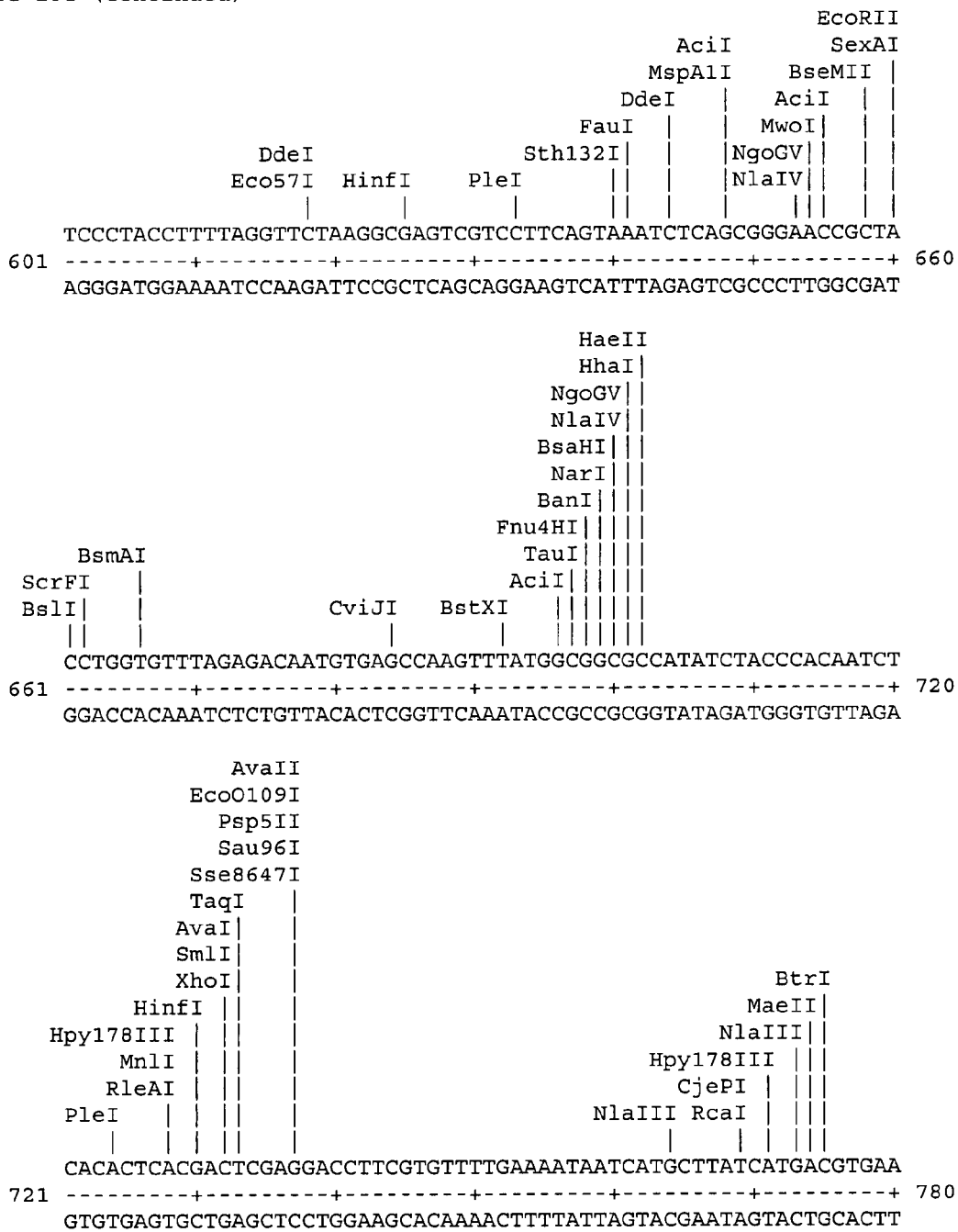
Figure 10D:
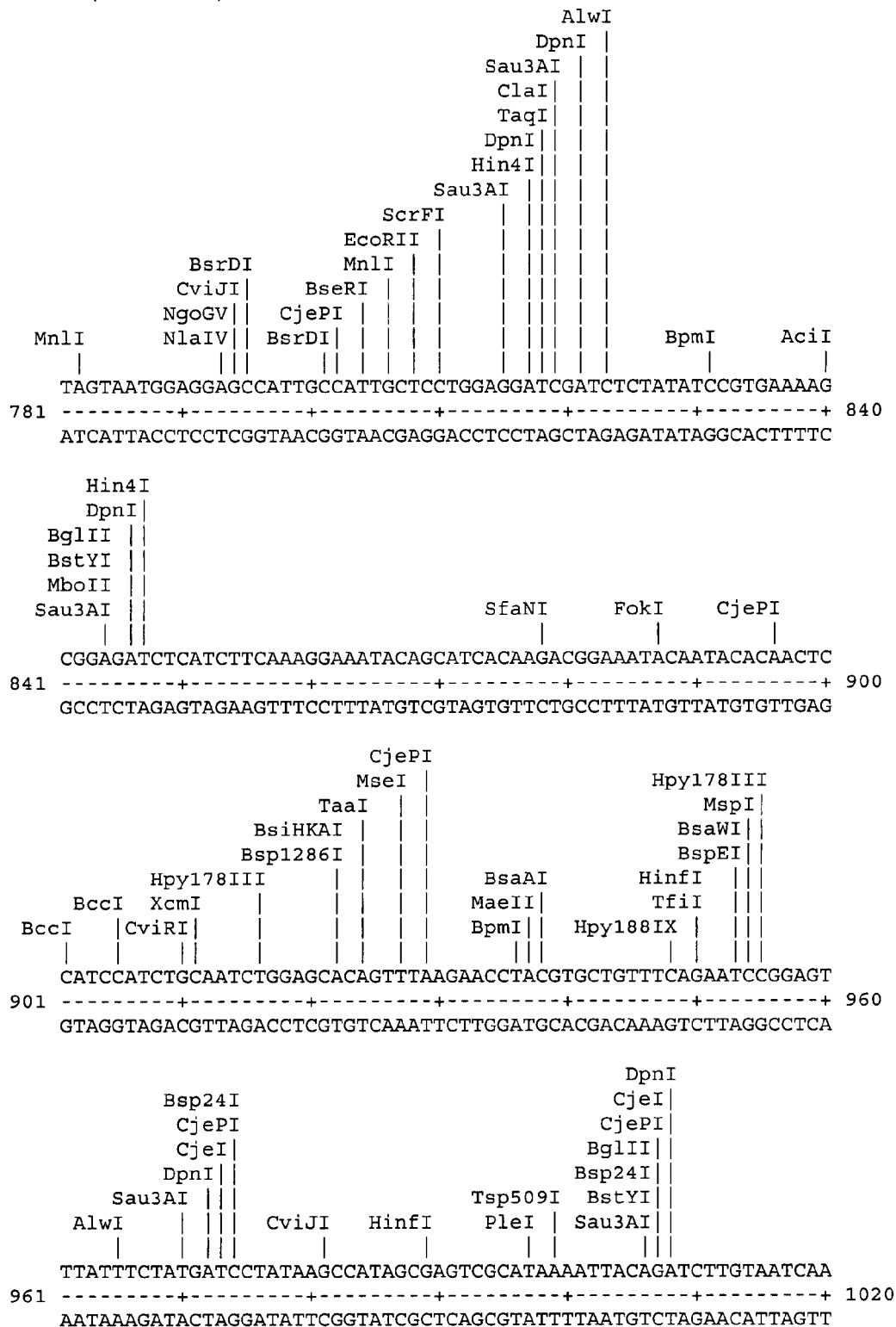
Figure 10E:
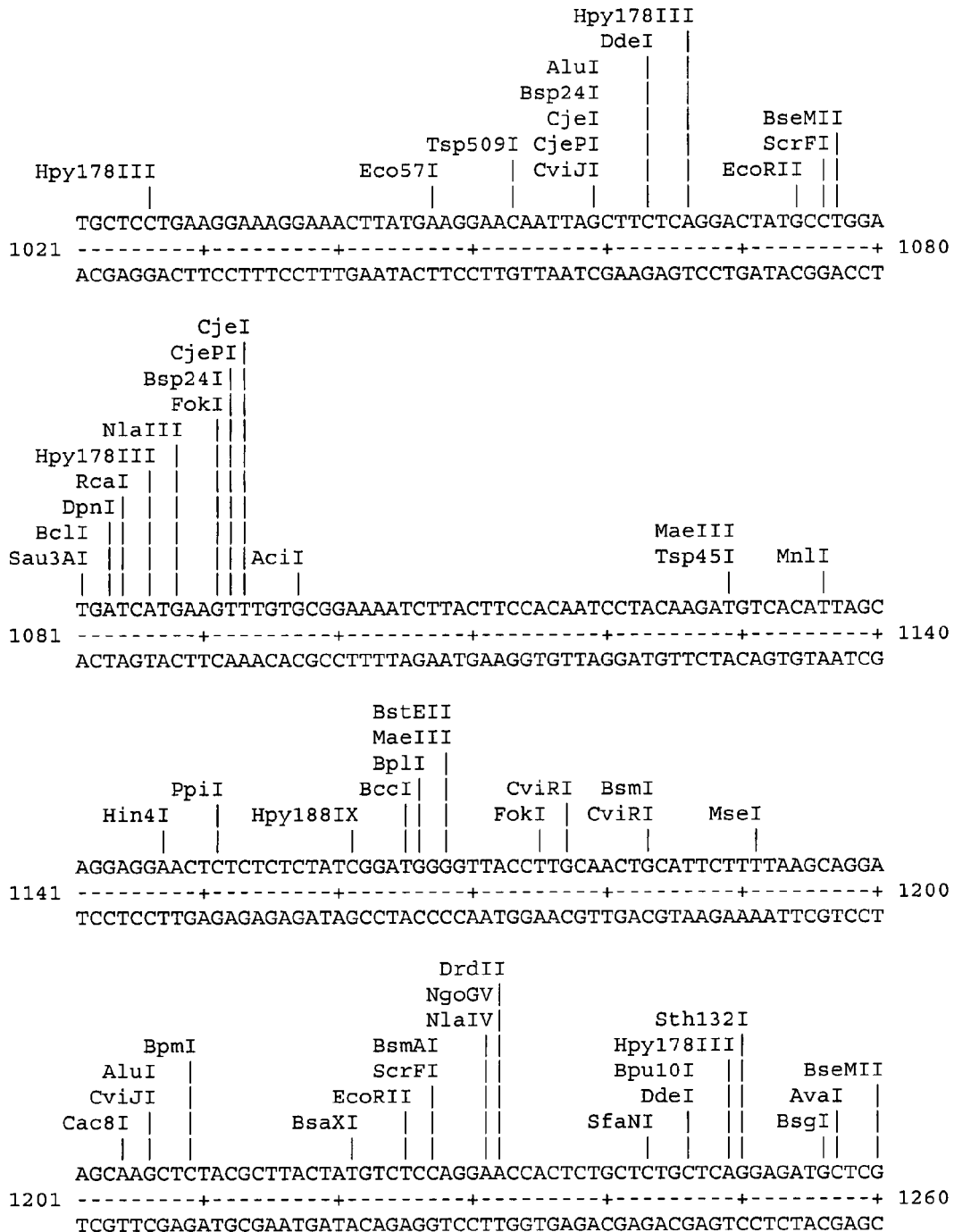
Figure 10F:
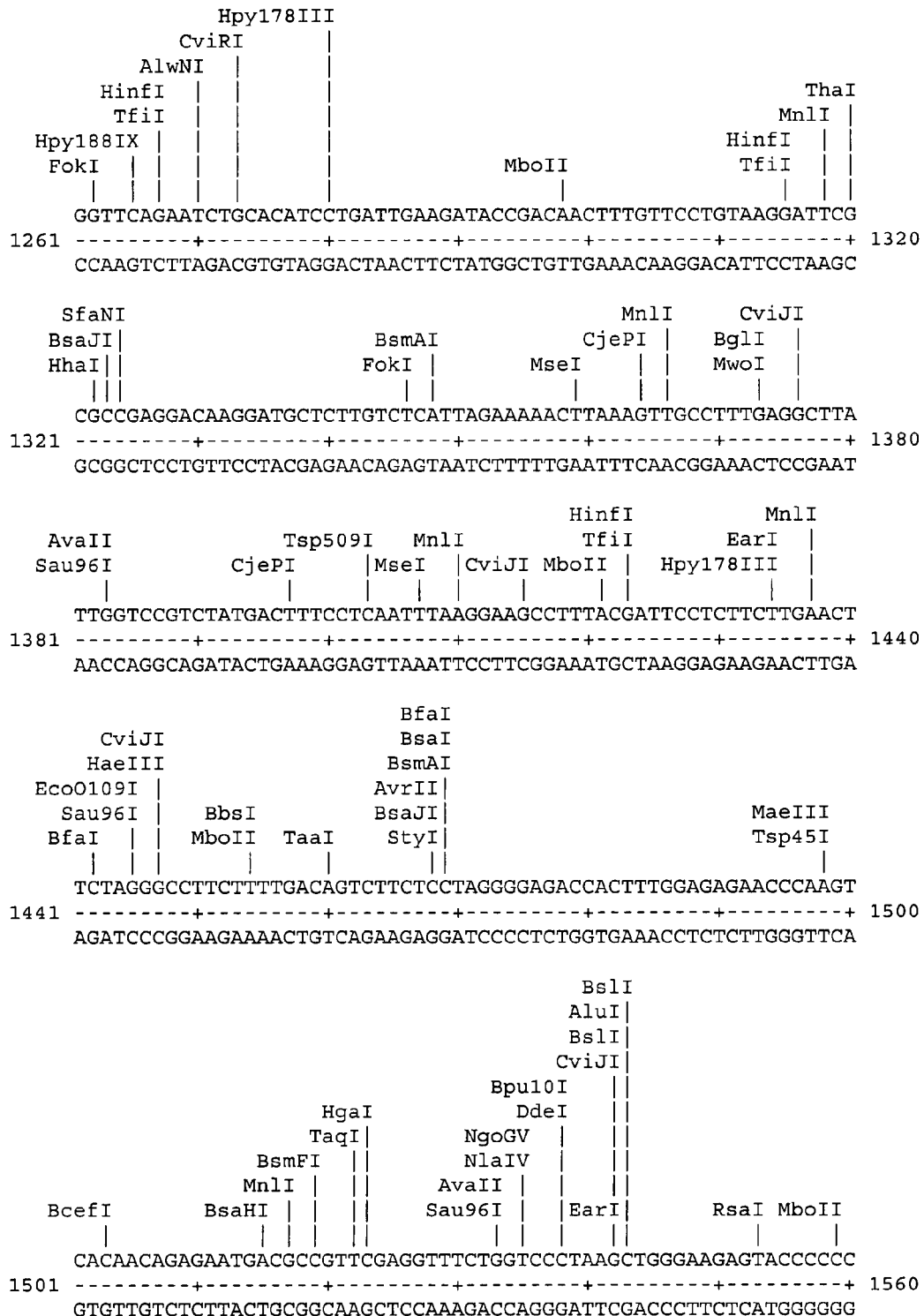
Figure 10G:
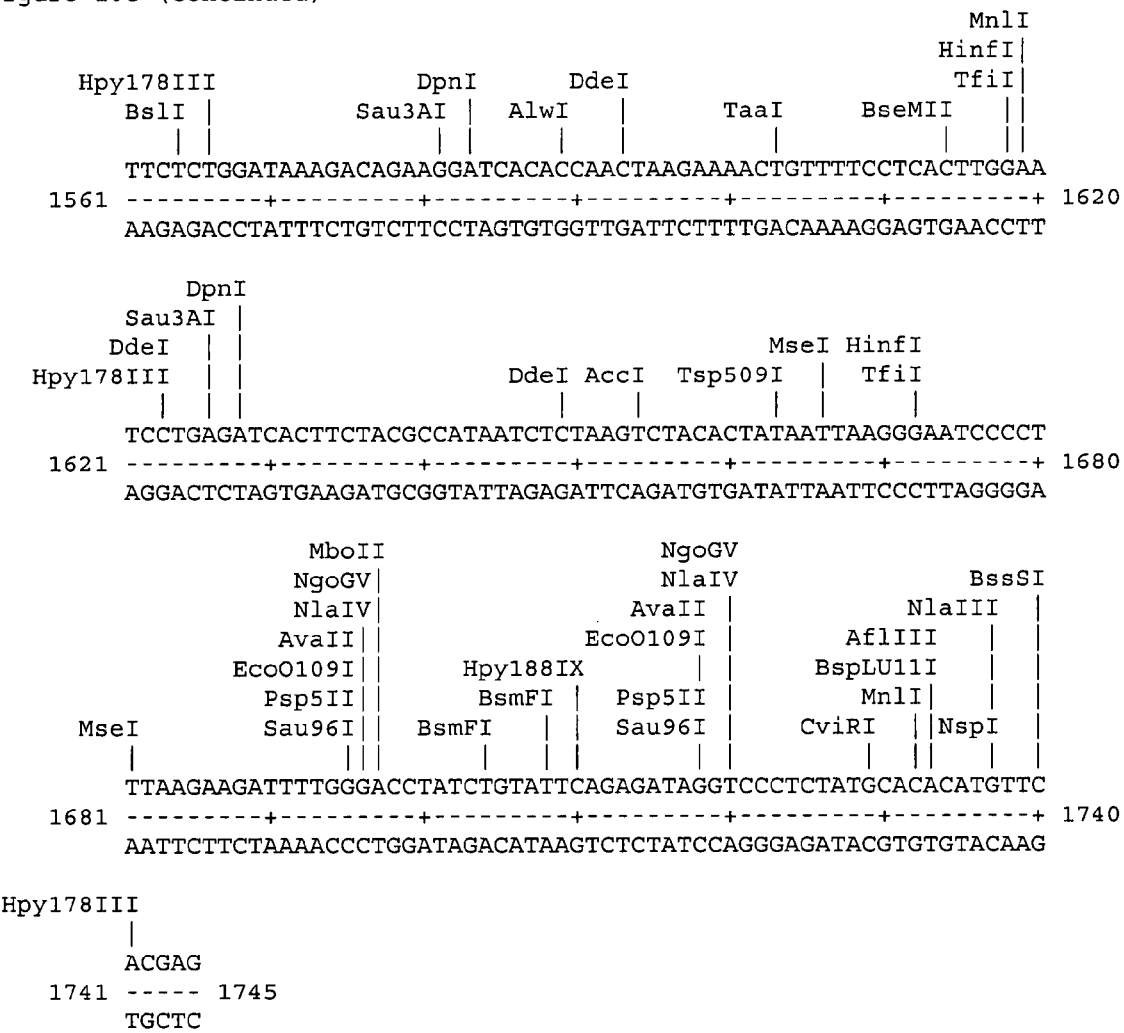

Open reading frames (ORFs) encoding chlamydial polypeptides have been identified from the *C. pneumoniae* genome. These polypeptides include polypeptides found permanently in the bacterial membrane structure, polypeptides present in the external vicinity of the bacterial membrane, polypeptides found permanently in the inclusion membrane structure, polypeptides present in the external vicinity of the inclusion membrane, and polypeptides released into the cytoplasm of the infected cell. These polypeptides can be used to prevent and treat *Chlamydia* infection.

The polypeptide CPN100686 RY 54 whose amino acid sequence is shown as SEQ ID No: 14 is a putative 98 kDa outer membrane protein; the polypeptide CPN100696 RY-55 (SEQ ID No: 15) is consistent with a sulfur-rich protein; the polypeptide CPN100709 RY-57 (SEQ ID No: 16) is a ABC transporter; the polypeptide CPN100710 RY-58 (SEQ ID No: 17) is an adhesion protein; the polypeptide CPN100711 RY-59 (SEQ ID No: 18) is a putative outer membrane protein; the polypeptide CPN100877 RY-61 (SEQ ID No: 19) is a putative 98 kDa outer membrane protein, and so are the polypeptides CPN100325 RY-62 (SEQ ID No: 20), CPN100368 RY-63 (SEQ ID No: 21), CPN100624 RY-64 (SEQ ID No: 22), and CPN100633 RY-65 (SEQ ID No: 23); the polypeptide CPN100985 RY-66 (SEQ ID No: 24) is yscT; and CPN100988 RY-68 (SEQ ID No: 26) is a flagellar protein.

According to a first aspect of the invention, isolated polynucleotides are provided which encode the precursor and mature forms of *Chlamydia* polypeptides, whose amino acid sequences are selected from the group consisting of SEQ ID Nos: 14 to 26.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotides of the invention are either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (antisense) strand. Any one of the sequences that encode the polypeptides of the invention as shown in SEQ ID Nos: 1 to 13 is (a) a coding sequence, (b) a ribonucleotide sequence derived from transcription of (a), or (c) a coding sequence which uses the redundancy or degeneracy of the genetic code to encode the same polypeptides. By "polypeptide" or "protein" is meant any chain of amino acids, regardless of length or post-translational modification (e.g., glycosylation or phosphorylation). Both terms are used interchangeably in the present application.

Consistent with the first aspect of the invention, amino acid sequences are provided which are homologous to any one of SEQ ID Nos: 14 to 26. As used herein, "homologous amino acid sequence" is any polypeptide which is encoded, in whole or in part, by a nucleic acid sequence which hybridizes at 25-35° C. below critical melting temperature (Tm), to any portion of the nucleic acid sequences of SEQ ID Nos: 1 to 13. A homologous amino acid sequence is one that differs from an amino acid sequence shown in any one of SEQ ID Nos: 13 to 26 by one or more conservative amino acid substitutions. Such a sequence also encompass serotypic variants (defined below) as well as sequences containing deletions or insertions which retain inherent characteristics of the polypeptide such as immunogenicity. Preferably, such a sequence is at least 75%, more preferably 80%, and most preferably 90% identical to any one of SEQ ID Nos: 14 to 26.

Homologous amino acid sequences include sequences that are identical or substantially identical to SEQ ID Nos: 14 to 26. By "amino acid sequence substantially identical" is meant a sequence that is at least 90%, preferably 95%, more preferably 97%, and most preferably 99% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 60%, and most preferably 85% identical to any one of coding sequences SEQ ID Nos: 1 to 13.

Consistent with the first aspect of the invention, polypeptides having a sequence homologous to any one of SEQ ID Nos: 14 to 26 include naturally-occurring allelic variants, as well as mutants or any other non-naturally occurring variants that retain the inherent characteristics of the polypeptide of SEQ ID Nos: 14 to 26.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. Biological function is distinct from antigenic property. A polypeptide can have more than one biological function.

Allelic variants are very common in nature. For example, a bacterial species such as *C. pneumoniae*, is usually represented by a variety of strains that differ from each other by minor allelic variations. Indeed, a polypeptide that fulfills the same biological function in different strains can have an amino acid sequence (and polynucleotide sequence) that is not identical in each of the strains. Despite this variation, an immune response directed generally against many allelic variants has been demonstrated. In studies of the Chlamydial MOMP antigen, cross-strain antibody binding plus neutralization of infectivity occurs despite amino acid sequence variation of MOMP from strain to strain, indicating that the MOMP, when used as an immunogen, is tolerant of amino acid variations.

Polynucleotides encoding homologous polypeptides or allelic variants are retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers are designed according to the nucleotide sequence information provided in SEQ ID Nos: 1 to 13. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 µL, 20 to 200 µM deoxynucleotide each, preferably at equivalent concentrations, 0.5 to 2.5 MM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for denaturation of G+C-rich targets. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: Tm=81.5+ 0.5×(% G+C)+1.6 log (positive ion concentration)–0.6×(% formamide). Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

For the polynucleotides of the invention, stringent conditions are achieved for both pre-hybridizing and hybridizing incubations (i) within 4-16 hours at 42° C., in 6×SSC containing 50% formamide, or (ii) within 4-16 hours at 65° C. in an aqueous 6×SSC solution (1 M NaCl, 0.1 M sodium citrate (pH 7.0)).

Useful homologs and fragments thereof that do not occur naturally are designed using known methods for identifying regions of an antigen that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed using the BLAST homology searching algorithm of Altschul et al., Nucleic Acids Res. 25:3389-3402 (1997). Alternatively, sequences are modified such that they become more reactive to T- and/or B-cells. (See FIGS. 11 to 15 below for identification of T- and B-epitopes). Yet another alternative is to mutate a particular amino acid residue or sequence within the polypeptide in vitro, then screen the mutant polypeptides for their ability to prevent or treat *Chlamydia* infection according to the method outlined below.

A person skilled in the art will readily understand that by following the screening process of this invention, it will be determined without undue experimentation whether a particular homolog of any of SEQ ID Nos: 14 to 26 may be useful in the prevention or treatment of *Chlamydia* infection. The screening procedure comprises the steps:

(i) immunizing an animal, preferably mouse, with the test homolog or fragment;

(ii) inoculating the immunized animal with *Chlamydia*; and, (iii) selecting those homologs or fragments which confer protection against *Chlamydia*.

By "conferring protection" is meant that there is a reduction in severity of any of the effects of *Chlamydia* infection, in comparison with a control animal which was not immunized with the test homolog or fragment.

It has been previously demonstrated (Yang, Z. P., Chi, E. Y., Kuo, C. C. and Grayston, J. T. 1993. A mouse model of *C. pneumoniae* strain TWAR pneumonitis. *Infect. Immun.* 61(5):2037-2040) that mice are susceptible to intranasal infection with different isolates of *C. pneumoniae*. Strain AR-39 (Chi, E. Y., Kuo, C. C. and Grayston, J. T., 1987. Unique ultrastructure in the elementary body of *Chlamydia* sp. strain TWAR. J. Bacteriol. 169(8):3757-63) is used in Balb/c mice as a challenge infection model to examine the capacity of chlamydia gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (6 to 10 per group) are immunized intramuscularly (i.m.) plus intranasally (i.n.) with plasmid DNA containing the coding sequence of a *C. pneumoniae* polypeptide. Saline or the plasmid vector lacking an inserted chlamydial gene is given to groups of control animals.

For i.m. immunization alternate left and right quadriceps are injected with 100 μg of DNA in 50 μl of PBS on three occasions at 0, 3 and 6 weeks. For i.n. immunization, anaesthetized mice aspirates 50 μl of PBS containing 50 μg DNA on three occasions at 0, 3 and 6 weeks. At week 8, immunized mice are inoculated i.n. with $5\times10^5$ IFU of *C. pneumoniae*, strain AR39 in 100 μl of SPG buffer to test their ability to limit the growth of a sublethal *C. pneumoniae* challenge.

Lungs are taken from mice at day 9 post-challenge and immediately homogenised in SPG buffer (7.5% sucrose, 5 mM glutamate, 12.5 mM phosphate pH7.5). The homogenate is stored frozen at −70° C. until assay. Dilutions of the homogenate are assayed for the presence of infectious chlamydia by inoculation onto monolayers of susceptible cells. The inoculum is centrifuged onto the cells at 3000 rpm for 1 hour, then the cells are incubated for three days at 35° C. in the presence of 1 μg/ml cycloheximide. After incubation the monolayers are fixed with formalin and methanol then immunoperoxidase stained for the presence of chlamydial inclusions using convalescent sera from rabbits infected with *C. pneumoniae* and metal-enhanced DAB as a peroxidase substrate.

Consistent with the first aspect of the invention, polypeptide derivatives are provided that are partial sequences of SEQ ID Nos: 14 to 26, partial sequences of polypeptide sequences homologous to SEQ ID Nos: 14 to 26, polypeptides derived from full-length polypeptides by internal deletion, and fusion proteins.

It is an accepted practice in the field of immunology to use fragments and variants of protein immunogens as vaccines, as all that is required to induce an immune response to a protein is a small (e.g., 8 to 10 amino acid) immunogenic region of the protein. Various short synthetic peptides corresponding to surface-exposed antigens of pathogens other than *Chlamydia* have been shown to be effective vaccine antigens against their respective pathogens, e.g. an 11 residue peptide of murine mammary tumor virus (Casey & Davidson, Nucl. Acid Res. (1977) 4:1539), a 16-residue peptide of Semliki Forest virus (Snijders et al., 1991. J. Gen. Virol. 72:557-565), and two overlapping peptides of 15 residues each from canine parvovirus (Langeveld et al., Vaccine 12(15):1473-1480, 1994).

Accordingly, it will be readily apparent to one skilled in the art, having read the present description, that partial sequences of SEQ ID Nos: 14 to 26 or their homologous amino acid sequences are inherent to the full-length sequences and are taught by the present invention. Such polypeptide fragments preferably are at least 12 amino acids in length. Advantageously, they are at least 20 amino acids, preferably at least 50 amino acids, more preferably at least 75 amino acids, and most preferably at least 100 amino acids in length.

Polynucleotides of 30 to 600 nucleotides encoding partial sequences of sequences homologous to SEQ ID Nos: 14 to 26 are retrieved by PCR amplification using the parameters outlined above and using primers matching the sequences upstream and downstream of the 5' and 3' ends of the fragment to be amplified. The template polynucleotide for such amplification is either the full length polynucleotide homologous to one of SEQ ID Nos: 1 to 13, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20-30 bases are to be obtained, the formula for calculating the Tm is as follows: Tm=4×(G+C)+2 (A+T). For example, an 18 nucleotide fragment of 50% G+C would have an approximate Tm of 54° C. Short peptides that are fragments of SEQ. ID Nos. 14 to 26 or their homologous sequences, are obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Figure 11A:
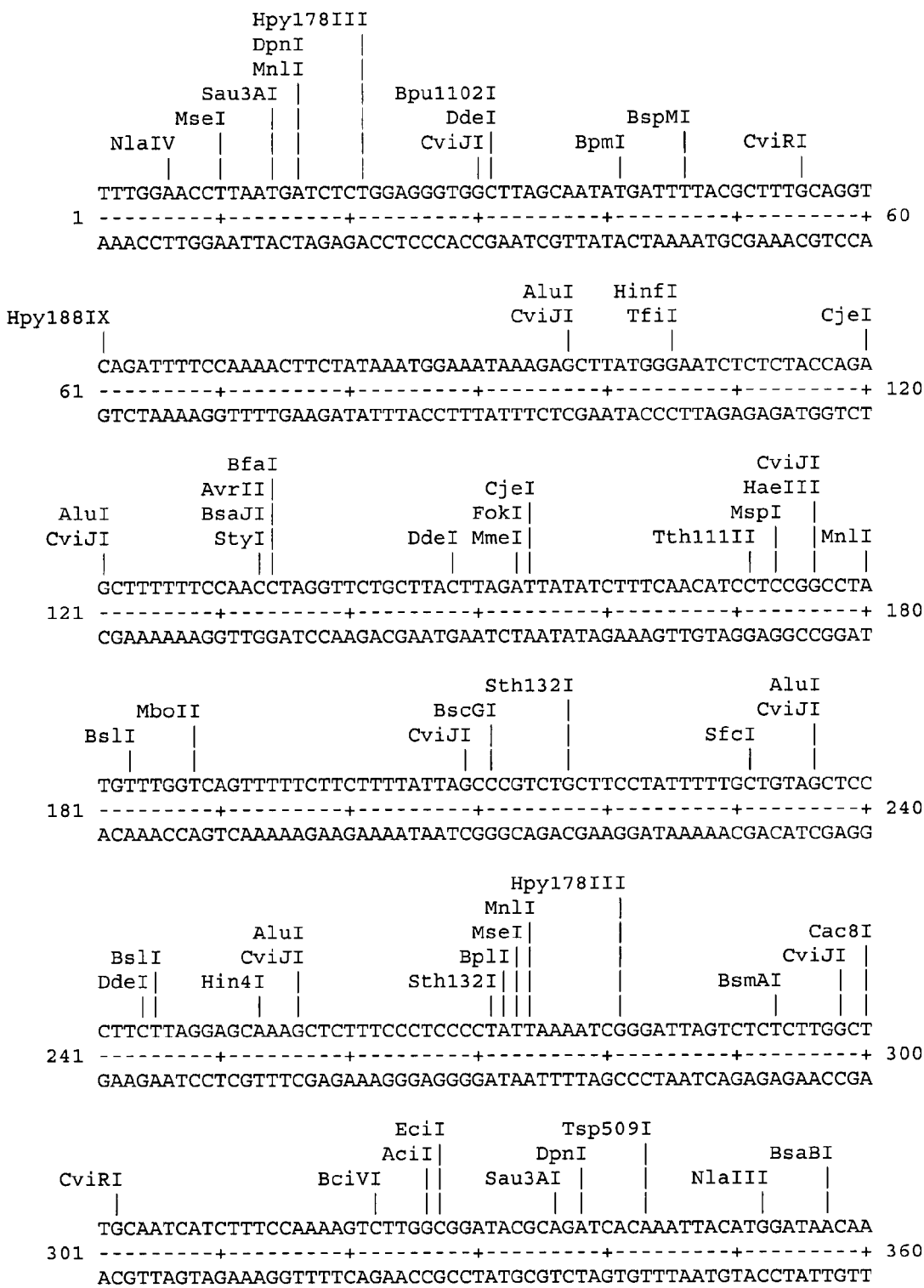
Figure 11C:
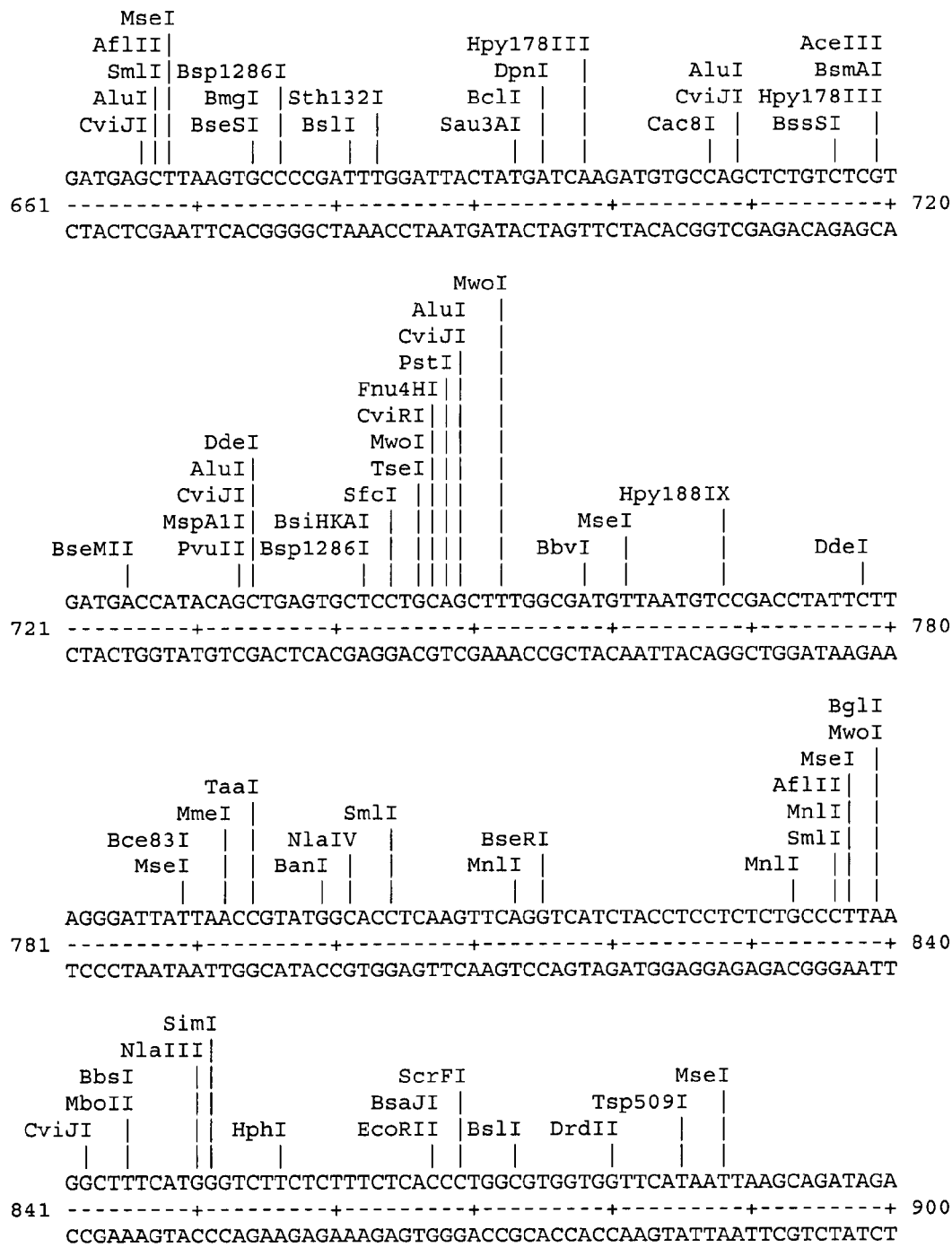
Figure 12A:
Figure 12B:
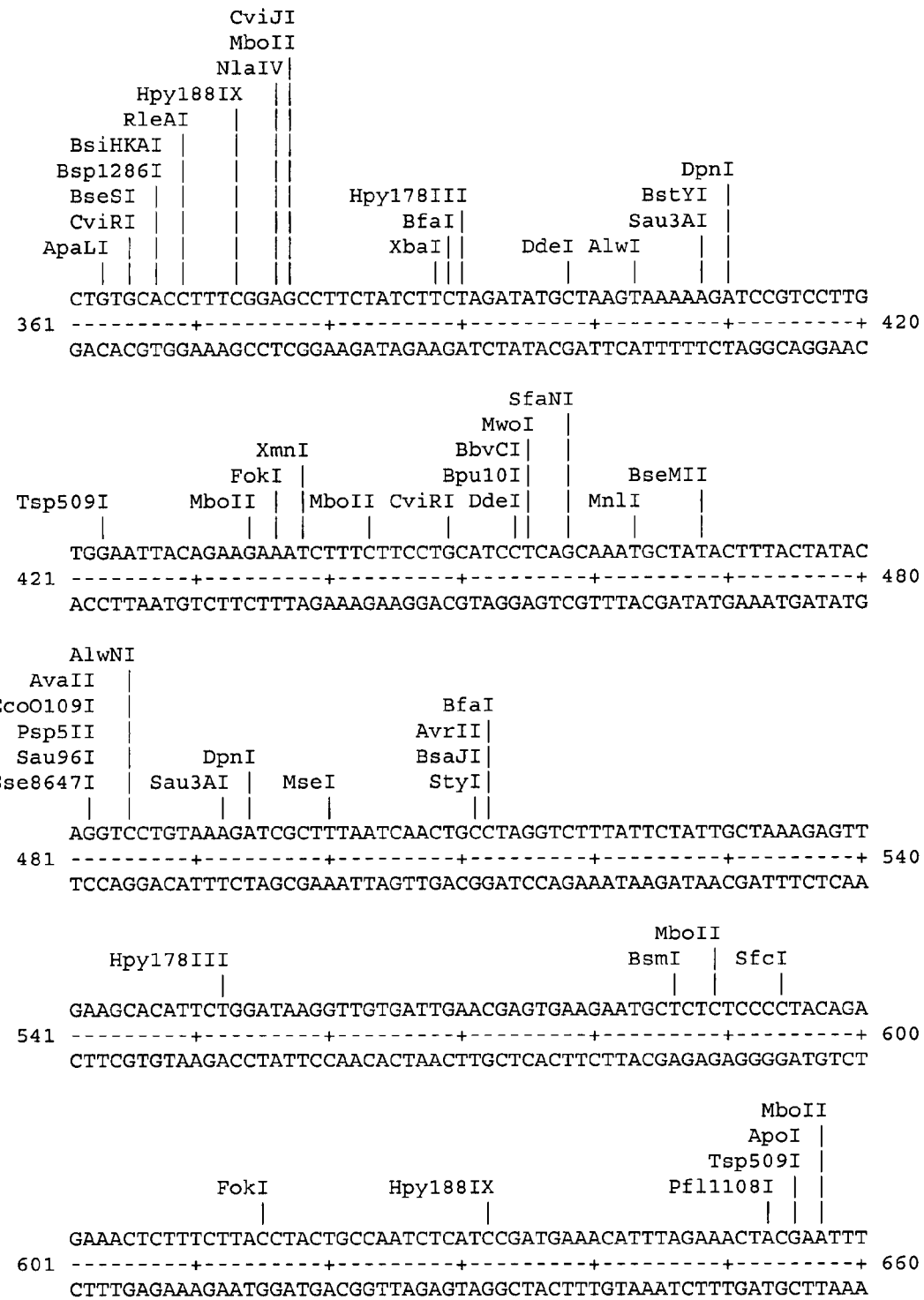
Figure 13A:
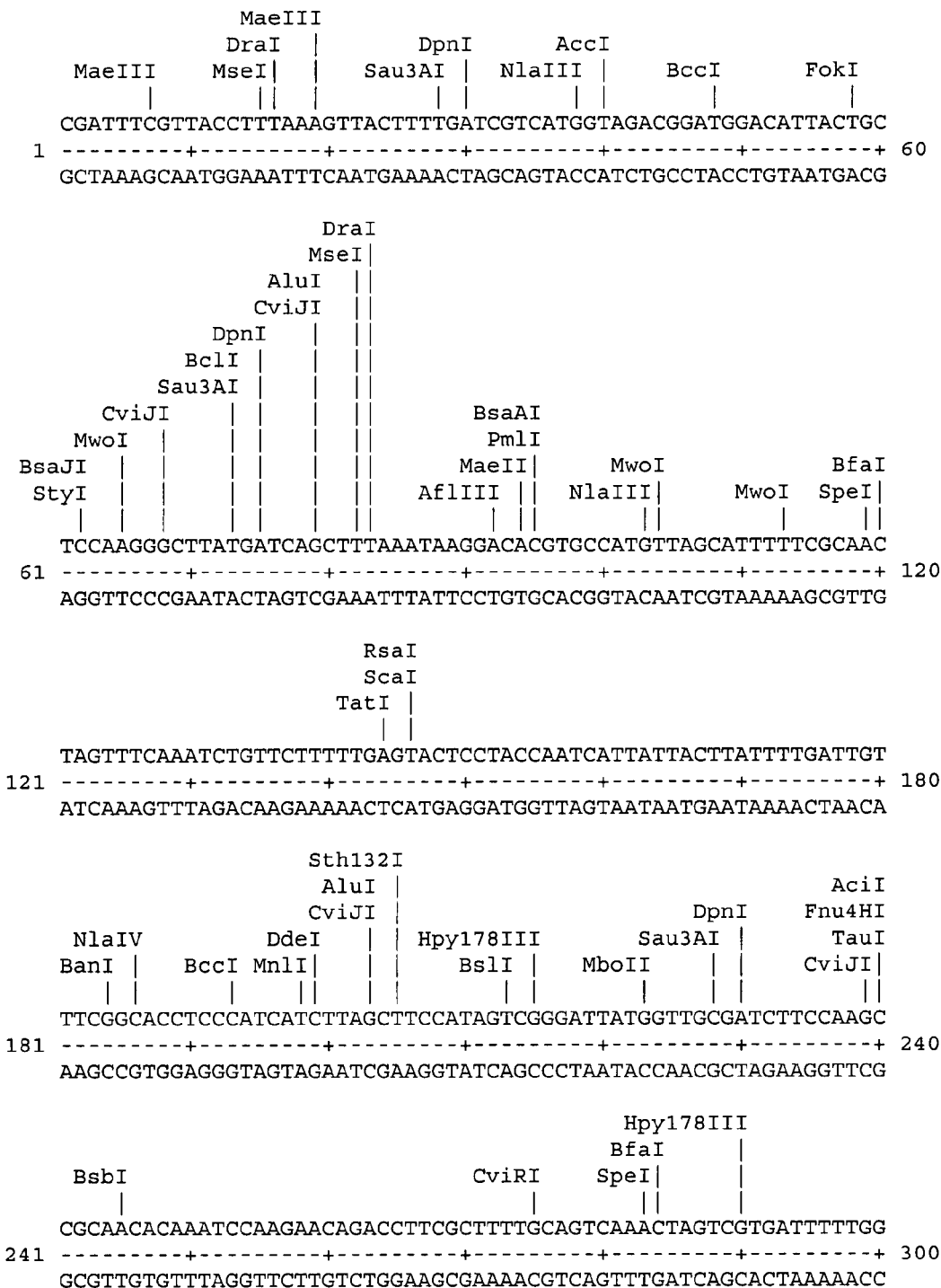

Useful polypeptide derivatives, e.g., polypeptide fragments, are designed using computer-assisted analysis of amino acid sequences. This identifies probable surface-exposed, antigenic regions (Hughes et al., 1992. Infect. Immun. 60(9):3497). An analysis of the 6 amino acid sequences contained in SEQ ID Nos: 14 to 26, based on the product of flexibility and hydrophobicity propensities using the program SEQSEE (Wishart D S, et al. "SEQSEE: a comprehensive program suite for protein sequence analysis." *Comput Appl Biosci*. 1994 April; 10(2):121-32), reveal a number of potential B- and T-cell epitopes which may be used as a basis for selecting useful immunogenic fragments and variants. The results are shown in FIGS. 11 to 15. This analysis uses a reasonable combination of external surface features that is likely to be recognized by antibodies. Probable T-cell epitopes for HLA-A0201 MHC subclass were revealed by an algorithm written at Connaught Laboratories that emulates an approach developed at the NIH (Parker K C, et al. "Peptide binding to MHC class I molecules: implications for antigenic peptide prediction." *Immunol Res* 1995; 14(1):34-57).

Epitopes which induce a protective T cell-dependent immune response are present throughout the length of the polypeptide. However, some epitopes may be masked by secondary and tertiary structures of the polypeptide. To reveal such masked epitopes large internal deletions are created which remove much of the original protein structure and expose the masked epitopes. Such internal deletions sometimes effect the additional advantage of removing immunodominant regions of high variability among strains.

Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources such as Stratagene. Once the deletion mutants have been constructed, they are tested for their ability to prevent or treat *Chlamydia* infection as described above.

As used herein, a fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

An advantageous example of a fusion polypeptide is one where the polypeptide or homolog or fragment of the invention is fused to a polypeptide having adjuvant activity, such as subunit B of either cholera toxin or *E. coli* heat-labile toxin. Another advantageous fusion is one where the polypeptide, homolog or fragment is fused to a strong T-cell epitope or B-cell epitope. Such an epitope may be one known in the art (e.g. the Hepatitis B virus core antigen, D. R. Millich et al., "Antibody production to the nucleocapsid and envelope of the Hepatitis B virus primed by a single synthetic T cell site", Nature. 1987. 329:547-549), or one which has been identified in another polypeptide of the invention (FIGS. 11-15). Consistent with this aspect of the invention is a fusion polypeptide comprising T- or B-cell epitopes from one of SEQ ID Nos: 14 to 26 or its homolog or fragment, wherein the epitopes are derived from multiple variants of said polypeptide or homolog or fragment, each variant differing from another in the location and sequence of its epitope within the polypeptide. Such a fusion is effective in the prevention and treatment of *Chlamydia* infection since it optimizes the T- and B-cell response to the overall polypeptide, homolog or fragment.

To effect fusion, the polypeptide of the invention is fused to the N-, or preferably, to the C-terminal end of the polypeptide having adjuvant activity or T- or B-cell epitope. Alternatively, a polypeptide fragment of the invention is inserted internally within the amino acid sequence of the polypeptide having adjuvant activity. The T- or B-cell epitope may also be inserted internally within the amino acid sequence of the polypeptide of the invention.

Consistent with the first aspect, the polynucleotides of the invention also encode hybrid precursor polypeptides containing heterologous signal peptides, which mature into polypeptides of the invention. By "heterologous signal peptide" is meant a signal peptide that is not found in naturally-occurring precursors of polypeptides of the invention.

A polynucleotide molecule according to the invention, including RNA, DNA, or modifications or combinations thereof, has various applications. A DNA molecule is used, for example, (i) in a process for producing the encoded polypeptide in a recombinant host system, (ii) in the construction of vaccine vectors such as poxviruses, which are further used in methods and compositions for preventing and/or treating *Chlamydia* infection, (iii) as a vaccine agent (as well as an RNA molecule), in a naked form or formulated with a delivery vehicle and, (iv) in the construction of attenuated *Chlamydia* strains that can over-express a polynucleotide of the invention or express it in a non-toxic, mutated form.

Accordingly, a second aspect of the invention encompasses (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system is selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. A preferred expression system is a procaryotic host such as *E. coli*. Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form.

One skilled in the art would readily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variable are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are compatible with the selected vector, tolerant of any possible toxic effects of the expressed product, able to secrete the expressed product efficiently if such is desired, to be able to express the product in the desired conformation, to be easily scaled up, and to which ease of purification of the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system. Promoters and signal peptide encoding regions are widely known and available to those skilled in the art and include, for example, the promoter of Salmonella typhimurium (and derivatives) that is inducible by arabinose (promoter araB) and is functional in Gram-negative bacteria such as E. coli (as described in U.S. Pat. No. 5,028,530 and in Cagnon et al., (Cagnon et al., Protein Engineering (1991) 4(7):843)); the promoter of the gene of bacteriophage T7 encoding RNA polymerase, that is functional in a number of E. coli strains expressing T7 polymerase (described in U.S. Pat. No. 4,952,496); OspA lipidation signal peptide; and RlpB lipidation signal peptide (Takase et al., J. Bact. (1987) 169:5692).

The expression cassette is typically part of an expression vector, which is selected for its ability to replicate in the chosen expression system. Expression vectors (e.g., plasmids or viral vectors) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Ausubel et al., Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained as described below.

A polynucleotide of the invention can also be useful as a vaccine. There are two major routes, either using a viral or bacterial host as gene delivery vehicle (live vaccine vector) or administering the gene in a free form, e.g., inserted into a plasmid. Therapeutic or prophylactic efficacy of a polynucleotide of the invention is evaluated as described below.

Accordingly, a third aspect of the invention provides (i) a vaccine vector such as a poxvirus, containing a DNA molecule of the invention, placed under the control of elements required for expression; (ii) a composition of matter comprising a vaccine vector of the invention, together with a diluent or carrier; specifically (iii) a pharmaceutical composition containing a therapeutically or prophylactically effective amount of a vaccine vector of the invention; (iv) a method for inducing an immune response against Chlamydia in a mammal (e.g., a human; alternatively, the method can be used in veterinary applications for treating or preventing Chlamydia infection of animals, e.g., cats or birds), which involves administering to the mammal an immunogenically effective amount of a vaccine vector of the invention to elicit a protective or therapeutic immune response to Chlamydia; and particularly, (v) a method for preventing and/or treating a Chlamydia (e.g., C. trachomatis, C. psittaci, C. pneumonia, C. pecorum) infection, which involves administering a prophylactic or therapeutic amount of a vaccine vector of the invention to an infected individual. Additionally, the third aspect of the invention encompasses the use of a vaccine vector of the invention in the preparation of a medicament for preventing and/or treating Chlamydia infection.

As used herein, a vaccine vector expresses one or several polypeptides or derivatives of the invention. The vaccine vector may express additionally a cytokine, such as interleukin-2 (IL-2) or interleukin-12 (IL-12), that enhances the immune response (adjuvant effect). It is understood that each of the components to be expressed is placed under the control of elements required for expression in a mammalian cell.

Consistent with the third aspect of the invention is a composition comprising several vaccine vectors, each of them capable of expressing a polypeptide or derivative of the invention. A composition may also comprise a vaccine vector capable of expressing an additional Chlamydia antigen, or a subunit, fragment, homolog, mutant, or derivative thereof, optionally together with a cytokine such as IL-2 or IL-12.

Vaccination methods for treating or preventing infection in a mammal comprises use of a vaccine vector of the invention to be administered by any conventional route, particularly to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. Treatment may be effected in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., *Shigella, Salmonella, Vibrio cholerae, Lactobacillus*, Bacille bilié de Calmette-Guérin (BCG), and *Streptococcus*.

An example of an adenovirus vector, as well as a method for constructing an adenovirus vector capable of expressing a DNA molecule of the invention, are described in U.S. Pat. No. 4,920,209. Poxvirus vectors include vaccinia and canary pox virus, described in U.S. Pat. No. 4,722,848 and U.S. Pat. No. 5,364,773, respectively. (Also see, e.g., Tartaglia et al., Virology (1992) 188:217) for a description of a vaccinia virus vector and Taylor et al, Vaccine (1995) 13:539 for a reference of a canary pox.) Poxvirus vectors capable of expressing a polynucleotide of the invention are obtained by homologous recombination as described in Kieny et al., Nature (1984) 312:163 so that the polynucleotide of the invention is inserted in the viral genome under appropriate conditions for expression in mammalian cells. Generally, the dose of vaccine viral vector, for therapeutic or prophylactic use, can be of from about $1 \times 10^4$ to about $1 \times 10^{11}$, advantageously from about $1 \times 10^7$ to about $1 \times 10^{10}$, preferably of from about $1 \times 10^7$ to about $1 \times 10^9$ plaque-forming units per kilogram. Preferably, viral vectors are administered parenterally; for example, in 3 doses, 4 weeks apart. It is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are known. Mekalanos et al., Nature (1983) 306:551 and U.S. Pat. No. 4,882,278 describe strains which have a substantial amount of the coding sequence of each of the two ctxA alleles deleted so that no functional *cholerae* toxin is produced. WO 92/11354 describes a strain in which the irgA locus is inactivated by mutation; this mutation can be combined in a single strain with ctxA mutations. WO 94/01533 describes a deletion mutant lacking functional ctxA and attRS1 DNA sequences. These mutant strains are genetically engineered to express heterologous antigens, as described in WO 94/19482. An effective vaccine dose of a *Vibrio cholerae* strain capable of expressing a polypeptide or polypeptide derivative encoded by a DNA molecule of the invention contains about $1 \times 10^5$ to about $1 \times 10^9$, preferably about $1 \times 10^6$ to about $1 \times 10^8$, viable bacteria in a volume appropriate for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al. (Bio/Technology (1988) 6:693) and WO 92/11361. Preferred routes of administration include all mucosal routes; most preferably, these vectors are administered intranasally or orally.

Other bacterial strains used as vaccine vectors in the context of the present invention are described for *Shigella flexneri* in High et al., EMBO (1992) 11:1991 and Sizemore et al., Science (1995) 270:299; for *Streptococcus gordonii* in Medaglini et al., Proc. Natl. Acad. Sci. USA (1995) 92:6868; and for Bacille Calmette Guerin in Flynn J. L., Cell. Mol. Biol. (1994) 40 (suppl. I):31, WO 88/06626, WO 90/00594, WO 91/13157, WO 92/01796, and WO 92/21376.

In bacterial vectors, the polynucleotide of the invention is inserted into the bacterial genome or remains in a free state as part of a plasmid.

The composition comprising a vaccine bacterial vector of the present invention may further contain an adjuvant. A number of adjuvants are known to those skilled in the art. Preferred adjuvants as provided below.

Accordingly, a fourth aspect of the invention provides (i) a composition of matter comprising a polynucleotide of the invention, together with a diluent or carrier; (ii) a pharmaceutical composition comprising a therapeutically or prophylactically effective amount of a polynucleotide of the invention; (iii) a method for inducing an immune response against *Chlamydia* in a mammal by administration of an immunogenically effective amount of a polynucleotide of the invention to elicit a protective immune response to *Chlamydia*; and particularly, (iv) a method for preventing and/or treating a *Chlamydia* (e.g., *C. trachomatis, C. psittaci, C. pneumoniae*, or *C. pecorum*) infection, by administering a prophylactic or therapeutic amount of a polynucleotide of the invention to an infected individual. Additionally, the fourth aspect of the invention encompasses the use of a polynucleotide of the invention in the preparation of a medicament for preventing and/or treating *Chlamydia* infection. A preferred use includes the use of a DNA molecule placed under conditions for expression in a mammalian cell, especially in a plasmid that is unable to replicate in mammalian cells and to substantially integrate in a mammalian genome.

Uses of the polynucleotides of the invention include their administration to a mammal as a vaccine, for therapeutic or prophylactic purposes. Such polynucleotides are used in the form of DNA as part of a plasmid that is unable to replicate in a mammalian cell and unable to integrate into the mammalian genome. Typically, such a DNA molecule is placed under the control of a promoter suitable for expression in a mammalian cell. The promoter functions either ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, Molec. Cell Biol. (1985) 5:281). An example of a tissue-specific promoter is the desmin promoter which drives expression in muscle cells (Li et al., Gene (1989) 78:243, Li & Paulin, J. Biol. Chem. (1991) 266:6562 and Li & Paulin, J. Biol. Chem. (1993) 268:10403). Use of promoters is well-known to those skilled in the art. Useful vectors are described in numerous publications, specifically WO 94/21797 and Hartikka et al., Human Gene Therapy (1996) 7:1205.

Polynucleotides of the invention which are used as vaccines encode either a precursor or a mature form of the corresponding polypeptide. In the precursor form, the signal peptide is either homologous or heterologous. In the latter case, a eucaryotic leader sequence such as the leader sequence of the tissue-type plasminogen factor (tPA) is preferred.

As used herein, a composition of the invention contains one or several polynucleotides with optionally at least one additional polynucleotide encoding another *Chlamydia* antigen such as urease subunit A, B, or both, or a fragment, derivative, mutant, or analog thereof. The composition may also contain an additional polynucleotide encoding a cytokine, such as interleukin-2 (IL-2) or interleukin-12 (IL-12) so that the immune response is enhanced. These additional polynucleotides are placed under appropriate control for expression. Advantageously, DNA molecules of the invention and/or additional DNA molecules to be included in the same composition, are present in the same plasmid.

Standard techniques of molecular biology for preparing and purifying polynucleotides are used in the preparation of polynucleotide therapeutics of the invention. For use as a vaccine, a polynucleotide of the invention is formulated according to various methods outlined below.

One method utilizes the polynucleotide in a naked form, free of any delivery vehicles. Such a polynucleotide is simply diluted in a physiologically acceptable solution such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

An alternative method utilizes the polynucleotide in association with agents that assist in cellular uptake. Examples of such agents are (i) chemicals that modify cellular permeability, such as bupivacaine (see, e.g., WO 94/16737), (ii) liposomes for encapsulation of the polynucleotide, or (iii) cationic lipids or silica, gold, or tungsten microparticles which associate themselves with the polynucleotides.

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy)propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N—(N',N'-dimethyl aminomethane)-carbamoyl)cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

Formulation containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles are used for gene delivery, as described in WO 91/00359, WO 93/17706, and Tang et al. Nature (1992) 356:152. The microparticle-coated polynucleotide is injected via intradermal or intraepidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 μg to about 1 mg, preferably, from about 10 μg to about 800 μg and, more preferably, from about 25 μg to about 250 μg, can be administered to human adults. The administration can be achieved in a single dose or repeated at intervals.

The route of administration is any conventional route used in the vaccine field. As general guidance, a polynucleotide of the invention is administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends on the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or sub-cutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that are used for diagnostic purposes. Accordingly, a fifth aspect of the invention provides a nucleotide probe or primer having a sequence found in or derived by degeneracy of the genetic code from a sequence shown in any one of SEQ ID Nos: 1 to 13.

The term "probe" as used in the present application refers to DNA (preferably single stranded) or RNA molecules (or modifications or combinations thereof) that hybridize under the stringent conditions, as defined above, to nucleic acid molecules having SEQ ID Nos: 1 to 13 or to sequences homologous to SEQ ID Nos: 1 to 13, or to their complementary or anti-sense sequences. Generally, probes are significantly shorter than full-length sequences. Such probes contain from about 5 to about 100, preferably from about 10 to about 80, nucleotides. In particular, probes have sequences that are at least 75%, preferably at least 85%, more preferably 95% homologous to a portion of any of SEQ ID Nos: 1 to 13 or that are complementary to such sequences. Probes may contain modified bases such as inosine, methyl-5-deoxycytidine, deoxyuridine, dimethylamino-5-deoxyuridine, or diamino-2,6-purine. Sugar or phosphate residues may also be modified or substituted. For example, a deoxyribose residue may be replaced by a polyamide (Nielsen et al., Science (1991) 254:1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used in diagnostic tests, as capture or detection probes. Such capture probes are conventionally immobilized on a solid support, directly or indirectly, by covalent means or by passive adsorption. A detection probe is labelled by a detection marker selected from: radioactive isotopes, enzymes such as peroxidase, alkaline phosphatase, and enzymes able to hydrolyze a chromogenic, fluorogenic, or luminescent substrate, compounds that are chromogenic, fluorogenic, or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, J. Mol. Biol. (1975) 98:503), northern blot (identical to Southern blot with the exception that RNA is used as a target), or the sandwich technique (Dunn et al., Cell (1977) 12:23). The latter technique involves the use of a specific capture probe and/or a specific detection probe with nucleotide sequences that at least partially differ from each other.

A primer is a probe of usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art.

As described herein, the invention also encompasses (i) a reagent comprising a probe of the invention for detecting and/or identifying the presence of *Chlamydia* in a biological material; (ii) a method for detecting and/or identifying the presence of *Chlamydia* in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of *Chlamydia* in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

It is apparent that disclosure of polynucleotide sequences of SEQ ID Nos: 1 to 13, their homolog, and partial sequences of either enable their corresponding amino acid sequences. Accordingly, a sixth aspect of the invention features a substantially purified polypeptide or polypeptide derivative having an amino acid sequence encoded by a polynucleotide of the invention.

A "substantially purified polypeptide" as used herein is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art would readily understand that the polypeptides of the invention may be purified from a natural source, i.e., a *Chlamydia* strain, or produced by recombinant means.

Consistent with the sixth aspect of the invention are polypeptides, homologs or fragments which are modified or treated to enhance their immunogenicity in the target animal, in whom the polypeptide, homolog or fragments are intended to confer protection against *Chlamydia*. Such modifications or treatments include: amino acid substitutions with an amino acid derivative such as 3-methylhistidine, 4-hydroxyproline, 5-hydroxylysine etc., modifications or deletions which are carried out after preparation of the polypeptide, homolog or fragment, such as the modification of free amino, carboxyl or hydroxyl side groups of the amino acids.

Identification of homologous polypeptides or polypeptide derivatives encoded by polynucleotides of the invention which have specific antigenicity is achieved by screening for cross-reactivity with an antiserum raised against the polypeptide of reference having an amino acid sequence of any one of SEQ ID Nos: 14 to 26. The procedure is as follows: a monospecific hyperimmune antiserum is raised against a purified reference polypeptide, a fusion polypeptide (for example, an expression product of MBP, GST, or His-tag systems), or a synthetic peptide predicted to be antigenic. Where an antiserum is raised against a fusion polypeptide, two different fusion systems are employed. Specific antigenicity can be determined according to a number of methods, including Western blot (Towbin et al., Proc. Natl. Acad. Sci. USA (1979) 76:4350), dot blot, and ELISA, as described below.

In a Western blot assay, the product to be screened, either as a purified preparation or a total *E. coli* extract, is submitted to SDS-Page electrophoresis as described by Laemmle (Nature (1970) 227:680). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 µl of a preparation at about 10 µg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 µl PBS containing 1% bovine serum albumin (BSA) to prevent non-specific antibody binding. After a 1 hour incubation at 37° C., the plate is washed with PBS/Tween buffer. The antiserum is serially diluted in PBS/Tween buffer containing 0.5% BSA. 100 µl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non-immune control serum.

In a dot blot assay, a purified product is preferred, although a whole cell extract can also be used. Briefly, a solution of the product at about 100 µg/ml is serially two-fold diluted in 50 mM Tris-HCl (pH 7.5). 100 µl of each dilution are applied to a nitrocellulose membrane 0.45 µm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below. A seventh aspect of the invention provides (i) a composition of matter comprising a polypeptide of the invention together with a diluent or carrier; specifically (ii) a pharmaceutical composition containing a therapeutically or prophylactically effective amount of a polypeptide of the invention; (iii) a method for inducing an immune response against *Chlamydia* in a mammal, by administering to the mammal an immunogenically effective amount of a polypeptide of the invention to elicit a protective immune response to *Chlamydia*; and particularly, (iv) a method for preventing and/or treating a *Chlamydia* (e.g., *C. trachomatis. C. psittaci, C. pneumoniae.* or *C. pecorum*) infection, by administering a prophylactic or therapeutic amount of a polypeptide of the invention to an infected individual. Additionally, the seventh aspect of the invention encompasses the use of a polypeptide of the invention in the preparation of a medicament for preventing and/or treating *Chlamydia* infection.

As used herein, the immunogenic compositions of the invention are administered by conventional routes known the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of administration route depends upon a number of parameters, such as the adjuvant associated with the polypeptide. If a mucosal adjuvant is used, the intranasal or oral route is preferred. If a lipid formulation or an aluminum compound is used, the parenteral route is preferred with the sub-cutaneous or intramuscular route being most preferred. The choice also depends upon the nature of the vaccine agent. For example, a polypeptide of the invention fused to CTB or LTB is best administered to a mucosal surface.

As used herein, the composition of the invention contains one or several polypeptides or derivatives of the invention. The composition optionally contains at least one additional *Chlamydia* antigen, or a subunit, fragment, homolog, mutant, or derivative thereof.

For use in a composition of the invention, a polypeptide or derivative thereof is formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach, RPC New Ed, IRL press (1990).

Adjuvants other than liposomes and the like are also used and are known in the art. Adjuvants may protect the antigen from rapid dispersal by sequestering it in a local deposit, or they may contain substances that stimulate the host to secrete factors that are chemotactic for macrophages and other components of the immune system. An appropriate selection can conventionally be made by those skilled in the art, for example, from those described below (see the eleventh aspect of the invention).

Treatment is achieved in a single dose or repeated as necessary at intervals, as can be determined readily by one skilled in the art. For example, a priming dose is followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention is administered by a mucosal route in an amount from about 10 μg to about 500 mg, preferably from about 1 mg to about 200 mg. For the parenteral route of administration, the dose usually does not exceed about 1 mg, preferably about 100 μg.

When used as vaccine agents, polynucleotides and polypeptides of the invention may be used sequentially as part of a multistep immunization process. For example, a mammal is initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention is also used for priming, with boosting being carried out mucosally using a soluble polypeptide or derivative of the invention in combination with a mucosal adjuvant (e.g., LT).

A polypeptide derivative of the invention is also used in accordance with the seventh aspect as a diagnostic reagent for detecting the presence of anti-Chlamydia antibodies, e.g., in a blood sample. Such polypeptides are about 5 to about 80, preferably about 10 to about 50 amino acids in length. They are either labeled or unlabeled, depending upon the diagnostic method. Diagnostic methods involving such a reagent are described below.

Upon expression of a DNA molecule of the invention, a polypeptide or polypeptide derivative is produced and purified using known laboratory techniques. As described above, the polypeptide or polypeptide derivative may be produced as a fusion protein containing a fused tail that facilitates purification. The fusion product is used to immunize a small mammal, e.g., a mouse or a rabbit, in order to raise antibodies against the polypeptide or polypeptide derivative (monospecific antibodies). Accordingly, an eighth aspect of the invention provides a monospecific antibody that binds to a polypeptide or polypeptide derivative of the invention.

By "monospecific antibody" is meant an antibody that is capable of reacting with a unique naturally-occurring *Chlamydia* polypeptide. An antibody of the invention is either polyclonal or monoclonal. Monospecific antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

Antibodies against the polypeptides, homologs or fragments of the present invention are generated by immunization of a mammal with a composition comprising said polypeptide, homolog or fragment. Scu antibodies may be polyclonal or monoclonal. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657-680. For monoclonal antibodies, see Kohler and Milstein (1975) Nature. 256:495-497.

The antibodies of the invention, which are raised to a polypeptide or polypeptide derivative of the invention, are produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies are used in diagnostic methods to detect the presence of a *Chlamydia* antigen in a sample, such as a biological sample. The antibodies are also used in affinity chromatography for purifying a polypeptide or polypeptide derivative of the invention. As is discussed further below, such antibodies may be used in prophylactic and therapeutic passive immunization methods.

Accordingly, a ninth aspect of the invention provides (i) a reagent for detecting the presence of *Chlamydia* in a biological sample that contains an antibody, polypeptide, or polypeptide derivative of the invention; and (ii) a diagnostic method for detecting the presence of *Chlamydia* in a biological sample, by contacting the biological sample with an antibody, a polypeptide, or a polypeptide derivative of the invention, such that an immune complex is formed, and by detecting such complex to indicate the presence of *Chlamydia* in the sample or the organism from which the sample is derived.

Those skilled in the art will readily understand that the immune complex is formed between a component of the sample and the antibody, polypeptide, or polypeptide derivative, whichever is used, and that any unbound material is removed prior to detecting the complex. It is understood that a polypeptide reagent is useful for detecting the presence of anti-*Chlamydia* antibodies in a sample, e.g., a blood sample, while an antibody of the invention is used for screening a sample, such as a gastric extract or biopsy, for the presence of *Chlamydia* polypeptides.

For diagnostic applications, the reagent (i.e., the antibody, polypeptide, or polypeptide derivative of the invention) is either in a free state or immobilized on a solid support, such as a tube, a bead, or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means may also employ a ligand-receptor system, for example, where a molecule such as a vitamin is grafted onto the polypeptide reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent is labeled with a detection means which allows for the detection of the reagent when it is bound to its target. The detection means may be a fluorescent agent such as fluorescein isocyanate or fluorescein isothiocyanate, or an enzyme such as horse radish peroxidase or luciferase or alkaline phosphatase, or a radioactive element such as $^{125}$I or $^{51}$Cr.

Accordingly, a tenth aspect of the invention provides a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody is either polyclonal or monospecific, and preferably is of the IgG type. Purified IgGs is prepared from an antiserum using standard methods (see, e.g., Coligan et al., Current Protocols in Immunology (1994) John Wiley & Sons, Inc., New York, N.Y.). Conventional chromatography supports, as well as standard methods for grafting antibodies, are described in, e.g., Antibodies: A Laboratory Manual, D. Lane, E. Harlow, Eds. (1988) and outlined below.

Briefly, a biological sample, such as a *C. pneumoniae* extract preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M MgCl$_2$). Eluted fractions are recovered and the presence of the antigen is detected, e.g., by measuring the absorbance at 280 nm.

An eleventh aspect of the invention provides (i) a composition of matter comprising a monospecific antibody of the invention, together with a diluent or carrier; (ii) a pharmaceutical composition comprising a therapeutically or prophylactically effective amount of a monospecific antibody of the invention, and (iii) a method for treating or preventing a *Chlamydia* (e.g., *C. trachomatis*, *C. psittaci*, *C. pneumoniae* or *C. pecorum*) infection, by administering a therapeutic or prophylactic amount of a monospecific antibody of the invention to an infected individual. Additionally, the eleventh aspect of the invention encompasses the use of a monospecific antibody of the invention in the preparation of a medicament for treating or preventing *Chlamydia* infection.

The monospecific antibody is either polyclonal or monoclonal, preferably of the IgA isotype (predominantly). In passive immunization, the antibody is administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, is carried out. A monospecific antibody of the invention is administered as a single active component or as a mixture with at least one monospecific antibody specific for a different *Chlamydia* polypeptide. The amount of antibody and the particular regimen used are readily determined by one skilled in the art. For example, daily administration of about 100 to 1,000 mg of antibodies over one week, or three doses per day of about 100 to 1,000 mg of antibodies over two or three days, are effective regimens for most purposes.

Therapeutic or prophylactic efficacy are evaluated using standard methods in the art, e.g., by measuring induction of a mucosal immune response or induction of protective and/or therapeutic immunity, using, e.g., the *C. pneumoniae* mouse model. Those skilled in the art will readily recognize that the *C. pneumoniae* strain of the model may be replaced with another *Chlamydia* strain. For example, the efficacy of DNA molecules and polypeptides from *C. pneumoniae* is preferably evaluated in a mouse model using *C. pneumoniae* strain. Protection is determined by comparing the degree of *Chlamydia* infection to that of a control group. Protection is shown when infection is reduced by comparison to the control group. Such an evaluation is made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen is precipitated with, or adsorbed onto, the aluminum compound according to standard protocols. Other adjuvants, such as RIBI (ImmunoChem, Hamilton, Mont.), are used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof such as a purified preparation of native cholera toxin subunit B (CTB). Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/06627 (Arg-192-Gly LT mutant), and WO 95/34323 (Arg-9-Lys and Glu-129-Gly PT mutant). Additional LT mutants that are used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium*, or *Shigella flexneri*; saponins, or polylactide glycolide (PLGA) microspheres, are also be used in mucosal administration.

Adjuvants useful for both mucosal and parenteral administrations include polyphosphazene (WO 95/02415), DC-chol (3 b-(N—(N',N'-dimethyl aminomethane)-carbamoyl)cholesterol; U.S. Pat. No. 5,283,185 and WO 96/14831) and QS-21 (WO 88/09336).

Any pharmaceutical composition of the invention containing a polynucleotide, a polypeptide, a polypeptide derivative, or an antibody of the invention, is manufactured in a conventional manner. In particular, it is formulated with a pharmaceutically acceptable diluent or carrier, e.g., water or a saline solution such as phosphate buffer saline. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which *Chlamydia* infection are treated by oral administration of a *Chlamydia* polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids). In addition, compounds containing more than one of the above-listed components coupled together, are used. The invention also includes compositions for carrying out these methods, i.e., compositions containing a *Chlamydia* antigen (or antigens) of the invention, an adjuvant, and one or more of the above-listed compounds, in a pharmaceutically acceptable carrier or diluent.

Amounts of the above-listed compounds used in the methods and compositions of the invention are readily determined by one skilled in the art. Treatment/immunization schedules are also known and readily designed by one skilled in the art. For example, the non-vaccine components can be administered on days 1-14, and the vaccine antigen+adjuvant can be administered on days 7, 14, 21, and 28.

The invention claimed is:

1. An isolated polypeptide comprising the amino acid sequence set forth in SEQ ID NO:26.

2. A fusion protein comprising the polypeptide defined in claim 1 and a second polypeptide.

3. The fusion protein of claim 2 wherein the second polypeptide is a heterologous signal peptide.

4. The fusion protein of claim 2 wherein the second polypeptide has adjuvant activity.

5. A composition comprising the polypeptide as defined in claim 1 and a pharmaceutically acceptable carrier.

6. A composition comprising the polypeptide as defined in claim 1, and a compound that facilitates delivery and/or enhance an immune response to the amino acid sequence set forth in SEQ ID NO:26.

7. A composition comprising the fusion protein as defined in claim 2.

8. The composition according to claim 6 wherein the compound is a liposome.

9. The composition according to claim 6 wherein the compound is an adjuvant.

10. The composition according to claim 5, further comprising at least one compound selected from the group consisting of an antibiotic, an antacid, sucralfate, and a cytokine immunomodulator.

11. The composition according to claim 6, further comprising at least one compound selected from the group consisting of an antibiotic, an antacid, sucralfate, and a cytokine immunomodulator.

12. The composition according to claim 9, further comprising at least one compound selected from the group consisting of an antibiotic, an antacid, sucralfate, and a cytokine immunomodulator.

13. An isolated polypeptide consisting of the amino acid sequence set forth in SEQ ID NO:26.

14. A fusion protein comprising the polypeptide defined in claim 13 and a second polypeptide.

15. The fusion protein of claim 14 wherein the second polypeptide is a heterologous signal peptide.

16. The fusion protein of claim 14 wherein the second polypeptide has adjuvant activity.

17. A composition comprising the polypeptide as defined in claim 13 and a pharmaceutically acceptable carrier.

18. A composition comprising the polypeptide as defined in claim 13 and a compound that facilitates delivery and/or enhance an immune response to the amino acid sequence set forth in SEQ ID NO:26.

19. A composition comprising the fusion protein as defined in claim 14.

20. The composition according to claim 18 wherein the compound is a liposome.

21. The composition according to claim 18 wherein the compound is an adjuvant.

22. The composition according to claim 17, further comprising at least one compound selected from the group consisting of an antibiotic, an antacid, sucralfate, and a cytokine immunomodulator.

23. The composition according to claim 18, further comprising at least one compound selected from the group consisting of an antibiotic, an antacid, sucralfate, and a cytokine immunomodulator.

24. The composition according to claim 20, further comprising at least one compound selected from the group consisting of an antibiotic, an antacid, sucralfate, and a cytokine immunomodulator.

* * * * *

SEQUENCE LISTING

```
<160> NUMBER OF SEQ ID NOS: 54

<210> SEQ ID NO 1
<211> LENGTH: 1864
<212> TYPE: DNA
<213> ORGANISM: Chlamydia pneumoniae
<220> FEATURE:
<221> NAME/KEY: CDS
<222> LOCATION: (101)..(1756)

<400> SEQUENCE: 1
atggacttcc gcatattgtc aggaggggat cagcggcact gctaatggac aatattctgc      60
aaaccgtgga tggcgtatgg ctgtagtgat tgacggttat atg gtc agc agc cct       115
                                            Met Val Ser Ser Pro
                                              1               5 att tta aac gtc cca ttg aaa aat cat gcc agt gtc tca ggg aaa ttt       163
Ile Leu Asn Val Pro Leu Lys Asn His Ala Ser Val Ser Gly Lys Phe
                10                  15                  20 acc cac cgt gaa gtg agc aaa ctc gcc tca gat tta aaa tct gga gcg       211
Thr His Arg Glu Val Ser Lys Leu Ala Ser Asp Leu Lys Ser Gly Ala
            25                  30                  35 atg tct ttt gtt ccc gag gtt ctc agt gaa gag acg atc tct tct gat       259
Met Ser Phe Val Pro Glu Val Leu Ser Glu Glu Thr Ile Ser Ser Asp
        40                  45                  50 ctt ggg aaa aaa caa tgt aca caa ggc att atc tca gca tgc tgt ggc       307
```

| | | |
|---|---|---|
| Leu Gly Lys Lys Gln Cys Thr Gln Gly Ile Ile Ser Ala Cys Cys Gly<br>55                   60                   65 | | |
| ttg gca atg ctt att gtt ttg atg agc gta tat tat aga ttt gga ggc<br>Leu Ala Met Leu Ile Val Leu Met Ser Val Tyr Tyr Arg Phe Gly Gly<br>70                  75                  80                   85 | | 355 |
| gtc atc gct tcg gga gct gtt ctt ctg aat ctt ttg ctt atc tgg gca<br>Val Ile Ala Ser Gly Ala Val Leu Leu Asn Leu Leu Leu Ile Trp Ala<br>                         90                  95                   100 | | 403 |
| gct cta cag tat ttg gat gcg cca ctc acc ttg tca gga ctc gct ggg<br>Ala Leu Gln Tyr Leu Asp Ala Pro Leu Thr Leu Ser Gly Leu Ala Gly<br>                  105                   110                   115 | | 451 |
| att gtt ctt gct atg ggg atg gcc gta gat gca aat gtt ctt gta ttc<br>Ile Val Leu Ala Met Gly Met Ala Val Asp Ala Asn Val Leu Val Phe<br>         120                   125                   130 | | 499 |
| gaa aga atc cga gag gaa ttt tta ttg tct caa agt ctt aaa aaa tct<br>Glu Arg Ile Arg Glu Glu Phe Leu Leu Ser Gln Ser Leu Lys Lys Ser<br>135                   140                   145 | | 547 |
| gta gaa aaa gga tat acc aag gct ttt gga gcc att ttt gat tct aac<br>Val Glu Lys Gly Tyr Thr Lys Ala Phe Gly Ala Ile Phe Asp Ser Asn<br>150                   155                   160                   165 | | 595 |
| ttg act aca gta ttg gcc tca gca ctt ctt ttc ttc cta gat aca ggg<br>Leu Thr Thr Val Leu Ala Ser Ala Leu Leu Phe Phe Leu Asp Thr Gly<br>                    170                   175                   180 | | 643 |
| cct att aaa ggg ttt gct ttg aca ttg att tta gga att ttc tct tca<br>Pro Ile Lys Gly Phe Ala Leu Thr Leu Ile Leu Gly Ile Phe Ser Ser<br>             185                   190                   195 | | 691 |
| atg ttt acg gct ctt ttc atg act aaa ttt ttc ttc atg ctg tgg atg<br>Met Phe Thr Ala Leu Phe Met Thr Lys Phe Phe Phe Met Leu Trp Met<br>         200                   205                   210 | | 739 |
| aat aag acc caa cat aca cag ttg cat atg atg aat aag ttc gtg ggg<br>Asn Lys Thr Gln His Thr Gln Leu His Met Met Asn Lys Phe Val Gly<br>215                   220                   225 | | 787 |
| ata aag cat gat ttc ttg aga gga tgc aaa aaa ctt tgg gct gtt tct<br>Ile Lys His Asp Phe Leu Arg Gly Cys Lys Lys Leu Trp Ala Val Ser<br>230                   235                   240                   245 | | 835 |
| gga agt gtt ttt ctt tta ggt tgc gtt gct ctc ggg ttt gga gcc tgg<br>Gly Ser Val Phe Leu Leu Gly Cys Val Ala Leu Gly Phe Gly Ala Trp<br>         250                   255                   260 | | 883 |
| aat tcc gtt ttg gga atg gat ttt aaa gga ggg tat gcc ttt acc ttt<br>Asn Ser Val Leu Gly Met Asp Phe Lys Gly Gly Tyr Ala Phe Thr Phe<br>             265                   270                   275 | | 931 |
| aat cca aaa gag cat ggc atc agc gat gtt gct caa atg cgt ggc aaa<br>Asn Pro Lys Glu His Gly Ile Ser Asp Val Ala Gln Met Arg Gly Lys<br>         280                   285                   290 | | 979 |
| gtt gtg cat aaa cta cag gaa gct ggt ctt tct tct aga gac ttc cgt<br>Val Val His Lys Leu Gln Glu Ala Gly Leu Ser Ser Arg Asp Phe Arg<br>295                   300                   305 | | 1027 |
| att caa aca ttt gga tct tca gaa aag atc aaa atc tat ttt agt gat<br>Ile Gln Thr Phe Gly Ser Ser Glu Lys Ile Lys Ile Tyr Phe Ser Asp<br>310                   315                   320                   325 | | 1075 |
| aaa gct tta agc tat act aag cag ata cga gcc tct ctc cta aaa tta<br>Lys Ala Leu Ser Tyr Thr Lys Gln Ile Arg Ala Ser Leu Leu Lys Leu<br>             330                   335                   340 | | 1123 |
| acg atc atg agc tgg cgt tat tgt ggg att gtt gtc aga aac agg cct<br>Thr Ile Met Ser Trp Arg Tyr Cys Gly Ile Val Val Arg Asn Arg Pro<br>         345                   350                   355 | | 1171 |
| aga ttt ctc tac gga aac tct aaa cga aac gca aaa ttt tgg tca aag<br>Arg Phe Leu Tyr Gly Asn Ser Lys Arg Asn Ala Lys Phe Trp Ser Lys<br>360                   365                   370 | | 1219 |

-continued

| | | |
|---|---|---|
| gta agc agc aaa cta tcg aag aaa atg cgt tat cag gcg acc atc ggg<br>Val Ser Ser Lys Leu Ser Lys Lys Met Arg Tyr Gln Ala Thr Ile Gly<br>375 380 385 | 1267 | |
| ctt tta gga gct ttg gca atc atc ttg ctc tat gtg agt ttg cgc ttt<br>Leu Leu Gly Ala Leu Ala Ile Ile Leu Leu Tyr Val Ser Leu Arg Phe<br>390 395 400 405 | 1315 | |
| gaa tgg caa tat gct ttc agt gcc gta tgc gct tta att cat gac ctt<br>Glu Trp Gln Tyr Ala Phe Ser Ala Val Cys Ala Leu Ile His Asp Leu<br>410 415 420 | 1363 | |
| ttg gct acc tgt gca gtc ttg ttt ata gca cat ttc ttt ttg aag aaa<br>Leu Ala Thr Cys Ala Val Leu Phe Ile Ala His Phe Phe Leu Lys Lys<br>425 430 435 | 1411 | |
| att caa ata gat ttg caa gcc att ggt gct tta atg act gta ttg ggg<br>Ile Gln Ile Asp Leu Gln Ala Ile Gly Ala Leu Met Thr Val Leu Gly<br>440 445 450 | 1459 | |
| tat tca tta aac aat act ttg atc att ttt gat cgt att cgt gaa gat<br>Tyr Ser Leu Asn Asn Thr Leu Ile Ile Phe Asp Arg Ile Arg Glu Asp<br>455 460 465 | 1507 | |
| cgc caa gcg aac ctg ttt acc cct atg cat gtt tta gtt aat gat gcc<br>Arg Gln Ala Asn Leu Phe Thr Pro Met His Val Leu Val Asn Asp Ala<br>470 475 480 485 | 1555 | |
| ctt caa aag acg ttc agc cgc acg gta atg aca aca gct aca act cta<br>Leu Gln Lys Thr Phe Ser Arg Thr Val Met Thr Thr Ala Thr Thr Leu<br>490 495 500 | 1603 | |
| tca gtt ttg tta atg ctt ttg ttt ata ggc ggc tcc tct gtc ttt aat<br>Ser Val Leu Leu Met Leu Leu Phe Ile Gly Gly Ser Ser Val Phe Asn<br>505 510 515 | 1651 | |
| ttt gca ttt att atg acc ata ggg att ctt cta gga act tta tcg tct<br>Phe Ala Phe Ile Met Thr Ile Gly Ile Leu Leu Gly Thr Leu Ser Ser<br>520 525 530 | 1699 | |
| ctt tat att gca cca cct ctg ttg ttg ttt atg gtc cgt aaa gaa aat<br>Leu Tyr Ile Ala Pro Pro Leu Leu Leu Phe Met Val Arg Lys Glu Asn<br>535 540 545 | 1747 | |
| cgc tca aaa taagtaccgt taaacttaat ctaacgtgta gcaatataaa<br>Arg Ser Lys<br>550 | 1796 | |
| aatctccttt gggactttag tcccaaaggc ccctgtggta ttaaatttat gacaaattca | 1856 | |
| gataatgc | 1864 | |

<210> SEQ ID NO 2
<211> LENGTH: 800
<212> TYPE: DNA
<213> ORGANISM: Chlamydia pneumoniae
<220> FEATURE:
<221> NAME/KEY: CDS
<222> LOCATION: (101)..(688)

<400> SEQUENCE: 2

| | |
|---|---|
| ttatttaaa agcccatctt tttaggtatg taattaaaat ttttaattaa tgttttccta | 60 |
| gtgtaacctg cttctttagg aactacacta ggagaacggt atg tca tca aat cta<br>Met Ser Ser Asn Leu<br>1 5 | 115 |
| cat ccc gta gga gga aca gga aca gga gca gct gct cct gag tct gtg<br>His Pro Val Gly Gly Thr Gly Thr Gly Ala Ala Ala Pro Glu Ser Val<br>10 15 20 | 163 |
| cta aac ata gta gag gaa ata gca gca tcg ggg agt gtc acc gct ggt<br>Leu Asn Ile Val Glu Glu Ile Ala Ala Ser Gly Ser Val Thr Ala Gly<br>25 30 35 | 211 |
| cta caa gca att acg tcc agt cca gga atg gtg aat cta ctc ata gga<br>Leu Gln Ala Ile Thr Ser Ser Pro Gly Met Val Asn Leu Leu Ile Gly | 259 |

```
                   40                  45                  50
tgg gca aag aca aaa ttt att caa cct ata cgt gaa tca aag ctc ttt    307
Trp Ala Lys Thr Lys Phe Ile Gln Pro Ile Arg Glu Ser Lys Leu Phe
     55                  60                  65 caa tcc aga gct tgc caa att acc ctg ctc gtt tta gga att ctt ttg    355
Gln Ser Arg Ala Cys Gln Ile Thr Leu Leu Val Leu Gly Ile Leu Leu
 70                  75                  80                  85 gtt gtt gct gga tta gca tgt atg ttt atc ttc cat agc cag tta ggg    403
Val Val Ala Gly Leu Ala Cys Met Phe Ile Phe His Ser Gln Leu Gly
                 90                  95                 100 gca aat gca ttt tgg ttg att att cct gct gcc ata gga ttg att aag    451
Ala Asn Ala Phe Trp Leu Ile Ile Pro Ala Ala Ile Gly Leu Ile Lys
                105                 110                 115 tta cta gtt aca tca tta tgt ttt gat gaa gct tgt aca tct gaa aaa    499
Leu Leu Val Thr Ser Leu Cys Phe Asp Glu Ala Cys Thr Ser Glu Lys
                120                 125                 130 ctc atg gtt ttc caa aaa tgg gca ggt gtt tta gaa gat cag ctc gat    547
Leu Met Val Phe Gln Lys Trp Ala Gly Val Leu Glu Asp Gln Leu Asp
 135                 140                 145 gat ggg atc ctt aat aac tca aat aag att ttt ggc cat gtg aaa aca    595
Asp Gly Ile Leu Asn Asn Ser Asn Lys Ile Phe Gly His Val Lys Thr
150                 155                 160                 165 gaa gga aat acc tct agg gct act acc cca gta ctt aat gat ggc cgc    643
Glu Gly Asn Thr Ser Arg Ala Thr Thr Pro Val Leu Asn Asp Gly Arg
                170                 175                 180 gga act cct gta ctt tca cct tta gta agt aaa ata gct cgc gtt         688
Gly Thr Pro Val Leu Ser Pro Leu Val Ser Lys Ile Ala Arg Val
                185                 190                 195 tagacgttca tctcacaagc atcctagaac ttgggatgct actttccacg tacgagatca    748
gatgtaaaga gcaacagtaa ttattttcta cactgttgta ataaaatcat gt            800

<210> SEQ ID NO 3
<211> LENGTH: 950
<212> TYPE: DNA
<213> ORGANISM: Chlamydia pneumoniae
<220> FEATURE:
<221> NAME/KEY: CDS
<222> LOCATION: (101)..(835)

<400> SEQUENCE: 3
tgctggcaga tcgtttccac atgcatactg tgaatctcga tccctatgcg gaaaatgtac    60
ttgtaaactt aaaaaccata gcgacgactt tttctagttt atg aca ata cga att     115
                                             Met Thr Ile Arg Ile
                                               1               5 ctt gct gaa ggc cta gct ttc cgt tac gga agc aag gga ccg aat atc    163
Leu Ala Glu Gly Leu Ala Phe Arg Tyr Gly Ser Lys Gly Pro Asn Ile
             10                  15                  20 att cat gat gtt tct ttc tct gtc tat gat ggc gac ttt ata gga atc    211
Ile His Asp Val Ser Phe Ser Val Tyr Asp Gly Asp Phe Ile Gly Ile
                 25                  30                  35 ata gga cca aac gga ggg ggg aaa agc acc tta acg atg tta att ttg    259
Ile Gly Pro Asn Gly Gly Gly Lys Ser Thr Leu Thr Met Leu Ile Leu
                 40                  45                  50 ggc ttg ctt act cct aca ttc gga tcc ttg aag act ttc cct tcg cat    307
Gly Leu Leu Thr Pro Thr Phe Gly Ser Leu Lys Thr Phe Pro Ser His
 55                  60                  65 tcc gcg ggg aaa caa acc cat tcc atg atc ggt tgg gtt ccc caa cat    355
Ser Ala Gly Lys Gln Thr His Ser Met Ile Gly Trp Val Pro Gln His
 70                  75                  80                  85
```

-continued

| | | |
|---|---|---|
| ttc tct tat gat cct tgt ttt cct atc tca gta aaa gat gtt gtc ctc<br>Phe Ser Tyr Asp Pro Cys Phe Pro Ile Ser Val Lys Asp Val Val Leu<br>                    90                  95                 100 | 403 |
| tca gga aga ttg tct caa ctc tcc tgg cat gga aaa tat aaa aag aaa<br>Ser Gly Arg Leu Ser Gln Leu Ser Trp His Gly Lys Tyr Lys Lys Lys<br>           105                 110                 115 | 451 |
| gat ttt gaa gct gta gat cac gct ttg gat ctt gtt gga ctt tct gac<br>Asp Phe Glu Ala Val Asp His Ala Leu Asp Leu Val Gly Leu Ser Asp<br>      120                 125                 130 | 499 |
| acc acc acc act gct ttc gcc cat ctc tca gga gga caa atc cag cgt<br>Thr Thr Thr Thr Ala Phe Ala His Leu Ser Gly Gly Gln Ile Gln Arg<br>135                 140                 145 | 547 |
| gta ctt ctg gca aga gcc tta gcc tcc tac cct gaa att tta att ctt<br>Val Leu Leu Ala Arg Ala Leu Ala Ser Tyr Pro Glu Ile Leu Ile Leu<br>150                 155                 160                 165 | 595 |
| gat gag ccg acg aca aac att gat cct gac aat caa caa aga att tta<br>Asp Glu Pro Thr Thr Asn Ile Asp Pro Asp Asn Gln Gln Arg Ile Leu<br>                    170                 175                 180 | 643 |
| agt atc cta aaa aag ctc aac cgt acg tgc acc att ctt atg gta act<br>Ser Ile Leu Lys Lys Leu Asn Arg Thr Cys Thr Ile Leu Met Val Thr<br>           185                 190                 195 | 691 |
| cac gat ctt cac cat acg acg aat tac ttt aat aaa gtt ttt tat atg<br>His Asp Leu His His Thr Thr Asn Tyr Phe Asn Lys Val Phe Tyr Met<br>      200                 205                 210 | 739 |
| aac aaa act ttg cac ttc att ggc aga cac ttc gac ctt aac aga cca<br>Asn Lys Thr Leu His Phe Ile Gly Arg His Phe Asp Leu Asn Arg Pro<br>215                 220                 225 | 787 |
| att ttg ttg tca tcc tat aaa aat cag gaa ttt tca tgc tct cct cac<br>Ile Leu Leu Ser Ser Tyr Lys Asn Gln Glu Phe Ser Cys Ser Pro His<br>230                 235                 240                 245 | 835 |
| taatccgtga ttcatttccc cttcttattt tacttcccac attcctagcg gcattaggag | 895 |
| cctccgtagc tggcggcgtt atgggaacct atatcgttgt aaaacgtatt gtttc | 950 |

<210> SEQ ID NO 4
<211> LENGTH: 1050
<212> TYPE: DNA
<213> ORGANISM: Chlamydia pneumoniae
<220> FEATURE:
<221> NAME/KEY: CDS
<222> LOCATION: (101)..(934)

<400> SEQUENCE: 4

| | | |
|---|---|---|
| gagaattttt tcctaagatc accgcttctt aggatattcg ttctttatta aaattatgcc | 60 |
| ccaatagaat aatagatcat cttatcaaac tgcttttgtc atg cat aaa gta ata<br>                                                  Met His Lys Val Ile<br>                                                   1               5 | 115 |
| gtt ttc att ttc ctt acc cta tat tcg tta aaa agt tat ggg aat gat<br>Val Phe Ile Phe Leu Thr Leu Tyr Ser Leu Lys Ser Tyr Gly Asn Asp<br>           10                  15                  20 | 163 |
| gta ata gat aag ccc cat gtt ctt gtc agt atc gcc ccc tat aaa ttc<br>Val Ile Asp Lys Pro His Val Leu Val Ser Ile Ala Pro Tyr Lys Phe<br>      25                  30                  35 | 211 |
| cta gtt gaa caa att gct gaa gag acc tgt ttt gtc tat gcg ata gtt<br>Leu Val Glu Gln Ile Ala Glu Glu Thr Cys Phe Val Tyr Ala Ile Val<br>40                  45                  50 | 259 |
| acg aat cac tat gat ccc cat acc tat gaa ctt cct cct cag caa atc<br>Thr Asn His Tyr Asp Pro His Thr Tyr Glu Leu Pro Pro Gln Gln Ile<br>   55                  60                  65 | 307 |
| aag gag tta cga caa gga gac ctt tgg ttc cgt ata gga gag gca ttt<br>Lys Glu Leu Arg Gln Gly Asp Leu Trp Phe Arg Ile Gly Glu Ala Phe | 355 |

-continued

```
                70                  75                  80                  85
gga aaa aac ttg tta gag aaa cct tac atg caa caa gtc gat ctt tcc       403
Gly Lys Asn Leu Leu Glu Lys Pro Tyr Met Gln Gln Val Asp Leu Ser
             90                  95                 100 caa aat gtc tcg ctg att caa gga aag cct tgc tgt aat caa cat acc       451
Gln Asn Val Ser Leu Ile Gln Gly Lys Pro Cys Cys Asn Gln His Thr
            105                 110                 115 acg aac tac gac acc cac act tgg tta agc cct aaa aac ctt aaa gtc       499
Thr Asn Tyr Asp Thr His Thr Trp Leu Ser Pro Lys Asn Leu Lys Val
            120                 125                 130 caa gtg gag act atc gtt acc act tta agt aaa aaa tat cct caa cac       547
Gln Val Glu Thr Ile Val Thr Thr Leu Ser Lys Lys Tyr Pro Gln His
    135                 140                 145 gcg act cta tat caa agc aat gga gag aaa ctt ctg tta gct ttg gac       595
Ala Thr Leu Tyr Gln Ser Asn Gly Glu Lys Leu Leu Leu Ala Leu Asp
150                 155                 160                 165 caa ctc aat gag gaa att ctt acg att acc tcc aaa gcg aaa caa cgc       643
Gln Leu Asn Glu Glu Ile Leu Thr Ile Thr Ser Lys Ala Lys Gln Arg
                170                 175                 180 cat att tta gtt tcc cat gga gcc ttt ggg tat ttt tgc cgt gat tac       691
His Ile Leu Val Ser His Gly Ala Phe Gly Tyr Phe Cys Arg Asp Tyr
            185                 190                 195 aat ttc tct cag cac act ata gag aaa agc agt cat gtt gag cct tct       739
Asn Phe Ser Gln His Thr Ile Glu Lys Ser Ser His Val Glu Pro Ser
        200                 205                 210 cct aaa gat gtg gct cgc gta ttt cgt gac att gaa cag tac aaa att       787
Pro Lys Asp Val Ala Arg Val Phe Arg Asp Ile Glu Gln Tyr Lys Ile
    215                 220                 225 tct tct gtg att ctt ctc gaa tac tct gga aga cga agt agt gct atg       835
Ser Ser Val Ile Leu Leu Glu Tyr Ser Gly Arg Arg Ser Ser Ala Met
230                 235                 240                 245 ctg gca gat cgt ttc cac atg cat act gtg aat ctc gat ccc tat gcg       883
Leu Ala Asp Arg Phe His Met His Thr Val Asn Leu Asp Pro Tyr Ala
                250                 255                 260 gaa aat gta ctt gta aac tta aaa acc ata gcg acg act ttt tct agt       931
Glu Asn Val Leu Val Asn Leu Lys Thr Ile Ala Thr Thr Phe Ser Ser
            265                 270                 275 tta tgacaatacg aattcttgct gaaggcctag ctttccgtta cggaagcaag            984
Leu ggaccgaata tcattcatga tgtttctttc tctgtctatg atggcgactt tataggaatc    1044
atagga                                                              1050
```

<210> SEQ ID NO 5
<211> LENGTH: 1550
<212> TYPE: DNA
<213> ORGANISM: Chlamydia pneumoniae
<220> FEATURE:
<221> NAME/KEY: CDS
<222> LOCATION: (10)..(1416)

<400> SEQUENCE: 5

```
acaatcact atg ggc cca gga tcg gtt ctt tcc aac cat agc aaa gaa gca       51
           Met Gly Pro Gly Ser Val Leu Ser Asn His Ser Lys Glu Ala
            1               5                  10 gga gga atc gct ata aac aat gtc atc att gat ttt agt gaa atc gtt          99
Gly Gly Ile Ala Ile Asn Asn Val Ile Ile Asp Phe Ser Glu Ile Val
 15                  20                  25                  30 cct act aaa gat aat gca aca gta gct cca ccc act ctt aaa tta gta        147
Pro Thr Lys Asp Asn Ala Thr Val Ala Pro Pro Thr Leu Lys Leu Val
                 35                  40                  45
```

```
tcg aga act aat gca gat agt aaa gat aag att gat att aca gga act        195
Ser Arg Thr Asn Ala Asp Ser Lys Asp Lys Ile Asp Ile Thr Gly Thr
             50                  55                  60 gtg act ctt cta gat cct aat ggc aac tta tat caa aat tct tat ctt        243
Val Thr Leu Leu Asp Pro Asn Gly Asn Leu Tyr Gln Asn Ser Tyr Leu
         65                  70                  75 ggt gaa gac cgc gat atc act ctt ttc aat ata gac aat tct gca agt        291
Gly Glu Asp Arg Asp Ile Thr Leu Phe Asn Ile Asp Asn Ser Ala Ser
 80                  85                  90 ggg gca gtt aca gcc acg aat gtc acc ctt caa ggg aat tta gga gct        339
Gly Ala Val Thr Ala Thr Asn Val Thr Leu Gln Gly Asn Leu Gly Ala
 95                 100                 105                 110 aaa aaa gga tat tta gga acc tgg aat ttg gat cca aat tcc tcg ggt        387
Lys Lys Gly Tyr Leu Gly Thr Trp Asn Leu Asp Pro Asn Ser Ser Gly
                115                 120                 125 tca aaa att att cta aaa tgg acc ttt gac aaa tac ctg cgc tgg ccc        435
Ser Lys Ile Ile Leu Lys Trp Thr Phe Asp Lys Tyr Leu Arg Trp Pro
            130                 135                 140 tac atc cct aga gac aac cac ttc tac atc aac tct att tgg gga gca        483
Tyr Ile Pro Arg Asp Asn His Phe Tyr Ile Asn Ser Ile Trp Gly Ala
                145                 150                 155 caa aac tct tta gtg act gtg aac caa ggg atc tta ggg aac atg ttg        531
Gln Asn Ser Leu Val Thr Val Asn Gln Gly Ile Leu Gly Asn Met Leu
        160                 165                 170 aac aat gca agg ttt gaa gat cct gct ttc aac aac ttc tgg gct tcg        579
Asn Asn Ala Arg Phe Glu Asp Pro Ala Phe Asn Asn Phe Trp Ala Ser
175                 180                 185                 190 gct ata gga tct ttc ctt agg aaa gaa gta tct cga aat tct gac tca        627
Ala Ile Gly Ser Phe Leu Arg Lys Glu Val Ser Arg Asn Ser Asp Ser
                195                 200                 205 ttc acc tat cat ggc aga ggc tat acc gct gct gtg gat gcc aaa cct        675
Phe Thr Tyr His Gly Arg Gly Tyr Thr Ala Ala Val Asp Ala Lys Pro
            210                 215                 220 cgc caa gaa ttt att tta gga gct gcc ttc agt cag gtt ttt ggt cac        723
Arg Gln Glu Phe Ile Leu Gly Ala Ala Phe Ser Gln Val Phe Gly His
                225                 230                 235 gcc gag tct gaa tat cac ctt gac aac tat aag cat aaa ggc tca ggt        771
Ala Glu Ser Glu Tyr His Leu Asp Asn Tyr Lys His Lys Gly Ser Gly
        240                 245                 250 cac tct aca caa gca tct ctt tat gct ggc aat atc ttc tat ttt cct        819
His Ser Thr Gln Ala Ser Leu Tyr Ala Gly Asn Ile Phe Tyr Phe Pro
255                 260                 265                 270 gcg ata cgg tct cgg cct att cta ttc caa ggt gtg gcg acc tat ggt        867
Ala Ile Arg Ser Arg Pro Ile Leu Phe Gln Gly Val Ala Thr Tyr Gly
                275                 280                 285 tat atg caa cat gac acc aca acc tac tat cct tct att gaa gaa aaa        915
Tyr Met Gln His Asp Thr Thr Thr Tyr Tyr Pro Ser Ile Glu Glu Lys
            290                 295                 300 aat atg gca aac tgg gat agc att gct tgg tta ttt gat ctg cgt ttc        963
Asn Met Ala Asn Trp Asp Ser Ile Ala Trp Leu Phe Asp Leu Arg Phe
                305                 310                 315 agt gtg gat ctt aaa gaa cct caa cct cac tct aca gca agg ctt acc       1011
Ser Val Asp Leu Lys Glu Pro Gln Pro His Ser Thr Ala Arg Leu Thr
        320                 325                 330 ttc tat aca gaa gct gag tat acc aga att cgc cag gag aaa ttc aca       1059
Phe Tyr Thr Glu Ala Glu Tyr Thr Arg Ile Arg Gln Glu Lys Phe Thr
335                 340                 345                 350 gag cta gac tat gat cct aga tct ttc tct gca tgc tct tat gga aac       1107
Glu Leu Asp Tyr Asp Pro Arg Ser Phe Ser Ala Cys Ser Tyr Gly Asn
```

-continued

```
                   355                 360                 365
tta gca att cct act gga ttc tct gta gac gga gca tta gct tgg cgt       1155
Leu Ala Ile Pro Thr Gly Phe Ser Val Asp Gly Ala Leu Ala Trp Arg
            370                 375                 380 gag att att cta tat aat aaa gta tca gct gcg tac ctc cct gtg att       1203
Glu Ile Ile Leu Tyr Asn Lys Val Ser Ala Ala Tyr Leu Pro Val Ile
        385                 390                 395 ctc agg aat aat cca aaa gcg acc tat gaa gtt ctc tct aca aaa gaa       1251
Leu Arg Asn Asn Pro Lys Ala Thr Tyr Glu Val Leu Ser Thr Lys Glu
    400                 405                 410 aag ggc aac gta gtc aac gtt ctc cct aca aga aac gca gct cgt gca       1299
Lys Gly Asn Val Val Asn Val Leu Pro Thr Arg Asn Ala Ala Arg Ala
415                 420                 425                 430 gag gtg agc tct caa att tat ctt gga agt tac tgg aca ctc tac ggc       1347
Glu Val Ser Ser Gln Ile Tyr Leu Gly Ser Tyr Trp Thr Leu Tyr Gly
                435                 440                 445 acg tat act att gat gct tca atg aat act tta gtg caa atg gcc aac       1395
Thr Tyr Thr Ile Asp Ala Ser Met Asn Thr Leu Val Gln Met Ala Asn
            450                 455                 460 gga ggg atc cgg ttt gta ttc tagggtatac aattaaagat tttatgaaat          1446
Gly Gly Ile Arg Phe Val Phe
        465 tgaggatacg gagagagtgg gattcgaacc cacggtacgc gttaacgcac acacgctttc     1506 caagcgtgct ccttaagcca ctcggacatc tctccatatt tata                      1550

<210> SEQ ID NO 6
<211> LENGTH: 2950
<212> TYPE: DNA
<213> ORGANISM: Chlamydia pneumoniae
<220> FEATURE:
<221> NAME/KEY: CDS
<222> LOCATION: (101)..(2866)

<400> SEQUENCE: 6
aattcttttt aagtgacaag aaattcttgt gctcggcttg ctttcttatt cttattgacg      60
tattgcttga tcagatattc attttgattt aggtactaaa atg cga ttt tcg ctc       115
                                              Met Arg Phe Ser Leu
                                                1               5 tgc gga ttt cct cta gtt ttt tct ttt aca ttg ctc tca gtc ttc gac       163
Cys Gly Phe Pro Leu Val Phe Ser Phe Thr Leu Leu Ser Val Phe Asp
            10                  15                  20 act tct ttg agt gct act acg att tct tta acc cca gaa gat agt ttt       211
Thr Ser Leu Ser Ala Thr Thr Ile Ser Leu Thr Pro Glu Asp Ser Phe
        25                  30                  35 cat gga gat agt cag aat gca gaa cgt tct tat aat gtt caa gct ggg       259
His Gly Asp Ser Gln Asn Ala Glu Arg Ser Tyr Asn Val Gln Ala Gly
    40                  45                  50 gat gtc tat agc ctt act ggt gat gtc tca ata tct aac gtc gat aac       307
Asp Val Tyr Ser Leu Thr Gly Asp Val Ser Ile Ser Asn Val Asp Asn
55                  60                  65 tct gca tta aat aaa gcc tgc ttc aat gtg acc tca gga agt gtg acg       355
Ser Ala Leu Asn Lys Ala Cys Phe Asn Val Thr Ser Gly Ser Val Thr
70                  75                  80                  85 ttc gca gga aat cat cat ggg tta tat ttt aat aat att tcc tca gga       403
Phe Ala Gly Asn His His Gly Leu Tyr Phe Asn Asn Ile Ser Ser Gly
            90                  95                 100 act aca aag gaa ggg gct gta ctt tgt tgc caa gat cct caa gca acg       451
Thr Thr Lys Glu Gly Ala Val Leu Cys Cys Gln Asp Pro Gln Ala Thr
        105                 110                 115
```

```
gca cgt ttt tct ggg ttc tcc acg ctc tct ttt att cag agc ccc gga      499
Ala Arg Phe Ser Gly Phe Ser Thr Leu Ser Phe Ile Gln Ser Pro Gly
        120                 125                 130 gat att aaa gaa cag gga tgt ctc tat tca aaa aat gca ctt atg ctc      547
Asp Ile Lys Glu Gln Gly Cys Leu Tyr Ser Lys Asn Ala Leu Met Leu
135                 140                 145 tta aac aat tat gta gtg cgt ttt gaa caa aac caa agt aag act aaa      595
Leu Asn Asn Tyr Val Val Arg Phe Glu Gln Asn Gln Ser Lys Thr Lys
150                 155                 160                 165 ggc gga gct att agt ggg gcg aat gtt act ata gta ggc aac tac gat      643
Gly Gly Ala Ile Ser Gly Ala Asn Val Thr Ile Val Gly Asn Tyr Asp
                170                 175                 180 tcc gtc tct ttc tat cag aat gca gcc act ttt gga ggt gct atc cat      691
Ser Val Ser Phe Tyr Gln Asn Ala Ala Thr Phe Gly Gly Ala Ile His
                185                 190                 195 tct tca ggt ccc cta cag att gca gta aat cag gca gag ata aga ttt      739
Ser Ser Gly Pro Leu Gln Ile Ala Val Asn Gln Ala Glu Ile Arg Phe
                200                 205                 210 gca caa aat act gcc aag aat ggt tct gga ggg gct ttg tac tcc gat      787
Ala Gln Asn Thr Ala Lys Asn Gly Ser Gly Gly Ala Leu Tyr Ser Asp
        215                 220                 225 ggt gat att gat att gat cag aat gct tat gtt cta ttt cga gaa aat      835
Gly Asp Ile Asp Ile Asp Gln Asn Ala Tyr Val Leu Phe Arg Glu Asn
230                 235                 240                 245 gag gca ttg act act gct ata ggt aag gga ggg gct gtc tgt tgt ctt      883
Glu Ala Leu Thr Thr Ala Ile Gly Lys Gly Gly Ala Val Cys Cys Leu
                250                 255                 260 ccc act tca gga agt agt act cca gtt cct att gtg act ttc tct gac      931
Pro Thr Ser Gly Ser Ser Thr Pro Val Pro Ile Val Thr Phe Ser Asp
                265                 270                 275 aat aaa cag tta gtc ttt gaa aga aac cat tcc ata atg ggt ggc gga      979
Asn Lys Gln Leu Val Phe Glu Arg Asn His Ser Ile Met Gly Gly Gly
        280                 285                 290 gcc att tat gct agg aaa ctt agc atc tct tca gga ggt cct act cta     1027
Ala Ile Tyr Ala Arg Lys Leu Ser Ile Ser Ser Gly Gly Pro Thr Leu
    295                 300                 305 ttt atc aat aat ata tca tat gca aat tcg caa aat tta ggt gga gct     1075
Phe Ile Asn Asn Ile Ser Tyr Ala Asn Ser Gln Asn Leu Gly Gly Ala
310                 315                 320                 325 att gcc att gat act gga ggg gag atc agt tta tca gca gag aaa gga     1123
Ile Ala Ile Asp Thr Gly Gly Glu Ile Ser Leu Ser Ala Glu Lys Gly
                330                 335                 340 aca att aca ttc caa gga aac cgg acg agc tta ccg ttt ttg aat ggc     1171
Thr Ile Thr Phe Gln Gly Asn Arg Thr Ser Leu Pro Phe Leu Asn Gly
        345                 350                 355 atc cat ctt tta caa aat gct aaa ttc ctg aaa tta cag gcg aga aat     1219
Ile His Leu Leu Gln Asn Ala Lys Phe Leu Lys Leu Gln Ala Arg Asn
        360                 365                 370 gga tac tct ata gaa ttt tat gat cct att act tct gaa gca gat ggg     1267
Gly Tyr Ser Ile Glu Phe Tyr Asp Pro Ile Thr Ser Glu Ala Asp Gly
    375                 380                 385 tct acc caa ttg aat atc aac gga gat cct aaa aat aaa gag tac aca     1315
Ser Thr Gln Leu Asn Ile Asn Gly Asp Pro Lys Asn Lys Glu Tyr Thr
390                 395                 400                 405 ggg acc ata ctc ttt tct gga gaa aag agt cta gca aac gat cct agg     1363
Gly Thr Ile Leu Phe Ser Gly Glu Lys Ser Leu Ala Asn Asp Pro Arg
                410                 415                 420 gat ttt aaa tct aca atc cct cag aac gtc aac ctg tct gca gga tac     1411
Asp Phe Lys Ser Thr Ile Pro Gln Asn Val Asn Leu Ser Ala Gly Tyr
        425                 430                 435
```

```
tta gtt att aaa gag ggg gcc gaa gtc aca gtt tca aaa ttc acg cag     1459
Leu Val Ile Lys Glu Gly Ala Glu Val Thr Val Ser Lys Phe Thr Gln
            440                 445                 450 tct cca gga tcg cat tta gtt tta gat tta gga acc aaa ctg ata gcc     1507
Ser Pro Gly Ser His Leu Val Leu Asp Leu Gly Thr Lys Leu Ile Ala
455                 460                 465 tct aag gaa gac att gcc atc aca ggc ctc gcg ata gat ata gat agc     1555
Ser Lys Glu Asp Ile Ala Ile Thr Gly Leu Ala Ile Asp Ile Asp Ser
470                 475                 480                 485 tta agc tca tcc tca aca gca gct gtt att aaa gca aac acc gca aat     1603
Leu Ser Ser Ser Ser Thr Ala Ala Val Ile Lys Ala Asn Thr Ala Asn
                490                 495                 500 aaa cag ata tcc gtg acg gac tct ata gaa ctt atc tcg cct act ggc     1651
Lys Gln Ile Ser Val Thr Asp Ser Ile Glu Leu Ile Ser Pro Thr Gly
            505                 510                 515 aat gcc tat gaa gat ctc aga atg aga aat tca cag acg ttc cct ctg     1699
Asn Ala Tyr Glu Asp Leu Arg Met Arg Asn Ser Gln Thr Phe Pro Leu
        520                 525                 530 ctc tct tta gag cct gga gcc ggg ggt agt gtg act gta act gct gga     1747
Leu Ser Leu Glu Pro Gly Ala Gly Gly Ser Val Thr Val Thr Ala Gly
535                 540                 545 gat ttc cta ccg gta agt ccc cat tat ggt ttt caa ggc aat tgg aaa     1795
Asp Phe Leu Pro Val Ser Pro His Tyr Gly Phe Gln Gly Asn Trp Lys
550                 555                 560                 565 tta gct tgg aca gga act gga aac aaa gtt gga gaa ttc ttc tgg gat     1843
Leu Ala Trp Thr Gly Thr Gly Asn Lys Val Gly Glu Phe Phe Trp Asp
                570                 575                 580 aaa ata aat tat aag cct aga cct gaa aaa gaa gga aat tta gtt cct     1891
Lys Ile Asn Tyr Lys Pro Arg Pro Glu Lys Glu Gly Asn Leu Val Pro
            585                 590                 595 aat atc ttg tgg ggg aat gct gta gat gtc aga tcc tta atg cag gtt     1939
Asn Ile Leu Trp Gly Asn Ala Val Asp Val Arg Ser Leu Met Gln Val
        600                 605                 610 caa gag acc cat gca tcg agc tta cag aca gat cga ggg ctg tgg atc     1987
Gln Glu Thr His Ala Ser Ser Leu Gln Thr Asp Arg Gly Leu Trp Ile
615                 620                 625 gat gga att ggg aat ttc ttc cat gta tct gcc tcc gaa gac aat ata     2035
Asp Gly Ile Gly Asn Phe Phe His Val Ser Ala Ser Glu Asp Asn Ile
630                 635                 640                 645 agg tac cgt cat aac agc ggt gga tat gtt cta tct gta aat aat gag     2083
Arg Tyr Arg His Asn Ser Gly Gly Tyr Val Leu Ser Val Asn Asn Glu
                650                 655                 660 atc aca cct aag cac tat act tcg atg gca ttt tcc caa ctc ttt agt     2131
Ile Thr Pro Lys His Tyr Thr Ser Met Ala Phe Ser Gln Leu Phe Ser
            665                 670                 675 aga gac aag gac tat gcg gtt tcc aac aac gaa tac aga atg tat tta     2179
Arg Asp Lys Asp Tyr Ala Val Ser Asn Asn Glu Tyr Arg Met Tyr Leu
        680                 685                 690 gga tcg tat ctc tat caa tat aca acc tcc cta ggg aat att ttc cgt     2227
Gly Ser Tyr Leu Tyr Gln Tyr Thr Thr Ser Leu Gly Asn Ile Phe Arg
695                 700                 705 tat gct tcg cgt aac cct aat gta aac gtc ggg att ctc tca aga agg     2275
Tyr Ala Ser Arg Asn Pro Asn Val Asn Val Gly Ile Leu Ser Arg Arg
710                 715                 720                 725 ttt ctt caa aat cct ctt atg att ttt cat ttt ttg tgt gct tat ggt     2323
Phe Leu Gln Asn Pro Leu Met Ile Phe His Phe Leu Cys Ala Tyr Gly
                730                 735                 740 cat gcc acc aat gat atg aaa aca gac tac gca aat ttc cct atg gtg     2371
His Ala Thr Asn Asp Met Lys Thr Asp Tyr Ala Asn Phe Pro Met Val
```

```
                  745                 750                 755
aaa aac agc tgg aga aac aat tgt tgg gct ata gag tgc gga ggg agc       2419
Lys Asn Ser Trp Arg Asn Asn Cys Trp Ala Ile Glu Cys Gly Gly Ser
            760                 765                 770 atg cct cta ttg gta ttt gag aac gga aga ctt ttc caa ggt gcc atc       2467
Met Pro Leu Leu Val Phe Glu Asn Gly Arg Leu Phe Gln Gly Ala Ile
775                 780                 785 cca ttt atg aaa cta caa tta gtt tat gct tat cat gga gat ttc aaa       2515
Pro Phe Met Lys Leu Gln Leu Val Tyr Ala Tyr His Gly Asp Phe Lys
790                 795                 800                 805 gag acg act gca gat ggc cgt aga ttt agt aat ggg agt tta aca tcg       2563
Glu Thr Thr Ala Asp Gly Arg Arg Phe Ser Asn Gly Ser Leu Thr Ser
            810                 815                 820 att tct gta cct cta ggc ata cgc ttt gag aag ctg gca ctt tct cag       2611
Ile Ser Val Pro Leu Gly Ile Arg Phe Glu Lys Leu Ala Leu Ser Gln
            825                 830                 835 gat gta ctc tat gac ttt agt ttc tcc tat att cct gat att ttc cgt       2659
Asp Val Leu Tyr Asp Phe Ser Phe Ser Tyr Ile Pro Asp Ile Phe Arg
            840                 845                 850 aag gat ccc tca tgt gaa gct gct ctg gtg att agc gga gac tcc tgg       2707
Lys Asp Pro Ser Cys Glu Ala Ala Leu Val Ile Ser Gly Asp Ser Trp
855                 860                 865 ctt gtt ccg gca gca cac gta tca aga cat gct ttt gta ggg agt gga       2755
Leu Val Pro Ala Ala His Val Ser Arg His Ala Phe Val Gly Ser Gly
870                 875                 880                 885 acg ggt cgg tat cac ttt aac gac tat act gag ctc tta tgt cga gga       2803
Thr Gly Arg Tyr His Phe Asn Asp Tyr Thr Glu Leu Leu Cys Arg Gly
            890                 895                 900 agt ata gaa tgc cgc ccc cat gct agg aat tat aat ata aac tgt gga       2851
Ser Ile Glu Cys Arg Pro His Ala Arg Asn Tyr Asn Ile Asn Cys Gly
            905                 910                 915 agc aaa ttt cgt ttt tagaaggttt ccattgcctg tgtggttccg gatcttaact       2906
Ser Lys Phe Arg Phe
            920 ataaatcctg gactatggat cataggcatt gggtttctcg aact                      2950

<210> SEQ ID NO 7
<211> LENGTH: 1328
<212> TYPE: DNA
<213> ORGANISM: Chlamydia pneumoniae
<220> FEATURE:
<221> NAME/KEY: CDS
<222> LOCATION: (101)..(1225)
<220> FEATURE:
<221> NAME/KEY: unsure
<222> LOCATION: (1254)...(1323)
<223> OTHER INFORMATION: n is a or g or c or t/u, unknown, or other

<400> SEQUENCE: 7
gtgggggcat tgctggggga aaagcacatt tcgatcgcat tgataatctt atcagtccaa       60
agcaaccaag caaagaaagg tggtggggtt tatcttgaag atg ccc tca tcc tgg       115
                                              Met Pro Ser Ser Trp
                                              1               5 aaa agg tta tta cag gtt ctg tct cac aaa ata gca gct aca gaa agt       163
Lys Arg Leu Leu Gln Val Leu Ser His Lys Ile Ala Ala Thr Glu Ser
                10                  15                  20 ggt ggg ggt atc tac gct aag gat att caa cta caa gct cta cct gga       211
Gly Gly Gly Ile Tyr Ala Lys Asp Ile Gln Leu Gln Ala Leu Pro Gly
            25                  30                  35 agc ttc aca att acc gat aat aaa gtc gaa act agt ctt act act agc       259
Ser Phe Thr Ile Thr Asp Asn Lys Val Glu Thr Ser Leu Thr Thr Ser
```

```
                40                      45                      50
act aat tta tat ggt ggg ggc atc tat tcc agt gga gct gtc acg cta        307
Thr Asn Leu Tyr Gly Gly Gly Ile Tyr Ser Ser Gly Ala Val Thr Leu
         55                      60                      65 acc aat ata tct gga acc ttt ggc att aca gga aac tct gtt atc aat        355
Thr Asn Ile Ser Gly Thr Phe Gly Ile Thr Gly Asn Ser Val Ile Asn
 70                      75                      80                 85 aca gcg aca tcc cag gat gca gat ata caa ggt ggg ggc att tat gca        403
Thr Ala Thr Ser Gln Asp Ala Asp Ile Gln Gly Gly Gly Ile Tyr Ala
             90                      95                     100 acc acg tct ctc tca ata aat caa tgt aat aca ccc att cta ttt agc        451
Thr Thr Ser Leu Ser Ile Asn Gln Cys Asn Thr Pro Ile Leu Phe Ser
                105                     110                     115 aac aac tct gct gcc act aaa aaa aca tca aca aca aag caa att gct        499
Asn Asn Ser Ala Ala Thr Lys Lys Thr Ser Thr Thr Lys Gln Ile Ala
            120                     125                     130 ggt ggg gct atc ttc tcc gct gca gta act atc gag aat aac tct cag        547
Gly Gly Ala Ile Phe Ser Ala Ala Val Thr Ile Glu Asn Asn Ser Gln
        135                     140                     145 ccc att att ttc tta aat aat tcc gca aag tcg gaa gca act aca gca        595
Pro Ile Ile Phe Leu Asn Asn Ser Ala Lys Ser Glu Ala Thr Thr Ala
150                     155                     160                 165 gca act gca gga aat aaa gat agc tgt gga gga gcc att gca gct aac        643
Ala Thr Ala Gly Asn Lys Asp Ser Cys Gly Gly Ala Ile Ala Ala Asn
                170                     175                     180 tct gtt act tta aca aat aac cct gaa ata acc ttt aaa gga aat tat        691
Ser Val Thr Leu Thr Asn Asn Pro Glu Ile Thr Phe Lys Gly Asn Tyr
            185                     190                     195 gca gaa act gga gga gcg att ggc tgt att gat ctt act aat ggc tca        739
Ala Glu Thr Gly Gly Ala Ile Gly Cys Ile Asp Leu Thr Asn Gly Ser
        200                     205                     210 cct ccc cgt aaa gtc tct att gca gac aac ggt tct gtc ctt ttt caa        787
Pro Pro Arg Lys Val Ser Ile Ala Asp Asn Gly Ser Val Leu Phe Gln
215                     220                     225 gac aac tct gcg tta aat cgc gga ggc gct atc tat gga gag act atc        835
Asp Asn Ser Ala Leu Asn Arg Gly Gly Ala Ile Tyr Gly Glu Thr Ile
230                     235                     240                 245 gat atc tcc agg aca ggt gcg act ttc atc ggt aac tct tca aaa cat        883
Asp Ile Ser Arg Thr Gly Ala Thr Phe Ile Gly Asn Ser Ser Lys His
                250                     255                     260 gat gga agt gca att tgc tgt tca aca gcc cta act ctt gcg cca aac        931
Asp Gly Ser Ala Ile Cys Cys Ser Thr Ala Leu Thr Leu Ala Pro Asn
            265                     270                     275 tcc caa ctt atc ttt gaa aac aat aag gtt acg gaa acc aca gcc act        979
Ser Gln Leu Ile Phe Glu Asn Asn Lys Val Thr Glu Thr Thr Ala Thr
        280                     285                     290 aca aaa gct tcc ata aat aat tta gga gct gca att tat gga aat aat        1027
Thr Lys Ala Ser Ile Asn Asn Leu Gly Ala Ala Ile Tyr Gly Asn Asn
295                     300                     305 gag act agt gac gtc act atc tct tta tca gct gag aat gga agt att        1075
Glu Thr Ser Asp Val Thr Ile Ser Leu Ser Ala Glu Asn Gly Ser Ile
310                     315                     320                 325 ttc ttt aaa aac aat cta tgc aca gca aca aac aaa tac tgc agt att        1123
Phe Phe Lys Asn Asn Leu Cys Thr Ala Thr Asn Lys Tyr Cys Ser Ile
                330                     335                     340 gct gga aac gta aaa ttt aca gca ata gaa gct tca gca ggg aaa gct        1171
Ala Gly Asn Val Lys Phe Thr Ala Ile Glu Ala Ser Ala Gly Lys Ala
            345                     350                     355 ata tct ttc tat gat gca gtt aac gtt cca cca aag aaa caa ttg ctc        1219
```

```
                Ile Ser Phe Tyr Asp Ala Val Asn Val Pro Pro Lys Lys Gln Leu Leu
                        360                 365                 370 aag agc taaattaaat gaaaaagcga caagtacang gacgtttcta ntttctgggg          1275
Lys Ser
    375 gacttcacgg aaataaatcc ctattccaca gaaagtcact tcgccctngg gat              1328

<210> SEQ ID NO 8
<211> LENGTH: 2816
<212> TYPE: DNA
<213> ORGANISM: Chlamydia pneumoniae
<220> FEATURE:
<221> NAME/KEY: CDS
<222> LOCATION: (101)..(2713)

<400> SEQUENCE: 8
ttacttgatt tatttaactg tattctctat tggtgcacca tgctcctaaa gccacatgct        60
atgggagtat ttttgataaa aagcttttcc ccaaagacac atg aaa tat tct tta        115
                                              Met Lys Tyr Ser Leu
                                                1               5 cct tgg cta ctt acc tct tcg gct tta gtt ttc tcc cta cat cca cta        163
Pro Trp Leu Leu Thr Ser Ser Ala Leu Val Phe Ser Leu His Pro Leu
             10                  15                  20 atg gct gct aac acg gat ctc tca tca tcc gat aac tat gaa aat ggt        211
Met Ala Ala Asn Thr Asp Leu Ser Ser Ser Asp Asn Tyr Glu Asn Gly
         25                  30                  35 agt agt ggt agc gca gca ttc act gcc aag gaa act tcg gat gct tca        259
Ser Ser Gly Ser Ala Ala Phe Thr Ala Lys Glu Thr Ser Asp Ala Ser
     40                  45                  50 gga act acc tac act ctc act agc gat gtt tct att acg aat gta tct        307
Gly Thr Thr Tyr Thr Leu Thr Ser Asp Val Ser Ile Thr Asn Val Ser
 55                  60                  65 gca att act cct gca gat aaa agc tgt ttt aca aac aca gga gga gca        355
Ala Ile Thr Pro Ala Asp Lys Ser Cys Phe Thr Asn Thr Gly Gly Ala
 70                  75                  80                  85 ttg agt ttt gtt gga gct gat cac tca ttg gtt ctg caa acc ata gcg        403
Leu Ser Phe Val Gly Ala Asp His Ser Leu Val Leu Gln Thr Ile Ala
             90                  95                 100 ctt acg cat gat ggt gct gca att aac aat acc aac aca gct ctt tct        451
Leu Thr His Asp Gly Ala Ala Ile Asn Asn Thr Asn Thr Ala Leu Ser
         105                 110                 115 ttc tca gga ttc tcg tca ctc tta atc gac tca gct cca gca aca gga        499
Phe Ser Gly Phe Ser Ser Leu Leu Ile Asp Ser Ala Pro Ala Thr Gly
     120                 125                 130 act tcg ggc ggc aag ggt gct att tgt gtg aca aat aca gag gga ggt        547
Thr Ser Gly Gly Lys Gly Ala Ile Cys Val Thr Asn Thr Glu Gly Gly
 135                 140                 145 act gcg act ttt act gac aat gcc agt gtc acc ctc caa aaa aat act        595
Thr Ala Thr Phe Thr Asp Asn Ala Ser Val Thr Leu Gln Lys Asn Thr
150                 155                 160                 165 tca gaa aaa gat gga gct gca gtt tct gcc tac agc atc gat ctt gct        643
Ser Glu Lys Asp Gly Ala Ala Val Ser Ala Tyr Ser Ile Asp Leu Ala
             170                 175                 180 aag act acg aca gca gct ctc tta gat caa aat act agc aca aaa aat        691
Lys Thr Thr Thr Ala Ala Leu Leu Asp Gln Asn Thr Ser Thr Lys Asn
         185                 190                 195 ggc ggg gcc ctc tgt agt aca gca aac act aca gtc caa gga aac tca        739
Gly Gly Ala Leu Cys Ser Thr Ala Asn Thr Thr Val Gln Gly Asn Ser
     200                 205                 210 gga acg gtg acc ttc tcc tca aat act gct aca gat aaa ggt ggg ggg        787
```

```
                                                                -continued

Gly Thr Val Thr Phe Ser Ser Asn Thr Ala Thr Asp Lys Gly Gly Gly
    215                 220                 225 atc tac tca aaa gaa aag gat agc acg cta gat gcc aat aca gga gtc        835
Ile Tyr Ser Lys Glu Lys Asp Ser Thr Leu Asp Ala Asn Thr Gly Val
230                 235                 240                 245 gtt acc ttc aaa tct aat act gca aag acg ggg ggt gct tgg agc tct        883
Val Thr Phe Lys Ser Asn Thr Ala Lys Thr Gly Gly Ala Trp Ser Ser
                250                 255                 260 gat gac aat ctt gct ctt acc ggc aac act caa gta ctt ttt cag gaa        931
Asp Asp Asn Leu Ala Leu Thr Gly Asn Thr Gln Val Leu Phe Gln Glu
            265                 270                 275 aat aaa aca acc ggc tca gca gca cag gca aat aac ccg gaa ggt tgt        979
Asn Lys Thr Thr Gly Ser Ala Ala Gln Ala Asn Asn Pro Glu Gly Cys
        280                 285                 290 ggt ggg gca atc tgt tgt tat ctt gct aca gca aca gac aaa act gga       1027
Gly Gly Ala Ile Cys Cys Tyr Leu Ala Thr Ala Thr Asp Lys Thr Gly
    295                 300                 305 tta gcc att tct cag aat caa gaa atg agc ttc act agt aat aca aca       1075
Leu Ala Ile Ser Gln Asn Gln Glu Met Ser Phe Thr Ser Asn Thr Thr
310                 315                 320                 325 act gcg aat ggt gga gcg atc tac gct act aaa tgt act ctg gat gga       1123
Thr Ala Asn Gly Gly Ala Ile Tyr Ala Thr Lys Cys Thr Leu Asp Gly
                330                 335                 340 aac aca act ctt acc ttc gat cag aat act gcg aca gca gga tgt ggc       1171
Asn Thr Thr Leu Thr Phe Asp Gln Asn Thr Ala Thr Ala Gly Cys Gly
            345                 350                 355 gga gct atc tat aca gaa act gaa gat ttt tct ctt aag gga agt acg       1219
Gly Ala Ile Tyr Thr Glu Thr Glu Asp Phe Ser Leu Lys Gly Ser Thr
        360                 365                 370 gga acc gtg acc ttc agc aca aat aca gca aag aca ggc ggc gcc tta       1267
Gly Thr Val Thr Phe Ser Thr Asn Thr Ala Lys Thr Gly Gly Ala Leu
    375                 380                 385 tat tct aaa gga aac agc tcg ctg act gga aat acc aac ctg ctc ttt       1315
Tyr Ser Lys Gly Asn Ser Ser Leu Thr Gly Asn Thr Asn Leu Leu Phe
390                 395                 400                 405 tca ggg aac aaa gct acg ggc ccg agt aat tct tca gca aat caa gag       1363
Ser Gly Asn Lys Ala Thr Gly Pro Ser Asn Ser Ser Ala Asn Gln Glu
                410                 415                 420 ggt tgc ggt ggg gca atc cta gcc ttt att gat tca gga tcc gta agc       1411
Gly Cys Gly Gly Ala Ile Leu Ala Phe Ile Asp Ser Gly Ser Val Ser
            425                 430                 435 gat aaa aca gga cta tcg att gca aac aac caa gaa gtc agc ctc act       1459
Asp Lys Thr Gly Leu Ser Ile Ala Asn Asn Gln Glu Val Ser Leu Thr
        440                 445                 450 agt aat gct gca aca gta agt ggt ggt gcg atc tat gct acc aaa tgt       1507
Ser Asn Ala Ala Thr Val Ser Gly Gly Ala Ile Tyr Ala Thr Lys Cys
    455                 460                 465 act cta act gga aac ggc tcc ctg acc ttt gac ggc aat act gct gga       1555
Thr Leu Thr Gly Asn Gly Ser Leu Thr Phe Asp Gly Asn Thr Ala Gly
470                 475                 480                 485 act tca gga ggg gcg atc tat aca gaa act gaa gat ttt act ctt aca       1603
Thr Ser Gly Gly Ala Ile Tyr Thr Glu Thr Glu Asp Phe Thr Leu Thr
                490                 495                 500 gga agt aca gga acc gtg acc ttc agc aca aat aca gca aag aca ggc       1651
Gly Ser Thr Gly Thr Val Thr Phe Ser Thr Asn Thr Ala Lys Thr Gly
            505                 510                 515 ggc gcc tta tat tct aaa gga aac aac tct ctg tct ggt aat acc aac       1699
Gly Ala Leu Tyr Ser Lys Gly Asn Asn Ser Leu Ser Gly Asn Thr Asn
        520                 525                 530
```

```
ctg ctc ttt tca ggg aac aaa gct acg ggc ccg agt aat tct tca gca    1747
Leu Leu Phe Ser Gly Asn Lys Ala Thr Gly Pro Ser Asn Ser Ser Ala
    535                 540                 545 aat caa gag ggt tgc ggt ggg gca atc cta tcg ttt ctt gag tca gca    1795
Asn Gln Glu Gly Cys Gly Gly Ala Ile Leu Ser Phe Leu Glu Ser Ala
550                 555                 560                 565 tct gta agt act aaa aaa gga ctc tgg att gaa gat aac gaa aac gtg    1843
Ser Val Ser Thr Lys Lys Gly Leu Trp Ile Glu Asp Asn Glu Asn Val
                570                 575                 580 agt ctc tct ggt aat act gca aca gta agt ggc ggt gcg atc tat gcg    1891
Ser Leu Ser Gly Asn Thr Ala Thr Val Ser Gly Gly Ala Ile Tyr Ala
            585                 590                 595 acc aag tgt gct ctg cat gga aac acg act ctt acc ttt gat ggc aat    1939
Thr Lys Cys Ala Leu His Gly Asn Thr Thr Leu Thr Phe Asp Gly Asn
        600                 605                 610 act gcc gaa act gca gga gga gcg atc tat aca gaa acc gaa gat ttt    1987
Thr Ala Glu Thr Ala Gly Gly Ala Ile Tyr Thr Glu Thr Glu Asp Phe
    615                 620                 625 act ctt acg gga agt acg gga acc gtg acc ttc agc aca aat aca gca    2035
Thr Leu Thr Gly Ser Thr Gly Thr Val Thr Phe Ser Thr Asn Thr Ala
630                 635                 640                 645 aag aca gca ggg gct cta cat act aaa gga aat act tcc ttt acc aaa    2083
Lys Thr Ala Gly Ala Leu His Thr Lys Gly Asn Thr Ser Phe Thr Lys
                650                 655                 660 aat aag gct ctt gta ttt tct gga aat tca gca aca gca aca gca aca    2131
Asn Lys Ala Leu Val Phe Ser Gly Asn Ser Ala Thr Ala Thr Ala Thr
            665                 670                 675 aca act aca gat caa gaa ggt tgt ggt gga gcg atc ctc tgt aat atc    2179
Thr Thr Thr Asp Gln Glu Gly Cys Gly Gly Ala Ile Leu Cys Asn Ile
        680                 685                 690 tca gag tct gac ata gct aca aaa agc tta act ctt act gaa aat gag    2227
Ser Glu Ser Asp Ile Ala Thr Lys Ser Leu Thr Leu Thr Glu Asn Glu
    695                 700                 705 agt tta agt ttc att aac aat acg gca aaa aga agt ggt ggt ggt att    2275
Ser Leu Ser Phe Ile Asn Asn Thr Ala Lys Arg Ser Gly Gly Gly Ile
710                 715                 720                 725 tat gct cct aag tgt gta atc tca ggc agt gaa tcc ata aac ttt gat    2323
Tyr Ala Pro Lys Cys Val Ile Ser Gly Ser Glu Ser Ile Asn Phe Asp
                730                 735                 740 ggc aat act gct gaa act tcg gga gga gcg att tat tcg aaa aac ctt    2371
Gly Asn Thr Ala Glu Thr Ser Gly Gly Ala Ile Tyr Ser Lys Asn Leu
            745                 750                 755 tcg att aca gct aac ggt cct gtc tcc ttt acc aat aat tct gga ggc    2419
Ser Ile Thr Ala Asn Gly Pro Val Ser Phe Thr Asn Asn Ser Gly Gly
        760                 765                 770 aag gga ggc gcc att tat ata gcc gat agc gga gaa ctt tcc tta gag    2467
Lys Gly Gly Ala Ile Tyr Ile Ala Asp Ser Gly Glu Leu Ser Leu Glu
    775                 780                 785 gct att gat ggg gat att act ttc tca ggg aac cga gcg act gag gga    2515
Ala Ile Asp Gly Asp Ile Thr Phe Ser Gly Asn Arg Ala Thr Glu Gly
790                 795                 800                 805 act tca act ccc aac tcg atc cat tta ggt gcc agg ggc aag atc act    2563
Thr Ser Thr Pro Asn Ser Ile His Leu Gly Ala Arg Gly Lys Ile Thr
                810                 815                 820 aag ctt gca gca gct cct ggt cat acg att tat ttt tat gat cct att    2611
Lys Leu Ala Ala Ala Pro Gly His Thr Ile Tyr Phe Tyr Asp Pro Ile
            825                 830                 835 acg atg gaa gct cct gca tct gga gga aca ata gag gag tta gtc atc    2659
Thr Met Glu Ala Pro Ala Ser Gly Gly Thr Ile Glu Glu Leu Val Ile
        840                 845                 850
```

-continued

```
aat cct gtt gtc aaa gct att gtt cct cct ccc caa cca aaa aat ggt     2707
Asn Pro Val Val Lys Ala Ile Val Pro Pro Pro Gln Pro Lys Asn Gly
    855                 860                 865 cct ata tagaagaaaa acgaatgctc tttgtaaggc tcaagagtaa aaaattctaa      2763
Pro Ile
870 aggtattctc tcaataggtt ctgaagtgct gccgtagaat tcataaatat ctc          2816

<210> SEQ ID NO 9
<211> LENGTH: 3092
<212> TYPE: DNA
<213> ORGANISM: Chlamydia pneumoniae
<220> FEATURE:
<221> NAME/KEY: CDS
<222> LOCATION: (101)..(2989)

<400> SEQUENCE: 9
tcaaatatat gagtttacta actctgtaat attcaacatg ttaataagca tatttaaata   60
taaatttata aacttctaga caacaaattg atgattttt atg aca aac tct att     115
                                             Met Thr Asn Ser Ile
                                              1               5 ttc ata tca aag ttt gga tgt tta tgc gac cca ttt gtc tca gca ttt    163
Phe Ile Ser Lys Phe Gly Cys Leu Cys Asp Pro Phe Val Ser Ala Phe
             10                  15                  20 tat ccc act gcg cta tgt tgt tcc tta tca gga aat gaa gtc cct aac    211
Tyr Pro Thr Ala Leu Cys Cys Ser Leu Ser Gly Asn Glu Val Pro Asn
         25                  30                  35 ctc gcc tct tgt cag atg tct aga aaa gac atc tct gct ttc cac acg    259
Leu Ala Ser Cys Gln Met Ser Arg Lys Asp Ile Ser Ala Phe His Thr
     40                  45                  50 tct cca agc ttc cgt ctg aat gta act cca gag ccc ttg gtt tcc tcc    307
Ser Pro Ser Phe Arg Leu Asn Val Thr Pro Glu Pro Leu Val Ser Ser
 55                  60                  65 ttt cgt ccc tct aat ctt ctt aat gga ttc ggt cac gat ata acc cag    355
Phe Arg Pro Ser Asn Leu Leu Asn Gly Phe Gly His Asp Ile Thr Gln
 70                  75                  80                  85 gac atc aca att aca gga aac tct atc aat tct gtt ata gat tat aac    403
Asp Ile Thr Ile Thr Gly Asn Ser Ile Asn Ser Val Ile Asp Tyr Asn
             90                  95                 100 tac cac tac gag gat gga ggc att ctt gca tgt aaa aat ttg ttc att    451
Tyr His Tyr Glu Asp Gly Gly Ile Leu Ala Cys Lys Asn Leu Phe Ile
        105                 110                 115 tct gaa aat aaa gga aac tta agt ttt gaa agg aat agc tcc cac agt    499
Ser Glu Asn Lys Gly Asn Leu Ser Phe Glu Arg Asn Ser Ser His Ser
    120                 125                 130 tct gga ggg gct ctc tac agt gtt cgg gaa tgc tgg att tct aag aat    547
Ser Gly Gly Ala Leu Tyr Ser Val Arg Glu Cys Trp Ile Ser Lys Asn
135                 140                 145 cag aac tac tcg ttt att tca aat gcg gct tcc tta gct act act aca    595
Gln Asn Tyr Ser Phe Ile Ser Asn Ala Ala Ser Leu Ala Thr Thr Thr
150                 155                 160                 165 act tca gga ttt ggt ggg gct ata cat gca cta gat agc tat att aca    643
Thr Ser Gly Phe Gly Gly Ala Ile His Ala Leu Asp Ser Tyr Ile Thr
            170                 175                 180 aat aac tta gga gaa gga caa ttc tta gat aat gtc tct aaa aat aga    691
Asn Asn Leu Gly Glu Gly Gln Phe Leu Asp Asn Val Ser Lys Asn Arg
        185                 190                 195 gga gga gct atc tat gtt ggg gtg agt tta tca atc aca gac aac tta    739
Gly Gly Ala Ile Tyr Val Gly Val Ser Leu Ser Ile Thr Asp Asn Leu
    200                 205                 210
```

-continued

| | |
|---|---|
| ggt cct atc gtt atc aag aaa aat caa aca tta gaa gat tcc agc ttt<br>Gly Pro Ile Val Ile Lys Lys Asn Gln Thr Leu Glu Asp Ser Ser Phe<br>215                     220                          225 | 787 |
| gga gga ggc atc ttc tgc aga gcc gta aat ata gaa agg aat tat caa<br>Gly Gly Gly Ile Phe Cys Arg Ala Val Asn Ile Glu Arg Asn Tyr Gln<br>230                   235                    240                      245 | 835 |
| aac atc caa atc aat gat aat gct tca gga caa ggg gtg gta tat ttt<br>Asn Ile Gln Ile Asn Asp Asn Ala Ser Gly Gln Gly Val Val Tyr Phe<br>               250                    255                   260 | 883 |
| ctg ccc cta gga gtc att atc tct tca aat aaa gaa att ata gag atc<br>Leu Pro Leu Gly Val Ile Ile Ser Ser Asn Lys Glu Ile Ile Glu Ile<br>265                     270                        275 | 931 |
| agc aat cac tcc gca tcc tca att aac aca gca tca gga aaa cta tat<br>Ser Asn His Ser Ala Ser Ser Ile Asn Thr Ala Ser Gly Lys Leu Tyr<br>               280                    285                   290 | 979 |
| ccc ggt ggt ggc ggt atc atg tgt acc tcc ctt agt cat gag aac aat<br>Pro Gly Gly Gly Gly Ile Met Cys Thr Ser Leu Ser His Glu Asn Asn<br>295                     300                    305 | 1027 |
| ccc aaa ggt ctt atc ttt aac aat aaa acg gca gca ctt agc ggc gga<br>Pro Lys Gly Leu Ile Phe Asn Asn Lys Thr Ala Ala Leu Ser Gly Gly<br>310                     315                    320                    325 | 1075 |
| gta tac aca cga gat ctt tca tct tcc aaa ata acg gtc cgc aca gca<br>Val Tyr Thr Arg Asp Leu Ser Ser Ser Lys Ile Thr Val Arg Thr Ala<br>               330                    335                   340 | 1123 |
| ttt att aat aac tct gcg act tca gga ggg gct ctc atc aat ctt tct<br>Phe Ile Asn Asn Ser Ala Thr Ser Gly Gly Ala Leu Ile Asn Leu Ser<br>345                     350                    355 | 1171 |
| ggt ata gga agt act cct caa aat ttc ttc ctc tct gca gac tac ggc<br>Gly Ile Gly Ser Thr Pro Gln Asn Phe Phe Leu Ser Ala Asp Tyr Gly<br>               360                    365                   370 | 1219 |
| gat att cta ttt aac aat aat aca atc aca tct tct tct cct caa ccc<br>Asp Ile Leu Phe Asn Asn Asn Thr Ile Thr Ser Ser Ser Pro Gln Pro<br>375                     380                    385 | 1267 |
| gga tat aga aat gca ctc tat gct gct ccg ggg att aac tta aaa cta<br>Gly Tyr Arg Asn Ala Leu Tyr Ala Ala Pro Gly Ile Asn Leu Lys Leu<br>390                     395                    400                    405 | 1315 |
| gga gca aga cag ggt tat aaa att ctc ttt tat gat cct ata gat cac<br>Gly Ala Arg Gln Gly Tyr Lys Ile Leu Phe Tyr Asp Pro Ile Asp His<br>               410                    415                   420 | 1363 |
| gat cag acg aca aca gat cct ata gta ttt aat tat gaa ccc cat cac<br>Asp Gln Thr Thr Thr Asp Pro Ile Val Phe Asn Tyr Glu Pro His His<br>425                     430                    435 | 1411 |
| ctt ggc acc gtg ttg ttt tcc gga atc aat gta gat tct aac gca aca<br>Leu Gly Thr Val Leu Phe Ser Gly Ile Asn Val Asp Ser Asn Ala Thr<br>440                     445                    450 | 1459 |
| aat cca ttg aac ttc cta tca aaa ttt tct aac tct tca cga ctt gaa<br>Asn Pro Leu Asn Phe Leu Ser Lys Phe Ser Asn Ser Ser Arg Leu Glu<br>455                     460                    465 | 1507 |
| agg ggt gtg ctc gct att gaa gat cgg gct gct att tct tgc aaa acc<br>Arg Gly Val Leu Ala Ile Glu Asp Arg Ala Ala Ile Ser Cys Lys Thr<br>470                     475                    480                    485 | 1555 |
| cta tcg caa act ggg ggc att cta cgt tta gga aac gca gca tta atc<br>Leu Ser Gln Thr Gly Gly Ile Leu Arg Leu Gly Asn Ala Ala Leu Ile<br>               490                    495                   500 | 1603 |
| agg acg aaa ggc ccg gga agc tcc ata aat ttt aat gca atc gcg atc<br>Arg Thr Lys Gly Pro Gly Ser Ser Ile Asn Phe Asn Ala Ile Ala Ile<br>505                     510                    515 | 1651 |
| aat ctt cct tct att tta caa tca gaa gcc tca gct cca aag ttc tgg<br>Asn Leu Pro Ser Ile Leu Gln Ser Glu Ala Ser Ala Pro Lys Phe Trp | 1699 |

-continued

```
              520                 525                 530
att tat cct aca tta aca gga tcc acc tat tct gaa gac act tct tct    1747
Ile Tyr Pro Thr Leu Thr Gly Ser Thr Tyr Ser Glu Asp Thr Ser Ser
535                 540                 545 act atc act ctc tca gga ccc ttg act ttt cta aac gat gaa aat gaa    1795
Thr Ile Thr Leu Ser Gly Pro Leu Thr Phe Leu Asn Asp Glu Asn Glu
550                 555                 560                 565 aac ccc tat gat agc tta gat ctc tct gaa cct cga aag gat atc ccc    1843
Asn Pro Tyr Asp Ser Leu Asp Leu Ser Glu Pro Arg Lys Asp Ile Pro
            570                 575                 580 cct cct cta cct cct cga tgt gac tgc aaa aaa atc gat act tcg aat    1891
Pro Pro Leu Pro Pro Arg Cys Asp Cys Lys Lys Ile Asp Thr Ser Asn
        585                 590                 595 ctc att gta gaa gcc atg aac tta gat gag cac tat gga tat cag gga    1939
Leu Ile Val Glu Ala Met Asn Leu Asp Glu His Tyr Gly Tyr Gln Gly
    600                 605                 610 atc tgg tct ccc tat tgg atg gaa act acg act aca aca agc tct aca    1987
Ile Trp Ser Pro Tyr Trp Met Glu Thr Thr Thr Thr Thr Ser Ser Thr
615                 620                 625 gta ccg gaa cag acc aat aca aac cac agg cag ctc tac gta gac tgg    2035
Val Pro Glu Gln Thr Asn Thr Asn His Arg Gln Leu Tyr Val Asp Trp
630                 635                 640                 645 act cct gta gga tac cgc cct aac ccg gaa cgt cac gga gaa ttt att    2083
Thr Pro Val Gly Tyr Arg Pro Asn Pro Glu Arg His Gly Glu Phe Ile
            650                 655                 660 gct aat acc tta tgg cag tct gcc tat aac gct ctg tta gga atc cgc    2131
Ala Asn Thr Leu Trp Gln Ser Ala Tyr Asn Ala Leu Leu Gly Ile Arg
        665                 670                 675 atc tta cct cca caa aac ctc aaa gag cat gac ctt gaa gcc tct ctg    2179
Ile Leu Pro Pro Gln Asn Leu Lys Glu His Asp Leu Glu Ala Ser Leu
    680                 685                 690 caa gga ctc ggg ctt cta att aac caa cat aat cgc gag gga cgc aaa    2227
Gln Gly Leu Gly Leu Leu Ile Asn Gln His Asn Arg Glu Gly Arg Lys
695                 700                 705 ggc ttc cga aac cat act acg ggc tat gca gca aca acc tca gca aaa    2275
Gly Phe Arg Asn His Thr Thr Gly Tyr Ala Ala Thr Thr Ser Ala Lys
710                 715                 720                 725 act gca gca cga cat agt ttc tct tta gga ttc gca caa atg ttc tcc    2323
Thr Ala Ala Arg His Ser Phe Ser Leu Gly Phe Ala Gln Met Phe Ser
            730                 735                 740 aaa act aga gaa cgt caa tct cca agt acg act tcc tcc cac aac tac    2371
Lys Thr Arg Glu Arg Gln Ser Pro Ser Thr Thr Ser Ser His Asn Tyr
        745                 750                 755 ttt gca gga ctc cgc ttc gac agt ctc ctc ttc agg gac ttc atc tct    2419
Phe Ala Gly Leu Arg Phe Asp Ser Leu Leu Phe Arg Asp Phe Ile Ser
    760                 765                 770 aca ggg cta tcc cta ggt tat agc tac gga gat cac cat atg ctt tgc    2467
Thr Gly Leu Ser Leu Gly Tyr Ser Tyr Gly Asp His His Met Leu Cys
775                 780                 785 cac tat aca gaa atc tta aaa ggg tcg tcc aaa gcc ttc ttt aat aac    2515
His Tyr Thr Glu Ile Leu Lys Gly Ser Ser Lys Ala Phe Phe Asn Asn
790                 795                 800                 805 cac act ttg gta gcc tct cta gac tgc aca ttc tta cca gct aga atc    2563
His Thr Leu Val Ala Ser Leu Asp Cys Thr Phe Leu Pro Ala Arg Ile
            810                 815                 820 acc cgc act ctc gaa ctc cag ccc ttt atc agt gca att gct ctg cgc    2611
Thr Arg Thr Leu Glu Leu Gln Pro Phe Ile Ser Ala Ile Ala Leu Arg
        825                 830                 835 tgt tcc cag gcc tcg ttc caa gaa act gga gac cat ata aga aaa ttc    2659
```

```
                Cys Ser Gln Ala Ser Phe Gln Glu Thr Gly Asp His Ile Arg Lys Phe
                    840                 845                 850 cat cca aaa cat ccc ctt aca gat ctt tcc tct ccc ata ggc ttc cgt             2707
His Pro Lys His Pro Leu Thr Asp Leu Ser Ser Pro Ile Gly Phe Arg
855                 860                 865 tct gaa tgg aaa act tca cat cat atc ccc atg cta tgg act acg gaa             2755
Ser Glu Trp Lys Thr Ser His His Ile Pro Met Leu Trp Thr Thr Glu
870                 875                 880                 885 ata tcc tac gta cct acc cta tac aga aaa aat cca gaa atg ttc acg             2803
Ile Ser Tyr Val Pro Thr Leu Tyr Arg Lys Asn Pro Glu Met Phe Thr
                890                 895                 900 aca cta ctc atc agc aat gga aca tgg aca aca caa gca act ccc gtc             2851
Thr Leu Leu Ile Ser Asn Gly Thr Trp Thr Thr Gln Ala Thr Pro Val
            905                 910                 915 tcc tat aat tcc gta gct gca aaa ata aaa aat act tcc caa ctt ttc             2899
Ser Tyr Asn Ser Val Ala Ala Lys Ile Lys Asn Thr Ser Gln Leu Phe
        920                 925                 930 tca aga gta acc tta tcc tta gat tat tca gct caa gtc tcc tcg tca             2947
Ser Arg Val Thr Leu Ser Leu Asp Tyr Ser Ala Gln Val Ser Ser Ser
    935                 940                 945 act gta ggt caa tac ctt aaa gct gag agt cat tgc aca ttt                     2989
Thr Val Gly Gln Tyr Leu Lys Ala Glu Ser His Cys Thr Phe
950                 955                 960 taaccacaaa gaaacatca aggaataaac agtgcaaaat aacagatccc ttagtaaatc            3049
ttccttcttt gttggagcct taattttagg taaaactaca ata                             3092

<210> SEQ ID NO 10
<211> LENGTH: 1745
<212> TYPE: DNA
<213> ORGANISM: Chlamydia pneumoniae
<220> FEATURE:
<221> NAME/KEY: CDS
<222> LOCATION: (101)..(1642)

<400> SEQUENCE: 10
aaacagttaa ataattaata gacaataatc tattcttatt gacttctttt tttcttgttt           60
attaaagttg cttcaacctt attgatttaa cgaggaaacc atg acc ata ctt cga            115
                                              Met Thr Ile Leu Arg
                                                1               5 aat ttt ctt acc tgc tcg gct tta ttc ctc gct ctc cct gca gca gca             163
Asn Phe Leu Thr Cys Ser Ala Leu Phe Leu Ala Leu Pro Ala Ala Ala
            10                  15                  20 caa gtt gta tat ctt cat gaa agt gat ggt tat aac ggt gct atc aat             211
Gln Val Val Tyr Leu His Glu Ser Asp Gly Tyr Asn Gly Ala Ile Asn
        25                  30                  35 aat aaa agc tta gaa cct aaa att acc tgt tat cca gaa gga act tct             259
Asn Lys Ser Leu Glu Pro Lys Ile Thr Cys Tyr Pro Glu Gly Thr Ser
    40                  45                  50 tac atc ttt cta gat gac gtg agg att tcc aac gtt aag cat gat caa             307
Tyr Ile Phe Leu Asp Asp Val Arg Ile Ser Asn Val Lys His Asp Gln
55                  60                  65 gaa gat gct ggg gtt ttt ata aat cga tct ggg aat ctt ttc ttc atg             355
Glu Asp Ala Gly Val Phe Ile Asn Arg Ser Gly Asn Leu Phe Phe Met
70                  75                  80                  85 ggc aac cgt tgc aac ttc act ttt cac aac ctt atg acc gag ggt ttt             403
Gly Asn Arg Cys Asn Phe Thr Phe His Asn Leu Met Thr Glu Gly Phe
            90                  95                  100 ggc gct gcc att tcg aac cgc gtt gga gac acc act ctc act ctc tct             451
Gly Ala Ala Ile Ser Asn Arg Val Gly Asp Thr Thr Leu Thr Leu Ser
        105                 110                 115
```

-continued

| | |
|---|---|
| aat ttt tct tac tta gcg ttc acc tca gca cct cta cta cct caa gga<br>Asn Phe Ser Tyr Leu Ala Phe Thr Ser Ala Pro Leu Leu Pro Gln Gly<br>      120                       125                     130 | 499 |
| caa gga gcg att tat agt ctt ggt tcc gtg atg atc gaa aat agt gag<br>Gln Gly Ala Ile Tyr Ser Leu Gly Ser Val Met Ile Glu Asn Ser Glu<br>135                     140                     145 | 547 |
| gaa gtg act ttc tgt ggg aac tac tct tcg tgg agt gga gct gcg att<br>Glu Val Thr Phe Cys Gly Asn Tyr Ser Ser Trp Ser Gly Ala Ala Ile<br>150                   155                   160                 165 | 595 |
| tat act ccc tac ctt tta ggt tct aag gcg agt cgt cct tca gta aat<br>Tyr Thr Pro Tyr Leu Leu Gly Ser Lys Ala Ser Arg Pro Ser Val Asn<br>              170                   175                     180 | 643 |
| ctc agc ggg aac cgc tac ctg gtg ttt aga gac aat gtg agc caa gtt<br>Leu Ser Gly Asn Arg Tyr Leu Val Phe Arg Asp Asn Val Ser Gln Val<br>185                     190                     195 | 691 |
| tat ggc ggc gcc ata tct acc cac aat ctc aca ctc acg act cga gga<br>Tyr Gly Gly Ala Ile Ser Thr His Asn Leu Thr Leu Thr Thr Arg Gly<br>              200                   205                     210 | 739 |
| cct tcg tgt ttt gaa aat aat cat gct tat cat gac gtg aat agt aat<br>Pro Ser Cys Phe Glu Asn Asn His Ala Tyr His Asp Val Asn Ser Asn<br>215                     220                     225 | 787 |
| gga gga gcc att gcc att gct cct gga gga tcg atc tct ata tcc gtg<br>Gly Gly Ala Ile Ala Ile Ala Pro Gly Gly Ser Ile Ser Ile Ser Val<br>230                     235                   240                 245 | 835 |
| aaa agc gga gat ctc atc ttc aaa gga aat aca gca tca caa gac gga<br>Lys Ser Gly Asp Leu Ile Phe Lys Gly Asn Thr Ala Ser Gln Asp Gly<br>              250                   255                     260 | 883 |
| aat aca ata cac aac tcc atc cat ctg caa tct gga gca cag ttt aag<br>Asn Thr Ile His Asn Ser Ile His Leu Gln Ser Gly Ala Gln Phe Lys<br>265                     270                     275 | 931 |
| aac cta cgt gct gtt tca gaa tcc gga gtt tat ttc tat gat cct ata<br>Asn Leu Arg Ala Val Ser Glu Ser Gly Val Tyr Phe Tyr Asp Pro Ile<br>              280                   285                     290 | 979 |
| agc cat agc gag tcg cat aaa att aca gat ctt gta atc aat gct cct<br>Ser His Ser Glu Ser His Lys Ile Thr Asp Leu Val Ile Asn Ala Pro<br>295                     300                     305 | 1027 |
| gaa gga aag gaa act tat gaa gga aca att agc ttc tca gga cta tgc<br>Glu Gly Lys Glu Thr Tyr Glu Gly Thr Ile Ser Phe Ser Gly Leu Cys<br>310                     315                   320                 325 | 1075 |
| ctg gat gat cat gaa gtt tgt gcg gaa aat ctt act tcc aca atc cta<br>Leu Asp Asp His Glu Val Cys Ala Glu Asn Leu Thr Ser Thr Ile Leu<br>              330                   335                     340 | 1123 |
| caa gat gtc aca tta gca gga gga act ctc tct cta tcg gat ggg gtt<br>Gln Asp Val Thr Leu Ala Gly Gly Thr Leu Ser Leu Ser Asp Gly Val<br>345                     350                   355 | 1171 |
| acc ttg caa ctg cat tct ttt aag cag gaa gca agc tct acg ctt act<br>Thr Leu Gln Leu His Ser Phe Lys Gln Glu Ala Ser Ser Thr Leu Thr<br>              360                   365                     370 | 1219 |
| atg tct cca gga acc act ctg ctc tgc tca gga gat gct cgg gtt cag<br>Met Ser Pro Gly Thr Thr Leu Leu Cys Ser Gly Asp Ala Arg Val Gln<br>375                     380                   385 | 1267 |
| aat ctg cac atc ctg att gaa gat acc gac aac ttt gtt cct gta agg<br>Asn Leu His Ile Leu Ile Glu Asp Thr Asp Asn Phe Val Pro Val Arg<br>390                     395                   400                 405 | 1315 |
| att cgc gcc gag gac aag gat gct ctt gtc tca tta gaa aaa ctt aaa<br>Ile Arg Ala Glu Asp Lys Asp Ala Leu Val Ser Leu Glu Lys Leu Lys<br>              410                   415                     420 | 1363 |
| gtt gcc ttt gag gct tat tgg tcc gtc tat gac ttt cct caa ttt aag<br>Val Ala Phe Glu Ala Tyr Trp Ser Val Tyr Asp Phe Pro Gln Phe Lys | 1411 |

-continued

```
                425                 430                 435
gaa gcc ttt acg att cct ctt ctt gaa ctt cta ggg cct tct ttt gac     1459
Glu Ala Phe Thr Ile Pro Leu Leu Glu Leu Leu Gly Pro Ser Phe Asp
        440                 445                 450 agt ctt ctc cta ggg gag acc act ttg gag aga acc caa gtc aca aca     1507
Ser Leu Leu Gly Glu Thr Thr Leu Glu Arg Thr Gln Val Thr Thr
    455                 460                 465 gag aat gac gcc gtt cga ggt ttc tgg tcc cta agc tgg gaa gag tac     1555
Glu Asn Asp Ala Val Arg Gly Phe Trp Ser Leu Ser Trp Glu Glu Tyr
470                 475                 480                 485 ccc cct tct ctg gat aaa gac aga agg atc aca cca act aag aaa act     1603
Pro Pro Ser Leu Asp Lys Asp Arg Arg Ile Thr Pro Thr Lys Lys Thr
                490                 495                 500 gtt ttc ctc act tgg aat cct gag atc act tct acg cca taatctctaa      1652
Val Phe Leu Thr Trp Asn Pro Glu Ile Thr Ser Thr Pro
                505                 510 gtctacacta taattaaggg aatccccttt aagaagattt gggacctat ctgtattcag    1712 agataggtcc ctctatgcac acatgttcac gag                                1745

<210> SEQ ID NO 11
<211> LENGTH: 1100
<212> TYPE: DNA
<213> ORGANISM: Chlamydia pneumoniae
<220> FEATURE:
<221> NAME/KEY: CDS
<222> LOCATION: (101)..(967)

<400> SEQUENCE: 11
tttggaacct taatgatctc tggagggtgg cttagcaata tgattttacg ctttgcaggt     60
cagattttcc aaaacttcta taaatggaaa taaagagctt atg gga atc tct cta     115
                                              Met Gly Ile Ser Leu
                                                1               5 cca gag ctt ttt tcc aac cta ggt tct gct tac tta gat tat atc ttt     163
Pro Glu Leu Phe Ser Asn Leu Gly Ser Ala Tyr Leu Asp Tyr Ile Phe
            10                  15                  20 caa cat cct ccg gcc tat gtt tgg tca gtt ttt ctt ctt tta tta gcc     211
Gln His Pro Pro Ala Tyr Val Trp Ser Val Phe Leu Leu Leu Leu Ala
        25                  30                  35 cgt ctg ctt cct att ttt gct gta gct ccc ttc tta gga gca aag ctc     259
Arg Leu Leu Pro Ile Phe Ala Val Ala Pro Phe Leu Gly Ala Lys Leu
    40                  45                  50 ttt ccc tcc cct att aaa atc ggg att agt ctc tct tgg ctt gca atc     307
Phe Pro Ser Pro Ile Lys Ile Gly Ile Ser Leu Ser Trp Leu Ala Ile
55                  60                  65 atc ttt cca aaa gtc ttg gcg gat acg cag atc aca aat tac atg gat     355
Ile Phe Pro Lys Val Leu Ala Asp Thr Gln Ile Thr Asn Tyr Met Asp
            70                  75                  80              85 aac aat ctc ttt tat gtt tta ctt gtg aag gag atg atc ata ggc att     403
Asn Asn Leu Phe Tyr Val Leu Leu Val Lys Glu Met Ile Ile Gly Ile
                90                  95                  100 gtg ata ggc ttt gtt tta gca ttt ccc ttt tat gct gca caa tcg gca     451
Val Ile Gly Phe Val Leu Ala Phe Pro Phe Tyr Ala Ala Gln Ser Ala
            105                 110                 115 gga tct ttc atc act aac caa caa ggg att cag ggt tta gag ggc gcg     499
Gly Ser Phe Ile Thr Asn Gln Gln Gly Ile Gln Gly Leu Glu Gly Ala
        120                 125                 130 aca tcc ctg att tcc att gag cag acc tct ccg cat ggc att tta tac     547
Thr Ser Leu Ile Ser Ile Glu Gln Thr Ser Pro His Gly Ile Leu Tyr
    135                 140                 145
```

```
cat tac ttc gtg act att att ttt tgg tta gtg ggt ggt cac cgt att      595
His Tyr Phe Val Thr Ile Ile Phe Trp Leu Val Gly Gly His Arg Ile
150                 155                 160                 165 gta atc tct ttg tta ttg caa act ctt gaa gtc att ccg atc cat agt      643
Val Ile Ser Leu Leu Leu Gln Thr Leu Glu Val Ile Pro Ile His Ser
                170                 175                 180 ttc ttt cct gcc gag atg atg agc tta agt gcc ccg att tgg att act      691
Phe Phe Pro Ala Glu Met Met Ser Leu Ser Ala Pro Ile Trp Ile Thr
185                 190                 195 atg atc aag atg tgc cag ctc tgt ctc gtg atg acc ata cag ctg agt      739
Met Ile Lys Met Cys Gln Leu Cys Leu Val Met Thr Ile Gln Leu Ser
    200                 205                 210 gct cct gca gct ttg gcg atg tta atg tcc gac cta ttc tta ggg att      787
Ala Pro Ala Ala Leu Ala Met Leu Met Ser Asp Leu Phe Leu Gly Ile
215                 220                 225 att aac cgt atg gca cct caa gtt cag gtc atc tac ctc ctc tct gcc      835
Ile Asn Arg Met Ala Pro Gln Val Gln Val Ile Tyr Leu Leu Ser Ala
230                 235                 240                 245 ctt aag gct ttc atg ggt ctt ctc ttt ctc acc ctg gcg tgg tgg ttc      883
Leu Lys Ala Phe Met Gly Leu Leu Phe Leu Thr Leu Ala Trp Trp Phe
                250                 255                 260 ata att aag cag ata gat tat ttc act ctt gct tgg ttc aaa gaa gtc      931
Ile Ile Lys Gln Ile Asp Tyr Phe Thr Leu Ala Trp Phe Lys Glu Val
            265                 270                 275 ccc att atg ctc cta ggt tcc aac cct caa gta ctc taatcccta            977
Pro Ile Met Leu Leu Gly Ser Asn Pro Gln Val Leu
            280                 285 ggctcttatc gtgactctta tctggagatg cgctcactta cgaatcttag cgcactgttt   1037
atggattatc ttagggaatc tctcgcatat tcttttgtaa tctaagaatc tataaattca   1097
aga                                                                 1100

<210> SEQ ID NO 12
<211> LENGTH: 950
<212> TYPE: DNA
<213> ORGANISM: Chlamydia pneumoniae
<220> FEATURE:
<221> NAME/KEY: CDS
<222> LOCATION: (101)..(895)

<400> SEQUENCE: 12
ccagtgataa agactctagt gataaagatg ctccagaagg aagcaatgaa attgagggtg     60
cttagtgact gccaacactt ttggaactct agacatcttg atg aag cac tcc aag      115
                                             Met Lys His Ser Lys
                                             1               5 gaa gat gac ctc tcc agg ttt ctt cct aaa aat ctt ctt gtt gaa tct      163
Glu Asp Asp Leu Ser Arg Phe Leu Pro Lys Asn Leu Leu Val Glu Ser
                10                  15                  20 cct cat ccc gaa gaa atc cct tta aaa tct tta tct ttt acg atg agt      211
Pro His Pro Glu Glu Ile Pro Leu Lys Ser Leu Ser Phe Thr Met Ser
            25                  30                  35 tgg cta cct aca att cat cct tca tgg att acc att gcc atg aaa gag      259
Trp Leu Pro Thr Ile His Pro Ser Trp Ile Thr Ile Ala Met Lys Glu
        40                  45                  50 ttc cct cct gaa atc caa ggt caa tta tta gcg tgg ttg cca gag cct      307
Phe Pro Pro Glu Ile Gln Gly Gln Leu Leu Ala Trp Leu Pro Glu Pro
    55                  60                  65 tta gtt caa gaa att cta ccc tta ctg cct ggc atc tct ata gcc cca      355
Leu Val Gln Glu Ile Leu Pro Leu Leu Pro Gly Ile Ser Ile Ala Pro
70                  75                  80                  85
```

-continued

| | |
|---|---|
| cat cgc tgt gca cct ttc gga gcc ttc tat ctt cta gat atg cta agt<br>His Arg Cys Ala Pro Phe Gly Ala Phe Tyr Leu Leu Asp Met Leu Ser<br>              90                            95                      100 | 403 |
| aaa aag atc cgt cct tgt gga att aca gaa gaa atc ttt ctt cct gca<br>Lys Lys Ile Arg Pro Cys Gly Ile Thr Glu Glu Ile Phe Leu Pro Ala<br>              105                       110                      115 | 451 |
| tcc tca gca aat gct ata ctt tac tat aca ggt cct gta aag atc gct<br>Ser Ser Ala Asn Ala Ile Leu Tyr Tyr Thr Gly Pro Val Lys Ile Ala<br>120                       125                       130 | 499 |
| tta atc aac tgc cta ggt ctt tat tct att gct aaa gag ttg aag cac<br>Leu Ile Asn Cys Leu Gly Leu Tyr Ser Ile Ala Lys Glu Leu Lys His<br>    135                     140                       145 | 547 |
| att ctg gat aag gtt gtg att gaa cga gtg aag aat gct ctc tcc cct<br>Ile Leu Asp Lys Val Val Ile Glu Arg Val Lys Asn Ala Leu Ser Pro<br>150                     155                     160                  165 | 595 |
| aca gag aaa ctc ttt ctt acc tac tgc caa tct cat ccg atg aaa cat<br>Thr Glu Lys Leu Phe Leu Thr Tyr Cys Gln Ser His Pro Met Lys His<br>              170                       175                      180 | 643 |
| tta gaa act acg aat ttt ctt tct tct tgg act act gat gca gaa tta<br>Leu Glu Thr Thr Asn Phe Leu Ser Ser Trp Thr Thr Asp Ala Glu Leu<br>    185                     190                       195 | 691 |
| cga cag ttc gtt cat aag caa ggg tta gag ttt tta ggt aaa gca tta<br>Arg Gln Phe Val His Lys Gln Gly Leu Glu Phe Leu Gly Lys Ala Leu<br>200                     205                     210 | 739 |
| aca aaa gaa aac gct tct ttt cta tgg tat ttt cta cgt agg tta gat<br>Thr Lys Glu Asn Ala Ser Phe Leu Trp Tyr Phe Leu Arg Arg Leu Asp<br>              215                     220                      225 | 787 |
| gtc ggt cga gca tat atc gtc gag cag act tta aaa aca tgg tat gac<br>Val Gly Arg Ala Tyr Ile Val Glu Gln Thr Leu Lys Thr Trp Tyr Asp<br>230                     235                     240                  245 | 835 |
| cat ccc tat gtg gat tat ttt aag tcc cgc cta gaa caa tgc atg aaa<br>His Pro Tyr Val Asp Tyr Phe Lys Ser Arg Leu Glu Gln Cys Met Lys<br>              250                     255                    260 | 883 |
| gtc tta gtg aaa taaaagcttt ataagtaaag atttagcttt atacaaagta<br>Val Leu Val Lys<br>           265 | 935 |
| tagaaaaata acacg | 950 |

<210> SEQ ID NO 13
<211> LENGTH: 500
<212> TYPE: DNA
<213> ORGANISM: Chlamydia pneumoniae
<220> FEATURE:
<221> NAME/KEY: CDS
<222> LOCATION: (101)..(385)

<400> SEQUENCE: 13

| | |
|---|---|
| cgatttcgtt acctttaaag ttacttttga tcgtcatggt agacggatgg acattactgc | 60 |
| tccaagggct tatgatcagc tttaaataag gacacgtgcc atg tta gca ttt ttc<br>                                                                               Met Leu Ala Phe Phe<br>                                                                                   1                   5 | 115 |
| gca act agt ttc aaa tct gtt ctt ttt gag tac tcc tac caa tca tta<br>Ala Thr Ser Phe Lys Ser Val Leu Phe Glu Tyr Ser Tyr Gln Ser Leu<br>              10                       15                      20 | 163 |
| tta ctt att ttg att gtt tcg gca cct ccc atc atc tta gct tcc ata<br>Leu Leu Ile Leu Ile Val Ser Ala Pro Pro Ile Ile Leu Ala Ser Ile<br>                    25                       30                      35 | 211 |
| gtc ggg att atg gtt gcg atc ttc caa gcc gca aca caa atc caa gaa<br>Val Gly Ile Met Val Ala Ile Phe Gln Ala Ala Thr Gln Ile Gln Glu<br>40                     45                     50 | 259 |

```
cag acc ttc gct ttt gca gtc aaa cta gtc gtg att ttt gga acc tta      307
Gln Thr Phe Ala Phe Ala Val Lys Leu Val Val Ile Phe Gly Thr Leu
        55                  60                  65 atg atc tct gga ggg tgg ctt agc aat atg att tta cgc ttt gca ggt      355
Met Ile Ser Gly Gly Trp Leu Ser Asn Met Ile Leu Arg Phe Ala Gly
 70                  75                  80                  85 cag att ttc caa aac ttc tat aaa tgg aaa taaagagctt atgggaatct        405
Gln Ile Phe Gln Asn Phe Tyr Lys Trp Lys
                 90                  95 ctctaccaga gctttttcc aacctaggtt ctgcttactt agattatatc tttcaacatc     465
ctccggccta tgtttggtca gttttctct ttta                                 500

<210> SEQ ID NO 14
<211> LENGTH: 552
<212> TYPE: PRT
<213> ORGANISM: Chlamydia pneumoniae

<400> SEQUENCE: 14
```

Met Val Ser Ser Pro Ile Leu Asn Val Pro Leu Lys Asn His Ala Ser
 1               5                  10                  15

Val Ser Gly Lys Phe Thr His Arg Glu Val Ser Lys Leu Ala Ser Asp
            20                  25                  30

Leu Lys Ser Gly Ala Met Ser Phe Val Pro Glu Val Leu Ser Glu Glu
         35                  40                  45

Thr Ile Ser Ser Asp Leu Gly Lys Lys Gln Cys Thr Gln Gly Ile Ile
     50                  55                  60

Ser Ala Cys Cys Gly Leu Ala Met Leu Ile Val Leu Met Ser Val Tyr
 65                  70                  75                  80

Tyr Arg Phe Gly Gly Val Ile Ala Ser Gly Ala Val Leu Leu Asn Leu
                 85                  90                  95

Leu Leu Ile Trp Ala Ala Leu Gln Tyr Leu Asp Ala Pro Leu Thr Leu
            100                 105                 110

Ser Gly Leu Ala Gly Ile Val Leu Ala Met Gly Met Ala Val Asp Ala
         115                 120                 125

Asn Val Leu Val Phe Glu Arg Ile Arg Glu Glu Phe Leu Leu Ser Gln
     130                 135                 140

Ser Leu Lys Lys Ser Val Glu Lys Gly Tyr Thr Lys Ala Phe Gly Ala
145                 150                 155                 160

Ile Phe Asp Ser Asn Leu Thr Thr Val Leu Ala Ser Ala Leu Leu Phe
                165                 170                 175

Phe Leu Asp Thr Gly Pro Ile Lys Gly Phe Ala Leu Thr Leu Ile Leu
            180                 185                 190

Gly Ile Phe Ser Ser Met Phe Thr Ala Leu Phe Met Thr Lys Phe Phe
         195                 200                 205

Phe Met Leu Trp Met Asn Lys Thr Gln His Thr Gln Leu His Met Met
     210                 215                 220

Asn Lys Phe Val Gly Ile Lys His Asp Phe Leu Arg Gly Cys Lys Lys
225                 230                 235                 240

Leu Trp Ala Val Ser Gly Ser Val Phe Leu Gly Cys Val Ala Leu
                245                 250                 255

Gly Phe Gly Ala Trp Asn Ser Val Leu Gly Met Asp Phe Lys Gly Gly
            260                 265                 270

Tyr Ala Phe Thr Phe Asn Pro Lys Glu His Gly Ile Ser Asp Val Ala
         275                 280                 285

Gln Met Arg Gly Lys Val Val His Lys Leu Gln Glu Ala Gly Leu Ser

-continued

```
                290                 295                 300
Ser Arg Asp Phe Arg Ile Gln Thr Phe Gly Ser Ser Glu Lys Ile Lys
305                 310                 315                 320

Ile Tyr Phe Ser Asp Lys Ala Leu Ser Tyr Thr Lys Gln Ile Arg Ala
                325                 330                 335

Ser Leu Leu Lys Leu Thr Ile Met Ser Trp Arg Tyr Cys Gly Ile Val
                340                 345                 350

Val Arg Asn Arg Pro Arg Phe Leu Tyr Gly Asn Ser Lys Arg Asn Ala
                355                 360                 365

Lys Phe Trp Ser Lys Val Ser Ser Lys Leu Ser Lys Lys Met Arg Tyr
                370                 375                 380

Gln Ala Thr Ile Gly Leu Leu Gly Ala Leu Ala Ile Ile Leu Leu Tyr
385                 390                 395                 400

Val Ser Leu Arg Phe Glu Trp Gln Tyr Ala Phe Ser Ala Val Cys Ala
                405                 410                 415

Leu Ile His Asp Leu Leu Ala Thr Cys Ala Val Leu Phe Ile Ala His
                420                 425                 430

Phe Phe Leu Lys Lys Ile Gln Ile Asp Leu Gln Ala Ile Gly Ala Leu
                435                 440                 445

Met Thr Val Leu Gly Tyr Ser Leu Asn Asn Thr Leu Ile Ile Phe Asp
                450                 455                 460

Arg Ile Arg Glu Asp Arg Gln Ala Asn Leu Phe Thr Pro Met His Val
465                 470                 475                 480

Leu Val Asn Asp Ala Leu Gln Lys Thr Phe Ser Arg Thr Val Met Thr
                485                 490                 495

Thr Ala Thr Thr Leu Ser Val Leu Leu Met Leu Leu Phe Ile Gly Gly
                500                 505                 510

Ser Ser Val Phe Asn Phe Ala Phe Ile Met Thr Ile Gly Ile Leu Leu
                515                 520                 525

Gly Thr Leu Ser Ser Leu Tyr Ile Ala Pro Pro Leu Leu Phe Met
                530                 535                 540

Val Arg Lys Glu Asn Arg Ser Lys
545                 550

<210> SEQ ID NO 15
<211> LENGTH: 196
<212> TYPE: PRT
<213> ORGANISM: Chlamydia pneumoniae

<400> SEQUENCE: 15

Met Ser Ser Asn Leu His Pro Val Gly Gly Thr Gly Thr Gly Ala Ala
1               5                   10                  15

Ala Pro Glu Ser Val Leu Asn Ile Val Glu Glu Ile Ala Ala Ser Gly
                20                  25                  30

Ser Val Thr Ala Gly Leu Gln Ala Ile Thr Ser Ser Pro Gly Met Val
            35                  40                  45

Asn Leu Leu Ile Gly Trp Ala Lys Thr Lys Phe Ile Gln Pro Ile Arg
        50                  55                  60

Glu Ser Lys Leu Phe Gln Ser Arg Ala Cys Gln Ile Thr Leu Leu Val
65              70                  75                  80

Leu Gly Ile Leu Leu Val Val Ala Gly Leu Ala Cys Met Phe Ile Phe
                85                  90                  95

His Ser Gln Leu Gly Ala Asn Ala Phe Trp Leu Ile Ile Pro Ala Ala
            100                 105                 110
```

```
Ile Gly Leu Ile Lys Leu Leu Val Thr Ser Leu Cys Phe Asp Glu Ala
            115                 120                 125
Cys Thr Ser Glu Lys Leu Met Val Phe Gln Lys Trp Ala Gly Val Leu
130                 135                 140
Glu Asp Gln Leu Asp Asp Gly Ile Leu Asn Asn Ser Asn Lys Ile Phe
145                 150                 155                 160
Gly His Val Lys Thr Glu Gly Asn Thr Ser Arg Ala Thr Thr Pro Val
                165                 170                 175
Leu Asn Asp Gly Arg Gly Thr Pro Val Leu Ser Pro Leu Val Ser Lys
                180                 185                 190
Ile Ala Arg Val
            195

<210> SEQ ID NO 16
<211> LENGTH: 245
<212> TYPE: PRT
<213> ORGANISM: Chlamydia pneumoniae

<400> SEQUENCE: 16

Met Thr Ile Arg Ile Leu Ala Glu Gly Leu Ala Phe Arg Tyr Gly Ser
  1               5                  10                  15
Lys Gly Pro Asn Ile Ile His Asp Val Ser Phe Ser Val Tyr Asp Gly
                 20                  25                  30
Asp Phe Ile Gly Ile Ile Gly Pro Asn Gly Gly Lys Ser Thr Leu
             35                  40                  45
Thr Met Leu Ile Leu Gly Leu Leu Thr Pro Thr Phe Gly Ser Leu Lys
 50                  55                  60
Thr Phe Pro Ser His Ser Ala Gly Lys Gln Thr His Ser Met Ile Gly
 65                  70                  75                  80
Trp Val Pro Gln His Phe Ser Tyr Asp Pro Cys Phe Pro Ile Ser Val
                 85                  90                  95
Lys Asp Val Val Leu Ser Gly Arg Leu Ser Gln Leu Ser Trp His Gly
                100                 105                 110
Lys Tyr Lys Lys Lys Asp Phe Glu Ala Val Asp His Ala Leu Asp Leu
            115                 120                 125
Val Gly Leu Ser Asp Thr Thr Thr Ala Phe Ala His Leu Ser Gly
130                 135                 140
Gly Gln Ile Gln Arg Val Leu Leu Ala Arg Ala Leu Ala Ser Tyr Pro
145                 150                 155                 160
Glu Ile Leu Ile Leu Asp Glu Pro Thr Thr Asn Ile Asp Pro Asp Asn
                165                 170                 175
Gln Gln Arg Ile Leu Ser Ile Leu Lys Lys Leu Asn Arg Thr Cys Thr
                180                 185                 190
Ile Leu Met Val Thr His Asp Leu His His Thr Thr Asn Tyr Phe Asn
            195                 200                 205
Lys Val Phe Tyr Met Asn Lys Thr Leu His Phe Ile Gly Arg His Phe
        210                 215                 220
Asp Leu Asn Arg Pro Ile Leu Leu Ser Ser Tyr Lys Asn Gln Glu Phe
225                 230                 235                 240
Ser Cys Ser Pro His
                245

<210> SEQ ID NO 17
<211> LENGTH: 278
<212> TYPE: PRT
<213> ORGANISM: Chlamydia pneumoniae
```

<400> SEQUENCE: 17

```
Met His Lys Val Ile Val Phe Ile Phe Leu Thr Leu Tyr Ser Leu Lys
 1               5                  10                  15

Ser Tyr Gly Asn Asp Val Ile Asp Lys Pro His Val Leu Val Ser Ile
            20                  25                  30

Ala Pro Tyr Lys Phe Leu Val Glu Gln Ile Ala Glu Thr Cys Phe
        35                  40                  45

Val Tyr Ala Ile Val Thr Asn His Tyr Asp Pro His Thr Tyr Glu Leu
    50                  55                  60

Pro Pro Gln Gln Ile Lys Glu Leu Arg Gln Gly Asp Leu Trp Phe Arg
65                  70                  75                  80

Ile Gly Glu Ala Phe Gly Lys Asn Leu Leu Glu Lys Pro Tyr Met Gln
                85                  90                  95

Gln Val Asp Leu Ser Gln Asn Val Ser Leu Ile Gln Gly Lys Pro Cys
            100                 105                 110

Cys Asn Gln His Thr Thr Asn Tyr Asp Thr His Thr Trp Leu Ser Pro
        115                 120                 125

Lys Asn Leu Lys Val Gln Val Glu Thr Ile Val Thr Thr Leu Ser Lys
130                 135                 140

Lys Tyr Pro Gln His Ala Thr Leu Tyr Gln Ser Asn Gly Glu Lys Leu
145                 150                 155                 160

Leu Leu Ala Leu Asp Gln Leu Asn Glu Glu Ile Leu Thr Ile Thr Ser
                165                 170                 175

Lys Ala Lys Gln Arg His Ile Leu Val Ser His Gly Ala Phe Gly Tyr
            180                 185                 190

Phe Cys Arg Asp Tyr Asn Phe Ser Gln His Thr Ile Glu Lys Ser Ser
        195                 200                 205

His Val Glu Pro Ser Pro Lys Asp Val Ala Arg Val Phe Arg Asp Ile
    210                 215                 220

Glu Gln Tyr Lys Ile Ser Ser Val Ile Leu Leu Glu Tyr Ser Gly Arg
225                 230                 235                 240

Arg Ser Ser Ala Met Leu Ala Asp Arg Phe His Met His Thr Val Asn
                245                 250                 255

Leu Asp Pro Tyr Ala Glu Asn Val Leu Val Asn Leu Lys Thr Ile Ala
            260                 265                 270

Thr Thr Phe Ser Ser Leu
        275
```

<210> SEQ ID NO 18
<211> LENGTH: 469
<212> TYPE: PRT
<213> ORGANISM: Chlamydia pneumoniae

<400> SEQUENCE: 18

```
Met Gly Pro Gly Ser Val Leu Ser Asn His Ser Lys Glu Ala Gly Gly
 1               5                  10                  15

Ile Ala Ile Asn Asn Val Ile Ile Asp Phe Ser Glu Ile Val Pro Thr
            20                  25                  30

Lys Asp Asn Ala Thr Val Ala Pro Pro Thr Leu Lys Leu Val Ser Arg
        35                  40                  45

Thr Asn Ala Asp Ser Lys Asp Lys Ile Asp Ile Thr Gly Thr Val Thr
    50                  55                  60

Leu Leu Asp Pro Asn Gly Asn Leu Tyr Gln Asn Ser Tyr Leu Gly Glu
65                  70                  75                  80
```

Asp Arg Asp Ile Thr Leu Phe Asn Ile Asp Asn Ser Ala Ser Gly Ala
                85                  90                  95

Val Thr Ala Thr Asn Val Thr Leu Gln Gly Asn Leu Gly Ala Lys Lys
            100                 105                 110

Gly Tyr Leu Gly Thr Trp Asn Leu Asp Pro Asn Ser Ser Gly Ser Lys
        115                 120                 125

Ile Ile Leu Lys Trp Thr Phe Asp Lys Tyr Leu Arg Trp Pro Tyr Ile
    130                 135                 140

Pro Arg Asp Asn His Phe Tyr Ile Asn Ser Ile Trp Gly Ala Gln Asn
145                 150                 155                 160

Ser Leu Val Thr Val Asn Gln Gly Ile Leu Gly Asn Met Leu Asn Asn
                165                 170                 175

Ala Arg Phe Glu Asp Pro Ala Phe Asn Asn Phe Trp Ala Ser Ala Ile
            180                 185                 190

Gly Ser Phe Leu Arg Lys Glu Val Ser Arg Asn Ser Asp Ser Phe Thr
        195                 200                 205

Tyr His Gly Arg Gly Tyr Thr Ala Ala Val Asp Ala Lys Pro Arg Gln
    210                 215                 220

Glu Phe Ile Leu Gly Ala Ala Phe Ser Gln Val Phe Gly His Ala Glu
225                 230                 235                 240

Ser Glu Tyr His Leu Asp Asn Tyr Lys His Lys Gly Ser Gly His Ser
                245                 250                 255

Thr Gln Ala Ser Leu Tyr Ala Gly Asn Ile Phe Tyr Phe Pro Ala Ile
            260                 265                 270

Arg Ser Arg Pro Ile Leu Phe Gln Gly Val Ala Thr Tyr Gly Tyr Met
        275                 280                 285

Gln His Asp Thr Thr Thr Tyr Pro Ser Ile Glu Glu Lys Asn Met
    290                 295                 300

Ala Asn Trp Asp Ser Ile Ala Trp Leu Phe Asp Leu Arg Phe Ser Val
305                 310                 315                 320

Asp Leu Lys Glu Pro Gln Pro His Ser Thr Ala Arg Leu Thr Phe Tyr
                325                 330                 335

Thr Glu Ala Glu Tyr Thr Arg Ile Arg Gln Glu Lys Phe Thr Glu Leu
            340                 345                 350

Asp Tyr Asp Pro Arg Ser Phe Ser Ala Cys Ser Tyr Gly Asn Leu Ala
        355                 360                 365

Ile Pro Thr Gly Phe Ser Val Asp Gly Ala Leu Ala Trp Arg Glu Ile
    370                 375                 380

Ile Leu Tyr Asn Lys Val Ser Ala Ala Tyr Leu Pro Val Ile Leu Arg
385                 390                 395                 400

Asn Asn Pro Lys Ala Thr Tyr Glu Val Leu Ser Thr Lys Glu Lys Gly
                405                 410                 415

Asn Val Val Asn Val Leu Pro Thr Arg Asn Ala Ala Arg Ala Glu Val
            420                 425                 430

Ser Ser Gln Ile Tyr Leu Gly Ser Tyr Trp Thr Leu Tyr Gly Thr Tyr
        435                 440                 445

Thr Ile Asp Ala Ser Met Asn Thr Leu Val Gln Met Ala Asn Gly Gly
    450                 455                 460

Ile Arg Phe Val Phe
465

<210> SEQ ID NO 19
<211> LENGTH: 922

<212> TYPE: PRT
<213> ORGANISM: Chlamydia pneumoniae

<400> SEQUENCE: 19

```
Met Arg Phe Ser Leu Cys Gly Phe Pro Leu Val Phe Ser Phe Thr Leu
  1               5                  10                  15

Leu Ser Val Phe Asp Thr Ser Leu Ser Ala Thr Thr Ile Ser Leu Thr
             20                  25                  30

Pro Glu Asp Ser Phe His Gly Asp Ser Gln Asn Ala Glu Arg Ser Tyr
         35                  40                  45

Asn Val Gln Ala Gly Asp Val Tyr Ser Leu Thr Gly Asp Val Ser Ile
     50                  55                  60

Ser Asn Val Asp Asn Ser Ala Leu Asn Lys Ala Cys Phe Asn Val Thr
 65                  70                  75                  80

Ser Gly Ser Val Thr Phe Ala Gly Asn His His Gly Leu Tyr Phe Asn
                 85                  90                  95

Asn Ile Ser Ser Gly Thr Thr Lys Glu Gly Ala Val Leu Cys Cys Gln
            100                 105                 110

Asp Pro Gln Ala Thr Ala Arg Phe Ser Gly Phe Ser Thr Leu Ser Phe
        115                 120                 125

Ile Gln Ser Pro Gly Asp Ile Lys Glu Gln Gly Cys Leu Tyr Ser Lys
    130                 135                 140

Asn Ala Leu Met Leu Leu Asn Asn Tyr Val Val Arg Phe Glu Gln Asn
145                 150                 155                 160

Gln Ser Lys Thr Lys Gly Gly Ala Ile Ser Gly Ala Asn Val Thr Ile
                165                 170                 175

Val Gly Asn Tyr Asp Ser Val Ser Phe Tyr Gln Asn Ala Ala Thr Phe
            180                 185                 190

Gly Gly Ala Ile His Ser Ser Gly Pro Leu Gln Ile Ala Val Asn Gln
        195                 200                 205

Ala Glu Ile Arg Phe Ala Gln Asn Thr Ala Lys Asn Gly Ser Gly Gly
    210                 215                 220

Ala Leu Tyr Ser Asp Gly Asp Ile Asp Ile Asp Gln Asn Ala Tyr Val
225                 230                 235                 240

Leu Phe Arg Glu Asn Glu Ala Leu Thr Thr Ala Ile Gly Lys Gly Gly
                245                 250                 255

Ala Val Cys Cys Leu Pro Thr Ser Gly Ser Thr Pro Val Pro Ile
            260                 265                 270

Val Thr Phe Ser Asp Asn Lys Gln Leu Val Phe Glu Arg Asn His Ser
        275                 280                 285

Ile Met Gly Gly Gly Ala Ile Tyr Ala Arg Lys Leu Ser Ile Ser Ser
    290                 295                 300

Gly Gly Pro Thr Leu Phe Ile Asn Ile Ser Tyr Ala Asn Ser Gln
305                 310                 315                 320

Asn Leu Gly Gly Ala Ile Ala Ile Asp Thr Gly Gly Glu Ile Ser Leu
                325                 330                 335

Ser Ala Glu Lys Gly Thr Ile Thr Phe Gln Gly Asn Arg Thr Ser Leu
            340                 345                 350

Pro Phe Leu Asn Gly Ile His Leu Leu Gln Asn Ala Lys Phe Leu Lys
        355                 360                 365

Leu Gln Ala Arg Asn Gly Tyr Ser Ile Glu Phe Tyr Asp Pro Ile Thr
    370                 375                 380

Ser Glu Ala Asp Gly Ser Thr Gln Leu Asn Ile Asn Gly Asp Pro Lys
385                 390                 395                 400
```

```
Asn Lys Glu Tyr Thr Gly Thr Ile Leu Phe Ser Gly Glu Lys Ser Leu
            405                 410                 415
Ala Asn Asp Pro Arg Asp Phe Lys Ser Thr Ile Pro Gln Asn Val Asn
        420                 425                 430
Leu Ser Ala Gly Tyr Leu Val Ile Lys Glu Gly Ala Glu Val Thr Val
    435                 440                 445
Ser Lys Phe Thr Gln Ser Pro Gly Ser His Leu Val Leu Asp Leu Gly
450                 455                 460
Thr Lys Leu Ile Ala Ser Lys Glu Asp Ile Ala Ile Thr Gly Leu Ala
465                 470                 475                 480
Ile Asp Ile Asp Ser Leu Ser Ser Ser Thr Ala Ala Val Ile Lys
            485                 490                 495
Ala Asn Thr Ala Asn Lys Gln Ile Ser Val Thr Asp Ser Ile Glu Leu
        500                 505                 510
Ile Ser Pro Thr Gly Asn Ala Tyr Glu Asp Leu Arg Met Arg Asn Ser
    515                 520                 525
Gln Thr Phe Pro Leu Leu Ser Leu Glu Pro Gly Ala Gly Gly Ser Val
530                 535                 540
Thr Val Thr Ala Gly Asp Phe Leu Pro Val Ser Pro His Tyr Gly Phe
545                 550                 555                 560
Gln Gly Asn Trp Lys Leu Ala Trp Thr Gly Thr Gly Asn Lys Val Gly
            565                 570                 575
Glu Phe Phe Trp Asp Lys Ile Asn Tyr Lys Pro Arg Pro Glu Lys Glu
        580                 585                 590
Gly Asn Leu Val Pro Asn Ile Leu Trp Gly Asn Ala Val Asp Val Arg
    595                 600                 605
Ser Leu Met Gln Val Gln Glu Thr His Ala Ser Ser Leu Gln Thr Asp
610                 615                 620
Arg Gly Leu Trp Ile Asp Gly Ile Gly Asn Phe Phe His Val Ser Ala
625                 630                 635                 640
Ser Glu Asp Asn Ile Arg Tyr Arg His Asn Ser Gly Gly Tyr Val Leu
            645                 650                 655
Ser Val Asn Asn Glu Ile Thr Pro Lys His Tyr Thr Ser Met Ala Phe
        660                 665                 670
Ser Gln Leu Phe Ser Arg Asp Lys Asp Tyr Ala Val Ser Asn Asn Glu
    675                 680                 685
Tyr Arg Met Tyr Leu Gly Ser Tyr Leu Tyr Gln Tyr Thr Thr Ser Leu
690                 695                 700
Gly Asn Ile Phe Arg Tyr Ala Ser Arg Asn Pro Asn Val Asn Val Gly
705                 710                 715                 720
Ile Leu Ser Arg Arg Phe Leu Gln Asn Pro Leu Met Ile Phe His Phe
            725                 730                 735
Leu Cys Ala Tyr Gly His Ala Thr Asn Asp Met Lys Thr Asp Tyr Ala
        740                 745                 750
Asn Phe Pro Met Val Lys Asn Ser Trp Arg Asn Asn Cys Trp Ala Ile
    755                 760                 765
Glu Cys Gly Gly Ser Met Pro Leu Leu Val Phe Glu Asn Gly Arg Leu
770                 775                 780
Phe Gln Gly Ala Ile Pro Phe Met Lys Leu Gln Leu Val Tyr Ala Tyr
785                 790                 795                 800
His Gly Asp Phe Lys Glu Thr Thr Ala Asp Gly Arg Arg Phe Ser Asn
            805                 810                 815
```

```
Gly Ser Leu Thr Ser Ile Ser Val Pro Leu Gly Ile Arg Phe Glu Lys
            820                 825                 830

Leu Ala Leu Ser Gln Asp Val Leu Tyr Asp Phe Ser Phe Ser Tyr Ile
            835                 840                 845

Pro Asp Ile Phe Arg Lys Asp Pro Ser Cys Glu Ala Ala Leu Val Ile
            850                 855                 860

Ser Gly Asp Ser Trp Leu Val Pro Ala Ala His Val Ser Arg His Ala
865                 870                 875                 880

Phe Val Gly Ser Gly Thr Gly Arg Tyr His Phe Asn Asp Tyr Thr Glu
                885                 890                 895

Leu Leu Cys Arg Gly Ser Ile Glu Cys Arg Pro His Ala Arg Asn Tyr
                900                 905                 910

Asn Ile Asn Cys Gly Ser Lys Phe Arg Phe
            915                 920

<210> SEQ ID NO 20
<211> LENGTH: 375
<212> TYPE: PRT
<213> ORGANISM: Chlamydia pneumoniae

<400> SEQUENCE: 20

Met Pro Ser Ser Trp Lys Arg Leu Leu Gln Val Leu Ser His Lys Ile
1               5                   10                  15

Ala Ala Thr Glu Ser Gly Gly Ile Tyr Ala Lys Asp Ile Gln Leu
            20                  25                  30

Gln Ala Leu Pro Gly Ser Phe Thr Ile Thr Asp Asn Lys Val Glu Thr
            35                  40                  45

Ser Leu Thr Thr Ser Thr Asn Leu Tyr Gly Gly Ile Tyr Ser Ser
        50                  55                  60

Gly Ala Val Thr Leu Thr Asn Ile Ser Gly Thr Phe Gly Ile Thr Gly
65                  70                  75                  80

Asn Ser Val Ile Asn Thr Ala Thr Ser Gln Asp Ala Asp Ile Gln Gly
                85                  90                  95

Gly Gly Ile Tyr Ala Thr Thr Ser Leu Ser Ile Asn Gln Cys Asn Thr
            100                 105                 110

Pro Ile Leu Phe Ser Asn Asn Ser Ala Ala Thr Lys Lys Thr Ser Thr
            115                 120                 125

Thr Lys Gln Ile Ala Gly Gly Ala Ile Phe Ser Ala Ala Val Thr Ile
        130                 135                 140

Glu Asn Asn Ser Gln Pro Ile Ile Phe Leu Asn Asn Ser Ala Lys Ser
145                 150                 155                 160

Glu Ala Thr Thr Ala Ala Thr Ala Gly Asn Lys Asp Ser Cys Gly Gly
                165                 170                 175

Ala Ile Ala Ala Asn Ser Val Thr Leu Thr Asn Asn Pro Glu Ile Thr
            180                 185                 190

Phe Lys Gly Asn Tyr Ala Glu Thr Gly Gly Ala Ile Gly Cys Ile Asp
            195                 200                 205

Leu Thr Asn Gly Ser Pro Pro Arg Lys Val Ser Ile Ala Asp Asn Gly
        210                 215                 220

Ser Val Leu Phe Gln Asp Asn Ser Ala Leu Asn Arg Gly Gly Ala Ile
225                 230                 235                 240

Tyr Gly Glu Thr Ile Asp Ile Ser Arg Thr Gly Ala Thr Phe Ile Gly
                245                 250                 255

Asn Ser Ser Lys His Asp Gly Ser Ala Ile Cys Cys Ser Thr Ala Leu
            260                 265                 270
```

```
Thr Leu Ala Pro Asn Ser Gln Leu Ile Phe Glu Asn Asn Lys Val Thr
        275                 280                 285

Glu Thr Thr Ala Thr Thr Lys Ala Ser Ile Asn Asn Leu Gly Ala Ala
        290                 295                 300

Ile Tyr Gly Asn Asn Glu Thr Ser Asp Val Thr Ile Ser Leu Ser Ala
305                 310                 315                 320

Glu Asn Gly Ser Ile Phe Phe Lys Asn Asn Leu Cys Thr Ala Thr Asn
                325                 330                 335

Lys Tyr Cys Ser Ile Ala Gly Asn Val Lys Phe Thr Ala Ile Glu Ala
            340                 345                 350

Ser Ala Gly Lys Ala Ile Ser Phe Tyr Asp Ala Val Asn Val Pro Pro
        355                 360                 365

Lys Lys Gln Leu Leu Lys Ser
        370                 375

<210> SEQ ID NO 21
<211> LENGTH: 871
<212> TYPE: PRT
<213> ORGANISM: Chlamydia pneumoniae

<400> SEQUENCE: 21

Met Lys Tyr Ser Leu Pro Trp Leu Leu Thr Ser Ser Ala Leu Val Phe
1               5                   10                  15

Ser Leu His Pro Leu Met Ala Ala Asn Thr Asp Leu Ser Ser Ser Asp
            20                  25                  30

Asn Tyr Glu Asn Gly Ser Ser Gly Ser Ala Ala Phe Thr Ala Lys Glu
        35                  40                  45

Thr Ser Asp Ala Ser Gly Thr Thr Tyr Thr Leu Thr Ser Asp Val Ser
    50                  55                  60

Ile Thr Asn Val Ser Ala Ile Thr Pro Ala Asp Lys Ser Cys Phe Thr
65                  70                  75                  80

Asn Thr Gly Gly Ala Leu Ser Phe Val Gly Ala Asp His Ser Leu Val
                85                  90                  95

Leu Gln Thr Ile Ala Leu Thr His Asp Gly Ala Ala Ile Asn Asn Thr
            100                 105                 110

Asn Thr Ala Leu Ser Phe Ser Gly Phe Ser Ser Leu Leu Ile Asp Ser
        115                 120                 125

Ala Pro Ala Thr Gly Thr Ser Gly Gly Lys Gly Ala Ile Cys Val Thr
    130                 135                 140

Asn Thr Glu Gly Gly Thr Ala Thr Phe Thr Asp Asn Ala Ser Val Thr
145                 150                 155                 160

Leu Gln Lys Asn Thr Ser Glu Lys Asp Gly Ala Ala Val Ser Ala Tyr
                165                 170                 175

Ser Ile Asp Leu Ala Lys Thr Thr Thr Ala Ala Leu Leu Asp Gln Asn
            180                 185                 190

Thr Ser Thr Lys Asn Gly Gly Ala Leu Cys Ser Thr Ala Asn Thr Thr
        195                 200                 205

Val Gln Gly Asn Ser Gly Thr Val Thr Phe Ser Ser Asn Thr Ala Thr
    210                 215                 220

Asp Lys Gly Gly Gly Ile Tyr Ser Lys Glu Lys Asp Ser Thr Leu Asp
225                 230                 235                 240

Ala Asn Thr Gly Val Val Thr Phe Lys Ser Asn Thr Ala Lys Thr Gly
                245                 250                 255

Gly Ala Trp Ser Ser Asp Asp Asn Leu Ala Leu Thr Gly Asn Thr Gln
```

-continued

```
            260                 265                 270
Val Leu Phe Gln Glu Asn Lys Thr Thr Gly Ser Ala Ala Gln Ala Asn
        275                 280                 285
Asn Pro Glu Gly Cys Gly Gly Ala Ile Cys Cys Tyr Leu Ala Thr Ala
    290                 295                 300
Thr Asp Lys Thr Gly Leu Ala Ile Ser Gln Asn Gln Glu Met Ser Phe
305                 310                 315                 320
Thr Ser Asn Thr Thr Thr Ala Asn Gly Gly Ala Ile Tyr Ala Thr Lys
                325                 330                 335
Cys Thr Leu Asp Gly Asn Thr Thr Leu Thr Phe Asp Gln Asn Thr Ala
                340                 345                 350
Thr Ala Gly Cys Gly Gly Ala Ile Tyr Thr Glu Thr Glu Asp Phe Ser
                355                 360                 365
Leu Lys Gly Ser Thr Gly Thr Val Thr Phe Ser Thr Asn Thr Ala Lys
        370                 375                 380
Thr Gly Gly Ala Leu Tyr Ser Lys Gly Asn Ser Ser Leu Thr Gly Asn
385                 390                 395                 400
Thr Asn Leu Leu Phe Ser Gly Asn Lys Ala Thr Gly Pro Ser Asn Ser
                405                 410                 415
Ser Ala Asn Gln Glu Gly Cys Gly Gly Ala Ile Leu Ala Phe Ile Asp
                420                 425                 430
Ser Gly Ser Val Ser Asp Lys Thr Gly Leu Ser Ile Ala Asn Asn Gln
            435                 440                 445
Glu Val Ser Leu Thr Ser Asn Ala Ala Thr Val Ser Gly Gly Ala Ile
    450                 455                 460
Tyr Ala Thr Lys Cys Thr Leu Thr Gly Asn Gly Ser Leu Thr Phe Asp
465                 470                 475                 480
Gly Asn Thr Ala Gly Thr Ser Gly Ala Ile Tyr Thr Glu Thr Glu
                485                 490                 495
Asp Phe Thr Leu Thr Gly Ser Thr Gly Thr Val Thr Phe Ser Thr Asn
                500                 505                 510
Thr Ala Lys Thr Gly Gly Ala Leu Tyr Ser Lys Gly Asn Asn Ser Leu
            515                 520                 525
Ser Gly Asn Thr Asn Leu Leu Phe Ser Gly Asn Lys Ala Thr Gly Pro
    530                 535                 540
Ser Asn Ser Ser Ala Asn Gln Glu Gly Cys Gly Gly Ala Ile Leu Ser
545                 550                 555                 560
Phe Leu Glu Ser Ala Ser Val Ser Thr Lys Lys Gly Leu Trp Ile Glu
                565                 570                 575
Asp Asn Glu Asn Val Ser Leu Ser Gly Asn Thr Ala Thr Val Ser Gly
                580                 585                 590
Gly Ala Ile Tyr Ala Thr Lys Cys Ala Leu His Gly Asn Thr Thr Leu
            595                 600                 605
Thr Phe Asp Gly Asn Thr Ala Glu Thr Ala Gly Gly Ala Ile Tyr Thr
    610                 615                 620
Glu Thr Glu Asp Phe Thr Leu Thr Gly Ser Thr Gly Thr Val Thr Phe
625                 630                 635                 640
Ser Thr Asn Thr Ala Lys Thr Ala Gly Ala Leu His Thr Lys Gly Asn
                645                 650                 655
Thr Ser Phe Thr Lys Asn Lys Ala Leu Val Phe Ser Gly Asn Ser Ala
                660                 665                 670
Thr Ala Thr Ala Thr Thr Thr Thr Asp Gln Glu Gly Cys Gly Gly Ala
            675                 680                 685
```

```
Ile Leu Cys Asn Ile Ser Glu Ser Asp Ile Ala Thr Lys Ser Leu Thr
    690                 695                 700
Leu Thr Glu Asn Glu Ser Leu Ser Phe Ile Asn Asn Thr Ala Lys Arg
705                 710                 715                 720
Ser Gly Gly Gly Ile Tyr Ala Pro Lys Cys Val Ile Ser Gly Ser Glu
                725                 730                 735
Ser Ile Asn Phe Asp Gly Asn Thr Ala Glu Thr Ser Gly Gly Ala Ile
                740                 745                 750
Tyr Ser Lys Asn Leu Ser Ile Thr Ala Asn Gly Pro Val Ser Phe Thr
            755                 760                 765
Asn Asn Ser Gly Gly Lys Gly Gly Ala Ile Tyr Ile Ala Asp Ser Gly
        770                 775                 780
Glu Leu Ser Leu Glu Ala Ile Asp Gly Asp Ile Thr Phe Ser Gly Asn
785                 790                 795                 800
Arg Ala Thr Glu Gly Thr Ser Thr Pro Asn Ser Ile His Leu Gly Ala
                805                 810                 815
Arg Gly Lys Ile Thr Lys Leu Ala Ala Ala Pro Gly His Thr Ile Tyr
                820                 825                 830
Phe Tyr Asp Pro Ile Thr Met Glu Ala Pro Ala Ser Gly Gly Thr Ile
            835                 840                 845
Glu Glu Leu Val Ile Asn Pro Val Val Lys Ala Ile Val Pro Pro Pro
        850                 855                 860
Gln Pro Lys Asn Gly Pro Ile
865                 870

<210> SEQ ID NO 22
<211> LENGTH: 963
<212> TYPE: PRT
<213> ORGANISM: Chlamydia pneumoniae

<400> SEQUENCE: 22

Met Thr Asn Ser Ile Phe Ile Ser Lys Phe Gly Cys Leu Cys Asp Pro
1               5                   10                  15
Phe Val Ser Ala Phe Tyr Pro Thr Ala Leu Cys Cys Ser Leu Ser Gly
            20                  25                  30
Asn Glu Val Pro Asn Leu Ala Ser Cys Gln Met Ser Arg Lys Asp Ile
        35                  40                  45
Ser Ala Phe His Thr Ser Pro Ser Phe Arg Leu Asn Val Thr Pro Glu
    50                  55                  60
Pro Leu Val Ser Ser Phe Arg Pro Ser Asn Leu Leu Asn Gly Phe Gly
65                  70                  75                  80
His Asp Ile Thr Gln Asp Ile Thr Ile Thr Gly Asn Ser Ile Asn Ser
                85                  90                  95
Val Ile Asp Tyr Asn Tyr His Tyr Glu Asp Gly Gly Ile Leu Ala Cys
            100                 105                 110
Lys Asn Leu Phe Ile Ser Glu Asn Lys Gly Asn Leu Ser Phe Glu Arg
        115                 120                 125
Asn Ser Ser His Ser Ser Gly Gly Ala Leu Tyr Ser Val Arg Glu Cys
    130                 135                 140
Trp Ile Ser Lys Asn Gln Asn Tyr Ser Phe Ile Ser Asn Ala Ala Ser
145                 150                 155                 160
Leu Ala Thr Thr Thr Thr Ser Gly Phe Gly Gly Ala Ile His Ala Leu
                165                 170                 175
Asp Ser Tyr Ile Thr Asn Asn Leu Gly Glu Gly Gln Phe Leu Asp Asn
```

-continued

```
                180                 185                 190
Val Ser Lys Asn Arg Gly Gly Ala Ile Tyr Val Gly Val Ser Leu Ser
            195                 200                 205

Ile Thr Asp Asn Leu Gly Pro Ile Val Ile Lys Lys Asn Gln Thr Leu
210                 215                 220

Glu Asp Ser Ser Phe Gly Gly Ile Phe Cys Arg Ala Val Asn Ile
225                 230                 235                 240

Glu Arg Asn Tyr Gln Asn Ile Gln Ile Asn Asp Asn Ala Ser Gly Gln
            245                 250                 255

Gly Val Val Tyr Phe Leu Pro Leu Gly Val Ile Ile Ser Ser Asn Lys
            260                 265                 270

Glu Ile Ile Glu Ile Ser Asn His Ser Ala Ser Ser Ile Asn Thr Ala
            275                 280                 285

Ser Gly Lys Leu Tyr Pro Gly Gly Gly Ile Met Cys Thr Ser Leu
            290                 295                 300

Ser His Glu Asn Asn Pro Lys Gly Leu Ile Phe Asn Asn Lys Thr Ala
305                 310                 315                 320

Ala Leu Ser Gly Gly Val Tyr Thr Arg Asp Leu Ser Ser Ser Lys Ile
                325                 330                 335

Thr Val Arg Thr Ala Phe Ile Asn Asn Ser Ala Thr Ser Gly Gly Ala
            340                 345                 350

Leu Ile Asn Leu Ser Gly Ile Gly Ser Thr Pro Gln Asn Phe Phe Leu
            355                 360                 365

Ser Ala Asp Tyr Gly Asp Ile Leu Phe Asn Asn Asn Thr Ile Thr Ser
370                 375                 380

Ser Ser Pro Gln Pro Gly Tyr Arg Asn Ala Leu Tyr Ala Ala Pro Gly
385                 390                 395                 400

Ile Asn Leu Lys Leu Gly Ala Arg Gln Gly Tyr Lys Ile Leu Phe Tyr
                405                 410                 415

Asp Pro Ile Asp His Asp Gln Thr Thr Thr Asp Pro Ile Val Phe Asn
                420                 425                 430

Tyr Glu Pro His His Leu Gly Thr Val Leu Phe Ser Gly Ile Asn Val
            435                 440                 445

Asp Ser Asn Ala Thr Asn Pro Leu Asn Phe Leu Ser Lys Phe Ser Asn
450                 455                 460

Ser Ser Arg Leu Glu Arg Gly Val Leu Ala Ile Glu Asp Arg Ala Ala
465                 470                 475                 480

Ile Ser Cys Lys Thr Leu Ser Gln Thr Gly Gly Ile Leu Arg Leu Gly
                485                 490                 495

Asn Ala Ala Leu Ile Arg Thr Lys Gly Pro Gly Ser Ser Ile Asn Phe
            500                 505                 510

Asn Ala Ile Ala Ile Asn Leu Pro Ser Ile Leu Gln Ser Glu Ala Ser
            515                 520                 525

Ala Pro Lys Phe Trp Ile Tyr Pro Thr Leu Thr Gly Ser Thr Tyr Ser
            530                 535                 540

Glu Asp Thr Ser Ser Thr Ile Thr Leu Ser Gly Pro Leu Thr Phe Leu
545                 550                 555                 560

Asn Asp Glu Asn Glu Asn Pro Tyr Asp Ser Leu Asp Leu Ser Glu Pro
                565                 570                 575

Arg Lys Asp Ile Pro Pro Leu Pro Pro Arg Cys Asp Cys Lys Lys
            580                 585                 590

Ile Asp Thr Ser Asn Leu Ile Val Glu Ala Met Asn Leu Asp Glu His
            595                 600                 605
```

```
Tyr Gly Tyr Gln Gly Ile Trp Ser Pro Tyr Trp Met Glu Thr Thr Thr
    610                 615                 620

Thr Thr Ser Ser Thr Val Pro Glu Gln Thr Asn Thr Asn His Arg Gln
625                 630                 635                 640

Leu Tyr Val Asp Trp Thr Pro Val Gly Tyr Arg Pro Asn Pro Glu Arg
            645                 650                 655

His Gly Glu Phe Ile Ala Asn Thr Leu Trp Gln Ser Ala Tyr Asn Ala
            660                 665                 670

Leu Leu Gly Ile Arg Ile Leu Pro Pro Gln Asn Leu Lys Glu His Asp
            675                 680                 685

Leu Glu Ala Ser Leu Gln Gly Leu Gly Leu Leu Ile Asn Gln His Asn
690                 695                 700

Arg Glu Gly Arg Lys Gly Phe Arg Asn His Thr Thr Gly Tyr Ala Ala
705                 710                 715                 720

Thr Thr Ser Ala Lys Thr Ala Ala Arg His Ser Phe Ser Leu Gly Phe
            725                 730                 735

Ala Gln Met Phe Ser Lys Thr Arg Glu Arg Gln Ser Pro Ser Thr Thr
            740                 745                 750

Ser Ser His Asn Tyr Phe Ala Gly Leu Arg Phe Asp Ser Leu Leu Phe
            755                 760                 765

Arg Asp Phe Ile Ser Thr Gly Leu Ser Leu Gly Tyr Ser Tyr Gly Asp
770                 775                 780

His His Met Leu Cys His Tyr Thr Glu Ile Leu Lys Gly Ser Ser Lys
785                 790                 795                 800

Ala Phe Phe Asn Asn His Thr Leu Val Ala Ser Leu Asp Cys Thr Phe
            805                 810                 815

Leu Pro Ala Arg Ile Thr Arg Thr Leu Glu Leu Gln Pro Phe Ile Ser
            820                 825                 830

Ala Ile Ala Leu Arg Cys Ser Gln Ala Ser Phe Gln Glu Thr Gly Asp
            835                 840                 845

His Ile Arg Lys Phe His Pro Lys His Pro Leu Thr Asp Leu Ser Ser
850                 855                 860

Pro Ile Gly Phe Arg Ser Glu Trp Lys Thr Ser His His Ile Pro Met
865                 870                 875                 880

Leu Trp Thr Thr Glu Ile Ser Tyr Val Pro Thr Leu Tyr Arg Lys Asn
            885                 890                 895

Pro Glu Met Phe Thr Thr Leu Leu Ile Ser Asn Gly Thr Trp Thr Thr
            900                 905                 910

Gln Ala Thr Pro Val Ser Tyr Asn Ser Val Ala Ala Lys Ile Lys Asn
            915                 920                 925

Thr Ser Gln Leu Phe Ser Arg Val Thr Leu Ser Leu Asp Tyr Ser Ala
930                 935                 940

Gln Val Ser Ser Ser Thr Val Gly Gln Tyr Leu Lys Ala Glu Ser His
945                 950                 955                 960

Cys Thr Phe
```

<210> SEQ ID NO 23
<211> LENGTH: 514
<212> TYPE: PRT
<213> ORGANISM: Chlamydia pneumoniae

<400> SEQUENCE: 23

```
Met Thr Ile Leu Arg Asn Phe Leu Thr Cys Ser Ala Leu Phe Leu Ala
 1               5                   10                  15
```

```
Leu Pro Ala Ala Ala Gln Val Val Tyr Leu His Glu Ser Asp Gly Tyr
            20                  25                  30

Asn Gly Ala Ile Asn Asn Lys Ser Leu Glu Pro Lys Ile Thr Cys Tyr
         35                  40                  45

Pro Glu Gly Thr Ser Tyr Ile Phe Leu Asp Asp Val Arg Ile Ser Asn
     50                  55                  60

Val Lys His Asp Gln Glu Asp Ala Gly Val Phe Ile Asn Arg Ser Gly
 65                  70                  75                  80

Asn Leu Phe Phe Met Gly Asn Arg Cys Asn Phe Thr Phe His Asn Leu
                 85                  90                  95

Met Thr Glu Gly Phe Gly Ala Ala Ile Ser Asn Arg Val Gly Asp Thr
                100                 105                 110

Thr Leu Thr Leu Ser Asn Phe Ser Tyr Leu Ala Phe Thr Ser Ala Pro
            115                 120                 125

Leu Leu Pro Gln Gly Gln Gly Ala Ile Tyr Ser Leu Gly Ser Val Met
        130                 135                 140

Ile Glu Asn Ser Glu Glu Val Thr Phe Cys Gly Asn Tyr Ser Ser Trp
145                 150                 155                 160

Ser Gly Ala Ala Ile Tyr Thr Pro Tyr Leu Leu Gly Ser Lys Ala Ser
                165                 170                 175

Arg Pro Ser Val Asn Leu Ser Gly Asn Arg Tyr Leu Val Phe Arg Asp
            180                 185                 190

Asn Val Ser Gln Val Tyr Gly Gly Ala Ile Ser Thr His Asn Leu Thr
        195                 200                 205

Leu Thr Thr Arg Gly Pro Ser Cys Phe Glu Asn Asn His Ala Tyr His
    210                 215                 220

Asp Val Asn Ser Asn Gly Gly Ala Ile Ala Ile Ala Pro Gly Gly Ser
225                 230                 235                 240

Ile Ser Ile Ser Val Lys Ser Gly Asp Leu Ile Phe Lys Gly Asn Thr
                245                 250                 255

Ala Ser Gln Asp Gly Asn Thr Ile His Asn Ser Ile His Leu Gln Ser
            260                 265                 270

Gly Ala Gln Phe Lys Asn Leu Arg Ala Val Ser Glu Ser Gly Val Tyr
        275                 280                 285

Phe Tyr Asp Pro Ile Ser His Ser Glu Ser His Lys Ile Thr Asp Leu
    290                 295                 300

Val Ile Asn Ala Pro Glu Gly Lys Glu Thr Tyr Glu Gly Thr Ile Ser
305                 310                 315                 320

Phe Ser Gly Leu Cys Leu Asp Asp His Glu Val Cys Ala Glu Asn Leu
                325                 330                 335

Thr Ser Thr Ile Leu Gln Asp Val Thr Leu Ala Gly Gly Thr Leu Ser
            340                 345                 350

Leu Ser Asp Gly Val Thr Leu Gln Leu His Ser Phe Lys Gln Glu Ala
        355                 360                 365

Ser Ser Thr Leu Thr Met Ser Pro Gly Thr Thr Leu Leu Cys Ser Gly
    370                 375                 380

Asp Ala Arg Val Gln Asn Leu His Ile Leu Ile Glu Asp Thr Asp Asn
385                 390                 395                 400

Phe Val Pro Val Arg Ile Arg Ala Glu Lys Asp Ala Leu Val Ser
                405                 410                 415

Leu Glu Lys Leu Lys Val Ala Phe Glu Ala Tyr Trp Ser Val Tyr Asp
        420                 425                 430
```

```
Phe Pro Gln Phe Lys Glu Ala Phe Thr Ile Pro Leu Leu Glu Leu Leu
            435                 440                 445

Gly Pro Ser Phe Asp Ser Leu Leu Gly Glu Thr Thr Leu Glu Arg
        450                 455                 460

Thr Gln Val Thr Thr Glu Asn Asp Ala Val Arg Gly Phe Trp Ser Leu
465                 470                 475                 480

Ser Trp Glu Glu Tyr Pro Pro Ser Leu Asp Lys Asp Arg Arg Ile Thr
                485                 490                 495

Pro Thr Lys Lys Thr Val Phe Leu Thr Trp Asn Pro Glu Ile Thr Ser
            500                 505                 510

Thr Pro

<210> SEQ ID NO 24
<211> LENGTH: 289
<212> TYPE: PRT
<213> ORGANISM: Chlamydia pneumoniae

<400> SEQUENCE: 24

Met Gly Ile Ser Leu Pro Glu Leu Phe Ser Asn Leu Gly Ser Ala Tyr
1               5                   10                  15

Leu Asp Tyr Ile Phe Gln His Pro Ala Tyr Val Trp Ser Val Phe
            20                  25                  30

Leu Leu Leu Leu Ala Arg Leu Leu Pro Ile Phe Ala Val Ala Pro Phe
            35                  40                  45

Leu Gly Ala Lys Leu Phe Pro Ser Pro Ile Lys Ile Gly Ile Ser Leu
        50                  55                  60

Ser Trp Leu Ala Ile Ile Phe Pro Lys Val Leu Ala Asp Thr Gln Ile
65                  70                  75                  80

Thr Asn Tyr Met Asp Asn Asn Leu Phe Tyr Val Leu Leu Val Lys Glu
                85                  90                  95

Met Ile Ile Gly Ile Val Ile Gly Phe Val Leu Ala Phe Pro Phe Tyr
            100                 105                 110

Ala Ala Gln Ser Ala Gly Ser Phe Ile Thr Asn Gln Gln Gly Ile Gln
            115                 120                 125

Gly Leu Glu Gly Ala Thr Ser Leu Ile Ser Ile Glu Gln Thr Ser Pro
        130                 135                 140

His Gly Ile Leu Tyr His Tyr Phe Val Thr Ile Ile Phe Trp Leu Val
145                 150                 155                 160

Gly Gly His Arg Ile Val Ile Ser Leu Leu Leu Gln Thr Leu Glu Val
                165                 170                 175

Ile Pro Ile His Ser Phe Phe Pro Ala Glu Met Met Ser Leu Ser Ala
            180                 185                 190

Pro Ile Trp Ile Thr Met Ile Lys Met Cys Gln Leu Cys Leu Val Met
            195                 200                 205

Thr Ile Gln Leu Ser Ala Pro Ala Ala Leu Ala Met Leu Met Ser Asp
        210                 215                 220

Leu Phe Leu Gly Ile Ile Asn Arg Met Ala Pro Gln Val Gln Val Ile
225                 230                 235                 240

Tyr Leu Leu Ser Ala Leu Lys Ala Phe Met Gly Leu Phe Leu Thr
                245                 250                 255

Leu Ala Trp Trp Phe Ile Ile Lys Gln Ile Asp Tyr Phe Thr Leu Ala
            260                 265                 270

Trp Phe Lys Glu Val Pro Ile Met Leu Leu Gly Ser Asn Pro Gln Val
        275                 280                 285
```

Leu

<210> SEQ ID NO 25
<211> LENGTH: 265
<212> TYPE: PRT
<213> ORGANISM: Chlamydia pneumoniae

<400> SEQUENCE: 25

Met Lys His Ser Lys Glu Asp Asp Leu Ser Arg Phe Leu Pro Lys Asn
1               5                   10                  15

Leu Leu Val Glu Ser Pro His Pro Glu Ile Pro Leu Lys Ser Leu
            20                  25                  30

Ser Phe Thr Met Ser Trp Leu Pro Thr Ile His Pro Ser Trp Ile Thr
            35                  40                  45

Ile Ala Met Lys Glu Phe Pro Pro Glu Ile Gln Gly Gln Leu Leu Ala
        50                  55                  60

Trp Leu Pro Glu Pro Leu Val Gln Glu Ile Leu Pro Leu Leu Pro Gly
65                  70                  75                  80

Ile Ser Ile Ala Pro His Arg Cys Ala Pro Phe Gly Ala Phe Tyr Leu
                85                  90                  95

Leu Asp Met Leu Ser Lys Lys Ile Arg Pro Cys Gly Ile Thr Glu Glu
            100                 105                 110

Ile Phe Leu Pro Ala Ser Ser Ala Asn Ala Ile Leu Tyr Tyr Thr Gly
        115                 120                 125

Pro Val Lys Ile Ala Leu Ile Asn Cys Leu Gly Leu Tyr Ser Ile Ala
    130                 135                 140

Lys Glu Leu Lys His Ile Leu Asp Lys Val Val Ile Glu Arg Val Lys
145                 150                 155                 160

Asn Ala Leu Ser Pro Thr Glu Lys Leu Phe Leu Thr Tyr Cys Gln Ser
                165                 170                 175

His Pro Met Lys His Leu Glu Thr Thr Asn Phe Leu Ser Ser Trp Thr
            180                 185                 190

Thr Asp Ala Glu Leu Arg Gln Phe Val His Lys Gln Gly Leu Glu Phe
        195                 200                 205

Leu Gly Lys Ala Leu Thr Lys Glu Asn Ala Ser Phe Leu Trp Tyr Phe
    210                 215                 220

Leu Arg Arg Leu Asp Val Gly Arg Ala Tyr Ile Val Glu Gln Thr Leu
225                 230                 235                 240

Lys Thr Trp Tyr Asp His Pro Tyr Val Asp Tyr Phe Lys Ser Arg Leu
                245                 250                 255

Glu Gln Cys Met Lys Val Leu Val Lys
            260                 265

<210> SEQ ID NO 26
<211> LENGTH: 95
<212> TYPE: PRT
<213> ORGANISM: Chlamydia pneumoniae

<400> SEQUENCE: 26

Met Leu Ala Phe Phe Ala Thr Ser Phe Lys Ser Val Leu Phe Glu Tyr
1               5                   10                  15

Ser Tyr Gln Ser Leu Leu Leu Ile Leu Ile Val Ser Ala Pro Pro Ile
            20                  25                  30

Ile Leu Ala Ser Ile Val Gly Ile Met Val Ala Ile Phe Gln Ala Ala
        35                  40                  45

Thr Gln Ile Gln Glu Gln Thr Phe Ala Phe Ala Val Lys Leu Val Val

```
                  50                  55                  60
Ile Phe Gly Thr Leu Met Ile Ser Gly Gly Trp Leu Ser Asn Met Ile
             65                  70                  75                  80
Leu Arg Phe Ala Gly Gln Ile Phe Gln Asn Phe Tyr Lys Trp Lys
                 85                  90                  95

<210> SEQ ID NO 27
<211> LENGTH: 9
<212> TYPE: PRT
<213> ORGANISM: Artificial Sequence
<220> FEATURE:
<223> OTHER INFORMATION: T-cell epitope from SEQ ID NO:14

<400> SEQUENCE: 27

Val Leu Phe Ile Ala His Phe Phe Leu
                 5

<210> SEQ ID NO 28
<211> LENGTH: 9
<212> TYPE: PRT
<213> ORGANISM: Artificial Sequence
<220> FEATURE:
<223> OTHER INFORMATION: B-cell epitope from SEQ ID NO:14

<400> SEQUENCE: 28

Arg Ile Arg Glu Asp Arg Gln Ala Asn
                 5

<210> SEQ ID NO 29
<211> LENGTH: 9
<212> TYPE: PRT
<213> ORGANISM: Artificial Sequence
<220> FEATURE:
<223> OTHER INFORMATION: T-cell epitope from SEQ ID NO:15

<400> SEQUENCE: 29

Lys Leu Met Val Phe Gln Lys Trp Ala
                 5

<210> SEQ ID NO 30
<211> LENGTH: 11
<212> TYPE: PRT
<213> ORGANISM: Artificial Sequence
<220> FEATURE:
<223> OTHER INFORMATION: B-cell epitope from SEQ ID NO:15

<400> SEQUENCE: 30

Val Lys Thr Glu Gly Asn Thr Ser Arg Ala Thr
                 5                  10

<210> SEQ ID NO 31
<211> LENGTH: 9
<212> TYPE: PRT
<213> ORGANISM: Artificial Sequence
<220> FEATURE:
<223> OTHER INFORMATION: T-cell epitope from SEQ ID NO:16

<400> SEQUENCE: 31

Tyr Met Asn Lys Thr Leu His Phe Ile
                 5

<210> SEQ ID NO 32
<211> LENGTH: 12
<212> TYPE: PRT
<213> ORGANISM: Artificial Sequence
<220> FEATURE:
```

<223> OTHER INFORMATION: B-cell epitope from SEQ ID NO:16

<400> SEQUENCE: 32

Ser Trp His Gly Lys Tyr Lys Lys Lys Asp Phe Glu
                5                   10

<210> SEQ ID NO 33
<211> LENGTH: 14
<212> TYPE: PRT
<213> ORGANISM: Artificial Sequence
<220> FEATURE:
<223> OTHER INFORMATION: B-cell epitope from SEQ ID NO:16

<400> SEQUENCE: 33

Asp Glu Pro Thr Thr Asn Ile Asp Pro Asp Asn Gln Gln Arg
                5                   10

<210> SEQ ID NO 34
<211> LENGTH: 9
<212> TYPE: PRT
<213> ORGANISM: Artificial Sequence
<220> FEATURE:
<223> OTHER INFORMATION: T-cell epitope from SEQ ID NO:17

<400> SEQUENCE: 34

Trp Leu Ser Pro Lys Asn Leu Lys Val
                5

<210> SEQ ID NO 35
<211> LENGTH: 22
<212> TYPE: PRT
<213> ORGANISM: Artificial Sequence
<220> FEATURE:
<223> OTHER INFORMATION: B-cell epitope from SEQ ID NO:17

<400> SEQUENCE: 35

Asn His Tyr Asp Pro His Thr Tyr Glu Leu Pro Pro Gln Gln Ile Lys
                5                   10                  15

Glu Leu Arg Gln Gly Asp
            20

<210> SEQ ID NO 36
<211> LENGTH: 9
<212> TYPE: PRT
<213> ORGANISM: Artificial Sequence
<220> FEATURE:
<223> OTHER INFORMATION: T-cell epitope from SEQ ID NO:18

<400> SEQUENCE: 36

Trp Leu Phe Asp Leu Arg Phe Ser Val
                5

<210> SEQ ID NO 37
<211> LENGTH: 18
<212> TYPE: PRT
<213> ORGANISM: Artificial Sequence
<220> FEATURE:
<223> OTHER INFORMATION: B-cell epitope from SEQ ID NO:18

<400> SEQUENCE: 37

Glu Ser Glu Tyr His Leu Asp Asn Tyr Lys His Lys Gly Ser Gly His
                5                   10                  15

Ser Thr

<210> SEQ ID NO 38

```
<211> LENGTH: 9
<212> TYPE: PRT
<213> ORGANISM: Artificial Sequence
<220> FEATURE:
<223> OTHER INFORMATION: T-cell epitope from SEQ ID NO:19

<400> SEQUENCE: 38

Ala Leu Met Leu Leu Asn Asn Tyr Val
                5

<210> SEQ ID NO 39
<211> LENGTH: 13
<212> TYPE: PRT
<213> ORGANISM: Artificial Sequence
<220> FEATURE:
<223> OTHER INFORMATION: B-cell epitope from SEQ ID NO:19

<400> SEQUENCE: 39

Asp Lys Ile Asn Tyr Lys Pro Arg Pro Glu Lys Glu Gly
                5                   10

<210> SEQ ID NO 40
<211> LENGTH: 9
<212> TYPE: PRT
<213> ORGANISM: Artificial Sequence
<220> FEATURE:
<223> OTHER INFORMATION: T-cell epitope from SEQ ID NO:20

<400> SEQUENCE: 40

Val Leu Phe Gln Asp Asn Ser Ala Leu
                5

<210> SEQ ID NO 41
<211> LENGTH: 7
<212> TYPE: PRT
<213> ORGANISM: Artificial Sequence
<220> FEATURE:
<223> OTHER INFORMATION: B-cell epitope from SEQ ID NO:20

<400> SEQUENCE: 41

Asn Ser Ser Lys His Asp Gly
                5

<210> SEQ ID NO 42
<211> LENGTH: 9
<212> TYPE: PRT
<213> ORGANISM: Artificial Sequence
<220> FEATURE:
<223> OTHER INFORMATION: T-cell epitope from SEQ ID NO:21

<400> SEQUENCE: 42

Trp Leu Leu Thr Ser Ser Ala Leu Val
                5

<210> SEQ ID NO 43
<211> LENGTH: 9
<212> TYPE: PRT
<213> ORGANISM: Artificial Sequence
<220> FEATURE:
<223> OTHER INFORMATION: B-cell epitope from SEQ ID NO:21

<400> SEQUENCE: 43

Gln Lys Asn Thr Ser Glu Lys Asp Gly
                5

<210> SEQ ID NO 44
<211> LENGTH: 16
```

```
<212> TYPE: PRT
<213> ORGANISM: Artificial Sequence
<220> FEATURE:
<223> OTHER INFORMATION: B-cell epitope from SEQ ID NO:21

<400> SEQUENCE: 44

Gly Asn Lys Ala Thr Gly Pro Ser Asn Ser Ser Ala Asn Gln Glu Gly
                 5                  10                  15

<210> SEQ ID NO 45
<211> LENGTH: 9
<212> TYPE: PRT
<213> ORGANISM: Artificial Sequence
<220> FEATURE:
<223> OTHER INFORMATION: T-cell epitope from SEQ ID NO:22

<400> SEQUENCE: 45

Gln Leu Tyr Val Asp Trp Thr Pro Val
                 5

<210> SEQ ID NO 46
<211> LENGTH: 17
<212> TYPE: PRT
<213> ORGANISM: Artificial Sequence
<220> FEATURE:
<223> OTHER INFORMATION: B-cell epitope from SEQ ID NO:22

<400> SEQUENCE: 46

Asn Gln His Asn Arg Glu Gly Arg Lys Gly Phe Arg Asn His Thr Thr
                 5                  10                  15
Gly

<210> SEQ ID NO 47
<211> LENGTH: 17
<212> TYPE: PRT
<213> ORGANISM: Artificial Sequence
<220> FEATURE:
<223> OTHER INFORMATION: B-cell epitope from SEQ ID NO:22

<400> SEQUENCE: 47

Ser Lys Thr Arg Glu Arg Gln Ser Pro Ser Thr Thr Ser Ser His Asn
                 5                  10                  15
Tyr

<210> SEQ ID NO 48
<211> LENGTH: 19
<212> TYPE: PRT
<213> ORGANISM: Artificial Sequence
<220> FEATURE:
<223> OTHER INFORMATION: B-cell epitope from SEQ ID NO:23

<400> SEQUENCE: 48

Trp Glu Glu Tyr Pro Pro Ser Leu Asp Lys Asp Arg Arg Ile Thr Pro
                 5                  10                  15
Thr Lys Lys

<210> SEQ ID NO 49
<211> LENGTH: 9
<212> TYPE: PRT
<213> ORGANISM: Artificial Sequence
<220> FEATURE:
<223> OTHER INFORMATION: T-cell epitope from SEQ ID NO:24

<400> SEQUENCE: 49

Tyr Met Asp Asn Asn Leu Phe Tyr Val
```

-continued

```
<210> SEQ ID NO 50
<211> LENGTH: 10
<212> TYPE: PRT
<213> ORGANISM: Artificial Sequence
<220> FEATURE:
<223> OTHER INFORMATION: B-cell epitope from SEQ ID NO:24

<400> SEQUENCE: 50

Thr Gln Ile Thr Asn Tyr Met Asp Asn Asn
                5                   10

<210> SEQ ID NO 51
<211> LENGTH: 9
<212> TYPE: PRT
<213> ORGANISM: Artificial Sequence
<220> FEATURE:
<223> OTHER INFORMATION: T-cell epitope from SEQ ID NO:25

<400> SEQUENCE: 51

Phe Leu Trp Tyr Phe Leu Arg Arg Leu
                5

<210> SEQ ID NO 52
<211> LENGTH: 11
<212> TYPE: PRT
<213> ORGANISM: Artificial Sequence
<220> FEATURE:
<223> OTHER INFORMATION: B-cell epitope from SEQ ID NO:25

<400> SEQUENCE: 52

Met Lys His Ser Lys Glu Asp Asp Leu Ser Arg
                5                   10

<210> SEQ ID NO 53
<211> LENGTH: 9
<212> TYPE: PRT
<213> ORGANISM: Artificial Sequence
<220> FEATURE:
<223> OTHER INFORMATION: T-cell epitope from SEQ ID NO:26

<400> SEQUENCE: 53

Leu Leu Leu Ile Leu Ile Val Ser Ala
                5

<210> SEQ ID NO 54
<211> LENGTH: 7
<212> TYPE: PRT
<213> ORGANISM: Artificial Sequence
<220> FEATURE:
<223> OTHER INFORMATION: B-cell epitope from SEQ ID NO:26

<400> SEQUENCE: 54

Gln Asn Phe Tyr Lys Trp Lys
                5
```